(12) United States Patent
Bruhlmann

(10) Patent No.: US 12,252,725 B2
(45) Date of Patent: Mar. 18, 2025

(54) METHOD FOR PRODUCING VANILLIN

(71) Applicant: FIRMENICH SA, Satigny (CH)

(72) Inventor: Fredi Bruhlmann, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 17/816,586

(22) Filed: Aug. 1, 2022

(65) Prior Publication Data

US 2023/0078975 A1    Mar. 16, 2023

Related U.S. Application Data

(63) Continuation of application No. 17/041,906, filed as application No. PCT/EP2019/058101 on Mar. 29, 2019, now Pat. No. 11,447,800.

(30) Foreign Application Priority Data

Mar. 29, 2018  (EP) ..................... 18165125

(51) Int. Cl.
  *C12P 7/24*   (2006.01)
  *C12N 1/21*   (2006.01)
  *C12N 9/04*   (2006.01)

(52) U.S. Cl.
  CPC .............. *C12P 7/24* (2013.01); *C12N 9/0006* (2013.01); *C12Y 101/01319* (2015.07)

(58) Field of Classification Search
  None
  See application file for complete search history.

(56) References Cited

U.S. PATENT DOCUMENTS

| 6,068,991 A | 5/2000 | Liu et al. |
| 2014/0178954 A1 | 6/2014 | Hitz et al. |

FOREIGN PATENT DOCUMENTS

| CN | 106754802 A |   | 5/2017 |
| KR | 20100054292 A | * | 5/2010 |
| WO | 03057897 A2 |   | 7/2003 |

OTHER PUBLICATIONS

Ryu et al., Isoeugenol monooxygenase and its putative regulatory gene are located in the eugenol metabolic gene cluster in Pseudomonas nitroreducens Jin1, Arch. Microbiol. 192, 2010, 201-09. (Year: 2010).*
GenBank, Accession No. FJ851547.1, 2010, www.ncbi.nlm.nih.gov. (Year: 2010).*
Yamada et al., Vanillin production using *Escherichia coli* cells over-expressing isoeugenol monooxygenase of Pseudomonas putida, Biotechnol. Lett. 30, 2008, 665-70. (Year: 2008).*
Yamada et al., Purification, characterization and gene cloning of isoeugenol-degrading enzyme from Pseudomonas putida IE27, Arch. Microbiol. 187, 2007, 511-17. (Year: 2007).*
GenBank, Accession No. AB291707.1, 2007, www.ncbi.nlm.nih.gov. (Year: 2007).*
Furuya et al., A Coenzyme-Independent Decarboxylase/Oxygenase Cascade for the Efficient Synthesis of Vanillin, ChemBioChem 15, 2014, 2248-54 (Year: 2014).*
Zhao et al., Efficient biotransformation of isoeugenol to vanillin in recombinant strains of *Escherichia coli* by using engineered isoeugenol monooxygenase and sol-gel chitosan membrane, Process Biochem. 71, 2018, 76-81. (Year: 2018).*
GenBank, Accession No. MF669473.1, 2018, www.ncbi.nlm.nih.gov. (Year: 2018).*
Puigbo et al., Optimizer, Nucleic Acids Res. 35, 2007, W126-W131. (Year: 2007).*
Lampman et al., The preparation of vanillin from eugenol and sawdust, J. Chem. Education 54, 1977, 776-78. (Year: 1977).*
GenBank, Accession No. BAF62888.1, 2007, www.ncbi.nlm.nih.gov. (Year: 2007).*
GenBank, Accession No. ACP17973.1, 2010, www.ncbi.nlm.nih.gov. (Year: 2010).*
International Search Report and Written Opinion for corresponding PCT/EP2019/058101 mailed Jun. 18, 2019, 17 pages.
Ryu et al., "Transcriptional Control of the Isoeugenol Monooxygenase of Pseudomonas nitroreducens Jin1 in *Escherichia coli*", Bioscience, Biotechnology, and Biochemistry, May 22, 2014, vol. 76, No. 10, pp. 1891-1896.
Yamada et al., "Vanillin production using *Escherichia coli* cells over-expressing isoeugenol monooxygenase of Pseudomonas putida", Biotechnology Letters, Nov. 27, 2007, vol. 30, pp. 665-670.
Yamada et al., Purification, characterization and gene cloning of isoeugenol-degrading enzyme from Pseudomonas putida IE27, Arch. Microbiol. 187, 2007, 511-17.
GenBank, Accession No. AB291707.1, 2007, www.ncbi.nlm.nih.gov.
Furuya et al., A Conenzyme-Independent Decarboxlase/Oxygenase Cascade for the Efficient Synthesis of Vanillin, ChemBioChem 15, 2014, 2248-54.
Ryu et al., Isoeugenol monooxygenase and its putative regulatory gene are located in the eugenol metabolic gene cluster in Pseudomonas nitroreducens Jin1, Arch. Microbiol. 192, 2010, 201-09.
UniProt, "Accession No. C3VA26", 2017; Retrieved on Sep. 4, 2023: https://rest.uniprot.org/unisave/C3VA26?format=txt&versions=16.

* cited by examiner

*Primary Examiner* — Todd M Epstein
(74) *Attorney, Agent, or Firm* — Armstrong Teasdale LLP

(57) ABSTRACT

The present disclosure relates to a novel method of producing vanillin and/or derivatives thereof by applying improved biocatalysts. Also provided herein are expression systems for preparing said improved biocatalysts. Moreover provided herewith are novel enzyme mutants, corresponding coding sequences and vectors applicable in the biochemical production of vanillin. The present disclosure further provides recombinant host cells or organisms genetically modified for improved functional expression of biocatalysts, as well as recombinant host cells or organisms useful to produce vanillin.

7 Claims, 9 Drawing Sheets

Specification includes a Sequence Listing.

Fig. 8

```
                        10         20         30         40         50         60         70
                        ....|....|....|....|....|....|....|....|....|....|....|....|....|....|
SEQ ID NO: 2 IEM_P.nitroreducens Jin1  MARLNRRNDRQLVGTLLPTRIEADLFDLEVDGEIPKSINGTFYRNTEEQVTPQKFWFTIDGDGMASAPHF
SEQ ID NO: 4 IEM_P.putida IE27         ..TFD.....A..MF......NV....IE.....RA...S.P........T.P........L.......

80         90        100        110        120        130        140
                        ....|....|....|....|....|....|....|....|....|....|....|....|....|....|
IEM_P.nitroreducens Jin1  EDGHVDFISRWVKTARFTAERRLARKSLFGMYRNPYTDDTSVKGLDRTVANTSTISHHGKVLAVKEDGLPY
IEM_P.putida IE27         ...Q...V.......C.P..E...S...........F...P..E.I.........T.......A.....

150        160        170        180        190        200        210
                        ....|....|....|....|....|....|....|....|....|....|....|....|....|....|
IEM_P.nitroreducens Jin1  ELDPRTLETRGRFDVDGQVTSQTHTAHPKYDPETGDLLFFGSAAKGEATPDMAYYIVDKHGKVTHETWFE
IEM_P.putida IE27         ...Q.....Y..K..........H.....F..Q..EM.L........R.L..........RY.......K 220        230        240        250        260        270        280
                        ....|....|....|....|....|....|....|....|....|....|....|....|....|....|
IEM_P.nitroreducens Jin1  QPYGAFMHDFAITRMWSTFPIMPATMSLSRLKAKQPIYMMEPELGSYIGVLPRRGQGSQIRWLKAPALMV
IEM_P.putida IE27         .............V.............E...........R..........KD...FR...........

290        300        310        320        330        340        350
                        ....|....|....|....|....|....|....|....|....|....|....|....|....|....|
IEM_P.nitroreducens Jin1  FHVVNAMEVGTKIYIDLMESETLPFFPFNSQNQPFAPEKAVPRLTRWEIDLDSSSDEIERTRLHDFFAEM
IEM_P.putida IE27         .E..NR.L................L..D.S.................N.GN.M...Q..EY.......

360        370        380        390        400        410        420
                        ....|....|....|....|....|....|....|....|....|....|....|....|....|....|
IEM_P.nitroreducens Jin1  PIMDFRRFALQCNRYGFMGVDDPRKPLAHQQAEKIFAYNSLGIWDNHRGDYDIWYSGEASAAQEPAFVPRS
IEM_P.putida IE27         .......DH..AY........R..................V......K..E..FT.KM..........

430        440        450        460        470
                        ....|....|....|....|....|....|....|....|....|....|....|
IEM_P.nitroreducens Jin1  PTAAEGDCYLLTVGRLDENRSDLVILDTQDIQSGFVATIKLPFFRLRAALHGCWVPRP
IEM_P.putida IE27         .D.P......S........D.........CLAA......V..........QSKN..
```

Feature Map pIEM2_C154_T222_A1318

| Name | Start | End |
|---|---|---|
| IEM_C154_T222_A1318 | 1528 | 2997 |
| Ori_p15a | 1 | 827 |
| Term_rpoC | 1009 | 1128 |
| Term_bla | 1129 | 1429 |
| P_T7_Inducible | 1456 | 1497 |
| LacO1 | 1477 | 1497 |
| Term_T7 | 3002 | 3049 |
| P_Amp | 3322 | 3439 |
| Kanamycin-r | 3450 | 4259 |
| P_lacI | 4260 | 4341 |
| lacI | 4342 | 5424 |

SEQUENCE LISTING

Sequence total quantity: 25
SEQ ID NO: 1    moltype = DNA  length = 1437
FEATURE            Location/Qualifiers
misc_feature       1..1437
                    note = codon modified Iseougenol monooxygenase of p.
                    nitroreducens Jin1
source              1..1437
                    mol_type = genomic DNA
                    organism = Pseudomonas nitroreducens
CDS                 1..1437
                    protein_id = 2
                    translation = MARLNRNDPQLVGTLLPTRIEADLFDLEVDGEIPKSINGTFYRNTP
                    EPQVTPQKFHTFIDGDGMASAFHFEDGHVDFISRWVKTARFTAERLARKSLFGMYRNPY
                    TDDTSVKGLDRTVANTSIISHHGKVLAVKEDGLPYELDPRTLETRGRFDYDGQVTSQTH
                    TAHPKYDPETGDLLFFGSAAKGEATPDMAYYIVDKHGKVTHETWFEQPYGAFMHDFAIT
                    RNWSIFPIMPATNSLSRLKAKQPIYMWEPELGSYIGVLPRRGQGSQIRWLKAPALWVFH
                    VVNAWEVGTKIYIDLMESEILPFPFPNSQNQPFAPEKAVPRLTRWEIDLDSSSDEIKRT
                    RLHDFFAEMPIMDFRFALQCNRYGFMGVDDPRKPLAHQQAEKIFAYNSLGIWDNHRGDY
                    DLWYSGEASAAQEPAFVPRSPTAAEGDGYLLTVVGRLDENRSDLVILDTQDIQSGPVAT
                    IKLPFRLRAALHGCWVPRP
SEQUENCE: 1
atggcacgtc tgaaccgtaa tgatccgcaa ctcgtcggca ccctgttacc aacccgtatt  60
gaggctgacc tgttcgacct ggaagtggac ggcgaaattc cgaagtccat caacggtacc 120
ttctaccgta acacgccgga gcctcaggtg acgccgcaga aattccacac cttcatcgat 180
ggtgacggca tggcgtctgc atttcatttt gaagatggcc acgtggactt catcagccgc 240
tgggttaaaa ccgcgcgttt cacggcggag agactggcac gtaaaagcct gttcggtatg 300
taccgtaatc cgtacaccga tgacacgtct gtgaaggtc tggatcgtac cgttgccaac 360
acgagcatca tcagccatca cggtaaggtt ctggcggtga agaagatgg cttgccgtac 420
gagctggacc cacgcactct ggaaacccgt ggtcgctttg actatgatgg ccaagtcacc 480
agccagacgc acaccgcgca tccgaagtat gacccggaaa ccggtgacct gttgttcttt 540
ggctccgcag ccaagggtga gcaacgcct gatatgcat attacatcgt tgataaacat 600
ggtaaggtaa cgcatgagac ttggttcgag caaccgtatg gcgcctttat gcatgatttt 660
gctattaccc gcaattggag catcttcccg atcatgccgg ctaccaattc gttgagccgc 720
ctgaaagcga agcagccgat ttacatgtgg agccggaac tgggttccta tattggtgtt 780
ctgccgcgtc gcggtcaagg tagccagatc cgctggctga agcaccagc gctgtgggtc 840
tttcacgtcg tcaacgcctg ggaagtgggc accaaaatct acattggcct tatggagagc 900
gaaattctgc cattcccgtt cccgaatagc caaaatcagc cgttcgctcc tgagaaagca 960
gtgccgcgtc tgacccgttg ggagattgat ctggatagca gcagcgatga gattaagcgt 1020
acgcgtctgc acgacttctt tgcagagatg ccgatcatgg attttcgttt tgcgctgcag 1080

```
tgcaaccgct acggttttat gggtgtcgat gacccgcgca agccgctggc gcaccaacaa   1140
gcggagaaga ttttttgcgta caatagcctg ggtatctggg acaaccaccg tggtgattat   1200
gatttgtggt acagcggcga agcctcagcg gcgcaagaac cggctttcgt tccgcgttct   1260
ccgactgcag cggaaggcga cggttatctg ctgaccgttg tgggccgttt ggacgagaac   1320
cgcagcgacc tggtcattct ggacacgcag gacatccaga gcggtccggt tgcgaccatt   1380
aaaactgccg ttcgcctgcg tgcggccctg cacggctgtt gggttccgcg tccgtaa     1437

SEQ ID NO: 2              moltype = AA  length = 478
FEATURE                   Location/Qualifiers
source                    1..478
                          mol_type = protein
                          organism = Pseudomonas nitroreducens
SEQUENCE: 2
MARLNRNDPQ LVGTLLPTRI EADLFDLEVD GEIPKSINGT FYRNTPEPQV TPQKFHTFID    60
GDGMASAFHF EDGHVDFISR WVKTARFTAE RLARKSLFGM YRNPYTDDTS VKGLDRTVAN   120
TSIISHHGKV LAVKEDGLPY ELDPRTLETR GRFDYDGQVT SQTHTAHPKY DPETGDLLFF   180
GSAAKGEATP DMAYYIVDKH GKVTHETWFE QPYGAFMHDF AITRNWSIFP IMPATNSLSR   240
LKAKQPIYMW EPELGSYIGV LPRRGQGSQI RWLKAPALWV FHVVNAWEVG TKIYIDLMES   300
EILPFPFPNS QNQPFAPEKA VPRLTRWEID LDSSSDEIKR TRLHDFFAEM PIMDFRFALQ   360
CNRYGFMGVD DPRKPLAHQQ AEKIFAYNSL GIWDNHRGDY DLWYSGEASA AQEPAFVPRS   420
PTAAEGDGYL LTVVGRLDEN RSDLVILDTQ DIQSGPVATI KLPFRLRAAL HGCWVPRP    478

SEQ ID NO: 3              moltype = DNA  length = 1437
FEATURE                   Location/Qualifiers
misc_feature              1..1437
                          note = Isoeugenol monooxygenase of p. putida IE27 at
                           GenBank AccessionAB291707
source                    1..1437
                          mol_type = genomic DNA
                          organism = Pseudomonas putida
CDS                       1..1437
                          protein_id = 4
                          translation = MATFDRNDPQLAGTMFPTRIEANVFDLEIEGEIPRAINGSFFRNTP
                           EPQVTTQPFHTFIDGDGLASAFHFEDGQVDFVSRWVCTPRFEAERSARKSLFGMYRNPF
                           TDDPSVEGIDRTVANTSIITHHGKVLAAKEDGLPYELDPQTLETRGRYDYKGQVTSHTH
                           TAHPKFDPQTGEMLLFGSAAKGERTLDMAYYIVDRYGKVTHETWFKQPYGAFMHDFAVT
                           RNWSIFPIMPATNSLERLKAKQPIYMWEPERGSYIGVLPRRGQGKDIRWFRAPALWVFH
                           VVNAWEEGNRILIDLMESEILPFPFPNSQNLPFDPSKAVPRLTRWEIDLNSGNDEMKRT
                           QLHEYFAEMPIMDFRFALQDHRYAYMGVDDPRRPLAHQQAEKIFAYNSLGVWDNHRKDY
                           ELWFTGKMSAAQEPAFVPRSPDAPEGDGYLLSVVGRLDEDRSDLVILDTQCLAAGPVAT
                           VKLPFRLRAALHGCWQSKN
SEQUENCE: 3
atggcaacgt ttgaccgcaa tgatccgcag ttggcaggaa cgatgttccc caccgaata     60
gaggcgaatg tctttgacct tgaaattgag ggcgagatcc cacgtgcaat caacgggagc   120
ttcttccgca acacccccga acctcaggtc accacgcaac cttccacac cttcatcgat    180
ggggatggtt tggcgtctgc tttcattc gaagatggcc aggtcgactt tgtcagccgt     240
tgggtatgta ctcctcgctt tgaagctgag cggtcggctc gtaaatcact cttcggtatg   300
taccgcaatc cgttcactga tgatccatcg gtagaaggta ttgatcgtac agtcgccaac   360
accagtatca tcactcatca cgggaaagta ctggccgcaa aggaagatgg actaccttat   420
gagcttgacc cccaaaccct ggaaacccga ggtcgttatg attacaaggg gcaggtaacc   480
agccatacac atacagcgca ccctaagttc gaccccagca caggtgaaat gttactcttc   540
ggctccgctg ctaaaggcga acgaacgctt gatatggcgt actatattgt tgatcgctac   600
ggcaaggtga cacatgagac ctggtttaag cagccttacg gtgcattcat gcacgacttt   660
gctgtcacgc gcaactggtc aatctttccg atcatgcctg cgacaaatag ccttgagcgt   720
cttaaagcaa agcagcccat ttacatgtgg gagcctgagc gaggaagcta tataggagta   780
cttcctcgtc gtggtcaggg caaggacatt cgttggttcc gtgccccggc gttgtgggtt   840
ttccatgtcg tgaatgcttg ggaggaaggg aatagaattc tgattgactt gatggaaagt   900
gagattttgc cgttcccatt cccgaactcg cagaaccttc catttgatcc ctccaaggct   960
gttccgcgtc taaccgttg gaaattgat ctcaatggtg gtaacgatga gatgaaacgt   1020
acgcagctac acgaatattt tgcagaaatg cctatcatgg atttccgttt tgcgctccaa   1080
gatcatcgct acgcctacat gggggttgac gatcctcgtc gccccttagc tcatcagcaa   1140
gctgaaaaa tctttgccta caattcgtta ggggtttggg acaaccatcg taaagattat   1200
gaactttggt ttacgggaaa aatgtctgca gcgcaggaac cggcgtttgt tcctagaagc   1260
ccagatcgcg ctgagggcga tggctaccta ctcagtgtag taggcggct cgatgaagat   1320
cgtagcgatc tagttatcct tgatacgcaa tgtttggcag ctgggcctgt ggccactgtc   1380
aagcttccct tccgtctccg agcagcgttg cacggttgtt ggcagtctaa gaactga    1437

SEQ ID NO: 4              moltype = AA  length = 478
FEATURE                   Location/Qualifiers
source                    1..478
                          mol_type = protein
                          organism = Pseudomonas putida
SEQUENCE: 4
MATFDRNDPQ LAGTMFPTRI EANVFDLEIE GEIPRAINGS FFRNTPEPQV TTQPFHTFID    60
GDGLASAFHF EDGQVDFVSR WVCTPRFEAE RSARKSLFGM YRNPFTDDPS VEGIDRTVAN   120
TSIITHHGKV LAAKEDGLPY ELDPQTLETR GRYDYKGQVT SHTHTAHPKF DPQTGEMLLF   180
GSAAKGERTL DMAYYIVDRY GKVTHETWFK QPYGAFMHDF AVTRNWSIFP IMPATNSLER   240
LKAKQPIYMW EPERGSYIGV LPRRGQGKDI RWFRAPALWV FHVVNAWEEG NRILIDLMES   300
EILPFPFPNS QNLPFDPSKA VPRLTRWEID LNSGNDEMKR TQLHEYFAEM PIMDFRFALQ   360
```

```
DHRYAYMGVD DPRRPLAHQQ AEKIFAYNSL GVWDNHRKDY ELWFTGKMSA AQEPAFVPRS   420
PDAPEGDGYL LSVVGRLDED RSDLVILDTQ CLAAGPVATV KLPFRLRAAL HGCWQSKN     478

SEQ ID NO: 5            moltype = DNA   length = 1437
FEATURE                 Location/Qualifiers
misc_feature            1..1437
                        note = codon modified Isoeugenol monoxygenase of p. putida
                        IE27
source                  1..1437
                        mol_type = genomic DNA
                        organism = Pseudomonas putida
CDS                     1..1437
                        protein_id = 6
                        translation = MATFDRNDPQLAGTMFPTRIEANVFDLEIEGEIPRAINGSFFRNTP
                        EPQVTTQPFHTFIDGDGLASAFHFEDGQVDFVSRWVCTPRFEAERSARKSLFGMYRNPF
                        TDDPSVEGIDRTVANTSIITHHGKVLAAKEDGLPYELDPQTLETRGRYDYKGQVTSHTH
                        TAHPKFDPQTGEMLLFGSAAKGERTLDMAYYIVDRYGKVTHETWFKQPYGAFMHDFAVT
                        RNWSIFPIMPATNSLERLKAKQPIYMWEPERGSYIGVLPRRGQGKDIRWFRAPALWVFH
                        VVNAWEEGNRILIDLMESEILPFPFPNSQNLPFDPSKAVPRLTRWEIDLNSGNDEMKRT
                        QLHEYFAEMPIMDFRFALQDHRYAYMGVDDPRRPLAHQQAEKIFAYNSLGVWDNHRKDY
                        ELWFTGKMSAAQEPAFVPRSPDAPEGDGYLLSVVGRLDEDRSDLVILDTQCLAAGPVAT
                        VKLPFRLRAALHGCWQSKN
SEQUENCE: 5
atggccactt tgaccgcaa tgacccgcaa ctggcaggca ccatgttccc gacgcgcatc   60
gaagcgaatg ttttgatct ggagattgaa ggtgagattc gcgtgcgat caacggtagc   120
ttttccgca acacgccaga gccgcaagtc accacgcagc cgtttcatac tttcatcgac   180
ggcgacggcc tggcgtcagc gttccacttc gaagatggcc aggtcgactt tgtgagccgc   240
tgggtctgca ccccgcgttt cgaggcagag cgcagcgcgc gtaaaagcct gtttggtatg   300
tatcgcaatc cgtttacgga tgacccgagc gttgaaggca ttgaccgtac cgtggcgaat   360
acctcgatca ttacccacca cggtaaggtc ctggcagcaa aagaagatgg cttgccgtac   420
gagttagatc cgcagaccct ggaaacgcgt ggtcgctatg actacaaggg ccaggttacc   480
agccataccc acacgctca ccctaagttt gatccgcaaa cgggtgagat gctgctgttc   540
ggcagcgcgg caaagggtga gcgtaccctg gacatggcgt actatatcgt tgaccgttac   600
ggtaaagtga cccatgaaac ctggttcaag caaccgtacg gcgcctttat gcacgactic   660
gcagtcacgc gcaactggtc tatctttccg attatgccga ccaccaatag cctggagcgt   720
ctgaaagcta agcaaccgat ttacatgtgg gaaccggagc gtggttccta catcggcgtg   780
ctgccgcgtc gtggtcaggg taaagatatc cgctggttcc gtcgcctgc cctctggtg   840
ttccacgttg tgaacgcatg ggaagagggc aatcgtattc tgatcgatct gatggagagc   900
gaaatcctgc cattcccgtt tccgaactct cagaatctgc cgttcgatcc gagcaaagcc   960
gtaccgcgct tgacccgttg ggagattgat ttgaacagcg gtaatgacga tgaagcgt   1020
actcagctgc acgaatactt cgctgagatg ccgattatgg actttcgttt cgcgctgcaa   1080
gatcaccgtt acgcgtatat gggtgttgat gatccacgcc gtccattggc gcatcaacaa   1140
gcggaaaaga ttttgcgta taacagcctg ggtgtttggg acaaccatcg taaagactat   1200
gagctgtggt ttacgggtaa aatgtccgcg gctcaggaac cggccttcgt gccgcgcagc   1260
ccggacgccc ctgagggtga tggttatttg ctgtccgtcg tgggtcgcct ggatgaagat   1320
cgtagcgacc tggttatcct ggacacccag tgccttgcgg caggcccggt tgcgaccgtc   1380
aagctgccgt tccgtctgcg tgcagctctg catggttgtt ggcagagcaa aaactaa     1437

SEQ ID NO: 6            moltype = AA   length = 478
FEATURE                 Location/Qualifiers
source                  1..478
                        mol_type = protein
                        organism = Pseudomonas putida
SEQUENCE: 6
MATFDRNDPQ LAGTMFPTRI EANVFDLEIE GEIPRAINGS FFRNTPEPQV TTQPFHTFID   60
GDGLASAFHF EDGQVDFVSR WVCTPRFEAE RSARKSLFGM YRNPFTDDPS VEGIDRTVAN   120
TSIITHHGKV LAAKEDGLPY ELDPQTLETR GRYDYKGQVT SHTHTAHPKF DPQTGEMLLF   180
GSAAKGERTL DMAYYIVDRY GKVTHETWFK QPYGAFMHDF AVTRNWSIFP IMPATNSLER   240
LKAKQPIYMW EPERGSYIGV LPRRGQGKDI RWFRAPALWV FHVVNAWEEG NRILIDLMES   300
EILPFPFPNS QNLPFDPSKA VPRLTRWEID LNSGNDEMKR TQLHEYFAEM PIMDFRFALQ   360
DHRYAYMGVD DPRRPLAHQQ AEKIFAYNSL GVWDNHRKDY ELWFTGKMSA AQEPAFVPRS   420
PDAPEGDGYL LSVVGRLDED RSDLVILDTQ CLAAGPVATV KLPFRLRAAL HGCWQSKN    478

SEQ ID NO: 7            moltype = DNA   length = 1647
FEATURE                 Location/Qualifiers
misc_feature            1..1647
                        note = chaperonin GroEL of e. coli at GenBank Accession
                        CP009685.1 inregion 3964433 to 3966079
source                  1..1647
                        mol_type = genomic DNA
                        organism = Escherichia coli
CDS                     1..1647
                        protein_id = 8
                        translation = MAAKDVKFGNDARVKMLRGVNVLADAVKVTLGPKGRNVVLDKSFGA
                        PTITKDGVSVAREIELEDKFENMGAQMVKEVASKANDAAGDGTTTATVLAQAIITEGLK
                        AVAAGMNPMDLKRGIDKAVTAAVEELKALSVPCSDSKAIAQVGTISANSDETVGKLIAE
                        AMDKVGKEGVITVEDGTGLQDELDVVEGMQFDRGYLSPYFINKPETGAVELESPFILLA
                        DKKISNIREMLPVLEAVAKAGKPLLIIAEDVEGEALATLVVNTMRGIVKVAAVKAPGFG
                        DRRKAMLQDIATLTGGTVISEEIGMELEKATLEDLGQAKRVVINKDTTTIIDGVGEEAA
```

```
                        IQGRVAQIRQQIEEATSDYDREKLQERVAKLAGGVAVIKVGAATEVEMKEKKARVEDAL
                        HATRAAVEEGVVAGGGVALIRVASKLADLRGQNEDQNVGIKVALRAMEAPLRQIVLNCG
                        EEPSVVANTVKGGDGNYGYNAATEEYGNMIDMGILDPTKVTRSALQYAASVAGLMITTE
                        CMVTDLPKNDAADLGAAGGMGGMGGMGGMM
SEQUENCE: 7
atggcagcta aagacgtaaa attcggtaac gacgctcgtg tgaaaatgct gcgcggcgta    60
aacgtactgg cagatgcagt gaaagttacc ctcggtccaa aaggccgtaa cgtagttctg   120
gataaatctt tcggtgcacc gaccatcacc aaagatggtg tttccgttgc tcgtgaaatc   180
gaactggaag acaagttcga aaatatgggt gcgcagatgg tgaaagaagt tgcctctaaa   240
gcaaacgacg ctgcaggcga cggtaccacc actgcaaccg tactggctca ggctatcatc   300
actgaaggtc tgaaagctgt tgctgcgggc atgaacccga tggacctgaa acgtggtatc   360
gacaaagcgg ttaccgctgc agttgaagaa ctgaaagcgc tgtccgtacc atgctctgac   420
tctaaagcga ttgctcaggt tggtaccatc tccgctaact ccgacgaaac cgtaggtaaa   480
ctgatcgctg aagcgatgga caaagtcggt aagaaggcg ttatcaccgt tgaagacggt   540
accggtctgc aggacgaact ggacgtggtt gaaggtatgc agttcgaccg tggctacctg   600
tctccttact tcatcaacaa gccggaaact ggcgcagtag aactgaaag cccgttcatc   660
ctgctggctg acaagaaaat ctccaacatc gcgaaatgc tgccggttct ggaagctgtt   720
gccaaagcag gcaaaccgct gctgatcatc gctgaagatg tagaaggcga agcgctggca   780
actctggttg ttaacaccat cgtggccatc gtgaaagtcg ctgcggttaa agcaccgggc   840
ttcggcgatc gtcgtaaagc tatgctgcag gatatcgcaa ccctgactgg cggtaccgtg   900
atctctgaag agatcggtat ggagctggaa aaagcaaccc tggaagacct gggtcaggct   960
aaacgtgttg tgatcaacaa agacaccacc actatcgacg atggcgtggg tgaagaagct  1020
gcaatccagg gccgtgttgc tcagatccgt cagcagattg aagaagcaac ttctgactac  1080
gaccgtgaaa aactgcagga acgcgtagcg aaactggcag cgggcgttgc agttatcaaa  1140
gtgggtgctg ctaccgaagt tgaaatgaaa gagaaaaaag cacgcgttga agatgccctg  1200
cacgccgaccc gtgctgcggt agaagaaggc gtggttggtg gtggtgtggt tgcgctgatc  1260
cgcgtagcgt ctaaactggc tgacctgcgt ggtcagaacg aagaccgaa cgtgggtatc  1320
aaagttgcac tgcgtgcaat ggaagctccg ctgcgtcaga tcgtattgaa ctgcggcgaa  1380
gaaccgtctg ttgttgctaa caccgttaaa ggcggcgacg gcaactacgg ttacaacgca  1440
gcaaccgaag aatacggcaa catgatcgac atgggtatcc tcgacccaac caaagtaact  1500
cgttctgctc tgcagtacgc agcttctgtg gctggcctga tgatcaccac cgaatgcatg  1560
gttaccgacc tgccgaaaaa cgatgcagct gacttaggcg ctgctggcgg tatgggcggc  1620
atgggtggca tgggcggcat gatgtaa                                      1647

SEQ ID NO: 8              moltype = AA  length = 548
FEATURE                   Location/Qualifiers
source                    1..548
                          mol_type = protein
                          organism = Escherichia coli
SEQUENCE: 8
MAAKDVKFGN DARVKMLRGV NVLADAVKVT LGPKGRNVVL DKSFGAPTIT KDGVSVAREI    60
ELEDKFENMG AQMVKEVASK ANDAAGDGTT TATVLAQAII TEGLKAVAAG MNPMDLKRGI   120
DKAVTAAVEE LKALSVPCSD SKAIAQVGTI SANSDETVGK LIAEAMDKVG KEGVITVEDG   180
TGLQDELDVV EGMQFDRGYL SPYFINKPET GAVELESPFI LLADKKISNI REMLPVLEAV   240
AKAGKPLLII AEDVEGEALA TLVVNTMRGI VKVAAVKAPG FGDRRKAMLQ DIATLTGGTV   300
ISEEIGMELE KATLEDLGQA KRVVINKDTT TIIDGVGEEA AIQGRVAQIR QQIEEATSDY   360
DREKLQERVA KLAGGVAVIK VGAATEVEMK EKKARVEDAL HATRAAVEEG VVAGGGVALI   420
RVASKLADLR GQNEDQNVGI KVALRAMEAP LRQIVLNCGE EPSVVANTVK GGDGNYGYNA   480
ATEEYGNMID MGILDPTKVT RSALQYAASV AGLMITTECM VTDLPKNDAA DLGAAGGMGG   540
MGGMGGMM                                                            548

SEQ ID NO: 9              moltype = DNA  length = 294
FEATURE                   Location/Qualifiers
misc_feature              1..294
                          note = chaperonin GroES of e. coli at GenBank Accession
                          CP009685.1 inregion 3966123 to 3966416
source                    1..294
                          mol_type = genomic DNA
                          organism = Escherichia coli
CDS                       1..294
                          protein_id = 10
                          translation = MNIRPLHDRVIVKRKEVETKSAGGIVLTGSAAAKSTRGEVLAVGNG
                          RILENGEVKPLDVKVGDIVIFNDGYGVKSEKIDNEEVLIMSESDILAIVEA
SEQUENCE: 9
atgaatattc gtccattgca tgatcgcgtg atcgtcaagc gtaaagaagt gaaaactaaa    60
tctgctggcg gcatcgttct gaccggctct gcagcggcta aatccaccg cggcgaagtg   120
ctggctgtcg gcaatggccg tatccttgaa aatggcgaag tgaagccgct ggatgtgaaa   180
gttggcgaca tcgttatttt caacgatggc tacggtgtga aatctgagaa gatcgacaat   240
gaagaagtgt tgatcatgtc cgaaagcgac attctggcaa ttgttgaagc gtaa         294

SEQ ID NO: 10             moltype = AA  length = 97
FEATURE                   Location/Qualifiers
source                    1..97
                          mol_type = protein
                          organism = Escherichia coli
SEQUENCE: 10
MNIRPLHDRV IVKRKEVETK SAGGIVLTGS AAAKSTRGEV LAVGNGRILE NGEVKPLDVK    60
VGDIVIFNDG YGVKSEKIDN EEVLIMSESD ILAIVEA                              97
```

| SEQ ID NO: 11 | moltype = DNA length = 3451 |
|---|---|
| FEATURE | Location/Qualifiers |
| misc_feature | 1..3451 |
| | note = Polycistroncic construct containing codon modified isoeugenolmonooxygenase of p. nitroreducens Jin1, GroES, GroEL |
| source | 1..3451 |
| | mol_type = other DNA |
| | organism = synthetic construct |

SEQUENCE: 11

```
gaaggagata tacatatggc acgtctgaac cgtaatgatc cgcaactcgt cggcaccctg    60
ttaccaaccc gtattgaggc tgacctgttc gacctggaag tggacggcga aattccgaag   120
tccatcaacg gtaccttcta ccgtaacacg ccggagcctc aggtgacgcc gcagaaattc   180
cacaccttca tcgatggtga cggcatggcg tctgcatttc attttgaaga tggccacgtg   240
gacttcatca gccgctgggt taaaaccgcg cgtttcacgg cggagagact ggcacgtaaa   300
agcctgttcg gtatgtaccg taatccgtac accgatgaca cgtctgtgaa gggtctggat   360
cgtaccgttg ccaacacgag catcatcagc catcacggta aggttctggc ggtgaaagaa   420
gatggcttgc cgtacgagct ggacccacgc actctggaaa cccgtggtcg ctttgactat   480
gatggccaag tcaccagcca gacgcacacc gcgcatccga agtatgaccc ggaaaccggt   540
gacctgttgt tctttggctc cgcagccaag ggtgaggcaa cgcctgatat ggcctattac   600
atcgttgata aacatggtaa ggtaacgcat gagacttggt tcgagcaacc gtatggcgcc   660
tttatgcatg attttgctat tacccgcaat tggagcattt tcccgatcat gccggctacc   720
aattcgttga gccgcctgaa agcgaagcag ccgatttaca tgtgggagcc ggaactgggt   780
tcctatattg tgttctgcc gcgtcgcggt caagtagcc agatccgctg gctgaaagca   840
ccagcgctgt gggtctttca cgtcgtcaac gcctgggaag tgggcaccaa aatctacatt   900
gaccttatgg agagcgaaat tctgccattc ccgttcccga atagccaaaa tcagccgttc   960
gctcctgaga aagcagtgcc ggtctgacc cgttgggaga ttgatctgga tagcagcagc  1020
gatgagatta agcgtacgcg tctgcacgac ttctttgcag agatgccgat catggatttt  1080
cgttttgcgc tgcagtgcaa ccgctacggt tttatgggtg tcgatgaccc gcgcaagccg  1140
ctggcgcacc aacaagcgga gaagattttt gcgtacaata gcctgggtat ctgggacaac  1200
caccgtggtg attatgattt gtggtacagc ggcgaagcct cagcggcgca agaaccggct  1260
ttcgttccgc gttctccgac tgcagcggaa ggcgacggtt atctgctgac cgttgtgggc  1320
cgtttggacg agaaccgcag cgacctggtc attctggaca cgcaggacat ccagagcggt  1380
ccggttgcga ccattaaact gccgtttcgc gccgtgctgc ggg ccctgcacgg ctgttgggtt  1440
ccgcgtccgt aagaaggaga tatacatatg aatattcgtc cattgcatga tcgcgtgatc  1500
gtcaagcgta aagaagttga aactaaatct gctggcggca tcgttctgac cggctctgca  1560
gcggctaaat ccacccgcgg cgaagtgctg gctgtcggca atggccgtat ccttgaaaat  1620
ggcgaagtga agccgctgga tgtgaaagtt ggcgacatcg ttattttcaa cgatggctac  1680
ggtgtgaaat ctgagaagat cgacaatgaa gaagtgttga tcatgtccga aagcgacatt  1740
ctggcaattg ttgaagcgta atccgcgcac gacactgaac atacgaattt aaggaataaa  1800
gataatggca gctaaagacg taaaattcgg taacgcgct cgtgtgaaaa tgctgcgcgg  1860
cgtaaacgta ctggcagatg cagtgaaagt taccctcggt ccaaaaggcc gtaacgtagt  1920
tctggataaa tctttcggtg caccgaccat caccaaagat ggtgtttccg ttgctcgtga  1980
aatcgaactg gaagacaagt tcgaaaatat gggtgcgcag atggtgaaag aagttgcctc  2040
taaagcaaac gacgctgcag cgacggtac caccactgca accgtactgg ctcaggctat  2100
catcactgaa ggtctgaaag ctgttgctgc gggcatgaac ccgatggacc tgaaacgtgg  2160
tatcgacaaa gcggttaccg ctgcagttga agaactgaaa gcgctgtccg taccatgctc  2220
tgactctaaa gcgattgctc aggttggtac catctccgct aactccgacg aaaccgtagg  2280
taaactgatc gctgaagcga tggacaaagt cggtaaagaa ggcgttatca ccgttgaaga  2340
cggtaccggt ctgcaggacg aactggacgt ggttgaaggt atgcagttcg accgtggcta  2400
cctgtctcct tacttcatca acaagccgga aactggcgca gtagaactgg aaagcccgtt  2460
catcctgctg gctgacaaga aaatctccaa catccgcgaa atgctgccgg ttctggaagc  2520
tgttgccaaa gcaggcaaac cgctgctgat catcgctgaa gatgtagaag cgaagcgct  2580
ggcaactctg gttgttaaca ccatgcgtgg catcgtgaaa gtcgctgcgg ttaaagcacc  2640
gggcttcgc gatcgtcgta aagctatgct gcaggatatc gcaaccctga ctggcggtac  2700
cgtgatctct gaagagatcg gtatggagct ggaaaaagca accctggaag acctgggtca  2760
ggctaaacgt gttgtgatca acaaagacac caccactatc atcgatgcg tgggtgaaga  2820
agctgcaatc cagggccgtg ttgctcagat ccgtcagcag attgaagaag caacttctga  2880
ctacgaccgt gaaaaactgc aggaacgcgt agcgaaactg gcaggcggcg ttgcagttat  2940
caaagtgggt gctgctaccg aagttgaaat gaaagagaaa aaagcacgcg ttgaagatgc  3000
cctgcacgcg acccgtctg cggtagaaga aggcgtggtt gctggtggtg tgttgcgct  3060
gatccgcgta gcgtctaaac tggctgacct gcgtggtcag aacgaagacc agaacgtggg  3120
tatcaaagtt gcactgcgtg caatggaagc tccgctgcgt cagatcgtat tgaactgcgg  3180
cgaagaaccg tctgttgttg ctaacaccgt taaggcggc gacaact acggttacaa  3240
cgcagcaacc gaagaatacg gcaacatgat cgacatgggt atcctggatc caaccaaagt  3300
aactcgttct gctctgcagt acgcagcttc tgtggctggc ctgatgatca ccaccgaatg  3360
catggttacc gacctgccga aaaacgatgc agctgactta ggcgctgctg gcggtatggg  3420
cggcatgggt ggcatgggcg gcatgatgta a                                 3451
```

| SEQ ID NO: 12 | moltype = DNA length = 3475 |
|---|---|
| FEATURE | Location/Qualifiers |
| misc_feature | 1..3475 |
| | note = Polycistroncic construct containing codon modified isoeugenolmonooxygenase of p. nitroreducens Jin1, GroES, GroEL |
| source | 1..3475 |
| | mol_type = other DNA |
| | organism = synthetic construct |

SEQUENCE: 12

```
gaaggagata tacatatggc acgtctgaac cgtaatgatc cgcaactcgt cggcaccctg    60
ttaccaaccc gtattgaggc tgacctgttc gacctggaag tggacggcga aattccgaag   120
tccatcaacg gtaccttcta ccgtaacacg ccggagcctc aggtgacgcc gcagaaattc   180
cacaccttca tcgatggtga cggcatggcg tctgcatttc attttgaaga tggccacgtg   240
gacttcatca gccgctgggt taaaaccgcg cgtttcacgg cggagagact ggcacgtaaa   300
agcctgttcg gtatgtaccg taatccgtac accgatgaca cgtctgtgaa gggtctggat   360
cgtaccgttg ccaacacgag catcatcagc catcacggta aggttctggc ggtgaaagaa   420
gatggcttgc cgtacgagct ggacccacgc actctggaaa cccgtggtcg ctttgactat   480
gatggccaag tcaccagcca gacgcacacc gcgcatccga agtatgaccc ggaaaccggt   540
gacctgttgt tctttggctc cgcagccaag ggtgaggcaa cgcctgatat ggcctattac   600
atcgttgata aacatggtaa ggtaacgcat gagacttggt tcgagcaacc gtatggcgcc   660
tttatgcatg attttgctat tacccgcaat tggagcatct cccgatcat gccggctacc   720
aattcgttga gccgcctgaa agcgaagcag ccgatttaca tgtgggagcc ggaactgggt   780
tcctatattg gtgttctgcc gcgtcgcggt caaggtagcc agatccgctg gctgaaagca   840
ccagcgctgt gggtctttca cgtcgtcaac gcctgggaag tgggcaccaa aatctacatt   900
gaccttatgc agagcgaaat tctgccattc ccgttcccga atagccaaaa tcagccgttc   960
gctcctgaga aagcagtgcc gcgtctgacc cgttgggaga ttgatctgga tagcagcagc  1020
gatgagatta agcgtacgcg tctgcacgac ttctttgcag agatgccgat catgatttt   1080
cgttttgcgc tgcagtgcaa ccgctacggt tttatgggtg tcgatgaccc gcgcaagccg  1140
ctggcgcacc aacaagcgga gaagattttt gcgtacaata gcctgggtat ctgggacaac  1200
caccgtggtg attatgattt gtggtacagc ggcgaagcct cagcggcgca agaaccggct  1260
ttcgttccgc gttctccgac tgcagcggaa ggcgacggtt atctgctgac cgttgtgggc  1320
cgtttggacg agaaccgcag cgacctggtc attcggaca cgcaggacat ccagagcggt  1380
ccggttgcga ccattaaact gccgtttcgc ctgcgtgcgg ccctgcacgg ctgttgggtt  1440
ccgcgtccgt aatccgcgca cgacactgaa catacggaag gagatataca tatgaatatt  1500
cgtccattgc atgatcgcgt gatctcaag cgtaaagaag ttgaaactaa atctgctggc  1560
ggcatcgttc tgaccggctc tgcagcggct aaatccaccc gcggcgaagt gctggctgtc  1620
ggcaatggcc gtatccttga aaatggcgaa gtgaagccgc tggatgtgaa agttggcgac  1680
atcgttattt tcaacgatgg ctacggtgtg aaatctgaga gatcgacaa tgaagaagtg  1740
ttgatcatgt ccgaaagcga cattctggca atgttgaaca cgtaatccgc gcacgacact  1800
gaacatacga atttaaggaa taaagataat ggcagctaaa gacgtaaaat tcggtaacga  1860
cgctcgtgtg aaaatgctgc gcggcgtaaa cgtactggca gatgcagtga agttaccct   1920
cggtccaaaa ggccgtaacg tagttctgga taaatctttc ggtgcaccga ccatcaccaa  1980
agatggtgtt tccgttgctc gtgaaatcga actggaagac aagttcgaaa atatgggtgc  2040
gcagatgtg aaagaagttg cctctaaagc aaacgacgct gcaggcgacg gtaccaccac  2100
tgcaaccgta ctggctcagg ctatcatcac tgaaggtctg aaagctgttg ctgcgggcat  2160
gaacccgatg gacctgaaac gtggtatcga caaagcggtt accgctgcag ttgaagaact  2220
gaaagcgctg tccgtaccat gctctgactc taaagcgatt gctcaggttg gtaccatctc  2280
cgctaactcc gacgaaaccg taggtaaact gatcgctgaa gcgatggaca aagtcggtaa  2340
agaaggcgtt atcaccgttg aagacggta cggtctgcag gacgaactgg acgtggttga  2400
aggtatgcag ttcgaccgtg gctacctgtc tccttacttc atcaacaagc cggaaactgg  2460
cgcagtagaa ctggaaagcc cgttcatcct gctggctgac aagaaaatct ccaacatccg  2520
cgaaatgctg ccggttctgg aagctgttgc caaagcaggc aaaccgctgc tgatcatcgc  2580
tgaagatgta gaaggcgaag cgctggcaac tctggttgtt aacaccatgc gtggcatcgt  2640
gaaagtcgct gcggttaaag caccgggctt cggcgatcgt cgtaaagcta tgctgcagga  2700
tatcgcaacc ctgactggcg gtaccgtgat ctctgaagag atcggtatgg agctggaaaa  2760
agcaacccctg gaagacctgg gtcaggctaa acgtgttgtg atcaacaaag acaccaccac  2820
tatcatcgat ggcgtgggtg aagaagctgc aatccagggc cgtgttgctc agatccgtca  2880
gcagattgaa gaagcaactt ctgactacga ccgtgaaaaa ctgcaggaac gcgtagcgaa  2940
actggcaggc ggcgttgcag ttatcaaagt gggtgctgct accgaagttg aaatgaaaga  3000
gaaaaaagca cgcgttgaag atgccctgca cgcgacccgt gctgcggtag aagaaggcgt  3060
ggttgctggt ggtggtgttg cgctgatccg cgtagcgtct aaactggctg acctgcgtgg  3120
tcagaacgaa gaccagaacg tgggtatcaa agttgcactg cgtgcaatgg aagctccgct  3180
gcgtcagatc gtattgaact gcggcgaaga accgtctgtt gttgctaaca ccgttaaagg  3240
cggcgacggc aactacggtt acaacgcagc aaccgaagaa tacggcaaca tgatcgacat  3300
gggtatcctg gatccaacca aagtaactgc ttctgctctg cagtacgcag cttctgtgcc  3360
tggcctgatg atcaccaccg aatgcatggt taccgacctg ccgaaaaacg atgcagctga  3420
cttaggcgct gctggcggta tgggcggcat gggtggcatg gcggcatga tgtaa          3475
```

SEQ ID NO: 13        moltype = DNA   length = 3456
FEATURE               Location/Qualifiers
misc_feature       1..3456
                       note = Polycistroncic construct containing codon modified
                       isoeugenolmonooxygenase of p. nitroreducens Jin1, GroES,
                       GroEL
source             1..3456
                       mol_type = other DNA
                       organism = synthetic construct
SEQUENCE: 13

```
gaaggagata tacatatggc acgtctgaac cgtaatgatc cgcaactcgt cggcaccctg    60
ttaccaaccc gtattgaggc tgacctgttc gacctggaag tggacggcga aattccgaag   120
tccatcaacg gtaccttcta ccgtaacacg ccggagcctc aggtgacgcc gcagaaattc   180
cacaccttca tcgatggtga cggcatggcg tctgcatttc attttgaaga tggccacgtg   240
gacttcatca gccgctgggt taaaaccgcg cgtttcacgg cggagagact ggcacgtaaa   300
agcctgttcg gtatgtaccg taatccgtac accgatgaca cgtctgtgaa gggtctggat   360
cgtaccgttg ccaacacgag catcatcagc catcacggta aggttctggc ggtgaaagaa   420
gatggcttgc cgtacgagct ggacccacgc actctggaaa cccgtggtcg ctttgactat   480
gatggccaag tcaccagcca gacgcacacc gcgcatccga agtatgaccc ggaaaccggt   540
gacctgttgt tctttggctc cgcagccaag ggtgaggcaa cgcctgatat ggcctattac   600
```

```
atcgttgata aacatggtaa ggtaacgcat gagacttggt tcgagcaacc gtatggcgcc  660
tttatgcatg attttgctat tacccgcaat tggagcatct tcccgatcat gccggctacc  720
aattcgttga gccgcctgaa agcgaagcag ccgatttaca tgtgggagcc ggaactgggt  780
tcctatattg gtgttctgcc gcgtcgcggt caaggtagcc agatccgctg gctgaaagca  840
ccagcgcgt gggtctttca cgtcgtcaac gcctgggaag tgggcaccaa aatctacatt  900
gaccttatgg agagcgaaat tctgccattc ccgttcccga atagccaaaa tcagccgttc  960
gctcctgaga aagcagtgcc gcgtctgacc cgttgggaga ttgatctgga tagcagcagc 1020
gatgagatta agcgtacgcg tctgcacgac ttctttgcag agatgccgat catggatttt 1080
cgttttgcgc tgcagtgcaa ccgctacggt tttatgggtg tcgatgaccc gcgcaagccg 1140
ctggcgcacc aacaagcgga gaagattttt gcgtacaata gcctgggtat ctgggacaac 1200
caccgtggtg attatgattt gtggtacagc ggcgaagcct cagcggcgca agaaccggct 1260
ttcgttccgc gttctccgac tgcagcggaa ggcgacggtt atctgctgac cgttgtgggc 1320
cgtttggacg agaaccgcag cgacctggtc attctggaca cgcaggacat ccagagcggt 1380
ccggttgcga ccattaaact gccgtttcgc ctgcgtgcgg ccctgcacgg ctgttgggtt 1440
ccgcgtccgt aaaattaggt aaaaaataaa aaatgaatat tcgtccattg catgatcgcg 1500
tgatcgtcaa gcgtaaagaa gttgaaacta aatctgctgg cggcatcgtt ctgaccggct 1560
ctgcagcgga taaatccacc cgcggcgaag tgctggctgt cggcaatggc cgtatccttg 1620
aaaatgcgaa agtgaagccg ctggatgtga aagttggcga catcgttatt ttcaacgatg 1680
gctacggtgt gaaatctgag aagatcgaca atgaagaagt gttgatcatg tccgaaagcc 1740
acattctggc aattgttgaa gcgtaatccg cgcacgacac tgaacatacg aatttaagga 1800
ataaagataa tggcagctaa agacgtaaaa ttcggtaacg acgctcgtgt gaaaatgctg 1860
cgcggcgtaa acgtactggc agatgcagtg aaagttcgcc tcggtccaaa aggccgtaac 1920
gtagttctgg ataaatcttt cggtgcaccg accatcacca agatggtgt ttccgttgct 1980
cgtgaaatcg aactggaaga caagttcgaa aatatgggtg cgcagatggt gaaagaagtt 2040
gcctctaaag caaacgacgc tgcaggcgac ggtaccacca ctgcaaccgt actggctcag 2100
gctatcatca ctgaaggtct gaaagctgtt gctgcgggca tgaacccgat ggacctgaaa 2160
cgtggtatcg acaaagcggt taccgctgca gttgaagaac tgaaagcgct gtccgtacca 2220
tgctctgact ctaaagcgat tgctcaggtt ggtaccatct ccgctaactc cgacgaaacc 2280
gtaggtaaac tgatcgctga agcgatggac aaagtcggta agaaggcgt tatcaccgtt 2340
gaagacggta ccggtctgca ggacgaactg gacgtggttg aaggtatgca gttcgaccgt 2400
ggctacctgt ctccttactt catcaacaag ccggaaactg gcgcagtaga actggaaagc 2460
ccgttcatcc tgctggctga caagaaaatc tccaacatcc gcgaaatgct gccggttctg 2520
gaagctgttg ccaaagcagg caaaccgctg ctgatcatcg ctgaagatgt agaaggcgaa 2580
gcgctggcaa ctctggttgt taacaccatg cgtggcatcg tgaaagtgc tgcggttaaa 2640
gcaccgggct tcggcgatcg tcgtaaagct atgctgcagg atatcgcaac cctgactgg 2700
ggtaccgtga tctctgaaga tctcggtatg gagctggaaa aagcaaccct ggaagacctg 2760
ggtcaggcta acgtgttgt gatcaacaaa gacaccacca ctatcatcga tggcgtgggt 2820
gaagaagctg caatccaggg ccgtgttgct cagatccgtc agcagattga agaagcaact 2880
tctgactacg accgtgaaaa actgcaggaa cgctagcga aactggcagg cggcgttgca 2940
gttatcaaag tgggtgctgc taccgaagtt gaaatgaaag agaaaaaagc acgcgttgaa 3000
gatgccctgc acgcgacccg tgctgcggta gaagaaggcg tggttgctgg tggtggtgtt 3060
gcgctgatcc gcgtagcgtc taaactggct gacctgcgtg gtcagaacga agaccagaac 3120
gtgggtatca aagttgcact gcgtgcaatg gaagctccag cgtattgaac 3180
tgcggcgaag aaccgtctgt tgttgctaac accgttaaag cggcgacgg caactacggt 3240
tacaacgcag caaccgaaga atacggcaac atgatcgaca tgggtatcct ggatccaacc 3300
aaagtaactc gttctgctct gcagtacgca gcttctgtgg ctggcctgat gatcaccacc 3360
gaatgcatgg ttaccgacct gccgaaaaac gatgcagctg acttaggcgc tgctggcggt 3420
atgggcggca tgggtgcat gggcggcatg atgtaa 3456

SEQ ID NO: 14           moltype = DNA  length = 3423
FEATURE                 Location/Qualifiers
misc_feature            1..3423
                        note = Polycistroncic construct containing codon modified
                          isoeugenolmonooxygenase of p. nitroreducens Jin1, GroES,
                          GroEL
source                  1..3423
                        mol_type = other DNA
                        organism = synthetic construct
SEQUENCE: 14
gaaggagata tacatatggc acgtctgaac cgtaatgatc cgcaactcgt cggcaccctg   60
ttaccaaccc gtattgaggc tgacctgttc gacctggaag tggacggcga aattccgaag  120
tccatcaacg gtaccttcta ccgtaacacg ccggagcctc aggtgacgcc gcagaaattc  180
cacaccttca tcgatggtga cggcatggcg tctgcatttc attttgaaga tggccacgtg  240
gacttcatca gccgctgggt taaaaccgcg cgtttcacgg cggagagact ggcacgtaaa  300
agcctgttcg gtatgtaccg taatccgtac accgatgaca cgtctgtgaa gggtctggat  360
cgtaccgttg ccaacacgag catcatcagc catcacggta aggttctggc ggtgaaagaa  420
gatggcttgc cgtacgagct ggaccacgc actctgaaa cccgtggtcg ctttgactat  480
gatggccaag tcaccagcca gacgcacacc gcgcatccga agtatgaccc ggaaaccggt  540
gacctgttgt tctttggctc cgcagccaag ggtgaggcaa gcctgtcgat ggcctattac  600
atcgttgata aacatggtaa ggtaacgcat gagacttggt tcgagcaacc gtatggcgcc  660
tttatgcatg attttgctat tacccgcaat tggagcatct tcccgatcat gccggctacc  720
aattcgttga gccgcctgaa agcgaagcag ccgatttaca tgtgggagcc ggaactgggt  780
tcctatattg gtgttctgcc gcgtcgcggt caaggtagcc agatccgctg gctgaaagca  840
ccagcgcgt gggtctttca cgtcgtcaac gcctgggaag tgggcaccaa aatctacatt  900
gaccttatgg agagcgaaat tctgccattc ccgttcccga atagccaaaa tcagccgttc  960
gctcctgaga aagcagtgcc gcgtctgacc cgttgggaga ttgatctgga tagcagcagc 1020
gatgagatta agcgtacgcg tctgcacgac ttctttgcag agatgccgat catggatttt 1080
cgttttgcgc tgcagtgcaa ccgctacggt tttatgggtg tcgatgaccc gcgcaagccg 1140
ctggcgcacc aacaagcgga gaagattttt gcgtacaata gcctgggtat ctgggacaac 1200
```

```
caccgtggtg attatgattt gtggtacagc ggcgaagcct cagcggcgca agaaccggct 1260
ttcgttccgc gttctccgac tgcagcggaa ggcgacggtt atctgctgac cgttgtgggc 1320
cgtttggacg agaaccgcag cgacctggtc attctggaca cgcaggacat ccagagcggt 1380
ccggttgcga ccattaaact gccgtttcgc ctgcgtgcgg ccctgcacgg ctgttggtt 1440
ccgcgtccgt aagaaggaga tatacatatg aatattcgtc cattcgatga tcgcgtgatc 1500
gtcaagcgta aagaagttga aactaaatct gctggcggca tcgttctgac cggctctgca 1560
gcggctaaat ccacccgcgg cgaagtgctg ctgtcggca atggccgtat ccttgaaaat 1620
ggcgaagtga agccgctgga tgtgaaagtt ggcgacatcg ttattttcaa cgatggctac 1680
ggtgtgaaat ctgagaagat cgacaatgaa gaagtgttga tcatgtccga aagcgacatt 1740
ctggcaattg ttgaagcgta agaaggagat atacatatgg cagctaaaga cgtaaaattc 1800
ggtaacgacg ctcgtgtgaa aatgctgcgc ggcgtaaacg tactggcaga tgcagtgaaa 1860
gttaccctcg gtccaaaagg ccgtaacgta gttctggata atctttcgg tgcaccgacc 1920
atcaccaaag atggtgtttc cgttgctcgt gaaatcgaac tggaagacaa gttcgaaaat 1980
atgggtgcgc agatggtgaa agaagttgcc tctaaagcaa acgacgctgc aggcgacggt 2040
accaccactg caaccgtact ggctcaggct atccatcactg aaggtctgaa agctgttgct 2100
gcgggcatga acccgatgga cctgaaacgt ggtatcgaca agcggttac cgctgcagtt 2160
gaagaactga aagcgctgtc cgtaccatgc tctgactcta aagcgattgc tcaggttggt 2220
accatctccg ctaactccga cgaaaccgta ggtaaactga tcgctgaagc tgtggacaaa 2280
gtcggtaaag aaggcgttat caccgttgaa gacggtaccg gtctgcagga cgaactggac 2340
gtggttgaag gtatgcagtt cgaccgtggc tacctgtctc cttacttcat caacaagccg 2400
gaaactggcg cagtagaact ggaaagcccg ttcatcctgc tggctgacaa gaaaatctcc 2460
aacatccgcg aaatgctgcc ggttctggaa gctgttgcca aagcaggcaa accgctgctg 2520
atcatcgctg aagatgtaga aggcgaagcg ctggcaactc tggttgttaa caccatgcgt 2580
ggcatcgtga aagtcgctgc ggttaaagca ccggggcttcg gcgatcgtcg taaagctatg 2640
ctgcaggata tcgcaaccct gactggcggt accgtgatct ctgaagagat cggtatggag 2700
ctggaaaaag caaccctgga agacctgggt caggctaaag gttgtgat caacaaagac 2760
accaccacta tcatcgatgg cgtgggtgaa gaagctgcaa tccagggccg tgttgctcag 2820
atccgtcagc agattgaaga agcaacttct gactacgacc gtgaaaaact gcaggaacgc 2880
gtagcgaaac tggcaggcgg cgttgcagtt atcaaagtgg gtgctgctac cgaagttgaa 2940
atgaaagaaa aaaaagcacg cgttgaagat gccctgcacg cgacccgtgc tgcggtgaaa 3000
gaaggcgtgg ttgctggtgg tggtgttgcg ctgatccgcg tagcgtctaa actggctgac 3060
ctgcgtggtc agaacgaaga ccagaacgtg ggtatcaaag ttgcactgcg tgcaatggaa 3120
gctccgctgc gtcagatcgt attgaactgc ggcgaagaac cgtctgttgt tgctaacacc 3180
gttaaaggcg gcgacggcaa ctacggttac aacgcagcag ccgaagaata cggcaacatg 3240
atcgacatgg gtatcctgga tccaaccaaa gtaactcgtt ctgctctgca gtacgcagct 3300
tctgtggctg gcctgatgat caccaccgaa tgcatggtta ccgacctgcc gaaaaacgat 3360
gcagctgact aggcgctgc tggcggtatg ggcggcatgg gtggcatggg cggcatgatg 3420
taa                                                                  3423
```

SEQ ID NO: 15        moltype = DNA   length = 3456
FEATURE              Location/Qualifiers
misc_feature         1..3456
                     note = Polycistroncic construct containing codon modified
                       isoeugenolmonooxygenase of p. nitroreducens Jin1, GroES,
                       GroEL
source               1..3456
                     mol_type = other DNA
                     organism = synthetic construct
SEQUENCE: 15

```
gaaggagata tacatatggc acgtctgaac cgtaatgatc gcaactcgt cggcaccctg 60
ttaccaaccc gtattgaggc tgacctgttc gacctgtgaa tggacggcga aattccgaag 120
tccatcaacg gtaccttcta ccgtaacacg ccggagcctc aggtgacgcc gcagaaattc 180
cacaccttca tcgatggtga cggcatggcg tctgcatttc attttgaaga tggccacgtg 240
gacttcatca gccgctgggt taaaaccgcg cgtttcacgg cggagagact ggcacgtaaa 300
agcctgttcg gtatgtaccg taatccgtac accgatgaca cgtctgtgaa gggtctggat 360
cgtaccgttg ccaacacgag catcatcagc catcacggta aggttctggc ggtgaaagaa 420
gatggcttgc cgtacgagct ggacccacgc actctggaaa cccgtggtcg ctttgactat 480
gatggccaag tcaccagcca gacgcacacc gcgcatccga gtatgaccc ggaaaccggt 540
gacctgttgt tctttggctc cgcagccaag ggtgaggcaa cgcctgatat ggcctattac 600
atcgttgata aacatggtaa ggtaacgcat gagacttggt tcgagcaacc gtatgcgcc 660
tttatgcatg attttgctat tacccgcaat tggagcatct tcccgatcat gccggctacc 720
aattcgttga gccgcctgaa agcgaagcag ccgatttaca tgtgggagcc ggaactgggt 780
tcctatattg tgtgttctgcc gcgtcgcggt caaggtagcc agatccgctg gctgaaagca 840
ccagcgctgt gggtctttca cgtcgtcaac gcctgggaag tgggcaccaa aatctacatt 900
gaccttatgg agagcgaaat tctgccattc ccgttcccga atagccaaaa tcagccgttc 960
gctcctgaga aagcagtgcc gcgtctgacc cgttgggaga ttgatctgga tagcagcagc 1020
gatgagatta agcgtacgcg tctgcacgac ttctttgcag agatgccgat catggatttt 1080
cgttttcgc tgcagtgcaa ccgctacggt tttatgggtg tcgatgaccc cgcgcaagcg 1140
ctggcgcacc aacaagcgga gaagattttt gcgtacaata gcctgggtat ctgggacaac 1200
caccgtggtg attatgattt gtggtacagc ggcgaagcct cagcggcgca agaaccggct 1260
ttcgttccgc gttctccgac tgcagcggaa ggcgacggtt atctgctgac cgttgtgggc 1320
cgtttggacg agaaccgcag cgacctggtc attctggaca cgcaggacat ccagagcggt 1380
ccggttgcga ccattaaact gccgtttcgc ctgcgtgcgg ccctgcacgg ctgttggtt 1440
ccgcgtccgt aaaagatagc aaaaaaataa aaatgaattac tgatgatcgcg 1500
tgatcgtcaa gcgtaaagaa gttgaaacta aatctgctgg cggcatcgtt ctgaccggct 1560
ctgcagcggc taaatccacc cgcggcgaag tgctggctgt cggcaatggc cgtatccttg 1620
aaaatggcga agtgaagccg ctggatgtga agttggcga catcgttatt ttcaacgatg 1680
gctacggtgt gaaatctgag aagatcgaca atgaagaagt gttgatcatg tccgaaagcg 1740
acattctggc aattgttgaa gcgtaatccg cgcacgacac tgaacatacg aatttaagga 1800
```

```
ataaagataa tggcagctaa agacgtaaaa ttcggtaacg acgctcgtgt gaaaatgctg    1860
cgcggcgtaa acgtactggc agatgcagtg aaagttaccc tcggtccaaa aggccgtaac    1920
gtagttctgg ataaatcttt cggtgcaccg accatcacca aagatggtgt ttccgttgct    1980
cgtgaaatcg aactggaaga caagttcgaa aatatgggtg cgcagatggt gaaagaagtt    2040
gcctctaaag caaacgacgc tgcaggcgac ggtaccacca ctgcaaccgt actggctcag    2100
gctatcatca ctgaaggtct gaaagctgtt gctgcgggca tgaacccgat ggacctgaaa    2160
cgtggtatcg acaaagcggt taccgctgca gttgaagaac tgaaagcgct gtccgtacca    2220
tgctctgact ctaaagcgat tgctcaggtt ggtaccatct ccgctaactc cgacgaaacc    2280
gtaggtaaac tgatcgctga agcgatgaaa aagtcggta aagaaggcgt tatcaccgtt    2340
gaagacggta ccggtctgca ggacgaactg gacgtggttg aaggtatgca gttcgaccgt    2400
ggctacctgt ctccttactt catcaacaag ccggaaactg gcgcagtaga actgaaagc     2460
ccgttcatcc tgctggctga caagaaaatc tccaacatcc gcgaaatgct gccggttctg    2520
gaagctgttg ccaaagcagg caaaccgctg ctgatcatcg ctgaagatgt agaaggcgaa    2580
gcgctggcaa ctctggttgt taacaccatg cgtggcactg tcgcggttaaa             2640
gcaccgggct tcggcgatcg tcgtaaagct atgctgcagg atatcgcaac cctgactggc    2700
ggtaccgtga tctctgaaga tcggtatg gagctggaaa aagcaaccct ggaagacctg     2760
ggtcaggcta acgtgttgt gatcaacaaa gacaccacca ctatcatcga tggcgtgggt    2820
gaagaagctg caatccaggg ccgtgttgct cagatccgtc agcagattga agaagcaact    2880
tctgactacg accgtgaaaa actgcaggaa cgcgtagcga aactggcagg cggcgttgca    2940
gttatcaaag tgggtgctgc taccgaagtt gaaatgaaag agaaaaaagc acgcgttgaa    3000
gatgccctgc acgcgacccg tgctgcggta gaagaaggcg tggttgctgg tggtggtgtt    3060
gcgctgatcc gcgtagcgtc taaactggct gacctgcgtg gtcagaacga agaccagaac    3120
gtgggtatca aagttgcact gcgtgcaatg gaagctccgc tgcgtcagat cgtattgaac    3180
tgcggcgaag aaccgtctgt tgttgctaac accgttaaag cggcgacgg caactacggt    3240
tacaacgcag caaccgaaga atacggcaac atgatcgaca tgggtatcct ggatccaacc    3300
aaagtaactc gttctgctct gcagtacgca gcttctgtgg ctggcctgat gatcaccacc    3360
gaatgcatgg ttaccgacct gccgaaaaac gatgcagctg acttaggcgc tgctggcggt    3420
atgggcggca tgggtggcat gggcggcatg atgtaa                              3456
```

| SEQ ID NO: 16 | moltype = DNA length = 5424 |
|---|---|
| FEATURE | Location/Qualifiers |
| misc_feature | 1..5424 |
| | note = e.coli modified with plasmids pIEM2_c154_t222_a1318 |
| misc_feature | 1..827 |
| | note = Ori_p15a |
| misc_feature | 1009..1128 |
| | note = Term_rpoC |
| misc_feature | 1129..1429 |
| | note = Term_bla |
| misc_feature | 1456..1497 |
| | note = P_T7_Inducible |
| misc_feature | 1477..1497 |
| | note = LacO1 |
| misc_feature | 1528..2997 |
| | note = IEM_C154_T222_A1318 |
| misc_feature | 3002..3049 |
| | note = Term_T7 |
| misc_feature | 3322..3439 |
| | note = P_Amp |
| misc_feature | 3450..4259 |
| | note = Kanamycin-r |
| misc_feature | 4260..4341 |
| | note = P-lacI |
| misc_feature | 4342..5424 |
| | note = lacI |
| source | 1..5424 |
| | mol_type = other DNA |
| | organism = synthetic construct |

```
SEQUENCE: 16
ttaataagat gatcttcttg agatcgtttt ggtctgcgcg taatctcttg ctctgaaaac     60
gaaaaaaccg ccttgcaggg cggtttttcg aaggttctct gagctaccaa ctctttgaac    120
cgaggtaact ggcttggagg agcgcagtca ccaaaacttg tcctttcagt ttagccttaa    180
ccggcgcatg acttcaagac taactcctct aaatcaatta ccagtggctg ctgccagtgg    240
tgcttttgca tgtctttccg ggttggactc aagacgatag ttaccgata aggcgcagcg    300
gtcggactga acgggggggtt cgtgcataca gtccagcttg gagcgaactg cctacccgga    360
actgagtgtc aggcgtggaa tgagacaaac gcggccataa cagcggaatg acaccggtaa    420
accgaaaggc aggaacagga gagcgcacga gggagccgcc aggggaaac gcctggtatc     480
tttatagtcc tgtcgggttt cgccaccact gatttgagcg tcagatttcg tgatgcttgt    540
caggggggga gagcgttatgg aaaaacggct ttgccgcgcc cctctcactt cctgttaag    600
tatcttcctg gcatcttcca ggaaatctcc gccccgttcg taagccattt ccgctcgccg    660
cagtcgaacg accgagcgta gcgagtcagt gagcgaggaa gcggaatata tcctgtatca    720
catattctgc tgacgcaccg gtgcagcctt ttttctcctg ccacatgaag cacttcactg    780
acaccctcat cagtgccaac atagtaagcc agtatacact ccgctagcgc tgaggtcccg    840
cagccgaacg accgagcgca gcgagtcagt gagcgaggaa gcggaaggcg agatagggga    900
actgccaggc atcaaactaa gcagaaggcc cctgacggat ggcctttttg cgtttctaca    960
aactctttct gtgttgtaaa acgacggcca gtcttaagct cgggcccct gggcggttct    1020
gataacgagt aatcgttaat ccgcaaataa cgtaaaaacc gcttcggcg ggttttttta    1080
tgggggggagt ttagggaaag agcatttgtc agaatatttta agggcgcctg tcactttgct    1140
tgatatatga gaattattta accttataaa tgagaaaaaa gcaacgcact ttaaataaga    1200
```

```
tacgttgctt tttcgattga tgaacaccta taattaaact attcatctat tatttatgat    1260
tttttgtata tacaatattt ctagtttgtt aaagagaatt aagaaaataa atctcgaaaa    1320
taataaaggg aaaatcagtt tttgatatca aaattataca tgtcaacgat aatacaaaat    1380
ataatacaaa ctataagatg ttatcagtat ttattatgca tttagaataa attttgtgtc    1440
gccctteege gaaattaata cgactcacta tagggaggt gtgagcggat aacaattccc    1500
ctctagaaat aattttgttt aacttttgaa ggagatatac atatggcaac gtttgaccgc    1560
aatgatccgc agttggcagg aacgatgttc cccacccgaa tagaggcgaa tgtcttttgac   1620
cttgaaattg agggcgagat cccacgtgca atcaacggga gcttcttccg caacaccccc    1680
gaacctcagg tcaccccgca acctttccac accttcatcg atgggatgg tttggcgtct    1740
gcttttcatt tcgaagatgg ccatgtcgac tttgtcagcg gttgggtatg tactcctcgc    1800
tttgaagctg agcggtcggc tcgtaaatca ctcttcggta tgtaccgcaa tccgttcact    1860
gatgatccat cggtagaagg tattgatcgt acagtcgcca acaccagtat catcactcat    1920
cacgggaaag tactggccgc aaaggaagat ggactacctt atgagcttga ccccaaacc    1980
ctggaaaccc gaggtcgtta tgattacaag gggcaggtaa ccagccatac acatacagcg    2040
caccctaagt tcgaccccca gacaggtgaa atgttactct tcggctccgc tgctaaaggc    2100
gaacgaacgc ttgatatggc gtactatatt gttgatcgct acggcaaggt gacacatgag    2160
acctggttta agcagcctta cggtgcattc atgcacgact ttgctgtcac gcgcaactgg    2220
tcaatctttc cgatcatgcc tgcgacaaat agccttgagc gtcttaaagc aaagcagccc    2280
atttacatgt gggagcctga gcgaggaagc tatataggag tacttcctcg tcgtggtcag    2340
ggcaaggaca ttcgttggtt ccgtgccccg gcgttgtggg ttttccatgt cgtgaatgct    2400
tgggaggaag gaatagaat tctgattgac ttgatggaaa gtgagatttt gccgttccca    2460
ttcccgaact cgcagaacct tccatttgat ccctccaagg ctgttccgcg tctaaacccgt   2520
tgggaaattg atctcaatag tggtaacgat gagatgaaac gtacgcagct acacgaatat    2580
tttgcagaaa tgcctatcat ggatttccgt tttgcgctcc aggatcatcg ctacgcctac    2640
atgggggtta cgatcctcg tcgcccctta gctcatcagc aagctgaaaa aatctttgcc    2700
tacaattcgt taggggttg ggacaaccat cgtaaagatt atgaactttg gtttacgggg    2760
aaaatgtctg cagcgcagga accgcgtttt gttcctagaa gcccagatgc gcctgagggc    2820
gatggctacc tactcagtgt agtagggcgg ctcgatgaaa atcgtagcga tctagttatc    2880
cttgatacgc aatgtttggc agctgggcct gtggccactg tcaagcttcc cttccgtctc    2940
cgagcagcgt tgcacggttg ttggcagtct aagaactgag gatccgaatt cgagctcccc    3000
cctagcataa cccccttggg cctctaaacg ggtcttgagg ggttttttgc ccctgagacg    3060
cgtcaatcga gttcgtacct aagggcgaca ccccctaatt agcccgggcg aaaggcccag    3120
tctttcgact gagcctttcg ttttatttga tgcctggcag ttccctactc tcgcatgggg    3180
agtccccaca ctaccatcgg cgctacggcg tttcacttct gagttcggca tggggtcagg    3240
tgggaccacc gcgctactgc cgccaggcaa acaaggggtg ttatgagcca tattcaggta    3300
taaatgggct cgcgataatg ttcagaattg gttaattggt tgtaaacactg accccctatt    3360
gtttattttt ctaaatacat tcaaatatgt atccgctcat gagacaataa ccctgataaa    3420
tgcttcaata atattgaaaa aggaagaata tgagccatat tcaacgggaa acgtcgaggc    3480
cgcgattaaa ttccaacatg gatgctgatt tatatgggta taatgggct ccgataatg    3540
tcggcaatc aggtgcgaca atctatcgct tgtatgggaa gcccgatgcg ccagagttgt    3600
ttctgaaaca tggcaaaggt agcgttgcca atgatgttac agatgagatg gtcagactaa    3660
actggctgac ggaatttatg ccacttccga ccatcaagca ttttatccgt actcctgatg    3720
atgcatggtt actcaccact gcgatccccg gaaaaacagc gttccaggta ttagaagaat    3780
atcctgattc aggtgaaaat attgttgatg cgctggcagt gttcctgcgc cggttgcact    3840
cgattcctgt ttgtaattgt cctttttaaca gcgatcgcgt atttcgcctc gctcaggcgc    3900
aatcacgaat gaataaccgt ttggttgatg cgagtgattt tgatgacgag cgtaatggct    3960
ggcctgttga acaagtctgg aaagaaatgc ataaacttttt gccattctca ccggattcag    4020
tcgtcactca tggtgatttc tcacttgata accttatttt tgacgagggg aaattaatag    4080
gttgtattga tgttggacga tcggaatcg cagaccgata ccaggatctt gccatcctat    4140
ggaactgcct ccggtgagttt tctccttcat tacagaaacg gcttttttcaa aaatatggta    4200
ttgataatcc tgatatgaat aaattgcagt ttcatttgat gctcgatgag ttttttctaag    4260
cggcgcgcca tcgaatggcg caaaaccttt cgcggtatgg catgatagcg cccggaagag    4320
agtcaattca gggtggtgaa tatgaaacca gtaacgttat acgatgtcgc agagtatgcc    4380
ggtgtctctt atcagaccgt ttcccgcgtg gtgaaccagg ccagccacgt ttctgcgaaa    4440
acgcgggaaa aagtggaagc ggcgatggcg gagctgaatt acattccaa ccgcgtggca    4500
caacaactgg cgggcaaaca gtcgttgctg attggcgttg ccacctccag tctggccctg    4560
cacgcgccgt cgcaaattgt cgcggcgatt aaatctcgcg ccgatcaact gggtgccagc    4620
gtggtggtgt cgatggtaga acgaagcggc gtcgaagcct gtaaagcggc ggtgcacaat    4680
cttctcgcgc aacgcgtcag tgggctgatc attaactatc cgctggatga ccaggatgcc    4740
attgctgtgg aagctgcctg cactaatgtt ccggcgttat ttcttgatgt ctctgaccag    4800
acacccatca acagtattat tttctcccat gaggacggta cgcgactggg cgtggagcat    4860
ctggtcgcat tgggtcacca gcaaatcgcg ctgttagcgg gcccattaag ttctgtctcg    4920
gcgcgtctgc gtctggctgg ctggcataaa tatctcactc gcaatcaaat tcagccgata    4980
gcggaacggg aaggcgactg gagtgccatg tccggttttc aacaaaccat gcaaatgctg    5040
aatgagggca tcgttcccac tgcgatgctg gttgccaacg atcagatggc gctgggcgca    5100
atgcgcgcca ttaccgagtc cgggctgcgc gttggtgcgg atatctcggt agtgggatac    5160
gacgataccg aagatagctc atgttatatc ccgccgttaa ccaccatcaa acaggatttt    5220
cgcctgctgg ggcaaaccag cgtggaccgc ttgctgcaac tctctcaggg ccaggcggtg    5280
aagggcaatc agctgttgcc agtctcactg gtgaaaagaa aaaccaccct ggcgcccaat    5340
acgcaaaccg cctctccccg cgcgttggcc gattcattaa tgcagctggc acgacaggtt    5400
tcccgactgg aaagcgggca gtga                                           5424

SEQ ID NO: 17       moltype = DNA  length = 7557
FEATURE             Location/Qualifiers
source              1..7557
                    mol_type = other DNA
                    organism = synthetic construct
SEQUENCE: 17
ttaataagat gatcttcttg agatcgtttt ggtctgcgcg taatctcttg ctctgaaaac      60
```

-continued

```
gaaaaaaccg ccttgcaggg cggttttcg aaggttctct gagctaccaa ctctttgaac    120
cgaggtaact ggcttggagg agcgcagtca ccaaaacttg tcctttcagt ttagccttaa    180
ccggcgcatg acttcaagac taactcctct aaatcaatta ccagtggctg ctgccagtgg    240
tgcttttgca tgtctttccg ggttggactc aagacgatag ttaccggata aggcgcagcg    300
gtcggactga acgggggtt cgtgcataca gtccagcttg gagcgaactg cctacccgga    360
actgagtgtc aggcgtgaa tgagacaaac gcggccataa cagcggaatg acaccggtaa    420
accgaaaggc aggaacagga gagcgcacga gggagccgcc aggggaaac gcctggtatc    480
tttatagtcc tgtcgggttt cgccaccact gatttgagcg tcagatttcg tgatgcttgt    540
caggggggcg gagcctatgg aaaaacggct ttgccgcggc cctctcactt ccctgttaag    600
tatcttcctg gcatcttcca ggaaatctcc gccccgttcg taagccattt ccgctcgccg    660
cagtcgaacg accgagcgta gcgagtcagt gagcgaggaa gcggaatata tcctgtatca    720
catattctgc tgacgcaccg gtgcagcctt ttttctcctg ccacatgaag cacttcactg    780
acaccctcat cagtgccaac atagtaagcc agtatacact ccgctagcgc tgaggtcccg    840
cagccgaacg accgagcgca gcgagtcagt gagcgaggaa gcggaaggcg agagtaggga    900
actgccaggc atcaaactaa gcagaaggcc cctgacggat ggccttttg cgttctaca    960
aactctttct gtgttgtaaa acgacggcca gtcttaagct cgggccccct gggcggttct   1020
gataacgagt aatcgttaat ccgcaaataa cgtaaaaacc cgcttcggcg ggttttttta   1080
tgggggagt ttagggaaag agcatttgtc agaatattta agggcgcctg tcactttgct   1140
tgatatatga gaattattta accttataaa tgagaaaaaa gcaacgcact ttaaataaga   1200
tacgttgctt tttcgattga tgaacaccta taattaaact attcatctat tatttatgat   1260
tttttgtata tacaatattt ctagtttgtt aaagagaatt aagaaaataa atctcgaaaa   1320
taataaaggg aaaatcagtt tttgatatca aaattataca tgtcaacgat aatacaaaat   1380
ataatacaaa ctataagatg ttatcagtat ttattatgca tttagaataa attttgtgtc   1440
gcccttccgc gaaattaata cgactcacta taggggaatt gtgagcggat aacaattccc   1500
ctctagaaat aattttgttt aacttttgaa ggagatatac atatggcaac gtttgaccgc   1560
aatgatccgc agttggcagg aacgatgttc cccacccgaa tagaggcgaa tgtctttgac   1620
cttgaaattg agggcgagat cccacgtgca atcaacggga gcttcttccg caacaccccc   1680
gaacctcagg tcaccccgca acctttccac accttcatcg atggggatgg tttggcgtct   1740
gcttttcatt tcgaagatgg ccatgtcgac tttgtcagcc gttgggtatg tactcctcgc   1800
tttgaagctg agcggtcggc tcgtaaatca ctcttcggta tgtaccgcaa tccgttcact   1860
gatgatccat cggtagaagg tattgatcgt acagtcgcca acaccagtat catcactcat   1920
cacgggaaag tactgccgc aaaggaagat ggactacctt atgagcttga ccccaaacc   1980
ctggaacccc gaggtcgtta tgattacaag gggcaggtaa ccagccatac acatacagcg   2040
caccctaagt tcgaccccca gacaggtgaa atgttactct tcggctccgc tgctaaaggc   2100
gaacgaacgt ttgatatggc gtactatatt gttgatcgct acggcaaggt gacacatgag   2160
acctggttta agcagcctta cggtgcattc atgcacgact tgctgtcac gcgcaactgg   2220
tcaatctttc cgatcatgcc tgcgacaaat agccttgagc gtcttaaagc aaagcagccc   2280
atttacatgt gggagcctga gcgaggaagc tatataggag tacttcctcg tcgtggtcag   2340
ggcaaggaca ttcgttggtt ccgtgccccg gcgttgttgg ttttccatgt cgtgaatgct   2400
tgggaggaag ggaatagaat tctgattgac ttgatggaaa gtgagatttt gccgttccca   2460
ttcccgaact cgcagaacct tccatttgat ccctccaagg ctgttccgcg tctaaccgt   2520
tgggaaattg atctcaatag tggtaacgat gagatgaaac gtacgcagct acacgaatat   2580
tttgcagaaa tgcctatcat ggatttccgt tttgcgctcc aggatcatcg ctacgcctac   2640
atggggggttg acgatcctcg tcgcccctta gctcatcagc aagctgaaaa aatctttgcc   2700
tacaattcgt taggggtttg ggacaaccat cgtaaagatt atgaactttg tttacgggga   2760
aaaatgtctg cagcgcagga accggcgttt gttcctagaa gcccagatgc gcctgagggc   2820
gatggctacc tactcagtgt agtagggcgg ctcgatgaaa atcgtagcga tctagtttatc   2880
cttgatacgc aatgtttggc agctgggcct gtggccactg tcaagcttcc cttccgtctc   2940
cgagcagcgt tgcacggttg ttggcagtct aagaactgac tagcataacc ccttggggcc   3000
tctaaacggg tcttgagggg tttttggca tcctgtccat gactcggtga caattaatta   3060
tccggctcgt ataatgtgtg gaattgtgag cggataacaa ttccctctag aaataattt   3120
gtttaacttt taaaggagag ttatcaatga atattcgtcc attgcatgat cgcgtgatcg   3180
tcaagcgtaa agaagttgaa actaaatctg ctggcggcat cgttctgacc ggctctgcag   3240
cggctaaatc caccccgcggc gaagtgctgg ctgtcggcaa tggccgtatc cttgaaaatg   3300
gcgaagtgaa gccgctggat gtgaaagttg gcgacatcgt tattttcaac gatggctacg   3360
gtgtgaaatc tgagaagatc gacaatgaag aagtgttgat catgtccgaa agcgacattc   3420
tggcaattgt tgaagcgtaa tccgcgcacg acactgaaca tacgaattta aggaataaag   3480
ataatgcag ctaaagacgt aaaattcggt aacgacgctc gtgtgaaaat gctgcgcggc   3540
gtaaacgtac tggcagatgc agtgaaagtt accctcggtc caaaaggccg taacgtagtt   3600
ctggataaat ctttcggtgc accgaccatc accaaagatg gtgtttccgt tgctcgtgaa   3660
atcgaactgg aagacaagtt cgaaaatatg ggtgcgcaga tggtgaaaga agttgcctct   3720
aaagcaaacg acgctgcagg cgacggtacc accactgcaa ccgtactggc tcaggctatc   3780
atcactgaag gtctgaaagc tgttgctgcg ggcatgaacc cgatggacct gaaacgtggt   3840
atcgacaaag cggttaccgc tgcagttgaa gaactgaaag ctctgtccgt accatgctct   3900
gactctaaag cgattgctca ggttggtacc atctccgcta actccgacga aaccgtaggt   3960
aaaactgatcg ctgaagcgat ggacaaagtc ggtaaagaag gcgttatcac cgttgaagac   4020
ggtaccggtc tgcaggacga actggacgtg gttgaaggta tgcagttcga ccgtggctac   4080
ctgtctcctt acttcatcaa caagccggaa actggcgcag tagaactgga aagcccgttc   4140
atcctgctgg ctgacaagaa aatctccaac atccgcgaaa tgctgccggt tctgaagct   4200
gttgccaaag caggcaaacc gctgctgatc atcgctgaag atgtagaagg cgaagcgctg   4260
gcaactctgt tgttaacac catcgtggc atcgtgaaag tcgctgcggt taaagcaccg   4320
ggcttcggcg atcgtcgtaa agctatgctg caggatatcg caaccctgac tggcggtacc   4380
gtgatctctg aagagatcgg tatggagctg gaaaaagcaa ccctggaaga cctgggtcag   4440
gctaaacgtg ttgtgatcaa caaagacacc accactatca tcgatggcgt gggtgaagaa   4500
gctgcaatcc agggccgtgt tgctcagatc cgtcagcaga ttgaagaagc aacttctgac   4560
tacgaccgtg aaaaactgca ggaacgcgta gcgaaactgg caggcggcgt tgcagttatc   4620
aaagtgggtg ctgctaccga agttgaaatg aaagagaaaa agcacgcgt tgaagatgcc   4680
ctgcacgcga cccgtgctgc ggtagaagaa ggcgtggttc tggtggtgg tgttgcgctg   4740
atccgcgtag cgtctaaact ggctgacctg cgtggtcaga acgaagacca gaacgtgggt   4800
```

```
atcaaagttg cactgcgtgc aatggaagct ccgctgcgtc agatcgtatt gaactgcggc   4860
gaagaaccgt ctgttgttgc taacaccgtt aaaggcggcg acggcaacta cggttacaac   4920
gcagcaaccg aagaatacgg caacatgatc gacatgggta tcctggatcc aaccaaagta   4980
actcgttctg ctctgcagta cgcagcttct gtggctggcc tgatgatcac caccgaatgc   5040
atggttaccg acctgccgaa aaacgatgca gctgacttag gcgctgctgg cggtatgggc   5100
ggcatgggtg gcatgggcgg catgatgtaa cccctagca taaccccttg gggcctctaa   5160
acgggtcttg aggggttttt tgcccctgag acgcgtcaat cgagttcgta cctaagggcg   5220
acaccccta attagcccgg gcgaaaggcc cagtctttcg actgagcctt tcgttttatt   5280
tgatgcctgg cagttcccta ctctcgcatg gggagtcccc acactaccat cggcgctacg   5340
gcgtttcact tctgagttcg catggggtc aggtgggacc accgcgctac tgccgccagg   5400
caaacaaggg gtgttatgag ccatattcag gtataaatgg gctcgcgata atgttcagaa   5460
ttggttaatt ggtgtaaca ctgaccccta tttgtttatt tttctaaata cattcaaata   5520
tgtatccgct catgagacaa taaccctgat aaatgcttca ataatattga aaaaggaaga   5580
atatgagcca tattcaacgg gaaacgtcga ggccgcgatt aaattccaac atggatgctg   5640
atttatatgg gtataaatgg gctcgcgata atgtcgggca atcaggtgcg acaatctatc   5700
gcttgtatgg gaagcccgat gcgccagagt tgtttctgaa acatggcaaa ggtagcgttg   5760
ccaatgatgt tacagatgag atggtcagac taaactggct gacggaattt atgccacttc   5820
cgaccatcaa gcatttatc cgtactcctg atgatgcatg gttactcacc actgcgatcc   5880
ccggaaaaac agcgttccag gtattagaag aatatcctga ttcaggtgaa atatattgtta   5940
atgcgctggc agtgttcctg cgccggttgc actcgattcc tgtttgtaat tgtcctttta   6000
acagcgatcg cgtatttcgc ctcgctcagg cgcaatcacg aatgaataac ggtttggttg   6060
atgcgagtga ttttgatgac gagcgtaatg gctggcctgt tgaacaagtc tggaaagaaa   6120
tgcataaact tttgccattc tcaccggatt cagtcgtcac tcatggtgat ttctcacttg   6180
ataaccttat ttttgacgag gggaaattaa taggttgtat tgatgttgga cgagtcggaa   6240
tcgcagaccg ataccaggat cttgccatcc tatggaactg cctcggtgag ttttctcctt   6300
cattacagaa acggctttt caaaaatatg gtattgataa tcctgatatg aataaattgc   6360
agtttcattt tgatgctcgat gagttttcct aagcggcgcg ccatcgaatg gcgcaaaacc   6420
tttcgcggta tggcatgata gcgcccgaa gagagtcaat tcagggtggt gaatatgaaa   6480
ccagtaacgt tatacgatgt cgcagagtat gccggtgtct cttatcagac cgtttcccgc   6540
gtggtgaacc aggccagcca cgtttctgcg aaaacgcggg aaaaagtgga agcggcgatg   6600
gcggagctga attacattcc caaccgcgtg gcacaacaac tggcgggcaa acagtcgttg   6660
ctgattggcg ttgccacctc cagtctggcc ctgcacgcgc cgtcgcaaat tgtcgcggcg   6720
attaaatctc gcgccgatca actgggtgcc agcgtggtgg tgtcgatggt agaacgaagc   6780
ggcgtcgaag cctgtaaagc ggcggtgcac aatcttctcg cgcaacgcgt cagtgggctg   6840
atcattaact atccgctgga tgaccaggat gccattgctg tggaagctgc ctgcactaat   6900
gttccggcgt tatttcttga tgtctctgac cagacaccca tcaacagtat tattttctcc   6960
catgaggacg gtacgcgact gggcgtggag catctggtcg cattgggtca ccagcaaatc   7020
gcgctgttag cgggcccatt aagttctgtc tcggcgcgtc tgcgtctggc tggctggcat   7080
aaatatctca ctcgcaatca aattcagccg atagcggaac gggaaggcga ctggagtgcc   7140
atgtccggtt ttcaacaaac catgcaaatg ctgaatgagg gcatcgttcc cactgcgatg   7200
ctggttgcca acgatcagat ggcgctgggc gcaatgcgcg ccattaccga gtcgggctg   7260
cgcgttggtg cggatatctc ggtagtggga tacgacgata ccgaagatag ctcatgttat   7320
atcccgccgt taaccaccat caaacgaggt tttcgcctgc tggggcaaac cagcgtggac   7380
cgcttgctgc aactctctca gggccaggcg gtgaagggca atcagctgtt gccagtctca   7440
ctggtgaaaa gaaaaaccac cctggcgccc aatacgcaaa ccgcctctcc ccgcgcgttg   7500
gccgattcat taatgcagct ggcacgacag gtttcccgac tggaaagcgg gcagtga      7557

SEQ ID NO: 18         moltype = DNA   length = 7556
FEATURE               Location/Qualifiers
source                1..7556
                      mol_type = other DNA
                      organism = synthetic construct
SEQUENCE: 18
ttaataagat gatcttcttg agatcgtttt ggtctgcgcg taatctcttg ctctgaaaac   60
gaaaaaccg ccttgcaggg cggttttcg aaggttctct gagctaccaa ctctttgaac   120
cgaggtaact ggcttggagg agcgcagtca ccaaaacttg tcctttcagt ttagccttaa   180
ccggcgcatg acttcaagac taactcctct aaatcaatta ccagtggctg ctgccagtgg   240
tgcttttgca tgtctttccg ggttggactc aagacgatag ttaccggata aggcgcagcg   300
gtcggactga acggggggtt cgtgcataca gtccagcttg gagcgaactg cctacccgga   360
actgagtgtc aggcgtgaa tgagacaaac gcggccataa cagcggaatg acaccgtaa   420
accgaaaggc aggaacagga gagcgcacga gggagccgcc aggggaaac gcctggtatc   480
tttatagtcc tgtcgggttt cgccaccact gatttgagcg tcagatttcg tgatgcttgt   540
cagggggcg gagcctatgg aaaaacggct ttgccgcggc cctctcactt ccctgttaag   600
tatcttcctg gcatcttcca ggaaatctcc gccccgttcg taagccattt ccgctccgtt   660
cagtcgaacg accgagcgta gcgagtcagt gagcgaggaa gcggaatata tcctgtatca   720
catattctgc tgacgcaccg gtgcagcctt ttttctcctg ccacatgaag cacttcactg   780
acaccctcat cagtgccaac atagtaagcc agtatacact ccgctagcgc tgaggtcccg   840
cagccgaacg accgagcgca gcgagtcagt gagcgaggaa gcggaaggcg agatgagga   900
actgccaggc atcaaaactaa cagaaggcc cctgacggat ggccttttg cgtttctaca   960
aactctttct gtgttgtaaa acgacggcca gtcttaagct cgggcccct gggcggttct   1020
gataacgagt aatcgttaat ccgcaataa cgtaaaaacc cgcttcggcg gttttttta   1080
tggggggagt ttagggaaag agcatttgtc agaatatta agggcgcctg tcactttgct   1140
tgatatatga gaattattta acctttataaa tgagaaaaat gcaacgcact ttaaataaga   1200
tacgttgctt tttcgattga tgaacacctaa taattaaact attcatctat tattttatgat  1260
tttttgtata tacaatattt ctagtttgtt aaagagaatt aagaaaataa atctcgaaaa   1320
taataaaggg aaaatcagtt tttgatatca aaattataca tgtcaacgat aatacaaaat   1380
ataatacaaa ctataagatg ttatcagtat ttattatgca tttagaataa attttgtgtc   1440
gcccttccgc gaaattaata cgactcacta taggggaatt gtgagcggat aacaattccc   1500
ctctagaaat aattttgttt aacttttgaa ggagatatac atatggcaac gtttgaccgc   1560
```

```
aatgatccgc agttggcagg aacgatgttc cccacccgaa tagaggcgaa tgtctttgac  1620
cttgaaattg agggcgagat cccacgtgca atcaacggga gcttcttccg caacacccccc 1680
gaacctcagg tcaccccgca accttttccac accttcatcg atggggatgg tttggcgtct  1740
gctttcatt tcgaagatgg ccatgtcgac tttgtcagcc gttgggtatg tactcctcgc  1800
tttgaagctg agccggtcgg c tcgtaaatca ctcttcggta tgtaccgcaa tccgttcact  1860
gatgatccat cggtagaagg tattgatcgt acagtcgcca acaccagtat catcactcat  1920
cacgggaaag tactgccgc aaaggaagat ggactacctt atgagcttga cccccaaacc  1980
ctggaaaccc gaggtcgtta tgattacaag gggcaggtaa ccagccatac acatacagcg  2040
caccctaagt tcgaccccca gacaggtgaa atgttactct tcggctccgc tgctaaaggc  2100
gaacgaacgc ttgatatggc gtactatatt gttgatcgct acggcaaggt gacacatgag  2160
acctggttta agcagcctta cggtgcattc atgcacgact ttgctgtcac gcgcaactgg  2220
tcaatctttc cgatcatgcc tgcgacaaat agccttgagc gtcttaaagc aaagcagccc  2280
atttacatgt gggagcctga gcgaggaagc tatataggag tacttcctcg tcgtggtcag  2340
ggcaaggaca ttcgttggtt ccgtgccccg gcgttgttgg tttccatgt cgtgaatgct  2400
tgggaggaag ggaatagaat tctgattgac ttgatggaaa gtgagatttt gccgttccca  2460
ttcccgaact cgcagaacct tccatttgat ccctccaagg ctgttccgcg tctaacccgt  2520
tgggaaattg atctcaatag tggtaacgat gagatgaaac gtaccgcagct acacgaatat  2580
tttgcagaaa tgcctatcat ggatttccgt tttgcgctcc aggatcatcg ctacgcctac  2640
atggggttg acgatcctcg tcgcccctta gctcatcagc aagctgaaaa aatctttgcc  2700
tacaattcgt taggggtttg ggacaaccat cgtaaagatt atgaactttg gtttacggga  2760
aaaatgtctg cagcgcagga accggcgttt gttcctagaa gcccagatgc gcctgagggc  2820
gatggctacc tactcagtgt agtagggcgg ctcgatgaaa atcgtagcga tctagtttatc  2880
cttgatacgc aatgtttggc agctgggcct gtggccactg tcaagcttcc cttccgtctc  2940
cgagcagcgt tgcacggttg ttggcagtct aagaactgac tagcataacc ccttggggcc  3000
tctaaacggg tcttgagggg ttttttgcca tcctgtccat gactcggtga caattaatca  3060
tcggctcgta taatgtgtgg aattgtgagc ggataacaat tccctctaga aataattttg  3120
tttaactttt aaaggagagt tatcaatgaa tattcgtcca ttgcatgatc gcgtgatcgt  3180
caagcgtaaa gaagttgaaa ctaaatctgc tggcggcatc gttctgaccg gctctgcagc  3240
ggctaaatcc acccgcggcg aagtgctggc tgtcggcaat ggccgtatcc ttgaaaatgg  3300
cgaagtgaag ccgctggatg tgaaagttgg cgacatcgtt atttttcaacg atggctacgg  3360
tgtgaaatct gagaagatcg acaatgaaga agtgttgatc atgtccgaaa gcgacattct  3420
ggcaattgtt gaagcgtaat ccgcgcacga cactgaacat acgaatttaa ggaataaaga  3480
taatggcagc taaagacgta aaattcggta acgacgctcg tgtgaaaatg ctgcgcggcg  3540
taaacgtact ggcagatgca gtgaaagtta ccctcggttc aaaaggccgt aacgtagttc  3600
tggataaatc tttcggtgca ccgaccatca ccaaagatgg tgtttccgtt gctcgtgaaa  3660
tcgaactgga agacaagttc gaaaatatgg gtgcgcagat ggtgaaagaa gttgcctcta  3720
aagcaaacga cgctgcaggc gacggtacca ccactgcaac cgtactggct caggctatca  3780
tcactgaagg tctgaaaagct gttgctgcgg gcatgaaccc gatggaactg aaacgtggta  3840
tcgacaaagc ggttaccgct gcagttgaag aactgaaagc gctgtccgta ccatgctctg  3900
actctaaagc gattgctcag gttggtacca tctccgctaa ctccgacgaa accgtaggta  3960
aactgatcgc tgaagcgatg gacaaagtcg gtaaagaagg cgttatcacc gttgaagacg  4020
gtaccggtct gcaggacgaa ctggacgtgg ttgaaggtat gcagttcgac cgtggctacc  4080
tgtctcctta cttcatcaac aagccggaaa ctggcgcagt agaactggaa agcccgttca  4140
tcctgctggc tgacaagaaa atctccaaca tccgcgaaat gctgccggtt ctggaagctg  4200
ttgccaaagc aggcaaaccg ctgctgatca tcgctgaaga tgtagaaggc gaagcgctgg  4260
caactctggt tgttaacacc atgcgtgcca tcgtgaaagt cgctgcggtt aaagcaccgg  4320
gcttcggcga tcgtcgtaaa gctatgctgc aggatatcgc aacccggact ggcggtaccg  4380
tgatcctctga agagatcggt atggagctgg aaaaagcaac cctggaagac ctgggtcagg  4440
ctaaacgtgt tgtgatcaac aaagacacca ccactatcat cgatggctg ggtgaagaag  4500
ctgcaatcca gggccgtgtt gctcagatcc gtcagcagat tgaagaagca acttctgact  4560
acgaccgtga aaaactgcag gaacgcgtag cgaaactggc aggcggcgtt gcagttatca  4620
aagtgggtgc tgctaccgaa gttgaaatga agagagaaaa agcacgcgtt gaagatgccc  4680
tgcacgcgac ccgtgctgcg gtagaagaag gcgtggttgc tggtggtggt gttgcgctga  4740
tccgcgtagc gtctaaactg gctgacctgc gtggtcagaa cgaagaccag aacgtgggta  4800
tcaaagttgc actgcgtgca atggaagctc cgctgcgtca gatcgtattg aactgcgggcg  4860
aagaaccgtc tgttgttgct aacaccgtta aaggcggcga cggcaactac ggttacaacg  4920
cagcaaccga agaatacggc aacatgatcg acatgggtat cctggatcca accaaagtaa  4980
ctcgttctgt tctgcagtac gcagcttctg tggctggcct gatgatcacc accgaatgca  5040
tggttaccga cctgccgaaa aacgatgcag ctacttagg cgctgctggc ggtatggggca  5100
gcatgggtgc catgggcggc atgatgtaac ccctagcat aacccccttgg ggcctctaaa  5160
cgggtcttga ggggttttt gccctgaga cgcgtcaatc gagttcgtac ctaagggcga  5220
caccccctaa ttagcccggg cgaaaggccc agtctttccga ctgagccttt cgttttattt  5280
gatgcctggc agttccctac tctcgcatgg ggagtcccca cactaccatc ggcgctacgg  5340
cgtttcactt ctgagttcgg catggggtca ggtgggaccca ccgctact gccgccagc  5400
aaacaagggg tgttatgagc catattcagg tataaatggg ctcgcgataa tgttcagaat  5460
tggttaattg gttgtaacac tgaccccctat ttgtttattt ttctaaatac attcaaatat  5520
gtatccgctc atgagacaat aaccctgata aatgcttcaa taatattgaa aaggaagaa  5580
tatgagccat attcaacggg aaacgtcgag gccgcgatta attccaaca tggatgctga  5640
tttatatggg tataaatggg ctcgcgataa tgtcgggcaa tcaggtgcga caatctatcg  5700
cttgtatggg aagcccgatg cgccagagtt gtttctgaaa catggcaaag gtagcgttgc  5760
caatgatgtt acagatgaga tggtcagact aaactggctg acggaattta tgccacttcc  5820
gaccatcaag cattttatcc gtactcctga tgatgcatgg ttactcacca ctgcgatccc  5880
cggaaaaaca gcgttccagg tattagaaga atatcctgat tcaggtgaaa atattgttga  5940
tgcgctggca gtgttcctgc gccggttgca ctcgattcct gtttgtaatt gtcctttaa  6000
cagcgatccg gtatttcgcc tcgctcaggc gcaatcacga tgaataacgg tttggttga  6060
tgcgagtgat tttgatgacg agcgtaatgg ctggcctgtt gaacaagtct ggaaagaaat  6120
gcataaactt ttgccattct caccggattc agtcgtcact catggtgatt tctcacttga  6180
taaccttatt tttgacgagg ggaaattaat aggttgtatt gatgttggac gagtcggaat  6240
cgcagaccga taccaggatc ttgccatcct atggaactgc ctcggtgagt tttctccttc  6300
```

```
attacagaaa cggcttttc  aaaaatatgg tattgataat cctgatatga ataaattgca 6360
gtttcatttg atgctcgatg agttttcta  agcggcgcgc catcgaatgg cgcaaaacct 6420
ttcgcggtat ggcatgatag cgcccggaag agagtcaatt cagggtggtg aatatgaaac 6480
cagtaacgtt atacgatgtc gcagagtatg ccggtgtctc ttatcagacc gtttcccgcg 6540
tggtgaacca ggccagccac gtttctgcga aaacgcggaa aaaagtggaa gcggcgatgg 6600
cggagctgaa ttacattccc aaccgcgtgg cacaacaact ggcgggcaaa cagtcgttgc 6660
tgattggcgt tgccacctcc agtctggccc tgcacgcgcc gtcgcaaatt gtcgcggcga 6720
ttaaatctcg cgccgatcaa ctgggtgcca gcgtggtggt gtcgatggta gaacgaagcg 6780
gcgtcgaagc ctgtaaagcg gcggtcgcaca atcttctcgc gcaacgcgtc agtgggcgga 6840
tcattaacta tccgctggat gaccaggatg ccattgctgt ggaagctgcc tgcactaatg 6900
ttccggcgtt atttcttgat gtctctgacc agacacccat caacagtatt attttctccc 6960
atgaggacgt tacgcgactg ggcgtggagc atctggtcgc attgggtcac cagcaaatcg 7020
cgctgttagc gggcccatta agttctgtct cggcgcgtct gcgtctggct ggctggcata 7080
aatatctcac tcgcaatcaa attcagccga tagcggaacg ggaaggcgac tggagtgcca 7140
tgtccggttt tcaacaaacc atgcaaatgc tgaatgaggg catcgttccc actgcgatgc 7200
tggttgccaa cgatcagatg gcgctgggcg caatgcgcgc cattaccgag tccgggctgc 7260
gcgttggtgc ggatatctcg gtagtgggat acgacgatac cgaagatagc tcatgttata 7320
tcccgccgtt aaccaccatc aaacaggatt ttcgcctgct ggggcaaacc agcgtggacc 7380
gcttgctgca actctctcag ggccaggcgg tgaagggcaa tcagctgttg ccagtctcac 7440
tggtgaaaag aaaaaccacc ctggcgccca atacgcaaac cgcctctccc cgcgcgttgg 7500
ccgattcatt aatgcagctg gcacgacagg tttcccgact ggaaagcggg cagtga      7556

SEQ ID NO: 19          moltype = DNA   length = 7544
FEATURE                Location/Qualifiers
source                 1..7544
                       mol_type = other DNA
                       organism = synthetic construct
SEQUENCE: 19
ttaataagat gatcttcttg agatcgtttt ggtctgcgcg taatctcttg ctctgaaaac  60
gaaaaaaccg ccttgcaggg cggtttttcg aaggttctct gagctaccaa ctctttgaac 120
cgaggtaact ggcttggagg agcgcagtca ccaaaacttg tcctttcagt ttagccttaa 180
ccggcgcatg acttcaagac taactcctct aaatcaatta ccagtggctg ctgccagtgg 240
tgcttttgca tgtcttccg  ggttggactc aagacgatag ttaccggata aggcgcagcg 300
gtcggactga acggggggtt cgtgcataca gtccagcttg gagcgaactg cctaccggaa 360
actgagtgtc aggcgtgaa  tgagacaaac gcggccataa cagcggaatg acaccggtaa 420
accgaaaggc aggaacagga gagcgcacga gggagccgcc aggggaaac  gcctggtatc 480
tttatagtcc tgtcgggttt cgccaccact gatttgagcg tcagatttcg tgatgcttgt 540
cagggggcg  gagcctatgg aaaaacggct ttgccgcggc cctctcactt ccctgttaag 600
tatcttcctg gcatcttcca ggaaatctcc gccccgttcg taagccattt ccgctcgccg 660
cagtcgaacg accgagcgta gcgagtcagt gagcgaggaa gcggaatata tcctgtatca 720
catattctgc tgacgcaccg gtgcagcctt ttttctcctg ccacatgaag cacttcactg 780
acaccctcat cagtgccaac atagtaagcc agtatacact ccgctagcgc tgaggtcccg 840
cagccgaacg accgagcgca gcgagtcagt gagcgaggaa gcggaaggcg agagtaggga 900
actgccaggc atcaaactaa gcagaaggcc cctgacggat ggcctttttg cgtttctaca 960
aactctttct gtgttgtaaa acgacggcca gtcttaagct cgggcccct  gggcggttct 1020
gataacgagt aatcgttaat ccgcaaataa cgtaaaaacc cgcttcggcg gttttttta  1080
tgggggagt  ttagggaaag agcatttgtc agaatattta aggggcctg  tcactttgct 1140
tgatatatga gaattattta accttataaa tgagaaaaaa gcaacgcact ttaaataaga 1200
tacgttgctt tttcgattga tgaacaccta taattaaact attcatctat tatttatgat 1260
ttttttgtata tacaatattt ctagtttgtt aaagagaatt aagaaaataa atctcgaaaa 1320
taataaaggg aaaatcagtt tttgatatca aaattataca tgtcaacgat aatacaaaat 1380
ataatacaaa ctataagatg ttatcagtat ttattatgca tttagaataa attttgtgtc 1440
gcccttccgc gaaattaata cgactcacta gggggaatt  gtgagcggat aacaattccc 1500
ctctagaaat aattttgttt aacttttgaa ggagatatac atatggcaac gtttgaccgc 1560
aatgatccgc agttggcagg aacgatgttc cccacccgaa tagaggcgaa tgtctttgac 1620
cttgaaattg agggcgagat cccacgtgca atcaacggga gcttcttccg caacaccccc 1680
gaacctcagg tcaccccgca accttttccac accttcatcg atgggggatgg tttggcgtct 1740
gcttttcatt tcgaagatgg ccatgtcgac tttgtcagcc gttgggtatg tactcctcgc 1800
tttgaagctg agccggtcggc tcgtaaatca ctcttcggta tgtaccgcaa tccgttcact 1860
gatgatccat cggtagaagg tattgatcgt acagtcgcca acaccgtat  catcactcat 1920
cacgggaaag tactggccgc aaaggaagat ggactacctt atgagcttga ccccaaaacc 1980
ctggaaaccc gaggtcgtta tgattacaag gggcaggtaa ccagccatac acatacagcg 2040
cacccctaagt tcgaccccca gacaggtgaa atgttactct tcggctccgc tgctaaaggc 2100
gaacgaacgc ttgatatggc gtactatatt gttgatcgct acggcaaggt gacacatgag 2160
acctggttta agcagcctta cggtgcattc atgcacgact ttgctgtcac gcgcaactgg 2220
tcaatctttc cgatcatgcc tgcgacaaat agccttgagc gtcttaaagc aaagcagccc 2280
atttacatgt gggagcctga gcgaggaagc tatataggag tacttcctcg tcgtggtcag 2340
ggcaaggaca ttcgttggtt ccgtgccccg gcgttgtggg ttttccatgt cgtgaatgct 2400
tgggaggaag ggaatagaat tctgattgac ttgatgaaga gatggttttt gccgttccga 2460
ttcccgaact cgcagaacct tccatttgat ccctccaagg ctgttccgcg tctaacccgt 2520
tgggaaattg atctcaatag tggtaacgat gagatgaaac gtacgcagct acacgaatat 2580
tttgcagaaa tgcctatcat ggatttccgt tttgcgctcc aggatcatcg ctacgcctac 2640
atgggggttg acgatcctcg tcgcccctta gctcatcagc aagctgaaaa aatctttgcc 2700
tacaattcgt taggggttttg ggacaaccat cgtaaagatt atgaacttgg gttttacggga 2760
aaaatgtctg cagcgcagga accggcgttt gttcctagaa gcccagatgc gcctgagggc 2820
gatggctacc tactcagtgt agtagggcgg ctcgatgaaa atcgtagcga tctagttatc 2880
cttgatacgt aatgtttggc agctgggcct gtggccactg tcaagcttcc cttccgtctc 2940
cgagcagcgt tgcacggttg ttggcagtct aagaactgac tagcataacc ccttgggggcc 3000
tctaaacggg tcttgagggg ttttttggca tcctgtccat gactcggtaa tacgactcac 3060
```

```
tataggggaa ttgtgagcgg ataacaattc cctctagaaa taattttgtt taacttttaa  3120
aggagagtta tcaatgaata ttcgtccatt gcatgatcgc gtgatcgtca agcgtaaaga  3180
agttgaaact aaatctgctg gcggcatcgt tctgaccggc tctgcagcgg ctaaatccac  3240
ccgcggcgaa gtgctggctg tcggcaatgg ccgtatcctt gaaaatggcg aagtgaagcc  3300
gctggatgtg aaagttggcg acatcgttat tttcaacgat ggctacggtg tgaaatctga  3360
gaagatcgac aatgaagaag tgttgatcat gtccgaaagc gacattctgg caattgttga  3420
agcgtaatcc gcgcacgaca ctgaacatac gaatttaagg aataaagata atggcagcta  3480
aagacgtaaa attcggtaac gacgctcgtg tgaaaatgct gcgcggcgta aacgtactgg  3540
cagatgcagt gaaagttacc ctcggtccaa aaggccgtaa cgtagttctg gataaatctt  3600
tcggtgcacc gaccatcacc aaagatggtg tttccgttgc tcgtgaaatc gaactggaag  3660
acaagttcga aaatatgggt gcgcagatgg tgaaagaagt tgcctctaaa gcaaacgacg  3720
ctgcaggcga cggtaccacc actgcaaccg tactggctca ggctatcatc actgaaggtc  3780
tgaaagctgt tgctgcgggc atgaacccga tggacctgaa acgtggtatc gacaaagcgg  3840
ttaccgctgc agttgaagaa ctgaaagcgc tgtccgtacc atgctctgac tctaaagcga  3900
ttgctcaggt tggtaccatc tccgctaact ccgacgaaac cgtaggtaaa ctgatcgctg  3960
aagcgatgga caaagtcggt aaagaaggcg ttatcaccgt tgaagacggt accggtctgc  4020
aggacgaact ggacgtggtt gaaggtatgc agttcgaccg tggctacctg tctccttact  4080
tcatcaacaa gccggaaact ggcgcagtag aactggaaaa cccgttcatc ctgctggctg  4140
acaagaaaat ctccaacatc cgcgaaatgc tgccggttct ggaagctgtt gccaaagcag  4200
gcaaaccgct gctgatcatc gctgaagatg tagaaggcga agcgctggca actctggttg  4260
ttaacaccat ccgtggcatc gtgaaagtcg ctgcggttaa agcaccgggc ttcggcgatc  4320
gtcgtaaagc tatgctgcag gatatcgcaa ccctgactgg cggtaccgtg atctctgaag  4380
agatcggtat ggagctggaa aaagcaaccc tggaagacct gggtcaggct aaacgtgttg  4440
tgatcaacaa agacaccacc actatcatcg atggcgtggg tgaagaagct gcaatccagg  4500
gccgtgttgc tcagatccgt cagcagattg aagaagcaac ttctgactac gaccgtgaaa  4560
aactgcagga acgcgtagcg aaactggcag gcggcgttgc agttatcaaa gtgggtgctg  4620
ctaccgaagt tgaaatgaaa gagaaaaaag cacgcgttga agatgccctg cacgcgaccc  4680
gtgctgcggt agaagaaggc gtggttgctg gtggtggtgt tgcgctgatc cgcgtagcgt  4740
ctaaactggc tgacctgcgt ggtcagaacg aagaccagaa cgtgggtatc aaagttgcac  4800
tgcgtgcaat ggaagctccg ctgcgtcaga tcgtattgaa ctgcggcgaa gaaccgtctg  4860
ttgttgctaa caccgttaaa ggcggcgacg gcaactacgg ttacaacgca gcaaccgaag  4920
aatacggcaa catgatcgac atgggtatcc tggatccaac caaagtaact cgttctgctc  4980
tgcagtacgc agcttctgtg gctggcctga tgatcaccac cgaatgcatg gttaccgacc  5040
tgccgaaaaa cgatgcagct gacttaggcg ctgctggcgg tatgggcggc atgggtggca  5100
tgggcggcat gatgtaaccc cctagcataa ccccttgggc cctctaaacg ggtcttgagg  5160
ggttttttgc ccctgagacg cgtcaatcga gttcgtacct aagggcgaca ccccctaatt  5220
agcccgggcg aaaggcccag tctttcgact gagccttttcg ttttatttga tgcctggcag  5280
ttccctactc tcgcatgggg agtccccaca ctaccatcgg cgctacgcg tttcacttct  5340
gagttcggca tggggtcagg tggggaccacc gcgctactgc cgccaggcaa acaagggtg  5400
ttatgagcca tattcaggta taatgggct cgcgataatg ttcagaattg gttaattggt  5460
tgtaacactg accccctattt gtttattttt ctaaatacat tcaaatatgt atccgctcat  5520
gagacaataa ccctgataaa tgcttcaata atattgaaaa aggaagaata tgagccatat  5580
tcaacgggaa acgtcgaggc cgcgattaaa ttccaacatg gatgctgatt tatatgggta  5640
taaatgggct cgcgataatg tcgggcaatc aggtgcgaca atctatcgct tgtatgggaa  5700
gcccgatgcg ccagagttgt ttctgaaaca tggcaaaggt agcgttgcca atgatgttac  5760
agatgagatg gtcagactaa actggctgac ggaatttatg ccacttccga ccatcaagca  5820
ttttatccgt actcctgatg atgcatggtt actcaccact gcgatccccg gaaaaacagc  5880
gttccaggta ttagaagaat atcctgattc aaggtgaaaat attgttgatg cgctggcagt  5940
gttcctgcgc cggttgcact cgattcctgt ttgtaattgt cctttttaaca gcgatcgcgt  6000
atttcgcctc gctcaggcgc aatcacgaat gaataacggt ttggttgatg cgagtgattt  6060
tgatgacgag cgtaatggct ggcctgttga acaagtctgg aaagaaatgc ataaactttt  6120
gccattctca ccggattcag tcgtcactca tggtgatttc tcacttgata accttatttt  6180
tgacgagggg aaattaatag gttgtattga tgttggacga gtcggaatcg cagaccgata  6240
ccaggatctt gccatcctat ggaactgcct cggtgagttt tctccttcat tacagaaacg  6300
gctttttcaa aaatatggta ttgataatcc tgatatgaat aaattgcagt ttcattttgat  6360
gctcgatgag ttttttctaag cggcgcgcca tcgaatggcg caaaacctt cgcggtatgg  6420
catgatagcg cccggaagag agtcaattca gggtggtgaa tatgaaacca gtaacgttat  6480
acgatgtcgc agagtatgcc ggtgtctctt atcagaccgt ttcccgcgtg gtgaaccagg  6540
ccagccacgt ttctgcgaaa acgcgggaaa aagtggaagc ggcgatggcg gagctgaatt  6600
acattcccaa ccgcgtggca caacaactgg cgggcaaaca gtcgttgctg attggcgttg  6660
ccacctccag tctggccctg cacgcgccgt cgcaaattgt cgcggcgatt aaatctcgcg  6720
ccgatcaact gggtgccagc gtggtggtgt cgatggtaga acgaagcggc gtcgaagcct  6780
gtaaagcggc ggtgcacaat cttctcgcgc aacgcgtcag tgggctgatc attaactatc  6840
cgctggatga ccaggatgcc attgctgtgg aagctgcctg cactaatgtt ccggcgttat  6900
ttcttgatgt ctctgaccag acacccatca acagtattat tttctcccat gaggacggta  6960
cgcgactggg cgtggagcat ctggtcgcat gggtcacca gcaaatcgcg ctgttagcgg  7020
gcccattaag ttctgtctcg gcgcgtctgc gtctggctgg ctggcataaa tatctcactc  7080
gcaatcaaat tcagccgata gcggaacggg aaggcgactg gagtgccatg tccggttttc  7140
aacaaaccat gcaaatgctg aatgagggca tcgttcccac tgcgatgctg gttgccaacg  7200
atcagatgcg gctgggcgca atgcgcgcca ttaccgagtc cgggctgcgc gttggtgcgg  7260
atatctcggt agtgggatac gacgataccg aagatagctc atgttatatc ccgccgttaa  7320
ccaccatcaa acaggatttt cgcctgctgg ggcaaaccag cgtggaccgc ttgctgcaac  7380
tctctcaggg ccaggcggtg aagggcaatc agctgttgcc agtctcactg gtgaaaagaa  7440
aaaccaccct ggcgcccaat acgcaaaccg cctctccccg cgcgttggcc gattcattaa  7500
tgcagctggc acgacaggtt tcccgactgg aaagcgggca gtga           7544
```

SEQ ID NO: 20    moltype = DNA  length = 7550
FEATURE          Location/Qualifiers
source           1..7550

```
                mol_type = other DNA
                organism = synthetic construct
SEQUENCE: 20
ttaataagat gatcttcttg agatcgtttt ggtctgcgcg taatctcttg ctctgaaaac    60
gaaaaaaccg ccttgcaggg cggttttttcg aaggttctct gagctaccaa ctctttgaac   120
cgaggtaact ggcttggagg agcgcagtca ccaaaacttg tcctttcagt ttagccttaa   180
ccggcgcatg acttcaagac taactcctct aaatcaatta ccagtggctg ctgccagtgg   240
tgcttttgca tgtctttccg ggttggactc aagacgatag ttaccggata aggcgcagcg   300
gtcggactga acgggggtt cgtgcataca gtccagcttg gagcgaactg cctacccgga   360
actgagtgtc aggcgtggaa tgagacaaac gcggccataa cagcggaatg acaccggtaa   420
accgaaaggc aggaacagga gagcgcacga gggagccgcc aggggaaac gcctggtatc   480
tttatagtcc tgtcgggttt cgccaccact gatttgagcg tcagatttcg tgatgcttgt   540
cagggggcg gagcctatgg aaaaacggct ttgccgcggc cctctcactt ccctgttaag   600
tatcttcctg gcatcttcca ggaaatctcc gcccgttcg taagccattt ccgctcgccg   660
cagtcgaacg accgagcgta gcgagtcagt gagcgaggaa gcgaatata tcctgtatca   720
catattctgc tgacgcaccg gtgcagcctt ttttctcctg ccacatgaag cacttcactg   780
acaccctcat cagtgccaac atagtaagcc agtatacact ccgctagcgc tgaggtcccg   840
cagccgaacg accgagcgca gcgagtcagt gagcgaggaa gcgaaggcg agagtaggga   900
actgccaggc atcaaactaa gcagaaggcc cctgacggat ggccttttg cgttctaca    960
aactctttct gtgttgtaaa acgacggcca gtcttaagct cgggcccct gggcggttct   1020
gataacgagt aatcgttaat ccgcaaataa cgtaaaaacc cgcttcggcg ggtttttta   1080
tggggggagt ttagggaaag agcatttgtc agaatattta agggcgcctg tcactttgct   1140
tgatatatga gaattattta accttataaa tgagaaaaaa gcaacgcact ttaaataaga   1200
tacgttgctt tttcgattga tgaacaccta taattaaact attcatctat tatttatgat   1260
tttttgtata tacaatattt ctagtttgtt aaagagaatt aagaaaataa atctcgaaaa   1320
taataaaggg aaaatcagtt tttgatatca aaattataca tgtcaacgat aatacaaaat   1380
ataatacaaa ctataagatg ttatcagtat ttattatgca tttagaataa attttgtgtc   1440
gcccttccgc gaaattaata cgactcacta taggggaatt gtgagcggat aacaattccc   1500
ctctagaaat aattttgttt aacttttgaa ggagatatac atatggcaac gtttgaccgc   1560
aatgatccgc agttggcagg aacgatgttc cccacccgaa tagaggcgaa tgtcttgac    1620
cttgaaattg agggcgagat cccacgtgca atcaacggga gcttcttccg caacaccccc   1680
gaacctcagg tcaccccgca acctttccac accttcatcg atggggatgg tttgcgtct   1740
gcttttcatt tcgaagatgg ccatgtcgac tttgtcagcc gttgggtatg tactcctcgc   1800
tttgaagctg agcggtcggc tcgtaaatca ctcttcggta tgtaccgcaa tccgttcact   1860
gatgatccat cggtagaagg tattgatcgt acagtcgcca acaccagtat catcactcat   1920
cacgggaaag tactgccgc aaaggaagat ggactacctt atgagcttga cccccaaacc   1980
ctggaaaccc gaggtcgtta tgattacaag gggcaggtaa ccagccatac acatacagcg   2040
caccctaagt tcgaccccca gacaggtgaa atgttactct tcggctccgc tgctaaaggc   2100
gaacgaacgc ttgatatggc gtactatatt gttgatcgct acggcaaggt gacacatgag   2160
acctggttta agcagcctta cggtgcattc atgcacgact ttgctgtcac gcgcaactgg   2220
tcaatctttc cgatcatgcc tgcgacaaat agccttgagc gtcttaaagc aaagcagccc   2280
atttacatgt gggagcctga gcgaggaagc tatataggag tacttcctcg tcgtggtcag   2340
ggcaaggaca ttcgttggtt ccgtgccccg gcgttgtggg ttttccatgt cgtgaatgct   2400
tgggaggaag ggaatagaat tctgattgac ttgatgaaa gtgagatttt gccgttccca   2460
ttcccgaact cgcagaacct tccatttgat ccctccaagg ctgttccgcg tctaacccgt   2520
tgggaaattg atctcaatag tggtaacgat gagatgaaac gtacgcagct acacgaatat   2580
tttgcagaaa tgcctatcat ggatttccgt tttgcgctcc aggatcatcg ctacgcctac   2640
atggggttg acgatcctcg tcgcccctta gctcatcagc aagctgaaaa aatctttgcc   2700
tacaattcgt taggggttg ggacaaccat cgtaaagatt atgaactttg gtttacggga   2760
aaaatgtctg cagcgcagga accggcgttt gttcctagaa gcccagatgc gcctgagggc   2820
gatgctacc tactcagtgt agtagggcgg ctcgatgaaa atcgtagcga tctagttatc   2880
cttgatacgc aatgtttggc agctgggcct gtgccactg tcaagcttcc cttccgtctc   2940
cgagcagcgt tgcacggttg ttggcagtct aagaactgac tagcataacc ccttgggcc   3000
tctaaacggg tcttgagggg ttttttggca tcctgtccat gactcggaaa tcataaaaaa   3060
tttattttgct ttgtgagcgg ataacaatta taatacccctc tagaaatat tttgtttaac   3120
ttttaaagga gagttatcaa tgaatattgc tccattgcat gatcgcgtga tcgtcaagcg   3180
taaagaagtt gaaactaaat ctgctggcgg catcgttctg accggctctg cagcggctaa   3240
atccaccgc ggcgaagtgc tggctgtcgg caatggccgt atccttgaaa atggcgaagt   3300
gaagccgctg gatgtgaaag ttggcgacat cgttatttc aacgatggct acggtgtgaa   3360
atctgagaag atcgacaatg aagaagtgtt gatcatgtcc gaaagcgaca ttctggcaat   3420
tgttgaagcg taatccgcgc acgacactga acatacgaat ttaaggaata aagataatgg   3480
cagctaaaga cgtaaaattc ggtaacgacg ctcgtgtgaa aatgctgcgc ggcgtaaacg   3540
tactggcaga tgcagtgaaa gttaccctcg gtccaaaagg ccgtaacgta gttctggata   3600
aatctttcgg tgcaccgacc atcaccaaag atggtgtttc cgttgctcgt gaaatcgaac   3660
tggaagacaa gttcgaaaat atgggtgcgc agatggttga agaagttgcc tctaaagcaa   3720
acgacgctgc aggcgacggt accaccactg caaccgtact ggctcaggct atcatcactg   3780
aaggtctgaa agctgttgct gcgggcatga acccgatgga cctgaaacgt ggtatcgaca   3840
aagcggttac cgctgcagtt gaagaactga aagcgctgtc cgtaccatgc tctgactcta   3900
aagcgattgt tcaggttggt tgccatctccg ctaactccga cgaaaccgta ggtaaactga   3960
tcgctgaagc gatggacaaa gtcggtaaag aaggcgttat caccgttgaa gacggtacct   4020
gtctgcagga cgaactggac gtggttgaag gtatgcagtt cgaccgtggc tacctgtctc   4080
cttacttcat caacaagccg gaaactggc cagtagaact ggaaagcccg ttcatcctgc   4140
tggctgacaa gaaaatctcc aacatccgcg aaatgctgcc ggttctggaa gctgttgcca   4200
aagcaggcaa accgctgctg atcatcgctg aagatgtaga aggcgaagct ctggctaccc   4260
tggttgttaa caccatgcgt ggcatcgtga agtcgctgc ggttaaagca ccgggcttcg   4320
gcgatcgtcg taagctatg ctgcaggata tcgcaaccct gactggcggt accgtgatct   4380
ctgaagagat cggtatggag ctggaaaaag caacccctgga agacctgggt caggctaaac   4440
gtgttgtgat caacaaagac accaccacta tcatcgatgg cgtgggtgaa gagctgcaa   4500
tccagggccg tgttgctcag atccgtcagc agattgaaga agcaacttct gactacgacc   4560
```

```
gtgaaaaact gcaggaacgc gtagcgaaac tggcaggcgg cgttgcagtt atcaaagtgg   4620
gtgctgctac cgaagttgaa atgaaagaga aaaaagcacg cgttgaagat gccctgcacg   4680
cgacccgtgc tgcggtagaa gaaggcgtgg ttgctggtgg tggtgttgcg ctgatccgcg   4740
tagcgtctaa actggctgac ctgcgtggtc agaacgaaga ccagaacgtg ggtatcaaag   4800
ttgcactgcg tgcaatggaa gctccgctgc gtcagatcgc attgaactgc ggcgaagaac   4860
cgtctgttgt tgctaacacc gttaaaggcg gcgacggcaa ctacggttac aacgcagcaa   4920
ccgaagaata cggcaacatg atcgacatgg gtatcctgga tccaaccaaa gtaactcgtt   4980
ctgctctgca gtacgcagct tctgtggctg gcctgatgat caccaccgaa tgcatggtta   5040
ccgacctgcc gaaaaacgat gcagctgact taggcgctgc tggcggtatg ggcggcatgg   5100
gtggcatggg cggcatgatg taaccccta gcataacccc ttggggcctc taaacgggtc   5160
ttgaggggtt ttttgcccct gagacgcgtc aatcgagttc gtacctaagg gcgacacccc   5220
ctaattagcc cgggcgaaag gcccagtctt tcgactgagc ctttcgtttt atttgatgcc   5280
tggcagttcc ctactctcgc atggggagtc cccacactac catcggcgct acggcgtttc   5340
acttctgagt tcggcatggg gtcaggtggg accaccgcgc tactgccgcc aggcaaacaa   5400
ggggtgttat gagccatatt caggtataaa tgggctcgcg ataatgttca gaattggtta   5460
attggttgta acactgaccc ctatttgttt attttttctaa atacattcaa atatggtatcc   5520
gctcatgaga caataaccct gataaatgct tcaataatat tgaaaaagga agaatatgag   5580
ccatattcaa cgggaaacgt cgaggccgcg attaaattcc aacatggatg ctgatttata   5640
tgggtataaa tgggctcgcg ataatgtcgg gcaatcaggt gcgacaatct atcgcttgta   5700
tgggaagccc gatgcgccag agttgtttct gaaacatggc aaaggtagcg ttgccaatga   5760
tgttacagat gagatggtca gactaaactg gctgacggaa tttatgccac ttccgaccat   5820
caagcatttt atccgtactc ctgatgatgc atggttactc accactgcga tccccggaaa   5880
aacagcgttc caggtattag aagaatatcc tgattcaggt gaaaatattg ttgatgcgct   5940
ggcagtgttc ctgcgccggt tgcactcgat tcctgtttgt aattgtcctt taacagcga   6000
tcgcgtattt cgcctcgctc aggcgcaatc acgaatgaat aacggtttgg ttgatgcgag   6060
tgattttgat gacgagcgta atggctggcc tgttgaacaa gtctggaaag aaatgcataa   6120
acttttgcca ttctcaccgg attcagtcgt cactcatggt gatttctcac ttgataacct   6180
tattttttgac gaggggaaat taataggttg tattgatgtt ggacgagtcg gaatcgcaga   6240
ccgataccag gatcttgcca tcctatgaa ctgcctcggt gagttttctc cttcattaca   6300
gaaacggctt tttcaaaaat atggtattga taatcctgat atgaataaat tgcagtttca   6360
tttgatgctc gatgagtttt tctaagcggc gcgccatcga atggcgcaaa acctttcgcg   6420
gtatggcatg atagcgcccg gaagagagtc aattcagggt ggtgaatatg aaaccagtaa   6480
cgttatacga tgtcgcagag tatgccggtg tctcttatca gaccgtttcc cgcgtggtga   6540
accaggccag ccacgtttct gcgaaaacgc gggaaaaagt ggaagcggcg atggcggagc   6600
tgaattacat tcccaaccgc gtggcacaac aactggcggg caaacagtcg ttgctgattg   6660
gcgttgccac ctccagtctg gccctgcacg cgccgtcgca aattgtcgcg gcgattaaat   6720
ctcgcgccga tcaactgggt gccagcgtgg tggtgtcgat ggtagaacga agcggcgtcg   6780
aagcctgtaa agcggcggtg cacaatcttc tcgcgcaacg cgtcagtggg ctgatcatta   6840
actatccgct ggatgaccag gatgccattg ctgtggaagc tgcctgcact aatgttccgg   6900
cgttatttct tgatgtctct gaccagacac ccatcaacag tattattttc tcccatgagg   6960
acggtacgcg actgggcgtg gagcatctgg tcgcattggg tcaccagcaa atcgcgctgt   7020
tagcgggccc attaagttct gtctcggcgc gtctgcgtct ggctggctgg cataaatatc   7080
tcactcgcaa tcaaattcag ccgatagcgg aacgggaagg cgactggagc gcatgtccga   7140
gttttcaaca aaccatgcaa atgctgaatg agggcatcgt tcccactgcg atgcggttg   7200
ccaacgatca gatggcgctg ggcgcaatgc gcgccattac cgagtccggg ctgcgcgttg   7260
gtgcggatat ctcggtagtg ggatacgacg ataccgaaga tagctcatgt tatatcccgc   7320
cgttaaccac catcaaacag gattttcgcc tgctggggca aaccagcgtg gaccgcttgc   7380
tgcaactctc tcagggccag gcggtgaagg gcaatcagct gttgccagtc tcactggtga   7440
aaagaaaaac caccctggcg cccaatacgc aaaccgcctc tccccgcgcg ttggccgatt   7500
cattaatgca gctggcacga caggtttccc gactggaaag cgggcagtga              7550
```

```
SEQ ID NO: 21         moltype = DNA   length = 7544
FEATURE               Location/Qualifiers
source                1..7544
                      mol_type = other DNA
                      organism = synthetic construct
SEQUENCE: 21
ttaataagat gatcttcttg agatcgtttt ggtctgcgcg taatctcttg ctctgaaaac     60
gaaaaaaccg ccttgcaggg cggttttttcg aaggttctct gagctaccaa ctctttgaac   120
cgaggtaact ggcttggagg agcgcagtca ccaaaacttg tcctttcagt ttagccttaa   180
ccggcgcatg acttcaagac taactcctct aaatcaatta ccagtggctg ctgccagtgg   240
tgcttttgca tgtcttccg ggttggactc aagacgatag ttaccggata aggcgcagcg   300
gtcggactga acggggggtt cgtgcataca gtccagcttg gagcgaactg cctacccgga   360
actgagtgtc aggcgtggaa tgagacaaac gcggccaaga cacccgtaa                420
accgaaaggc aggaacagga gagcgcacga gggagccgcc aggggaaac gcctggtatc    480
tttatagtcc tgtcgggttt cgccaccact gatttgagcg tcagatttcg tgatgcttgt    540
caggggggcg gagcctatgg aaaaacggct ttgccgcggc cctctcactt ccctgttaag    600
tatcttcctg gcatcttcca ggaaatctcc gccccgttcg taagccattt ccgctcgccg    660
cagtcgaacg accgagcgta gcgagtcagt gagcgaggaa gcggaatata tcctgtatca    720
catattctgc tgacgcaccg gtgcagcctt ttttctcctg ccacatgaag cacttcactg    780
acaccctcat cagtgccaac atagtaagcc agtatacact ccgctagcgc tgaggtcccg    840
cagccgaacg accgagcgca gcgagtcagt gagcgaggaa gcggaaggcg agagtaggga   900
actgccaggc atcaaactaa gcagaaggcc ctgacggat ggcttttg cgtttctaca      960
aactcttttct gtgttgtaaa acgacggcca gtcttaagct cgggccccct gggcggttct  1020
gataacgagt aatcgttaat ccgcaaataa cgtaaaaacc cgcttcggcg gttttttta   1080
tgggggagt ttagggaaag agcatttgtc agaatattta agggcgcctg tcactttgct   1140
tgatatatga gaattattta acctataaa tgagaaaaaa gcaacgcact ttaaataaga   1200
tacgttgctt tttcgattga tgaacaccta taattaaact attcatctat tattatgat   1260
tttttgtata tacaatattt ctagtttgtt aaagagaatt aagaaaataa atctcgaaaa   1320
```

```
taataaaggg aaaatcagtt tttgatatca aaattataca tgtcaacgat aatacaaaat   1380
ataatacaaa ctataagatg ttatcagtat ttattatgca tttagaataa attttgtgtc   1440
gcccttccgc gaaattaata cgactcacta taggggaatt gtgagcggat aacaattccc   1500
ctctagaaat aattttgttt aacttttgaa ggagatatac atatggcaac gtttgaccgc   1560
aatgatccgc agttggcagg aacgatgttc cccacccgca tagaggcgaa tgtctttgac   1620
cttgaaattg agggcgagat cccacgtgca atcaacggga gcttcttccg caacaccccc   1680
gaacctcagg tcaccccgca acctttccac accttcatcg atggggatgg tttggcgtct   1740
gcttttcatt tcgaagatgg ccatgtcgac tttgtcagcc gttgggtatg tactcctcgc   1800
tttgaagctg agcggtcggc tcgtaaatca ctcttcggta tgtaccgcaa tccgttcact   1860
gatgatccat cggtagaagg tattgatcgt acagtcgcca acaccagtat catcactcat   1920
cacgggaaag tactggccgc aaaggaagat ggactacctt atgagcttga cccccaaacc   1980
ctggaaaccc gaggtcgtta tgattacaag gggcaggtaa ccagccatac acatacagcg   2040
caccctaagt tcgaccccca gacaggtgaa atgttactct tcggctccgc tgctaaaggc   2100
gaacgaacgc ttgatatggc gtactatatt gttgatcgac acggcaaggt gacacatgag   2160
acctggttta agcagcctta cggtgcattc atgcacgact ttgctgtcac gcgcaactgg   2220
tcaatctttc cgatcatgcc tgcgacaaat agccttgagc gtcttaaagc aaagcagccc   2280
atttacatgt gggagcctga gcgaggaagc tatataggag tacttcctcg tcgtggtcag   2340
ggcaaggaca ttcgttggtt ccgtgccccg gcgttgtggg ttttccatgt cgtgaatgct   2400
tgggaggaag ggaatagaat tctgattgac ttgatggaaa gtgagatttt gccgttccca   2460
ttcccgaact cgcagaacct tccatttgat ccctccaagg ctgttccgcg tctaaccccgt   2520
tgggaaattg atctcaatag tggtaacgat gagatgaaac gtacgcagct acacgaatat   2580
tttgcagaaa tgcctatcat ggatttccgt tttgcgctcc aggatcatcg ctacgcctac   2640
atggggttg acgatcctcg tcgccccta gctcatcagc aagctgaaaa aatctttgcc   2700
tacaattcgt taggggtttg ggacaaccat cgtaaagatt atgaactttg gtttacggga   2760
aaaatgtctc agcgcagga accggcgttt gttcctagaa gcccagatgc gcctgagggc   2820
gctggctacc tactcagtgt agtagggcgg ctcgatgaaa atcgtagcga tctagtttatc   2880
cttgatacgc aatgtttggc agctgggcct gtggccactg tcaagcttcc cttccgtctc   2940
cgagcagcgt tgcacggttg ttggcagtct aagaactgac tagcataacc ccttggggcc   3000
tctaaacggg tcttgagggg ttttttggca tcctgtccat gactcggtaa tacgactcac   3060
tacggaagaa ttgtgagcgg ataacaattc cctctagaaa taattttgtt taacttttaa   3120
aggagagtta tcaatgaata ttcgtccatt gcatgatcgc gtgatcgtca agcgtaaaga   3180
agttgaaact aaatctgctg gcggcatcgt tctgaccggc tctgcagcgg ctaaatccac   3240
ccgcggcgaa gtgctggctg tcggcaatgg ccgtatcctt gaaaatggcg aagtgaagcc   3300
gctggatgtg aaagttggcg acatcgttat tttcaacgat ggctacggtg tgaaatctga   3360
gaagatcgac aatgaagaag tgttgatcat gtccgaaagc gacattctgg caattgttga   3420
agcgtaatcc gcgcacgaca ctgaacatac gaatttaagg aataaagata atggcagcta   3480
aagacgtaaa attcggtaac gacgctcgtg tgaaaatgct gcgcggcgta aacgtactgg   3540
cagatgcagt gaaagttacc ctcggtccaa aaggccgtaa cgtagttctg gataaatctt   3600
tcggtgcacc gaccatcacc aaagatggtg tttccgttgc tcgtgaaatc gaactggaag   3660
acaagttcga aaatatgggg gcgcagatgg tgaagaagt tgcctctaaa gcaaacgacg   3720
ctgcaggcga cggtaccacc actgcaaccg tactggctca ggctatcatc actgaaggtc   3780
tgaaagctgt tgctgcgggc atgaacccga tggacctgaa acgtggtatc gacaaagcgg   3840
ttaccgctgc agttgaagaa ctgaaagcgc tgtccgtacc atgctctgac tctaaagcga   3900
ttgctcaggt tggtaccatc tccgctaact ccgacgaaac cgtaggtaaa ctgatcgctg   3960
aagcgatgga caaagtcggt aaagaaggcg ttatcaccgt tgaagacggt accggtctgc   4020
aggacgaact ggacgtggtt gaaggtatgc agttcgaccg tggctacctg tctccttact   4080
tcatcaacaa gccggaaact ggcgcagtga actggaaag cccgttcatc ctgctggctg   4140
acaagaaaat ctccaacatc cgcgaaatgc tgccggttct ggaagctgtt gccaaagcag   4200
gcaaaccgct gctgatcatc gctgaagatg tagaaggcga agcgctggca actctggttg   4260
ttaacaccat gcgtggcatc gtgaaagtcg ctgcggttaa agcaccgggc ttcggcgatc   4320
gtcgtaaagc tatgctgcag gatatcgcaa ccctgactgg cggtaccgtg atctctgaag   4380
agatcggtat ggagctggaa aaagcaaccc tggaagacct gggtcaggct aaacgtgttg   4440
tgatcaacaa agacaccacc actatcatcg atggcgtggg tgaagaagct gcaatccagg   4500
gccgtgttgc tcagatccgt cagcagattg aagaagcaac ttctgactac gaccgtgaaa   4560
aactgcagga acgcgtagcg aaactggcag cggcgttgca agttatcaaa gtgggtgctg   4620
ctaccgaagt tgaaatgaaa gagaaaaaag cacgcgttga agatgccctg cacgcgaccc   4680
gtgctgcggt agaagaaggc gtggttgctg gtgtggtgt tgcgctgatc cgcgtagcgt   4740
ctaaactggc tgacctgcgt ggtcagaacg aagaccagaa cgtgggtatc aaagttgcac   4800
tgcgtgcaat ggaagctccg ctgcgtcaga tcgtattgaa ctgccgcgaa gaaccgtctg   4860
ttgttgctaa caccgttaaa ggcggcgacg gcaactacgg ttacaacgca gcaaccgaag   4920
aatacggcaa catgatcgac atgggtatcc tggatccaac caaagtaact cgttctgctc   4980
tgcagtacgc agcttctgtg gctggcctga tgatcaccac cgaatgcatg gttaccgacc   5040
tgccgaaaaa cgatgcagct gacttaggcg ctgctggcgg tatgggcggc atgggtggca   5100
tgggccgcat gatgtaaccc cctagcataa cccctttggg cctctaaacg ggtcttgagg   5160
ggttttttgc ccctgagacg cgtcaatcga gttcgtacct aagggcgaca ccccctaatt   5220
agcccggggcg aaaggcccag tctttcgact gagcctttcg ttttatttga tgcctggcag   5280
ttccctactc tcgcatgggg agtccccaca ctaccatcgg cgctacgcg tttcacttct   5340
gagttcggca tggggtcagg tggaccacc gcgctactgc cgccaggcaa caaggggtg   5400
ttatgagcca tattcaggta taaatgggct cgcgataatg ttcagaattg gttaattgat   5460
tgtaacactg acccctattt gtttattttt ctaaatacat tcaaatatgt atccgctcat   5520
gagacaataa ccctgataaa tgcttcaata atattgaaaa aggaagaata tgagccatat   5580
tcaacggaa acgtcgaggc cgcgattaaa ttccaacatg gatgctgatt tatatgggta   5640
taaatgggct cgcgataatg tcgggcaatc aggtgcgaca atctatcgct tgtatgggaa   5700
gcccgatgcg ccagagttgt ttctgaaaca tggcaaaggt agcgttgcca atgatgttac   5760
agatgagatg gtcagactaa actggctgac ggaatttatg ccacttccga ccatcaagca   5820
ttttatccgt actcctgatg atgcatggtt actcaccact gcgatccccg gaaaaacagc   5880
gttccaggta ttagaagaat atcctgattc aggtgaaaat attgttgatg cgctggcagt   5940
gttcctgcgc cggttgcact cgattcctgt ttgtaattgt cctttttaaca gcgatcgcgt   6000
atttcgcctc gctcaggcgc aatcacgaat gaataacggt ttggttgatg cgagtgattt   6060
```

```
tgatgacgag cgtaatggct ggcctgttga acaagtctgg aaagaaatgc ataaactttt    6120
gccattctca ccggattcag tcgtcactca tggtgatttc tcacttgata acctattttt    6180
tgacgagggg aaattaatag gttgtattga tgttggacga gtcggaatcg cagaccgata    6240
ccaggatctt gccatcctat ggaactgcct cggtgagttt tctccttcat acagaaacg    6300
gcttttcaa aaatatggta ttgataatcc tgatatgaat aaattgcagt ttcatttgat    6360
gctcgatgag tttttctaag cggcgcgcca tcgaatggcg caaaaccttt cgcggtatgg    6420
catgatagcg cccggaagag agtcaattca gggtggtgaa tatgaaacca gtaacgttat    6480
acgatgtcgc agagtatgcc ggtgtctctt atcagaccgt ttcccgcgtg gtgaaccagg    6540
ccagccacgt ttctgcgaaa acgcgggaaa aagtggaagc ggcgatggcg gagctgaatt    6600
acattcccaa ccgcgtggca caacaactgg cgggcaaaca gtcgttgctg attggcgttg    6660
ccacctccag tctggccctg cacgcgccgt cgcaaattgt cgcggcgatt aaatctcgcg    6720
ccgatcaact gggtgccagc gtggtggtgt cgatggtaga acgaagcggc gtcgaagcct    6780
gtaaagcggc ggtgcacaat cttctcgcgc aacgcgtcag tgggctgatc attaactatc    6840
cgctgatga ccaggatgcc attgctgtgg aagctgactg cactaatgtt ccggcgttat    6900
ttcttgatgt ctctgaccag acacccatca acagtattat tttctcccat gaggacggta    6960
cgcgactggg cgtggagcat ctggtcgcat gggtcacca gcaaatcgcg ctgttagcgg    7020
gcccattaag ttctgtctcg gcgcgtctgc gtctggctgg ctggcataaa tatctcactc    7080
gcaatcaaat tcagccgata gcggaacggg aaggcgactg gagtgccatc tccggtttc    7140
aacaaaccat gcaaatgctg aatgagggca tcgttcccac tgcgatgctg gttgccaacg    7200
atcagatggc gctgggcgca atgcgcgcca ttaccgagtc cgggctgcgc gttggtgcgg    7260
atatctcggt agtgggatac gacgataccg aagatagctc atgttatatc cgccgcgttaa    7320
ccaccatcaa acaggatttt cgcctgctgg gcaaaccagc ctggaccgc ttgctgcaac    7380
tctctcaggg ccaggcgtg aagggcaatc agctcgttgcc agtctcactg gtgaaaagaa    7440
aaaccaccct ggcgcccaat acgcaaaccg cctctcccg cgcgttggcc gattcattaa    7500
tgcagctggc acgacaggtt tcccgactgg aaagcgggca gtga                    7544
```

SEQ ID NO: 22        moltype = DNA  length = 7544
FEATURE              Location/Qualifiers
source               1..7544
                     mol_type = other DNA
                     organism = synthetic construct
SEQUENCE: 22

```
ttaataagat gatcttcttg agatcgtttt ggtctgcgcg taatctcttg ctctgaaaac      60
gaaaaaccg ccttgcaggg cggtttttcg aaggttctct gagctaccaa ctctttgaac     120
cgaggtaact ggcttggagg agcgcagtca ccaaaacttg tcctttcagt ttagccttaa     180
ccggcgcatg acttcaagac taactcctct aaatcaatta ccagtggctg ctgccagtgg     240
tgcttttgca tgtcttccg ggttggactc aagacgatag ttaccggata aggcgcagcg     300
gtcggactga acggggggtt cgtgcataca gtccagcttg agcgaactg cctacccgga     360
actgagtgtc aggcgtgaa tgagacaaac gcggccataa cagcggaatg acaccggtaa     420
accgaaaggc aggaacagga gagcgcacga gggagccgcc aggggaaac gcctggtatc     480
tttatagtcc tgtcgggttt cgccaccact gatttgagcg tcagatttcg tgatgcttgt     540
cagggggcg gagcctatgg aaaaacggct ttgccgcggc cctctcactt ccctgttaag     600
tatcttcctg gcatcttcca ggaaatctcc gccccgttcg taagccattt ccgctcgccg     660
cagtcgaacg accgagcgta gcgagtcagt gagcgaggaa gcggaatata tcctgtatca     720
catattctgc tgacgcaccg gtgcagcctt ttttctcctg ccacatgaag cacttcactg     780
acaccctcat cagtgccaac atagtaagcc agtatacact ccgctagcgc tgaggtcccg     840
cagccgaacg accgagcgca gcgagtcagt gagcgaggaa gcggaaggcg agagtaggga     900
actgccaggc atcaaactaa gcagaaggcc cctgacggat ggccttttg cgtttctaca     960
aactctttct gtgttgtaaa acgacggcca gtcttaagct cgggcccct gggcggttct    1020
gataacgagt aatcgttaat ccgcaaataa cgtaaaaacc cgcttcggcg gtttttta    1080
tgggggagt ttagggaaag agcatttgtc agaatatta agggcgcctg tcactttgc    1140
tgatatatga gaattattta accttataaa tgagaaaaaa gcaacgcact ttaaataaga    1200
tacgttgctt tttcgattga tgaacaccta taattaaact attcatctat tatttatgat    1260
tttttgtata tacaatattt ctagtttgtt aaagagaatt aagaaaataa atctcgaaaa    1320
taataaaggg aaaatcagtt tttgatatca aaattatcaa tgtcaacgat aatacaaaat    1380
ataatacaaa ctataagatg ttatcagtat ttattatgca tttagaataa attttgtgtc    1440
gcccttccgc gaaattaata cgactcacta gggggaatt gtgagcggat aacaattccc    1500
ctctagaaat aattttgttt aactttgaa ggagatatac atatggcaac gtttgaccgc    1560
aatgatccgc agttggcagg aacgatgttc cccacccgaa tagagcgaa tgtctttgac    1620
cttgaaattg aggggagat ccccacgtgca atcaacggga gcttcttccg caacacccc    1680
gaacctcagg tcacccccgca accttttccac accttcatcg atggggatgg tttgcgtct    1740
gcttttcatt tcgaagatgg ccatgtcgac tttgtcagcc gttgggtatg tactcctcgc    1800
tttgaagctg agcggtcggc tcgtaaatca ctcttcggta tgtaccgcaa tccgttcact    1860
gatgatccat cggtagaagg tattgatcgt acagtcgcca acactagtat catcactgat    1920
cacgggaaag tactgccgc aaaggaagat ggactacctt atgagcttga cccccaaacc    1980
ctggaaaccc gaggtcgtta tgattacaag gggcaggtaa ccagccatac acatacagcg    2040
caccctaagt tcgaccccca gacaggtgaa atgttactct tcggctccgc tgctaaaggc    2100
gaacgacgc ttgatatggc gtactatatt gttgatcgct acggcaaggt gacacatgag    2160
acctggttta agcagcctta cggtgcattc atgcacgagt ttgctgtcac gcgcaactgg    2220
tcaatctttc cgatcatgcc tgcgacaaat agccttgagc gtcttaaagc aaagcagccc    2280
atttacatgt gggagcctga gcgaggaagc tatataggag tacttcctcg tcgtggtcag    2340
ggcaaggaca ttcgttggtt ccgtgccccg cgttgtggg ttttccatgt cgtgaatgct    2400
tgggaggaag ggaatagaat tctgattgac ttgatggaaa gtgagatttt gccgttccca    2460
ttcccgaact ccagaacct tccatttgat ccctcaaggc ctgttccgcg tctaacccgt    2520
tgggaaattg atctcaatag tggtaacgat gagatgaaac gtacgcagct acacgaatat    2580
tttgcagaaa tgcctatcat ggattttcgt tttgcgctcc aggatcatcg ctacgcctac    2640
atgggggttg acgatcctcg tcgcccctta gctcatcagc aagctgaaaa aatctttgcc    2700
tacaattcgt taggggtttg ggacaaccat cgtaaagatt atgaactttg gtttacggga    2760
aaaatgtctg cagcgcagga accggcgttt gttcctagaa gcccagatgc gcctgagggc    2820
```

```
gatggctacc tactcagtgt agtagggcgg ctcgatgaaa atcgtagcga tctagttatc  2880
cttgatacgc aatgtttggc agctgggcct gtggccactg tcaagcttcc cttccgtctc  2940
cgagcagcgt tgcacggttg ttggcagtct aagaactgac tagcataacc ccttggggcc  3000
tctaaacggg tcttgagggg ttttttggca tcctgtccat gactcggtaa tacgactcac  3060
taatactgaa ttgtgagcgg ataacaattc cctctagaaa taattttgtt taacttttaa  3120
aggagagtta tcaatgaata ttcgtccatt gcatgatcgc gtgatcgtca agcgtaaaga  3180
agttgaaact aaatctgctg gcggcatcgt tctgaccggc tctgcagcgg ctaaatccac  3240
ccgcggcgaa gtgctggctg tcggcaatgg ccgtatcctt gaaaatggcg aagtgaagcc  3300
gctggatgtg aaagttggcg acatcgttat tttcaacgat ggctacggtg tgaaatctga  3360
gaagatcgac aatgaagaag tgttgatcat gtccgaaagc gacattctgg caattgttga  3420
agcgtaatcc gcgcacgaca ctgaacatac gaatttaagg aataaagata atggcagcta  3480
aagacgtaaa attcggtaac gacgctcgtg tgaaaatgct gcgcggcgta aacgtactgg  3540
cagatgcagt gaaagttacc ctcggtccaa aaggccgtaa cgtagttctg gataaatctt  3600
tcggtgcacc gaccatcacc aaagatggtg tttccgttgc tcgtgaaatc gaactggaag  3660
acaagttcga aaatatgggt gcgcagatgg tgaagaagt tgcctctaaa gcaaacgacg  3720
ctgcaggcga cggtaccacc actgcaaccg tactggctca ggctatcatc actgaaggtc  3780
tgaaagctgt tgctgcgggc atgaacccga tggacctgaa acgtggtatc gacaaagcgg  3840
ttaccgctgc agttgaagaa ctgaaagcgc tgtccgtacc atgctctgac tctaaagcga  3900
ttgctcaggt tggtaccatc tccgctaact ccgacgaaac cgtaggtaaa ctgatcgctg  3960
aagcgatgga caaagtcggt aaagaaggcg ttatcaccgt tgaagacggt accggtctgc  4020
aggacgaact ggacgtggtt gaaggtatgc agttcgaccg tggctacctg tctccttact  4080
tcatcaacaa gccggaaact ggcgcagtag aactggaaag ccgttcatc ctgctggctg  4140
acaagaaaat ctccaacatc cgcgaaatgc tgccggttct ggaagctgtt gccaaagcag  4200
gcaaaccgct gctgatcatc gctgaagatg tagaaggcga agcgctggca actctggttg  4260
ttaacaccat gcgtggcatc gtgaaagtcg ctgcggttaa agcaccgggc ttcggcgatc  4320
gtcgtaaagc tatgctgcag gatatcgcaa ccctgactgg cggtaccgtg atctctgaag  4380
agatcggtat ggagctggaa aaagcaaccc tggaagacct gggtcaggtc aaacgtgttg  4440
tgatcaacaa agacaccacc actatcatcg atggcgtggg tgaagaagct gcaatccagg  4500
gccgtgttgc tcagatccgt cagcagattg aagaagcaac ttctgactac gaccgtgaaa  4560
aactgcagga acgcgtagcg aaactgcagg gcggcgttgc agttatcaaa gtgggtgctg  4620
ctaccgaagt tgaaatgaaa gagaaaaaag cacgcgttga agatgccctg cacgcgaccc  4680
gtgctgcggt agaagaaggc gtggttgctg tgtgtggtgt tgcgctgatc cgcgtagcgt  4740
ctaaactggc tgacctgcgt ggtcagaacg aagaccagaa cgtgggtatc aaagttgcac  4800
tgcgtgcaat ggaagctccg ctgcgtcaga tcgtattgaa ctgcggcgaa gaaccgtctg  4860
ttgttgctaa caccgttaaa ggcggcgacg gcaactacgg ttacaacgca gcaaccgaag  4920
aatacggcaa catgatcgac atgggtatcc tggatccaac caaagtaact cgttctgctc  4980
tgcagtacgc agcttctgtg gctggcctga tgatcaccac cgaatgcatg gttaccgacc  5040
tgccgaaaaa cgatgcagct gacttaggcg ctgctggcgg tatgggcggc atgggtggca  5100
tgggcggcat gatgtaaccc cctagcataa cccccttggg cctctaaacg ggtcttgagg  5160
ggttttttgc ccctgagacg cgtcaatcga gttcgtacct aagggcgaca ccccctaatt  5220
agcccgggcg aaaggcccag tctttcgact gagcctttcg ttttatttga tgcctggcag  5280
ttccctactc tcgcatgggg agtccccaca ctaccatcgg cgctacgcg tttcacttct  5340
gagttcggca tggggtcagg tgggaccacc gcgctactgc gccaggcaa acaagggtg  5400
ttatgagcca tattcaggta taaatgggct cgcgataatg ttcagaattg gttaattggt  5460
tgtaacactg accccctatt tgtttatttt ctaaatacat tcaaatatgt atccgctcat  5520
gagacaataa ccctgataaa tgcttcaata atattgaaaa aggaagaata tgagccatat  5580
tcaacgggaa acgtcgaggc cgcgattaaa ttccaacatg gatgctgatt tatatgggta  5640
taaatgggct cgcgataatg tcgggcaatc aggtgcgaca atctatcgct tgtatgggaa  5700
gcccgatgcg ccagagttgt ttctgaaaca tggcaaaggt agcgttgcca atgatgttac  5760
agatgagatg gtcagactaa actggctgac ggaatttatg ccacttccga ccatcaagca  5820
ttttatccgt actcctgatg atgcatggtt actcaccact cgatcccccg gaaaaacagc  5880
gttccaggta ttagaagaat atcctgattc aggtgaaaat attgttgatg cgctggcagt  5940
gttcctgcgc cggttgcact cgattcctgt ttgtaattgt cctttaaca gcgatcgcgt  6000
atttcgcctc gctcaggcgc aatcacgaat gaataacggt ttggttgatg cgagtgattt  6060
tgatgacgag cgtaatggct ggcctgttga acaagtctgg aaagaaatgc ataaactttt  6120
gccattctca ccggattcag tcgtcactca tggtgatttc tcacttgata accttatttt  6180
tgacgagggg aaattaatag gttgtattga tgttggacga gtcggaatcg cagaccgata  6240
ccaggatctt gccatcctat ggaactgcct cggtgagttt tctccttcat tacagaaacg  6300
gctttttcaa aaatatggta ttgataatcc tgatatgaat aaattgcagt ttcatttgat  6360
gctcgatgag ttttctaag cggcgcgcca tcgaatggcg caaaacccttt cgcggtatgg  6420
catgatagcg cccggaagag agtcaattca gggtggtgaa tatgaaacca gtaacgttat  6480
acgatgtcgc agagtatgcc ggtgtctctt atcagaccgt ttcccgcgtg gtgaaccagg  6540
ccagccacgt ttctgcgaaa acgcgggaaa aagtggaagc ggcgatggcg gagctgaatt  6600
acattcccaa ccgcgtggca caactcctggg cgggcaaaca gtcgttgctg attggcgttg  6660
ccacctccag tctggccctg cacgcgccgt cgcaaattgt cgcggcgatt aaatctcgcg  6720
ccgatcaact gggtgccagc gtggtggtgt cgatggtaga acgaagcggc gtcgaagcct  6780
gtaaagcggc ggtgcacaat cttctcgcgc aacgcgtcag tgggctgatc attaactatc  6840
cgctggatga ccaggatgcc attgctgtgg aagctgcctg cactaatgtt ccggcgttat  6900
ttcttgatgt ctctgaccag acacccatca acagtattat tttctcccat gaggacgtta  6960
cgcgactggg cgtggagcat ctggtcgcat tgggtcacca gcaaatcgcg ctgttagcgg  7020
gcccattaag ttctgtctcg gcgcgtctcg cgtctggctgg ctggcataaa tatctcactc  7080
gcaatcaaat tcagccgata gcggaacggg aaggcgactc gagtgccatg tccggttttc  7140
aacaaaccat gcaaatgctg aatgagggca tcgttcccac tgcgatgctg gttgccaacg  7200
atcagatggc gctgggcgca atgcgcgcca ttaccgagtc gggctgcg gttggtgcgg  7260
atatctcggt agtgggatac gacgataccg aagatagctc atgttatatc ccgccgttaa  7320
ccaccatcaa acaggatttt cgcctgctgg ggcaaaccag cgtggaccgc ttgctgcaac  7380
tctctcaggg ccaggcggtg aagggcaatc agctgttgcc agtctcactg gtgaaaagaa  7440
aaaccaccct ggcgcccaat acgcaaaccg cctctccccg cgcgttggcc gattcattaa  7500
tgcagctggc acgacaggtt tcccgactgg aaagcgggca gtga                  7544
```

| SEQ ID NO: 23 | moltype = DNA length = 7545 |
|---|---|
| FEATURE | Location/Qualifiers |
| source | 1..7545 |
| | mol_type = other DNA |
| | organism = synthetic construct |

SEQUENCE: 23

```
ttaataagat gatcttcttg agatcgtttt ggtctgcgcg taatctcttg ctctgaaaac   60
gaaaaaaccg ccttgcaggg cggtttttcg aaggttctct gagctaccaa ctctttgaac  120
cgaggtaact ggcttggagg agcgcagtca ccaaaacttg tcctttcagt ttagccttaa  180
ccggcgcatg acttcaagac taactcctct aaatcaatta ccagtggctg ctgccagtgg  240
tgcttttgca tgtctttccg ggttggactc aagacgatag ttaccggata aggcgcagcg  300
gtcggactga acgggggtt cgtgcataca gtccagcttg gagcgaactg cctaccggga  360
actgagtgtc aggcgtgaa tgagacaaac gcggccataa cagcggaatg acaccggtaa  420
accgaaaggc aggaacagga gagcgcacga gggagccgcc aggggaaac gcctggtatc  480
tttatagtcc tgtcgggttt cgccaccact gatttgagcg tcagatttcg tgatgcttgt  540
caggggggcg gagcctatgg aaaaacggct ttgccgcggc cctctcactt ccctgttaag  600
tatcttcctg gcatcttcca ggaaatctcc gccccgttcg taagccattt ccgctccgcg  660
cagtcgaacg accgagcgta gcgagtcagt gagcgaggaa gcggaatata tcctgtatca  720
catattctgc tgacgcaccg gtgcagcctt ttttctcctg ccacatgaag cacttcactg  780
acaccctcat cagtgccaac atagtaagcc agtatacact ccgctagcgc tgaggtcccg  840
cagccgaacg accgagcgca gcgagtcagt gagcgaggaa gcggaaggcg agagtaggga  900
actgccaggc atcaaactaa gcagaaggcc cctgacggat ggccttttg cgttctaca  960
aactctttct gtgttgtaaa acgacggcca gtcttaagct cgggcccct gggcggttct 1020
gataacgagt aatcgttaat ccgcaaataa cgtaaaaacc cgcttcggcg ggttttttta 1080
tggggggagt ttagggaaag agcatttgtc agaatattta agggcgcctg tcacttgct 1140
tgatatatga gaattattta accttataaa tgagaaaaaa gcaacgcact ttaaataaga 1200
tacgttgctt tttcgattga tgaacaccta taattaaact attcatctat tatttatgat 1260
ttttttgtata tacaatattt ctagtttgtt aaagagaatt aagaaaataa atctcgaaaa 1320
taataaaggg aaaatcagtt tttgatatca aaattatca tgtcaacgat aatacaaaat 1380
ataatacaaa ctataagatg ttatcagtat ttattatgca tttagaataa attttgtgtc 1440
gcccttccgc gaaattaata cgactcacta taggggaatt gtgagcggat aacaattccc 1500
ctctagaaat aattttgttt aacttttgaa ggagatatac atatggcaac gtttgaccgc 1560
aatgatccgc agttggcagg aacgatgttc cccaccgaa tagagcgaa tgtctttgac 1620
cttgaaattg agggcgagat cccacgtgca atcaacggga gcttcttccg caacacccc 1680
gaacctcagg tcaccccgca acctttccac accttcatcg atgggatgg tttggcgtct 1740
gcttttcatt tcgaagatgg ccatgtcgac tttgtcagcc gttgggtatg tactcctcgc 1800
tttgaagctg agcggtcggc tcgtaaatca ctcttcggta tgtaccgcaa tccgttcact 1860
gatgatccat cggtagaagg tattgatcgt acagtcgcca acaccagtat catcactcat 1920
cacgggaaag tactgccgc aaaggaagat ggactacctt atgagcttga cccccaaacc 1980
ctggaaaccc gaggtcgtta tgattacaag gggcaggtaa ccagccatac acatacagcg 2040
caccctaagt tcgaccccca gacaggtgaa atgttactct tcggctccgc tgctaaaggc 2100
gaacgaacgc ttgatatggc gtactatatt gttgatcgct acgccaaggt gacacatgag 2160
acctggttta gcagcctta cggtgcattc atgcacgact ttgctgtcac gcgcaactgc 2220
tcaatctttc cgatcatgcc tgcgacaaat agccttgagc gtcttaaagc aaagcagccc 2280
atttacatgt gggagcctga gcgaggaagc tatataggag tacttcctcg tcgtggtcag 2340
ggcaaggaca ttcgttggtt ccgtgccccg gcgttgttgg ttttccatgt cgtgaatgct 2400
tgggaggaag ggaatagaat tctgattgac ttgatgaaa gtgagatttt gccgttccca 2460
ttcccgaact cgcagaacct tccatttgat ccctccaagg ctgttccgcg tctaacccgt 2520
tgggaaattg atctcaatag tggtaacgat gagatgaaac gtacgcagct acacgaatat 2580
tttgcagaaa tgcctatcat ggatttccgt tttgcgctcc aggatcatcg ctacgcctac 2640
atgggggttg acgatcctcg tcgcccctta gctcatcagc aagctgaaaa aatctttgcc 2700
tacaattcgt taggggtttg ggacaaccat cgtaaagatt atgaactttg gtttacggga 2760
aaaatgtctg cagcgcagga accggcgttt gttcctagaa gcccagatgc gcctgagggc 2820
gatgctacc tactcagtgt agtagggcgg ctcgatgaaa atcgtagcga tctagtttatc 2880
cttgatacgc aatgtttggc agctgggcct gtggccactg tcaagcttcc cttccgtctc 2940
cgagcagcgt tgcacggttg ttggcagtct aagaactgac tagcataacc ccttggggcc 3000
tctaaacggg tcttgagggg ttttttggca tccctgtcca tgactcggta atacgactca 3060
ctatttcgga attgtgagcg gataacaatt ccctctagaa ataattttgt ttaactttta 3120
aaggagagtt atcaatgaat attcgtccat tgcatgatcg cgtgatcgtc aagcgtaaag 3180
aagttgaaac taaatctgct ggcggcatcg ttctgaccgg ctctgcagcg ctaaatcca 3240
cccgcggcga agtgctggct gtcggcaatg gccgtatcct tgaaaatggc gaagtgaagc 3300
cgctggatgt gaaagttggc gacatcgtta ttttcaacga tggctacggt gtgaaatctg 3360
agaagatcga caatgaagaa gtgttgatca tgtccgaaag cgacattctg gcaattgctg 3420
aagcgtaatc cgcgcacgac actgaacata cgaatttaag gaataaagat aatggcagct 3480
aaagacgtaa aattcggtaa cgacgctcgt gtgaaatgc tgcgcggcgt aaacgtactg 3540
gcagatgcag tgaaagttac cctcggtcca aaagccgta acgtagttct ggataaatct 3600
ttcggtgcac cgaccatcac caaagatggt gtttccgttg ctcgtgaaat cgaactggaa 3660
gacaagttcg aaaatatggg tgcgcagatg gtgaaagaag ttgcctctaa agcaaacgac 3720
gctgcaggcg acgtaccac cactgcaacc gtactggctc aggctatcat cactgaaggt 3780
ctgaaagctg ttgctgcggg catgaacccg atggacctga aacgtggtat cgacaaagcg 3840
gttaccgctg cagttgaaga actgaaagcg ctgtccgtac catgctctga ctctaaagcg 3900
attgctcagg ttggtaccat ctccgctaac tccgacgaaa ccgtaggtaa actgatcgct 3960
gaagcgatgg acaaagtcgg taaagaaggc gttatcaccg ttgaagacgg taccggtctg 4020
caggacgaac tggacgtggt tgaaggtatg cagttcgacc gtggctacct gtctccttac 4080
ttcatcaaca agccggaaac tggtgcagta gaactgaaaa gccgttcat cctgctggct 4140
gacaagaaaa tctccaacat ccgcgaaatg ctgccggttc tggaagctgt tgccaaagca 4200
ggcaaaccgc tgctgatcat cgctgaagat gtagaaggcg aagcgctggc aactctggtt 4260
gttaacacca tgcgtggcat cgtgaaagtc gctgcggtta agcaccgg cttcggcgat 4320
```

```
cgtcgtaaag ctatgctgca ggatatcgca accctgactg gcggtaccgt gatctctgaa    4380
gagatcggta tggagctgga aaaagcaacc ctgaagacc  tgggtcaggc taaacgtgtt    4440
gtgatcaaca aagacaccac cactatcatc gatggcgtgg gtgaagaagc tgcaatccag    4500
ggccgtgttg ctcagatccg tcagcagatt gaagaagcaa cttctgacta cgaccgtgaa    4560
aaactgcagg aacgcgtagc gaaactggca ggcggcgttg cagttatcaa agtgggtgct    4620
gctaccgaag ttgaaatgaa agagaaaaaa gcacgcgttg aagatgccct gcacgcgacc    4680
cgtgctgcgg tagaagaagg cgtggttgct ggtggtggtg ttgcgctgat ccgcgtagcg    4740
tctaaactgg ctgacctgcg tggtcagaac gaagaccaga acgtgggtat caaagttgca    4800
ctgcgtgcaa tggaagctcc gctgcgtcag atcgtattga actgcggcga agaaccgtct    4860
gttgttgcta acaccgttaa aggcggcgac ggcaactacg gttacaacgc agcaaccgag    4920
gaatacggca acatgatcga catgggtatc ctggatccaa ccaaagtaac tcgttctgct    4980
ctgcagtacg cagcttctgt ggctggcctg atgatcacca ccgaatgcat ggttaccgac    5040
ctgccgaaaa acgatgcagc tgacttaggc gctgctggcg tatgggcgg  catgggtggc    5100
atgggcggca tgatgtaacc ccctagcata accccttggg gcctctaaac gggtcttgag    5160
gggttttttg cccctgagac gcgtcaatcg agttcgtacc taagggcgac accccctaat    5220
tagcccgggc gaaaggccca gtctttcgac tgagcctttc gttttatttg atgcctggca    5280
gttccctact ctcgcatggg gagtccccac actaccatcg gcgctacggc gtttcacttc    5340
tgagttcggc atggggtcag gtgggaccac cgcgctactg ccgccaggca aacaagggt    5400
gttatgagcc atattcaggt ataaatgggc tcgcgataat gttcagaatt ggttaattgg    5460
ttgtaacact gacccctatt tgtttatttt tctaaataca ttcaaatatg tatccgctca    5520
tgagacaata accctgataa atgcttcaat aatattgaaa aaggaagaat atgagccata    5580
ttcaacggga aacgtcgagg ccgcgattaa attccaacat ggatgctgat ttatatgggt    5640
ataaatgggc tcgcgataat gtcgggcaat caggtgcgac aatctatcgc ttgtatggga    5700
agcccgatgc gccagagttg tttctgaaac atggcaaagg tagcgttgcc aatgatgtta    5760
cagatgagat ggtcagacta aactggctga cggaatttat gccacttccg accatcaagc    5820
attttatccg tactcctgat gatgcatggt tactcaccac tgcgatcccc ggaaaaacag    5880
cgttccaggt attagaagaa tatcctgatt caggtgaaaa tattgttgat gcgctggcag    5940
tgttcctgcg ccgttgcac  tcgattcctg tttgtaattg tccttttaac agcgatcgcg    6000
tatttcgcct cgctcaggcg caatcacgaa tgaataacgg tttggttgat gcgagtgatt    6060
ttgatgacga gcgtaatggc tggcctgttg aacaagtctg gaaagaaatg cataaacttt    6120
tgccattctc accggattca gtcgtcactc atggtgattt ctcacttgat aaccttattt    6180
ttgacgaggg gaaattaata ggttgtattg atgttggacg agtcggaatc gcagaccgat    6240
accaggatct tgccatccta tggaactgcc tcggtgagtt ttctccttca ttacagaaac    6300
ggcttttcca aaaatatggt attgataatc ctgatatgaa taaattgcag tttcatttga    6360
tgctcgatga gttttctaa  gcggcgcgcc atcgaatggc gcaaaaccttt tcgcggtatg   6420
gcatgatagc gcccggaaga gagtcaattc agggtggtga atatgaaacc agtaacgtta    6480
tacgatgtcg cagagtatgc cggtgtctct tatcagaccg tttcccgcgt ggtgaaccag    6540
gccagccacg tttctgcgaa aacgcgggaa aaagtgaaag cggcgatggc ggagctgaat    6600
tacattccca accgcgtggc acaacaactg gcgggcaaca agtcgttgct gattggcgtt    6660
gccacctcca gtctggccct gcacgcgccg tcgcaaattg tcggcgcgat taaatctcgc    6720
gccgatcaac tgggtgccag cgtggtggtg tcgatggtag aacgaagcgg cgtcgaagcc    6780
tgtaaagcgg cggtgcacaa tcttctcgcg caacgcgtca gtgggctgat cattaactat    6840
ccgctggatg accaggatgc cattgctgtg gaagctgcct gcactaatgt tccgacgtta    6900
tttcttgatg tctctgacca gacacccatc aacagtatta ttttctccca tgaggacggt    6960
acgcgactgg gcgtggagca tctggtcgca ttgggtcacc agcaaatcgc gctgttagcg    7020
ggcccattaa gttctgtctc ggcgcgtctg cgtctggctg gctggcataa atatctcact    7080
cgcaatcaaa ttcagccgat agcggaacgg gaaggcgact ggagtgccat gtccggtttt    7140
caacaaacca tgcaaatgct gaatgagggc atcgttccca ctgcgatgct ggttgccaac    7200
gatcagatgc cgctgggcgc aatgcgcgcc attaccgagt ccgggctgcg cgttggtgcg    7260
gatatctcgg tagtgggata cgacgatacc gaagatagct catgttatat cccgccgtta    7320
accaccatca aacaggattt tcgcctgctg gggcaaacca gcgtggaccg cttgctgcaa    7380
ctctctcagg gccaggcggt gaagggcaat cagctgttgc cagtctcact ggtgaaaaga    7440
aaaaccaccc tggcgcccaa tacgcaaacc gcctctcccc gcgcgttggc cgattcatta    7500
atgcagctgg cacgacaggt ttcccgactg gaaagcgggc agtga                    7545

SEQ ID NO: 24        moltype = DNA   length = 7544
FEATURE              Location/Qualifiers
source               1..7544
                     mol_type = other DNA
                     organism = synthetic construct
SEQUENCE: 24
ttaataagat gatcttcttg agatcgtttt ggtctgcgcg taatctcttg ctctgaaaac     60
gaaaaaaccg ccttgcaggg cggttttttcg aaggttctct gagctaccaa ctctttgaac   120
cgaggtaact ggcttggagg agcgcagtca ccaaaacttg tcctttcagt ttagccttaa   180
ccggcgcatg acttcaagac taactcctct aaatcaatta ccagtggctg ctgccagtgg   240
tgcttttgca tgtctttccg ggttggactc aagacgatag ttaccggata aggcgcagcg   300
gtcggactga acgggggggtt cgtgcataca gtccagcttg gagcgaactg cctacccgga   360
actgagtgtc aggcgtggaa tgagacaaac gcggccataa cagcggaatg acaccggtaa   420
accgaaaggc aggaacagga gagcgcacga gggagccgcc aggggggaaac gcctggtatc   480
tttatagtcc tgtcgggttt cgccaccact gatttgagcg tcagatttcg tgatgcttgt   540
cagggggggcg gagcctatgg aaaaacggct ttgccgcggc cctctcactt ccctgttaag   600
tatcttcctg gcatcttcca ggaaatctcc gccccgttcg taagccattt ccgctcgccg   660
cagtcgaacg accgagcgta gcgagtcagt gagcgaggaa gcggaatata tcctgtatca   720
catattctgc tgacgcaccg gtgcagcctt ttttctcctg ccacatgaag cacttcactg   780
acaccctcat cagtgccaac atagtaagcc agtatacact ccgctagcgc tgaggtcccg   840
cagccgaacg accgagcgca gcgagtcagt gagcgaggaa gcggaaggcg agagtaggga   900
actgccaggc atcaaactaa gcagaaggcc cctgacggat ggccttttttg cgtttctaca   960
aactctttct gtgttgtaaa acgacggcca gtcttaagct cgggccccct gggcggttct   1020
gataacgagt aatcgttaat ccgcaaataa cgtaaaaacc cgcttcggcg gtttttttta   1080
```

```
tgggggggagt ttagggaaag agcatttgtc agaatattta agggcgcctg tcactttgct    1140
tgatatatga gaattattta acctataaaa tgagaaaaaa gcaacgcact ttaaataaga    1200
tacgttgctt tttcgattga tgaacaccta taattaaact attcatctat tatttatgat    1260
tttttgtata tacaatattt ctagtttgtt aaagagaatt aagaaaataa atctcgaaaa    1320
taataaaggg aaaatcagtt tttgatatca aaattatcca tgtcaacgat aatacaaaat    1380
ataatacaaa ctataagatg ttatcagtat ttattatgca tttagaataa attttgtgtc    1440
gcccttccgc gaaattaata cgactcacta tagggaatt gtgagcggat aacaattccc    1500
ctctagaaat aattttgttt aacttttgaa ggagatatac atatggcaac gtttgaccgc    1560
aatgatccgc agttggcagg aacgatgttc cccaccgaa tagaggcgaa tgtctttgac    1620
cttgaaattg agggcgagat cccacgtgca atcaacggga gcttcttccg caacaccccc    1680
gaacctcagg tcaccccgca accttttcca ccttcatcg atggggatgg tttggcgtct    1740
gcttttcatt tcgaagatgg ccatgtcgac tttgtcagcc gttgggtatg tactcctcgc    1800
tttgaagctg agcggtcggc tcgtaaatca ctcttcggta tgtaccgcaa tccgttcact    1860
gatgatccat cggtagaagg tattgatcgt acagtcgcca tcactcactcat    1920
cacgggaaag tactggccgc aaaggaagat ggactacctt atgagcttga cccccaaacc    1980
ctggaaaccc gaggtcgtta tgattacaag gggcaggtaa ccagccatac acatacagcg    2040
caccctaagt tcgaccccca gacaggtgaa atgttactct tcggctccgc tgctaaaggc    2100
gaacgaacgc ttgatatggc tgactatatt gttgatcgct acggcaaggt gacacatgag    2160
acctggttta agcagcctta cggtgcattc atgcacgact ttgctgtcac gcgcaactgg    2220
tcaatctttc cgatcatgcc tgcgacaaat agccttgagc gtcttaaagc aaagcagccc    2280
atttacatgt gggagcctga gcgaggaagc tatataggag tacttcctcg tcgtggtcag    2340
ggcaaggaca ttcgttggtt ccgtgccccg gcgttgttgg ttttccatgt gctgaatgct    2400
tgggaggaag ggaatagaat tctgattgac ttgatgaaa gtgagatttt gccgttccca    2460
ttcccgaact cgcagaacct tccatttgat ccctccaagg ctgttccgcg tctaacccgt    2520
tgggaaattg atctcaatag tggtaacgat gagatgaaac gtacgcagct acacgaatat    2580
tttgcagaaa tgcctatcat ggatttccgt tttgcgctcc aggatcatcg ctacgcctac    2640
atggggggttg acgatcctcg tcgcccctta gctcatcagc aagctgaaaa aatctttgcc    2700
tacaattcgt taggggttg ggacaaccat cgtaaagatt atgaactttg gtttacggga    2760
aaaatgtctg cagcgcagga accggcgttt gttcctagaa gcccagatgc gcctgagggc    2820
gatggctacc tactcagtgt agtagggcgg tctgatgaaa atcgtagcga tctagtttatc    2880
cttgatacgc aatgtttggc agctgggcct gtggccactg tcaagcttcc cttccgtctc    2940
cgagcagcgt gcacggttg ttggcagtct aagaactgac tagcataacc ccttggggcc    3000
tctaaacggg tcttgagggg ttttttggca tcctgtccat gactcggtaa tacgactcac    3060
tatcaaggaa ttgtgagcgg ataacaattc cctctagaaa taattttgtt taactttaa    3120
aggagagtta tcaatgaata ttcgtccatt gcatgatcgc gtgatcgtca agcgtaaaga    3180
agttgaaact aaatcgctg gcggcatcgt tctgaccggc tctgcagcgg ctaaatccac    3240
ccgcggcgaa gtgctggctg tcggcaatgg ccgtatcctt gaaaatggcg aagtgaagcc    3300
gctggatgtg aaagttggcg acatcgttat tttcaacgat ggctacggtg tgaaatctga    3360
gaagatcgac aatgaagaag tgttgatcat gtccgataacc gacattctgg caattgttga    3420
agcgtaatcc gcgcacgaca ctgaacatac gaatttaagg aataaagata atggcagcta    3480
aagacgtaaa attcggtaac gacgctcgtg tgaaaatgct gcgcggcgta aacgtactgg    3540
cagatgcagt gaaagttacc ctcggtccaa aaggccgtaa cgtagttctg gataaatctt    3600
tcggtgcacc gaccatcacc aaagatggtg tttccgttgc tcgtgaaatc gaactggaag    3660
acaagttcga aaatatgggt gcgcagatgg tgaaagaagt tgcctctaaa gcaaacgacg    3720
ctgcaggcga cggtaccacc actgcaaccg tactggctca ggctatcatc actgaaggtc    3780
tgaaagctgt tgctgcggc atgaacccga tggacctgaa acgtggtatc gacaaagcgg    3840
ttaccgctgc agttgaagaa ctgaaagcgc tgtccgtacc atgctctgac tctaaagcga    3900
ttgctcaggt tggtaccatc tccgctaact ccgacgaaac cgtaggtaaa ctgatcgctg    3960
aagcgatgga caaagtcggt aaagaaggcg ttatcaccgt tgaagacggt accggtctgc    4020
aggacgaact ggacgtggtt gaaggtatgc agttcgaccg tggctacctg tctccttact    4080
tcatcaacaa gccggaaact ggcgcagtaa aactggaaag cccgttcatc ctgctgctga    4140
acaagaaaat ctccaacatc cgcgaaatgc tgcggttct ggaagctgtt gccaaagcag    4200
gcaaaccgct gctgatcatc gctgaagatg tagaaggcga agcgctggca actctgttg    4260
ttaacaccat gcgtggcatc gtgaaagtcg ctgcggttaa agcaccgggc ttcggcgatc    4320
gtcgtaaagc tatgctgcag gatatcgcaa ccctgactgg cggtaccgtg atctctgaag    4380
agatcggtat ggagctggag aaagcaaccc tggaagacct gggtcaggtg aaacgtgttg    4440
tgatcaacaa agacaccacc actatcatcg atggcgtggg tgaagaagct gcaatccagg    4500
gccgtgttgc tcagatccgt cagcagattg aagaagcaac ttctgactac gaccgtgaaa    4560
aactgcagga acgcgtagcg aaactggcag gcggcgttgc agttatcaaa gtgggtgctg    4620
ctaccgaagt tgaaatgaaa gagaaaaaag cacgcgttga agatgccctg cacgcgaccc    4680
gtgctgcggt agaagaaggc gtggttcctg gtgtggtgt tgcgctgatc cgcgtagcgt    4740
ctaaactggc tgacctgcgt ggtcagaacg aagaccagaa cgtgggtatc aaagttgcac    4800
tgcgtgcaat ggaagctccg ctgcgtcaga tcgtattgaa ctgcggcgaa gaaccgtctg    4860
ttgttgctaa caccgttaaa ggcggcgacg gcaactacgg caactacgaa gaaccgaagg    4920
aatacggcaa catgatcgac atgggtatcc tggatccaac caaagtaact cgttctgctc    4980
tgcagtacgc agcttctgtg gctggcctga tgatcaccac cgaatgcatg gttaccgacc    5040
tgccgaaaaa cgatgcagct gacttaggcg ctgctggcgg tatgggcggc atgggtggca    5100
tgggcggcat gatgtaaccc cctagcataa ccccttgggg cctctaaacg ggtcttgagg    5160
ggttttttgc ccctgagacg cgtcgtacct gttcgtacct aagggcgaca cccctaatt    5220
agcccgggcg aaaggcccag tctttcgact gagcctttcg ttttatttga tgcctggcag    5280
ttccctactc tcgcatgggg agtccccaca ctaccatcgg cgctacgcg tttcacttct    5340
gagttcggca tggggtcagg tgggaccacc gcgctactgc cgccaggcaa acaagggggtg    5400
ttatgagcca tattcaggta aaatgggct cgcgataatg ttcagaattg gttaattggt    5460
tgtaacactg acccctattt gtttattttt ctaaatacat tcaaatatgt atccgctcat    5520
gagacaataa ccctgataaa tgcttcaata atattgaaaa aggaagaata tgagccatat    5580
tcaacgggaa acgtcgaggc cgcgattaaa ttccaacatg gatgctgatt tatatgggta    5640
taaatgggct cgcgataatg tcgggcaatc aggtgcgaca atctatcgct tgtatgggaa    5700
gcccgatgcg ccagagttgt ttctgaaaca tggcaaaggt agcgttgcca atgatgttac    5760
agatgagatg gtcagactaa actggctgac ggaatttatg ccacttccga ccatcaagca    5820
```

```
ttttatccgt actcctgatg atgcatggtt actcaccact gcgatcccg gaaaaacagc  5880
gttccaggta ttagaagaat atcctgattc aggtgaaaat attgttgatg cgctggcagt  5940
gttcctgcgc cggttgcact cgattcctgt ttgtaattgt ccttttaaca gcgatcgcgt  6000
atttcgcctc gctcaggcgc aatcacgaat gaataacggt ttggttgatg cgagtgattt  6060
tgatgacgag cgtaatggct ggcctgttga acaagtctgg aaagaaatgc ataaacttt   6120
gccattctca ccggattcag tcgtcactca tggtgatttc tcacttgata accttatttt  6180
tgacgagggg aaattaatag gttgtattga tgttggacga gtcggaatcg cagaccgata  6240
ccaggatctt gccatcctat ggaactgcct cggtgagttt tctccttcat tacagaaacg  6300
gcttttcaa aaatatggta ttgataatcc tgatatgaat aaattgcagt ttcatttgat   6360
gctcgatgag tttttctaag cggcgcgcca tcgaatggcg caaaacccttt cgcggtatgg  6420
catgatagcg cccggaagag agtcaattca gggtggtgaa tatgaaacca gtaacgttat  6480
acgatgtcgc agagtatgcc ggtgtctctt atcagaccgt ttcccgcgtg gtgaaccagg  6540
ccagccacgt ttctgcgaaa acgcgggaaa agtggaagc ggcgatggcg gagctgaatt   6600
acattcccaa ccgcgtgca caacaactgg cgggcaaaca gtcgttgctg attggcgttg  6660
ccacctccag tctggccctg cacgcgccgt cgcaaattgt cgcggcgatt aaatctcgcg  6720
ccgatcaact gggtgccagc gtggtggtgt cgatggtaga acgaagcggc gtcgaagcct  6780
gtaaagcggc ggtgcacaat cttctcgcgc aacgcgtcag tgggctgatc attaactatc  6840
cgctggatga ccaggatgcc attgctgtgg aagctgcctg cactaatgtt ccggcgttat  6900
ttcttgatgt ctctgaccag acacccatca acagtattat tttctcccat gaggacggta  6960
cgcgactggg cgtggagcat ctggtcgcat gggtcacca gcaaatcgcg ctgttagcgg   7020
gcccattaag ttctgtctcg gcgcgtctgc gtctggctgg ctggcataaa tatctcactc  7080
gcaatcaaat tcagccgata gcggaacggg aaggcgactg gagtgccatg tccggttttc  7140
aacaaaccat gcaaatgctg aatgagggca tcgttcccac tgcgatgctg gttgccaacg  7200
atcagatggc gctggcgca atgcgcgcca ttaccgagtc cgggctgcgc gttggtgcgg   7260
atatctcggt agtgggatac gacgataccg aagatagctc atgttatatc cgccgttaa   7320
ccaccatcaa acaggatttt cgcctgctgg gcaaaccag cgtggaccgc ttgctgcaac  7380
tctctcaggg ccaggcggtg aagggcaatc agctgttgcc agtctcactg gtgaaaagaa  7440
aaaccaccct ggcgcccaat acgcaaaccg cctctcccg cgcgttggcc gattcattaa   7500
tgcagctggc acgacaggtt tcccgactgg aaagcgggca gtga                  7544

SEQ ID NO: 25         moltype = DNA  length = 7405
FEATURE               Location/Qualifiers
source                1..7405
                      mol_type = other DNA
                      organism = synthetic construct
SEQUENCE: 25
ttaataagat gatcttcttg agatcgtttt ggtctgcgcg taatctcttg ctctgaaaac  60
gaaaaaaccg ccttgcaggg cggttttttcg aaggttctct gagctaccaa ctctttgaac  120
cgaggtaact ggcttggagg agcgcagtca ccaaaacttg tcctttcagt ttagccttaa  180
ccggcgcatg acttcaagac taactcctct aaatcaatta ccagtggctg ctgccagtgg  240
tgcttttgca tgtctttccg ggttggactc aagacgatag ttaccggata aggcgcagcg  300
gtcggactga acgggggtt cgtgcataca gtccagcttg gagcgaactg cctacccgga  360
actgagtgtc aggcgtggaa tgagacaaac gcggccataa cagcggtaag acaccggtaa  420
accgaaaggc aggaacagga gagcgcacga gggagccgcc aggggaaac gcctggtatc  480
tttatagtcc tgtcgggttt cgccaccact gatttgagcg tcagatttcg tgatgcttgt  540
cagggggcg gagcctatgg aaaaacggct ttgccgcggc cctctcactt ccctgttaag  600
tatcttcctg gcatcttcca ggaaatctcc gccccgttcg taagccattt cgctctcgcg  660
cagtcgaacg accgagcgta gcgagtcagt gagcgaggaa gcggaatata tcctgtatca  720
catattctgc tgacgcaccg gtgcagcctt tttctcctg ccacatgaag cacttcactg   780
acaccctcat cagtgccaac atagtaagcc agtatacact ccgctagcgc tgaggtcccg  840
cagccgaacg accgagcgca gcgagtcagt gagcgaggaa gcggaaggcg agagtaggga  900
actgccaggc atcaaactaa gcagaaggcc cctgacggat ggccttttg cgtttctaca   960
aactctttct gtgttgtaaa acgacggcca gtcttaagct cgggcccct gggcggttct  1020
gataacgagt aatcgttaat ccgcaaataa cgtaaaaacc cgcttcggcg gtttttta    1080
tgggggagt ttagggaaag agcatttgtc agaatattta agggcgcctg tcacttttgct  1140
tgatatatga gaattattta acctttataaa tgagaaaaaa gcaacgcact ttaaataaga  1200
tacgttgctt tttcgattga tgaacaccta aattaaact attcatctat tatttatgat   1260
tttttgtata tacaatattt ctagtttgtt aaagagaatt aagaaaataa atctcgaaaa   1320
taataaaggg aaaatcagtt tttgatatca aaattataca tgtcaacgat aatacaaaat  1380
ataatacaaa ctataagatg ttatcagtat ttattatgca tttagaataa attttgtgtc  1440
gcccttccgc gaaattaata cgactcacta taggggaatt gtgagcggat aacaattccc  1500
ctctagaaat aattttgttt aacttttgaa ggagatatac atatggcaac gtttgaccgc  1560
aatgatccgc agttggcagg aacgatgttc cccacccgaa tagaggcgaa tgtctttgac  1620
cttgaaattg agggcgagat cccacgtgca atcaacggga gcttcttccg caacacccat  1680
gaacctcagg tcaccccgca accttttcca accttcatcg atggggatgg tttggcgtct  1740
gctttttcatt tcgaagatgg ccatgtcgac tttgtcagcc gttgggtatg tactcctcgc  1800
tttgaagctg agcggtcggc tcgtaaatca ctcttcggta tgtaccgcaa tccgttcact  1860
gatgatccat cggtagaagg tattgatcgt acagtcgatg acaccagtat catcactcat  1920
cacgggaaag tactggccgc aaaggaagat ggactacctt atgacttga ccccaaaccc   1980
ctggaaaccc gaggtcgtta tgattacaag gggcaggtaa ccagccatac acatacagcg  2040
cacccctaagt tcgaccccca gacaggtgaa atgttactct cggctccgc tgctaaaggc  2100
gaacgaacgc ttgatatggc gtactatatt gttgatcgct acggcaaggt gacacatgag  2160
acctggttta gcagcctta cggtgcattc atgcacgact ttgctgtcac gcgcaactgg  2220
tcaatctttc cgatcatgcc tgcgacaaat gccttgagc gtcttaaagc aaagcagccc  2280
atttacatgt gggagcctga gcgaggaagc tatatagggag tacttcctcg tcgtggtcag  2340
ggcaaggaca ttcgttggtt ccgtgccccg gcgttgtggg ttttcatgt cgtgaatgct  2400
tgggaggaag ggaatagaat tctgattgac ttgatgaaa gtgagattt gccgttccca   2460
ttcccgaact cgcagaacct tccatttgat ccctccaagg ctgttccgcg tctaacccgt  2520
tgggaaattg atctcaatag tggtaacgat gagatgaac gtacgcagct acacgaatat  2580
```

```
tttgcagaaa tgcctatcat ggatttccgt tttgcgctcc aggatcatcg ctacgcctac  2640
atggggttg  acgatcctcg tcgcccctta gctcatcagc aagctgaaaa aatctttgcc   2700
tacaattcgt taggggtttg ggacaaccat cgtaaagatt atgaactttg gtttacggga   2760
aaaatgtctg cagcgcagga accggcgttt gttcctagaa gcccagatgc gcctgagggc   2820
gatggctacc tactcagtgt agtagggcgg ctcgatgaaa atcgtagcga tctagttatc   2880
cttgatacgc aatgtttggc agctgggcct gtggccactg tcaagcttcc cttccgtctc   2940
cgagcagcgt tgcacggttg ttggcagtct aagaactgag aaggagatat acatatgaat   3000
attcgtccat tgcatgatcg cgtgatcgtc aagcgtaaag aagttgaaac taaatctgct   3060
ggcggcatcg ttctgaccgg ctctgcagcg gctaaatcca cccgcggcga agtgctggct   3120
gtcggcaatg gccgtatcct tgaaaatggc gaagtgaagc cgctggatgt gaaagttggc   3180
gacatcgtta ttttcaacga tggctacggt gtgaaatctg agaagatcga caatgaagaa   3240
gtgttgatca tgtccgaaag cgacattctg gcaattgttg aagcgtaatc cgcgcacgac   3300
actgaacata cgaatttaag gaataaagat aatggcagct aaagacgtaa aattcggtaa   3360
cgacgctcgt gtgaaaatgc tgcgcggcgt aaacgtactg gcagatgcag tgaaagttac   3420
cctcggtcca aaaggccgta acgtagttct ggatcaaatct ttcggtgcac cgaccatcac   3480
caaagatggt gtttccgttg ctcgtgaaat cgaactggaa gacaagttcg aaaatatggg   3540
tgcgcagatg gtgaaagaag ttgcctctaa agcaaacgac gctgcaggcg acggtaccac   3600
cactgcaacc gtactggctc aggctatcat cactgaaggt ctgaaagctg ttgctgcgga   3660
catgaacccg atggacctga aacgtggtat cgacaaagcg gttaccgctg cagttgaaga   3720
actgaaagcg ctgtccgtac catgctctga ctctaaagcg attgctcagg ttggtaccat   3780
ctccgctaac tccgacgaaa ccgtaggtaa actgatcgct gaagcgatgg acaaagtcgg   3840
taaagaggc  gttatcaccg ttgaagacgg taccggtctg caggacgaac tggacgtggt   3900
tgaaggtatg cagttcgacc gtggctacct gtctccttac ttcatcaaca gccggaaac    3960
tggcgcagta gaactggaaa gcccgttcat cctgctggct gacaagaaaa tctccaacat   4020
ccgcgaaatg ctgccggttc tggaagctgt tgccaaagca ggcaaaccgc tgctgatcat   4080
cgctgaagat gtagaaggcg aagcgctggc aactctgtt  gttaacacca tgcgtggcat   4140
cgtgaaagtc gctgcggtta agcaccggg  cttcggcgat cgtcgtaaag ctatgctgca   4200
ggatatcgca accctgactg gcggtaccgt gatcctgaa  gagatcgta  tggagctgga   4260
aaaagcaacc ctggaagacc tgggtcaggc taaacgtgtt gtgatcaaca agacaccac    4320
cactatcatc gatggcgtgg gtgaagaagc tgcaatccag ggccgtgttg ctcagatccg   4380
tcagcagatt gaagaagcaa cttctgacta cgaccgtgaa aaactgcagg aacgcgtagc   4440
gaaactggca ggcggcgttg cagttatcaa agtgggtgct gctaccgaag ttgaaatgaa   4500
agagaaaaaa gcacgcgttg aagatgccct gcacgcgacc cgtgctgcgg tagaagaagg   4560
cgtggttgct ggtggtggtg ttgcgctgat ccgcgtagcg tctaaactgg ctgacctgcg   4620
tggtcagaac gaagaccaga acgtgggtat caaagttgca ctgcgtgcaa tggaagctcc   4680
gctgcgtcag atcgtattga actgcggcga agaaccgtct gttgttgcta acaccgttaa   4740
aggcggcgac ggcaactacg gttacaacgc agcaaccgaa gaatacgca  acatgatcga   4800
catgggtatc ctggatccaa ccaaagtaac tcgttctgct ctgcagtacg cagcttctgt   4860
ggctggcctg atgatcacca ccgaatgcat ggttaccgac ctgccgaaaa acgatgcagc   4920
tgacttaggc gctgctggcg gtatgggcgg catgggtggc atgggcggca tgatgtaacc   4980
ccctagcata accccttggg gcctctaaac gggtcttgag gggttttttg cccctgagac   5040
gcgtcaatcg agttcgtacc taagggcgac acccctaat  tagcccgggc gaaaggccca   5100
gtctttcgac tgagcctttc gttttatttg atgcctggca gttccctact ctcgcatggg   5160
gagtccccac actaccatcg gcgctacggc gtttcacttc tgagttcggc atggggtcag   5220
gtgggaccac cgcgctactg ccgccaggca acaaggggg  gttatgagcc atattcaggt   5280
ataaatgggc tcgcgataat gttcagaatt ggttaattgg ttgtaacact gaccccctat   5340
tgtttatttt tctaaataca ttcaaatatg tatccgctca tgagacaata accctgataa   5400
atgcttcaat aatattgaaa aaggaagaat atgagccata ttcaacggga aacgtcgagg   5460
ccgcgattaa attccaacat ggatgctgat ttatatgggt ataaatgggc tcgcgataat   5520
gtcgggcaat caggtgcgac aatctatcgc ttgtatggga agcccgatgc gccagagttg   5580
tttctgaaac atggcaaagg tagccgttgcc aatgatgtta cagatgagat ggtcagacta   5640
aactggctga cggaatttat gccacttccg accatcaagc attttatccg tactcctgat   5700
gatgcatggt tactcaccac tgcgatcccg ggaaaaacag cgttccaggt attagaagaa   5760
tatcctgatt caggtgaaaa tattgttgat gcgctggcag tgttcctgcg ccggttgcac   5820
tcgattcctg tttgtaattg tccttttaac agcgatcgcg tatttcgcct cgctcaggcg   5880
caatcacgaa tgaataacgg tttggttgat gcgagtgatt ttgatgacga gcgtaatggc   5940
tggcctgttg aacaagtctg aaagaaatg  cataaacttt tgccattctc accggattca   6000
gtcgtcactc atggtgattt ctcacttgat aaccttattt ttgacgaggg gaaattaata   6060
ggttgtattg atgttggacg agtcggaatc gcagaccgat accaggatct tgccatccta   6120
tggaactgcc tcggtgagtt ttctccttca ttacagaaac ggcttttca  aaaatatggt   6180
attgataatc ctgatatgaa taaattgcag tttcatttga tgctcgatga gttttttcta   6240
gcggcgcgcc atcgaatggc gcaaaacctt tcgcggtatg gcatgatagc gcccggaaga   6300
gagtcaattc agggtggtga atatgaaacc agtaacgtta tacgatgtcg cagagtatgc   6360
cggtgtctct tatcagaccg tttcccgcgt ggtgaaccag gccagccacg tttctgcgaa   6420
aacgcggaa  aaagtggaag cggcgatggc ggagctgaat tacattccca accgcgtggc   6480
acaacaactg gcgggcaaac agtcgttgct gattggcgtt gccacctcca gtctggccct   6540
gcacgcgccg tcgcaaattg tcgcggcgat taaatctcgc gccgatcaac tgggtgccag   6600
cgtggtggtg tcgatggtag aacgaagcgg cgtcgaagcc tgtaaagcgg cggtgcacaa   6660
tcttctcgcg caacgcgtca gtgggctgat cattaactat ccgctggatg accaggatgc   6720
cattgctgtg gaagctgcct gcactaatgt tccggcgtta tttcttgatg tctctgacca   6780
gacacccatc aacagtatta ttttctccca tgaggacggt acgcgactgg gcgtggagca   6840
tctggtcgca ttgggtcacc agcaaatcgc gctgttactg cgccattaa  gttctgtctc   6900
ggcgcgtctg cgtctggctg gctggcataa atatctcact cgcaatcaaa ttcagccgat   6960
agcggaacgg gaaggcgact ggagtgccat gtccggtttt caacaaacca tgcaaatgct   7020
gaatgagggc atcgttccca ctgcgatgct ggttgccaac gatcagatgg cgctgggcgc   7080
aatgcgcgcc attaccgagt ccgggctgcg cgttggtgcg gatatctcgg tagtgggata   7140
cgacgatacc gaagatagct catgttatat cccgccgtta accaccatca aacaggattt   7200
```

-continued

```
tcgcctgctg gggcaaacca gcgtggaccg cttgctgcaa ctctctcagg gccaggcggt    7260
gaagggcaat cagctgttgc cagtctcact ggtgaaaaga aaaaccaccc tggcgcccaa    7320
tacgcaaacc gcctctcccc gcgcgttggc cgattcatta atgcagctgg cacgacaggt    7380
ttcccgactg gaaagcgggc agtga                                          7405
```

METHOD FOR PRODUCING VANILLIN

CROSS-REFERENCE TO RELATED APPLICATIONS

This application is a continuation of U.S. patent application Ser. No. 17/041,906, filed on Sep. 25, 2020, which is a U.S. National Phase Application of PCT/EP2019/058101, filed on Mar. 29, 2019, which claims the benefit of priority to European Patent Application Number 18165125.8, filed Mar. 29, 2018, the entire contents of which are hereby incorporated by reference herein.

REFERENCE TO AN ELECTRONIC SEQUENCE LISTING

The contents of the electronic sequence listing (Filename: 36803-364_updated_sequence_listing.xml; Date of Creation: Sep. 27, 2022; and Size: 135,254 bytes) are herein incorporated by reference in their entirety.

TECHNICAL FIELD

Provided herein are biochemical methods of producing vanillin and related compounds and derivatives, which method comprises the use of a novel combination of polypeptides. Moreover provided herewith are novel enzyme mutants applicable in the biochemical production of vanillin.

BACKGROUND

Vanillin is an important compound globally for use in foods, beverages, and pharmaceuticals. Only a small portion of the world's production is derived naturally through extraction from vanilla pods; however, the availability of these natural plant sources is low and the production methods are laborious and slow. Whereas complex extracts derived from the pods of the orchids *V. planifolia*, or *V. tahitensis* offer unique and complex mixtures and olfactory qualities at high costs, the majority of vanillin (>99% i.e. 16,000 tons per year) is produced from petrochemical feed stocks, with a minor fraction still obtained from lignin waste of the paper industry. However, there is a small but growing market for natural 'vanillin not from the bean' (NFB), which mainly serves North America and Europe. The regulatory requirements for claiming natural status are different for these two markets.

Different starting materials including ferulic acid, curcumin, eugenol, or isoeugenol can be converted into vanillin using different biochemistries. Biotechnical methods for producing vanillin have been reviewed [Gallage N J, Møller B L. 2015. Mol Plant 8, 40-57; Kaur, B, Chakraborty, D. 2013. Appl Biochem Biotechnol 169, 1353-1372; Walton N J, Mayer M J, Narbad A. 2003. Phytochem 63, 505-515].

More recently, microorganisms have been engineered that can convert simple carbon sources such as sugars like glucose into vanillin [Hansen E H, Lindberg Moller B, Kock G R, Bünner C M, C Kristensen, Jensen O R, Okkels F T, Olsen C E, Motawia M S, Hansen J. 2009. Appl Environ Microbiol 75, 2765-2774; Ni J, Tao F, Du H, Xu P. 2015. Sci Rep 5, 1-11]

Isoeugenol is a phenyl propenoid found in many plants. However, it seems less abundant than eugenol, from which it has been traditionally obtained by isomerization under heat in presence of a strong base. That method is no longer compatible with the European legislation for natural flavoring substances. However, botanicals rich in isoeugenol could be identified.

Isoeugenol can be converted into vanillin via an array of different biochemical methods. For example non-heme iron containing enzymes such as lipoxygenases, or iron-porphyrin containing enzymes (e.g. horse radish peroxidase) have been used for oxidatively cleaving isoeugenol into vanillin. Recently, it was found that purified hemin alone was as good as nonspecific, heme containing enzymes for such biotransformation [Mutti F G. 2012. Bioorg Chem Appl 2012, 1-13; Li Y-H, Sun Z-H, Zhao L-Q, Xu Y. 2005. Appl Biochem Biotechnol 125, 1-10; Mutti F G, Lara M, Kroutil M, Kroutil W. 2010. Chem Eur J 16, 14142-14148]. However, these methods are prone to formation of side products.

Interestingly, isoeugenol oxidizing enzymes of microbial origin including but not limited to isoeugenol monooxygenases have been described for converting isoeugenol into vanillin [Ryu J-Y, J Seo, S Park, J-H Ahn, Y Chong, M J Sadowsky, H-G Hur. 2013. Biosci Biotechnol Biochem 77, 289-294; Yamada M, Y Okada, T Yoshida, T Nagasawa. 2007. Appl Microbiol Biotechnol 73, 1025-1030; Yamada M, Y Okada, T Yoshida, T Nagasawa 2008. Biotechnol Lett 30, 665-670]. Oxidation of isoeugenol with such enzymes showed formation of vanillin and acetaldehyde as main products [Yamada M, Y Okada, T Yoshida, T Nagasawa. 2007. Arch Microbiol 187, 511-517; Ryu J-Y, J Seo, S Park, J-H Ahn, Y Chong, M J Sadowsky, H-G Hur. 2013. Biosci Biotechnol Biochem 77, 289-294]. The approaches described therein are, however, not directed to an industrial scale production of vanillin.

For an industrial process it is often necessary to overproduce one or several functional enzymes in a recombinant bacterium such as *E. coli*. The overproduction of an enzyme in a suitable bacterium provides a secure and economic source of that enzyme. Overproduction of key enzymes also helps to minimize side activities caused by endogenous enzyme activities of the host organism (e.g. enzymes that could reduce or oxidize vanillin into vanillyl alcohol, or vanillic acid, respectively).

The correct folding of an enzyme in the host organism is critical for catalytic activity. Non-correctly folded enzymes have reduced or no catalytic activity as they are prone to aggregation (e.g. inclusion bodies) or degradation in the host. Different strategies can be applied to ensure correctly folded enzyme in the host organism. For example reducing the expression level in a recombinant host organism by low gene dosage, low transcript level by low inducer concentration (in case of an inducible system) or low promotor strength can be beneficial. Low temperature during enzyme synthesis can also help to improve folding of a recombinant protein. Alternatively, a non-correctly folded enzyme can sometimes get unfolded by strong denaturing chemicals, followed by refolding under physiological conditions. However, such procedure is time consuming and expensive.

In molecular biology, the large class of molecular chaperones represents proteins that assist the covalent folding or unfolding and the assembly or disassembly of other macromolecular structures. The group of chaperonin proteins belongs to said large class of chaperon molecules. The structure of these chaperonins resembles two donut-like structures stacked on top of one another to create a barrel. Each ring is composed of either 7, 8 or 9 subunits depending on the organism in which the chaperonin is found.

Group I chaperonins are found in bacteria as well as organelles of endosymbiotic origin: chloroplasts and mitochondria. Group II chaperonins, as found in the eukaryotic cytosol and in archaea, are more poorly characterized. The GroEL/GroES complex is a Group I chaperonin. Group II chaperonins are not thought to utilize a GroES-type cofactor to fold their substrates.

As mentioned, the chaperonin system GroES/GroEL forms a barrel like structure with a cavity that allows the up-take of misfolded proteins for refolding at the expense of ATP [Gragerov A, E Nudler, N Komissarova, G A Gaitanaris, M E Gottesman, V Nikiforov. 1992. Proc Nat Acad Sci 89, 10341-10344; Keskin O, Bahar I, Flatow D, Covell D G, Jernigan R L. 2002. Biochem 41, 491-501].

The applicability of any member of the large class of chaperons for recombinant production of monooxygenases, in particular of isoeugenol monooxygenases for the enzymatic synthesis of vanillin, has so far not been investigated.

Although there have been several reports of natural vanillin production through bioengineering (for example, WO2013/022881, KR101163542 (B1)), there still remains a need for the discovery of simpler, efficient and cost/or effective processes for production of natural vanillin. In particular, higher specific activity of the enzyme would allow lower catalyst loading for improved process performance and economics. Moreover, there is a need of further improved enzymes applicable in the biochemical production of vanillin, in particular from isoeugenol as starting material.

SUMMARY

The present invention addresses the above-mentioned drawbacks associated with the known systems so far applied for the biochemical production of vanillin.

The present inventors surprisingly observed that certain helper polypeptides may be successfully used in the large scale production of certain known and even of certain novel isoeugenol oxidizing enzymes of high functional activity. In particular, it was surprisingly found by the present inventors, that the coexpression with chaperonins GroES and GroEL significantly improved the amount of catalytically active isoeugenol monooxygenase enzymes produced in the bacterium *E. coli.*

Moreover, the present inventors surprisingly were able to genetically modify a microbial oxidase enzyme from a microorganism of the species *Pseudomonas putida*, so that it is applicable for the first time in the conversion of isoeugenol, in particular (E)-isoeugenol, to vanillin in the presence of molecular oxygen.

Thus the present inventors could surprisingly improve the biochemical approach of production of vanillin via isoeugenol by applying the isoeugenol oxidizing enzymes produced and/or genetically modified as herein below described in more detail.

DESCRIPTION OF THE DRAWINGS

FIG. 8: Amino acid sequence alignment of IEM1 of *Pseudomonas nitroreducens* Jin1 and IEM2 of *Pseudomonas putida* IE27.

Figure 11:
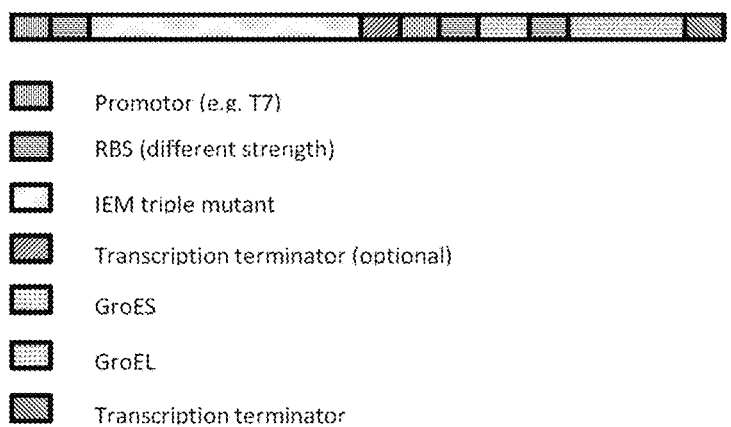
FIG. 11: General scheme of modified insert architectures for expressing an IEM, like the triple mutant of the isoeugenol monooxygenase IE27 as described herein, and the chaperonins GroES and GroEL.

FIG. 12: Normalized product titers of vanillin obtained under standard assay conditions with strains of *E. coli* containing different plasmid constructs, prepared by following the general scheme of FIG. 11, for expressing the triple mutant of the isoeugenol monooxygenase IE27 together with the chaperonins GroES and GroEL. The plasmid constructs varied in the promotor sequences for expressing the chaperonins and contained optionally a transcription terminator after the ORF of the isoeugenol monooxygenase indicated as + term, or − term, respectively. The polycistronic construct PC1_triple is shown as reference C+.

ABBREVIATIONS USED bp base pair
kb kilo base
DNA deoxyribonucleic acid
cDNA complementary DNA
DTT dithiothreitol
GC gas chromatograph
IPTG isopropyl-D-thiogalacto-pyranoside
IEM isoeugenol monooxygenase
LB lysogeny broth
MS mass spectrometer/mass spectrometry
PCR polymerase chain reaction
RBS ribosomal binding site
RNA ribonucleic acid
mRNA messenger ribonucleic acid
miRNA micro RNA
siRNA small interfering RNA
rRNA ribosomal RNA
tRNA transfer RNA
P. *Pseudomonas*

Specific Definitions

The term "isoeugenol" relates 2-methoxy-4-(prop-1-en-1-yl)phenol (CAS Registry Number: 97-54-1) and to any isomer mixture of trans- and cis-isoeugenol, or (E)- and (Z)-isoeugenol, respectively.

The terms "isoeugenol monooxygenase" or "polypeptide having isoeugenol monooxygenase activity" or "isoeugenol monooxygenase protein" or "isoeugenol oxidizing enzyme" or "polypeptide having isoeugenol oxidizing activity" or "isoeugenol oxidizing protein" or "IEM" relate to a polypeptide capable of catalyzing the synthesis of vanillin, starting from an isoeugenol, in the presence of molecular oxygen under formation of acetaldehyde, without being limited to any particular molecular mechanism of action of said enzyme. Preferably said enzyme converts stereospecifically the (E)- or trans-isomer of isoeugenol. Vanillin preferably is obtained as the main product.

"Isoeugenol oxidizing activity" is determined under "standard conditions" as described herein below in more detail in the examples: They can be determined using recombinant IEM expressing cells, disrupted IEM expressing cells, fractions of these or enriched or purified IEM enzyme, in a reaction medium, preferably buffered, having a pH in the range of 8.5 to 11, preferably 9 to 10, in the presence of molecular oxygen, at a temperature in the range of about 20 to 30° C. and in the presence of a reference substrate, here isoeugenol, in particular trans-isoeugenol, at an initial concentration in the range of 1 to 40 mg/ml, preferably 1 to 10 mg/ml more preferably 3 to 7 mg/ml.

The terms "biological function," "function," "biological activity" or "activity" refer to the ability of the isoeugenol oxidizing enzyme to catalyze the formation of vanillin from isoeugenol.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a polypeptide for use as described herein. The host cell is particularly a bacterial cell, a fungal cell or a plant cell. The host cell may contain a recombinant gene which has been integrated into the nuclear or organelle genomes of the host cell. Alternatively, the host may contain the recombinant gene extra-chromosomally.

"Homologous" sequences include orthologous or paralogous sequences. Methods of identifying orthologs or paralogs including phylogenetic methods, sequence similarity and hybridization methods are known in the art and are described herein.

"Paralogs" or paralogous sequences result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing isoeugenol monooxygenase.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing vanillin" when it produces vanillin naturally or when it does not produce vanillin naturally but is transformed to produce vanillin, either prior to the transformation with a nucleic acid as described herein or together with said nucleic acid. Organisms or cells transformed to produce a higher amount of vanillin than the naturally occurring organism or cell are also encompassed by the "organisms or cells capable of producing vanillin".

The terms "purified," "substantially purified," and "isolated" as used herein refer to the state of being free of other, dissimilar compounds with which a compound of the invention is normally associated in its natural state, so that the "purified," "substantially purified," and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified," "substantially purified," and "isolated" when referring to a nucleic acid or protein, of nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (1) the purification from other associated structures or compounds or (2) the association with structures or compounds to which it is not normally associated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

In the context of the descriptions provided herein and of the appended claims, the use of "or" means "and/or" unless stated otherwise.

Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 98.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes in particular conformational isomers.

Included in general are, according to the invention, all "stereoisomeric forms" of the compounds described herein, such as constitutional isomers and, in particular, stereoisomers and mixtures thereof, e.g. optical isomers, or geometric isomers, such as E- and Z-isomers, and combinations thereof. If several asymmetric centers are present in one molecule, the invention encompasses all combinations of different conformations of these asymmetry centers, e.g. enantiomeric pairs "Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\% \ ee = [X_A - X_B]/[X_A + X_B] * 100,$$

wherein $X_A$ and $X_B$ represent the molar ratio (Molenbruch) of the stereoisomers A and B.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product, like Vanillin, that is produced per h and L fermentation broth per g of biomass. The amount of wet cell weight stated as WCW describes the quantity of biologically active microorganism in a biochemical reaction. The value is given as g product per g WCW per h (i.e. $g/gWCW^{-1} \ h^{-1}$). Alternatively, the quantity of biomass can also be expressed as the amount of dry cell weight stated as DCW. Furthermore, the biomass concentration can be more easily determined by measuring the optical density at 600 nm ($OD_{600}$) and by using an experimentally determined correlation factor for estimating the corresponding wet cell or dry cell weight, respectively.

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

The terms "selectively converting" or "increasing the selectivity" in general means that a particular stereoisomeric form as for example the E-form, of an unsaturated hydrocarbon, is converted in a higher proportion or amount (compared on a molar basis) than the corresponding Z-form, either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60, or 40 to 50% conversion of the initial amount of the substrate. Said higher proportion or amount may, for example, be expressed in terms of:

a higher maximum yield of an isomer observed during the entire course of the reaction or said interval thereof;
a higher relative amount of an isomer at a defined % degree of conversion value of the substrate; and/or
an identical relative amount of an isomer at a higher % degree of conversion value;
each of which preferably being observed relative to a reference method, said reference method being performed under otherwise identical condition with known chemical obr biochemical means.

"E-stereoselectivity" or "E-selectivity" describes the ability to produce an E-Isomer of a particular C=C-double bond in an E-isomerically pure or essentially pure or enriched form or to specifically or essentially specifically convert an E-isomer in an enzymatically catalyzed method as described herein out of a plurality of other isomers or a mixture of E- and Z-isomers at said particular position of the double-bond.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

"Polycistronic" refers to nucleic acid molecules, in particular mRNAs or corresponding cDNAs that can encode more than one polypeptide separately within the same nucleic acid molecule.

"Derived from" a "polycistronic" construct or nucleic acid molecule means that molecule may be modified by introducing one or more identical or different regulatory sequences at appropriate position, like promotors, RBS and/or terminators, in order to influence or modulate the transcription and/or translation of at least one coding sequence contained in said nucleic acid molecule.

DETAILED DESCRIPTION a. Particular Embodiments of the Invention

The present invention particularly refers to the following embodiments:
1. An expression system for the recombinant expression of a polypeptide having isoeugenol oxidizing activity, which expression system comprises a combination of at least two different nucleic acid sequences contained in at least one recombinant nucleic acid construct; wherein said expression system comprises:
   a. a nucleotide sequence (A) encoding a polypeptide having enzymatic isoeugenol oxidizing activity, particularly catalyzing in the presence of oxygen, in particular molecular oxygen, the formation of vanillin and acetaldehyde from isoeugenol, and
   b. at least one nucleotide sequence (B) encoding at least one, like 1, 2, or 3, preferably 2, helper polypeptide which alone or, preferably in cooperation assist in the functional expression of the polypeptide, in particular the correct folding of said expressed polypeptide, encoded by said nucleotide sequence (A);
   wherein said expression system provides for the co-expression of said nucleotide sequences (A) and (B).
2. The expression system of embodiment 1, which is selected from
   a. a combination of at least two, preferably independently of each other acting or working nucleic acid constructs carrying said nucleic acid sequence (A) and said at least one nucleic acid (B), respectively; and
   b. a single nucleic acid construct carrying said nucleic acid sequence (A) and said at least one nucleic acid (B), which may be for example a nucleic acid construct or vector carrying multiple cloning sites or may more preferably be a polycistronic nucleic acid construct, which is ultimately transcribed in a single mRNA molecule containing the coding sequences (A) for the polypeptide having enzymatic isoeugenol oxidizing activity and (B) for the helper polypeptide(s). Said single nucleic acid construct carrying said nucleic acid sequence (A) and said at least one nucleic acid (B), may also be derived from a polycistronic nucleic acid construct. It may be derived therefrom, for example, by introducing one or more identical or different regulatory sequences at appropriate position, like promotors, RBS and/or terminators, in order to influence or modulate the transcription and/or translation of at least one coding sequence of (A) and (B) contained in said nucleic acid molecule, as further exemplified in the experimental section.
3. The expression system of one of the preceding embodiments, wherein said nucleotide sequence (A) encodes
   a. a polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO:2 (i.e. IEM1, as originally isolated from *Pseudomonas nitroreducens* Jin1); or
   b. a polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO: 4 (i.e. IEM2, as originally isolated from *Pseudomonas putida* IE27), wherein the amino acid sequence having at least 70%, 75%, 80%, 85%, 90%, 95%, 96%, 97%, 98%, 99% or 100% identity to SEQ ID NO: 4 comprises at least one mutation in an amino acid sequence position selected from T52, Q74, D440, and optionally at least one, like 1, 2, 3, 4 or 5, further mutation in an amino acid sequence position selected from N120, T121, F281, M298, and L470, in particular selected from N120I, T121P, F281Q, M298K, and L470S.

4. The expression system of embodiment 3, wherein the polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO: 4 is a mutant polypeptide comprising at least one mutation in an amino acid sequence position selected from T52, Q74 and D440.

5. The expression system of embodiment 4, wherein said mutant is selected from the following IEM2 mutants:
   a. the single mutants (T52$X_1$), (Q74$X_2$) and (D440$X_3$)
   b. the double mutants (T52$X_1$,Q74$X_2$), (T52$X_1$,D440$X_3$) and (Q74$X_2$,D440$X_3$) and
   c. the triple mutant (T52$X_1$,Q74$X_2$,D440$X_3$)
   wherein
   $X_1$ is P, K or M or any other natural or non-natural, in particular natural amino acid substitution resulting in a functional, vanillin producing enzyme mutant; preferably $X_1$ is P or M, and most preferably P;
   $X_2$ is H or A or any other natural or non-natural, in particular natural amino acid substitution resulting in a functional, vanillin producing enzyme mutant; most preferably $X_2$ is H; and;
   $X_3$ is N, A, C, E, F, G, H, I, K, L, M, Q, R, S, T, V, W or Y or any other natural or non-natural, in particular natural amino acid substitution resulting in a functional, vanillin producing enzyme mutant; preferably $X_3$ is N, A, C, E, F, G, H, K, L, M, Q, R, S, T, V, or Y; and most preferably N As non-limiting examples of such double-mutants to be expressed by such expression system there may be mentioned:
(T52$X_1$,Q74$X_2$):
   wherein $X_1$ is P, and $X_2$ is H or A; or
   wherein $X_1$ is K, and $X_2$ is H or A; or
   wherein $X_1$ is M, and $X_2$ is H or A.
(T52$X_1$,D440$X_3$)
   wherein $X_1$ is P, and $X_3$ is N, A, C, E, F, G, H, I, K, L, M, Q, R, S, T, V, W or Y; or
   wherein $X_1$ is K, and $X_3$ is N, A, C, E, F, G, H, I, K, L, M, Q, R, S, T, V, W or Y; or
   wherein $X_1$ is M, and $X_3$ is N, A, C, E, F, G, H, I, K, L, M, Q, R, S, T, V, W or Y.
(Q74$X_2$,D440$X_3$)
   wherein $X_2$ is H, and $X_3$ is N, A, C, E, F, G, H, I, K, L, M, Q, R, S, T, V, W or Y; or
   wherein $X_2$ is A, and $X_3$ is N, A, C, E, F, G, H, I, K, L, M, Q, R, S, T, V, W or Y.

Preferred double mutants are:
(T52P,Q74H);
(T52P,D440$X_3$) wherein $X_3$ is N, A, C, E, F, G, H, K, L, M, Q, R, S, T, V or Y
(Q74H,D440$X_3$) wherein $X_3$ is N, A, C, E, F, G, H, K, L, M, Q, R, S, T, V or Y As non-limiting examples of such triple-mutants to be expressed by such expression system there may be mentioned:
(T52$X_1$,Q74$X_2$,D440$X_3$)
   wherein $X_1$ is P, $X_2$ is H and $X_3$ is N, A, C, E, F, G, H, I, K, L, M, Q, R, S, T, V, W or Y;
   wherein $X_1$ is K, $X_2$ is H and $X_3$ is N, A, C, E, F, G, H, I, K, L, M, Q, R, S, T, V, W or Y;
   wherein $X_1$ is M, $X_2$ is H and $X_3$ is N, A, C, E, F, G, H, I, K, L, M, Q, R, S, T, V, W or Y;
   wherein $X_1$ is P, $X_2$ is A and $X_3$ is N, A, C, E, F, G, H, I, K, L, M, Q, R, S, T, V, W or Y;
   wherein $X_1$ is K, $X_2$ is A and $X_3$ is N, A, C, E, F, G, H, I, K, L, M, Q, R, S, T, V, W or Y;
   wherein $X_1$ is M, $X_2$ is A and $X_3$ is N, A, C, E, F, G, H, I, K, L, M, Q, R, S, T, V, W or Y.

Preferred triple mutants are:
(T52P,Q74H,D440$X_3$) wherein $X_3$ is N, A, C, E, F, G, H, K, L, M, Q, R, S, T, V or Y Said above-mentioned single, double or triple mutant may optionally be further modified by at least one, like 1, 2, 3, 4 or 5, preferably 1, 2 or 3, most preferably 1 further mutation in an amino acid sequence position of SEQ ID NO: 4 selected from N120, T121, F281, M298, and L470, in particular selected from the mutations N120I, T121P, F281Q, M298K, and L470S.

6. The expression system of one of the preceding embodiments, wherein said at least nucleotide sequence (B) comprises nucleotide sequences (B1) and (B2), wherein
   a. (B1) encodes a polypeptide having chaperonin activity comprising an amino acid sequence having at least 70%, 75%, 80%, 85%, 90%, 95%, 96%, 97%, 98%, 99% or 100% sequence identity to SEQ ID NO:8 (GroEL); and
   b. (B2) encodes a polypeptide having chaperonin activity comprising an amino acid sequence having at least 70%, 75%, 80%, 85%, 90%, 95%, 96%, 97%, 98%, 99% or 100% sequence identity to SEQ ID NO:10 (GroES).

Non-limiting examples of preferred expression systems of the invention are IEM1-expressing systems, that comprise a nucleotide sequence having at least 70%, 75%, 80%, 85%, 90%, 95%, 96%, 97%, 98%, 99% or 100% sequence identity to a sequence selected from SEQ ID NO: 11 (PC1); SEQ ID NO: 12 (PC2); SEQ ID NO: 13 (PC3); SEQ ID NO: 14 (PC4); SEQ ID NO: 15 (PC5); which are applicable according to the invention for expressing a functional polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO:2 (IEM1);
   Further non limiting examples of preferred expression systems may be derived from such IEM-1 expressing systems of SEQ ID NO: 11, 12, 13, 14, or 15 by replacing the coding sequence of IEM1 by a nucleotide sequence encoding a functional IEM2 mutant derived from SEQ ID NO:4 as described above for embodiment 5. Such IEM2-expressing systems are also preferred.

7. A polypeptide having isoeugenol oxidizing activity and being obtainable by recombinant expression utilizing an expression system as defined in anyone of the preceding embodiments.

8. A polypeptide having isoeugenol oxidizing activity and comprises an amino acid sequence having at least 70%, 75%, 80%, 85%, 90%, 95%, 96%, 97%, 98%, 99% or 100% sequence identity to SEQ ID NO: 4 (i.e. IEM2), wherein the amino acid sequence having at least 70%, 75%, 80%, 85%, 90%, 95%, 96%, 97%, 98%, 99% or 100% identity to SEQ ID NO: 4 comprises at least one mutation in an amino acid sequence position selected from T52, Q74, D440 optionally at least one, like 1, 2, 3, 4 or 5, further mutation in an amino acid sequence position selected from N120, T121, F281, M298, and L470, in particular selected from N120I, T121P, F281Q, M298K, and L470S.

9. The polypeptide of embodiment 8, which is a mutant polypeptide comprising at least one mutation in an amino acid sequence position selected from T52, Q74 and D440 of SEQ ID NO: 4.

10. The polypeptide of embodiment 9, wherein said mutant is selected from
    a. the single mutants ($T52X_1$), ($Q74X_2$) and ($D440X_3$)
    b. the double mutants ($T52X_1,Q74X_2$), ($T52X_1,D440X_3$) and ($Q74X_2,D440X_3$) and
    c. the triple mutant ($T52X_1,Q74X_2,D440X_3$)
    wherein
    $X_1$ is P, K or M or any other natural or non-natural, in particular natural amino acid substitution resulting in a functional, vanillin producing enzyme mutant, preferably $X_1$ is P or M, and most preferably P;
    $X_2$ is H or A or any other natural or non-natural, in particular natural amino acid substitution resulting in a functional, vanillin producing enzyme mutant, most preferably $X_2$ is H; and
    $X_3$ is N, A, C, E, F, G, H, I, K, L, M, Q, R, S, T, V, W Y or any other natural or non-natural, in particular natural amino acid substitution resulting in a functional, vanillin producing enzyme mutant; preferably $X_3$ is N, A, C, E, F, G, H, K, L, M, Q, R, S, T, V, or Y; and most preferably N.

As regards non-limiting examples of such double-mutants and triple mutants of the invention reference is made to embodiment 5 above.

Said single, double or triple mutant may optionally be further modified by at least one, like 1, 2, 3, 4 or 5, preferably 1, 2 or 3, most preferably 1 further mutation in an amino acid sequence position of SEQ ID NO: 4 selected from N120, T121, F281, M298, and L470, in particular selected from N120I, T121P, F281Q, M298K, and L470S.

11. A recombinant nucleic acid comprising a nucleotide sequence encoding a polypeptide of anyone of the embodiments 8 to 10.

12. A recombinant nucleic acid comprising a nucleotide sequence having at least 70%, 75%, 80%, 85%, 90%, 95%, 96%, 97%, 98%, 99% or 100%, or less than 100% like 99.9% sequence identity to SEQ ID NO:1, 3 or 5 or the reverse complement thereof.

A related embodiment provides a nucleic acid sequence which is complementary to the nucleic acid sequence according to SEQ ID NO:1, 3 or 5, or nucleic acid sequence which hybridizes under stringent conditions to at least part of the nucleotide sequence according to SEQ ID NO: 1, 3 or 5.

Particular examples of recombinant nucleic acids are those comprising a nucleotide sequence having at least 70%, 75%, 80%, 85%, 90%, 95%, 96%, 97%, 98%, 99% or 100%, or less than 100% like 99.9% sequence identity to SEQ ID NO: 3 or 5 and which encodes an IEM2 mutant as described above for embodiment 5; or the reverse complement thereof.

Such recombinant nucleic acids may be included in monocistronic or polycistronic expression vectors as further described herein.

13. A recombinant nucleic acid construct comprising the recombinant nucleic acid of embodiment 11 or embodiment 12 or the reverse complement thereof.

14. An expression vector comprising
    a. the recombinant expression system of anyone of the embodiments 1 to 6 or one of said partial nucleic acid constructs or the reverse complement thereof; or
    b. a nucleic acid as defined in embodiments 11 or 12; or
    c. a construct of embodiment 13.

15. The expression vector of embodiment 14, wherein the vector is a prokaryotic vector, viral vector, a eukaryotic vector, or one or more plasmids.

The above mentioned nucleic acid molecules or vectors may be such that monocistronic mRNAs or in particular a polycistronic mRNA, encoding an isoeugenol oxidizing enzyme of the invention and one or more helper polypeptides as described herein is transcribed upon expression.

16. A non-human host organism or host cell comprising, optionally stably integrated into its genome,
    a. the recombinant expression system of anyone of the embodiments 1 to 6 or one of said partial nucleic acid constructs; or
    b. a nucleic acid as defined in embodiments 11 or 12 or the reverse complement thereof; or
    c. the construct of embodiment 13; or
    d. the vector of embodiment 14 or 15.

17. The non-human host organism or host cell of embodiment 16, selected from a prokaryotic or eukaryotic microorganism, a plant, or a cell derived therefrom.

18. The non-human host organism or host cell of embodiment 17, wherein the microorganism is a bacterium or a fungus, in particular yeast.

19. The non-human host organism or host cell of embodiment 18, wherein said bacterium is selected from the genus *Escherichia*, in particular from the species *E. coli* and said yeast is selected from the genus *Saccharomyces* or *Pichia*, in particular from the species *Saccharomyces cerevisiae* or *Pichia pastoris*.

20. A method for producing an isolated catalytically active polypeptide having isoeugenol oxidizing activity, which method comprises the co-expression, like for example the substantially simultaneous, and in particular the simultaneous expression of said polypeptide having isoeugenol oxidizing activity and of at least one helper polypeptide each encoded by an expression system as defined in anyone of the embodiments 1 to 6 in a host cell system; and optionally isolating said polypeptide having isoeugenol oxidizing activity.

"Co-expression" or "co-expressing should be understood broadly as long as it is performed in a manner which results in a cooperative action of the helper polypeptide assisting the functional expression of the polypeptide having isoeugenol oxidizing activity (IEM), in particular the correct folding of said expressed IEM polypeptide. A simultaneous or substantially simultaneous co-expression of both polypeptides represents one non-limiting alternative among others. Another non-limiting alternative might be seen in the timely sequential expression of both polypeptides starting with expression of the helper polypeptide followed by the IEM polypeptide expression. Another non-limiting alternative might be seen a timely overlapping co-expression of both polypeptides, wherein in the initial phase merely the helper polypeptide is expressed and in the overlapping phase both polypeptides are expressed. Other alternatives may be developed by a skilled reader without inventive effort.
21. The method of embodiment 20, wherein an isoeugenol oxidizing enzyme as defined in anyone of the embodiments 7 to 10 is prepared.
22. The method of embodiment 20 or 21, wherein a non-human host organism or host cell as defined in anyone of the embodiments 16 to 19 is applied for expression.
23. A method of producing vanillin comprising
   a. contacting isoeugenol with a polypeptide having isoeugenol oxidizing activity as defined in anyone of the embodiments 7 to 10, or a polypeptide having isoeugenol oxidizing activity as prepared by a method of anyone of the embodiments 20 to 22 in the presence of oxygen, in particular molecular oxygen, to produce vanillin and acetaldehyde; and
   b. optionally isolating the vanillin produced in step a.
   In preferred embodiment vanillin is isolated.
   In another preferred embodiment vanillin (and acetaldehyde) is obtained as the main product of the isoeugenol oxygenation process.
   The vanillin produced in any of the method described herein can be converted to derivatives such as, but not limited to hydrocarbons, esters, amides, glycosides, ethers, epoxides, aldehydes, ketons, alcohols, diols, acetals or ketals.
   The vanillin derivatives can be obtained by a chemical method such as, but not limited to oxidation, reduction, alkylation, acylation and/or rearrangement.
   Alternatively, the vanillin derivatives can be obtained using a biochemical method by contacting vanillin with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells.
24. The method of embodiment 23, comprising transforming a non-human host organism or host cell with an expression system as defined in anyone of the embodiments 1 to 6, expressing the coding nucleotide sequences (A) and (B) thereof.
25. The method of any one of embodiments 23 or 24, wherein the isoeugenol is contacted with a host cell, with a cell lysate of the host cell, or a culture medium containing said host cell and/or with the polypeptide having isoeugenol oxidizing activity as defined in anyone of the embodiments 7 to 10, isolated from the host cell, cell lysate or culture medium.
   The isoeugenol substrate may either be added to reaction medium applied or, in an alternative embodiment, a non-human host organism or a host cell already capable of producing isoeugenol is transformed with an expression system as defined in anyone of the embodiments 1 to 6 to express at least one polypeptide having isoeugenol monooxygenase activity, and is cultivated under conditions conducive to the production of vanillin.
26. The method of embodiment 25, wherein vanillin is fermentatively produced by said non-human host organism or host cell.
27. The method of embodiment 25, wherein vanillin is enzymatically produced by the conversion of isoeugenol with an isolated polypeptide having isoeugenol oxidizing activity as defined in anyone of the embodiments 7 to 10, in the presence of oxygen, and optionally further adjuvants.
28. The method of anyone of the embodiments 23 to 27, which method further comprises in advance of step a. the step of chemical or biochemical isomerization of eugenol to isoeugenol, and optionally isolating isoeugenol from the reaction medium.
29. A method for preparing a mutant polypeptide having isoeugenol oxidizing activity comprising the steps of:
   a. selecting a nucleic acid according to any one of the embodiments 11 and 12;
   b. modifying the selected nucleic acid to obtain at least one mutant nucleic acid;
   c. providing host cells or unicellular organisms with the mutant nucleic acid sequence to express a polypeptide encoded by the mutant nucleic acid sequence;
   d. screening for at least one mutant polypeptide with activity in oxidizing isoeugenol;
   e. optionally, if the mutated polypeptide has no desired activity, repeating the process steps a. to d. until a polypeptide with a desired activity is obtained; and,
   f. optionally, if a mutant polypeptide having a desired activity was identified in step d. or e., isolating the corresponding mutant nucleic acid.

Further aspects and embodiments of the present invention as described above by reference to particular, preferred embodiments are described in the subsequent sections.

b. Polypeptides Applicable According to the Invention

In this context the following definitions apply:

The generic terms "polypeptide" or "peptide", which may be used interchangeably, refer to a natural or synthetic, linear chain or sequence of consecutive, peptidically linked amino acid residues, comprising about 10 up to more than 1.000 residues. Short chain polypeptides with up to 30 residues are also designated as "oligopeptides".

The term "protein" refers to a macromolecular structure consisting of one or more polypeptides. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spacial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity.

Thus, unless otherwise indicated the term "polypeptide" also encompasses the terms "protein" and "enzyme".

Similarly, the term "polypeptide fragment" encompasses the terms "protein fragment" and "enzyme fragment".

The term "isolated polypeptide" refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic isoeugenol oxidizing activity or, more particularly IEM activity, display at least a 1 to 10%, or at least 20%, or at least 50%, or at least 75%, or at least 90% higher or lower IEM activity, as that of the respective polypeptide specifically defined herein.

"Functional equivalents" may also be derived from helper polypeptides as described therein which assist in the functional expression of another, preferably enzymatically active, polypeptide, in particular the correct folding of said expressed polypeptide, as for example of a polypeptide with isoeugenol oxidizing activity or, more particularly IEM activity. Such modified helper polypeptide may still be regarded as functional, as long as it improves the correct expression or folding said enzymatically active polypeptide relative the expression of the same enzymatically active polypeptide under otherwise identical conditions but in the absence of such helper polypeptide.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |

-continued

| Original residue | Examples of substitution |
| --- | --- |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

Several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material. The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual,* 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, N.Y., Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3' non-translated sequence comprising, e.g., transcription termination sites.

"Polycistronic" refers to nucleic acid molecules, in particular mRNAs or corresponding cDNAs that can encode more than one polypeptide separately within the same nucleic acid molecule. A polycistronic gene allows for the translation initiation at two or more sites on one single sequence.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. ((1989))) with the following settings:

| Multiple alignment parameter: | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: http://www.ebi.ac.uk/Tools/clustalw/index.html# and the following settings

| | |
| --- | --- |
| DNA Gap Open Penalty | 15.0 |
| DNA Gap Extension Penalty | 6.66 |
| DNA Matrix | Identity |
| Protein Gap Open Penalty | 10.0 |

-continued

| | |
|---|---|
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoramidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences ac-cording to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual,* 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes. Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

Moreover, a person skilled in the art is familiar with methods for generating functional mutants, that is to say nucleotide sequences which code for a polypeptide with at least 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example

- site-specific mutagenesis, where individual or several nucleotides of a gene are replaced in a directed fashion (Trower M K (Ed.) 1996; In vitro mutagenesis protocols. Humana Press, New Jersey),
- saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1),
- error-prone polymerase chain reaction, where nucleotide sequences are mutated by error-prone DNA polymerases (Eckert K A, Kunkel T A (1990) Nucleic Acids Res 18:3739);
- the SeSaM method (sequence saturation method), in which preferred exchanges are prevented by the polymerase. Schenk et al., Biospektrum, Vol. 3, 2006, 277-279
- the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an E. coli mutator strain. In: Trower M K (Ed.) In vitro mutagenesis protocols. Humana Press, New Jersey), or
- DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, CA (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of vanillin in the cell or organism. Particularly, the nucleotide sequence encodes an IEM.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacI$^q$, T7, T5, T3, H9, H10, G6, C4, gal, trc, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation. See for example also Jones et al. ePathOptimize: A Combinatorial Approach for Transcriptional Balancing of Metabolic Pathways. Sci. Rep. 2015, 5, 11301.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in E. coli pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in Streptomyces pIJ101, pIJ364, pIJ702 or pIJ361, in Bacillus pUB110, pC194 or pBD214, in Corynebacterium pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity. In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Microorganisms to be Applied for the Present Invention

Depending on the context, the term "microorganism" can mean the wild-type microorganism or a genetically altered, recombinant microorganism or both.

In one embodiment, using the vectors according to the invention, recombinant microorganisms can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example coprecipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, NY, 1989.

In principle, all prokaryotic or eukaryotic organisms may be considered as recombinant host organisms for the nucleic acid according to the invention or the nucleic acid construct. Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

For the expression of mutants according to the invention, reference may be made to the description of expression of the wild-type enzyme EbN1 and the expression systems usable for this in WO2005/108590 and WO2006/094945, to which reference is hereby expressly made.

h. Polypeptide Immobilization

The enzymes or polypeptides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The at least one polypeptide/enzyme which is present during a method of the invention or an individual step of a multistep-method as defined herein above, can be present in living cells naturally or recombinantly producing the enzyme or enzymes, in harvested cells, in dead cells, in permeabilized cells, in crude cell extracts, in purified extracts, or in essentially pure or completely pure form. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger and Crueger, Biotechnologie—Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

Instead of living cells, biomass of non-living cells containing the required biocatalyst(s) may be applied to the biotransformation reactions of the invention as well.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butylether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

k. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

l. Fermentative Production of Vanillin

The invention also relates to methods for the fermentative production of vanillin.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einfuhrung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The methodology of the present invention can further include a step of recovering Vanillin.

The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The following examples are illustrative only and are not meant to limit the scope of invention as set forth in the Summary, Description or in the Claims.

The numerous possible variations that will become immediately evident to a person skilled in the art after heaving considered the disclosure provided herein also fall within the scope of the invention.

EXAMPLES

Materials:
Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, NY, 1989.
Methods:
In a typical isoeugenol monooxygenase assay reactions were centrifuged and extracted with MTBE as described in the following examples prior to the analysis by gas chromatography.

Gas chromatography was carried out with Agilent Technologies' 6850 equipped with an FID detector and a DB-WAX column (30 m, 250 microM, 0.25 microM) using the following program: 100° C. (1 min), 245° C. at 20° C. min', 245° C. (10 min). Carrier gas: Hydrogen, 75 cm $sec^{-1}$, split=50, injection volume=1 µL.

Example 1: Preparation and Testing of $1^{st}$ Generation Isoeugenol Monooxygenase (IEM1)

The following $1^{st}$ generation biocatalyst was used:

| E. coli strain | Plasmid construct |
| --- | --- |
| BL21(DE3):pIEM1 | Codon modified isoeugenol monooxygenase of P. nitroreducens |

| E. coli strain | Plasmid construct |
| --- | --- |
| | Jin1 in pJ414 (T7, $amp^R$, high copy, strong RBS). The wild type sequence originated from Genbank #FJ851547 |

A freshly grown colony of strain BL21(DE3):pIEM1 was picked from an LB agar plate and transferred into 20 mL of LB medium containing 100 mg/L of ampicillin. Cultivation was under shaking at 225 rpm at 37° C. for 20 h. 1 mL of that culture was taken to inoculate 200 mL of sterile LB medium with 100 mg $L^{-1}$ of ampicillin using a 1 L Erlenmeyer flask. Growth was under shaking at 220 rpm and at 37° C. till an $OD_{600}$ of 0.4 was reached. Temperature was reduced to 20° C. while the culture continued to grow till an $OD_{600}$ of 0.6 was reached. The culture was induced with 1 mM IPTG and grown for another 18 h. Typically an $OD_{600}$ of 5.5 to 7 was reached after an overnight incubation.

Figure 3:
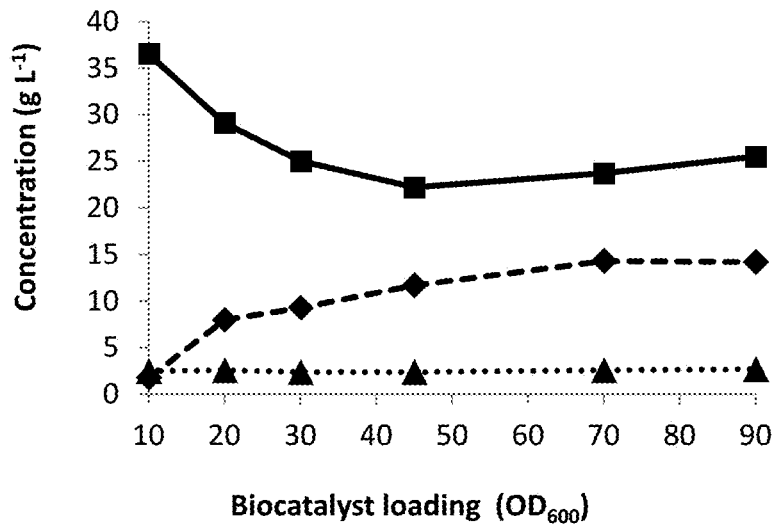
FIG. 3: $1^{st}$ generation catalyst based on IEM1: Product titers at different biocatalyst loadings under non-limiting substrate concentrations at pH 10.5. Symbols: Vanillin (♦), remaining trans-isoeugenol (■), remaining (Z)-isoeugenol (▲). Averaged data of two experiments are shown.

Cells were centrifuged at 9000 g and at 4° C. for 20 minutes. The supernatant was discarded and cells were resuspended in 100 mM glycine-NaOH buffer pH 10.5 containing 10 v/v % DMSO (the optimum pH was later found to be around pH 9 for the isoeugenol monooxygenase of P. nitroreducens Jin1). Suspensions of different cell densities were prepared corresponding to an $OD_{600}$ of 10 to 90. Into a 20 mL vial were added: 2 mL cell suspension of a defined optical density, 75 mg of isoeugenol (Sigma Aldrich #I17206). Reactions were stirred at 500 rpm at room temperature (24° C.) for 20 hours using vial closures made with a punctured membrane of aluminum for oxygenation. Reactions were acidified with 6 drops of 15% HCl and extracted with 10 mL of MTBE containing 1 g $L^{-1}$ of tridecane as the internal standard prior to analysis by gas chromatography. A negative control was carried out the same way with empty cells. The time curve for the formation of vanillin is shown in FIG. 3.

Example 2: Vanillin Production by $1^{st}$ Generation Isoeugenol Monooxygenase (IEM1)

Vanillin was prepared as follows: Cells of E. coli expressing the isoeugenol monooxygenase of P. nitroreducens Jin1 (see Example 1) were transferred from an ampicillin containing LB agar plate into 50 mL of an ampicillin containing mineral salt medium with 15 g $L^{-1}$ of glucose as the carbon source and grown under shaking at 225 rpm and at 37° C. for 20 h. The mineral salt medium was composed of 15 g $L^{-1}$ of glucose 5 g $L^{-1}$ of $(NH_4)_2HPO_4$, 16 g $L^{-1}$ of $K_2HPO_4$, 2 g $L^{-1}$ of citric acid, 1 g $L^{-1}$ of $MgSO_4$, and 30 mg $L^{-1}$ of $CaCl_2$ besides trace elements, vitamins and 100 mg $L^{-1}$ of ampicillin. Then 0.4 mL of this culture was taken to inoculate 200 mL of mineral salt medium of the same composition using a 1-L-flask. Several flasks were run in parallel. The culture was grown under shaking at 37° C., 180 rpm till an $OD_{600}$ of 2.5 was reached. The temperature was lowered to 20° C. The culture was induced with 1 mM IPTG at $OD_{600}$ of 3 and grown under shaking at 20° C. and at 180 rpm for another 17 h. An $OD_{600}$ of 24 was observed at the end of cultivation. The culture was centrifuged at 4000 g at 4° C. for 50 min. Cells were re-suspended in 100 mM glycine-NaOH buffer pH 9 to give a final $OD_{600}$ of 45.

Into a 2 L reaction flasks were added 1.3 L of the cell suspension of an $OD_{600}$ of 45 and 19.5 g of isoeugenol. The reaction was stirred at room temperature for 20 h. Analysis of the reaction by gas chromatography showed 7.3 g $L^{-1}$ of vanillin, 1.2 g $L^{-1}$ of (Z)-isoeugenol, and 4.1 g $L^{-1}$ of remaining (E)-isoeugenol. The temperature of the reaction broth was lowered to 12° C. and the pH was adjusted to pH 12.5 prior to extraction with distilled ethyl acetate (1 L). After phase separation and removal of the organic phase the water phase was again adjusted to 12° C. and pH 12.5. A second extraction with 700 mL of ethyl acetate was carried out and the organic phase was discarded. The pH of the water phase was then adjusted to pH 7 with 15% of HCl. The water phase was extracted twice with 1 L of distilled ethyl acetate. These combined extracts contained 7.7 g of vanillin based on GC analysis. The combined organic extract was then washed with 600 mL of water before evaporation under vacuum. A yellow residue of 7.7 g was obtained. Efforts to remove the yellow color by another extraction with ethyl acetate at 10° C. and pH 12.5 failed. About 0.8 g of vanillin was lost in this effort leaving a remaining 6.9 g of a slightly yellow, solid residue. The residue was dissolved in 153 mL of hot water at 55° C. Once all crude vanillin was dissolved the solution was left at room temperature for 1 h. The temperature was lowered to 4° C. and kept at this temperature for 3 h. Finally, the solution was cooled in an ice-water bath for 18 h. The solution with the precipitated vanillin was passed through a precooled paper filter. The crystals were washed with ice cold water (30 mL). The crystals were then dried in a desiccator under vacuum at room temperature for 6 h. A slightly yellowish solid residue of 5.4 g was recovered containing 99.7% of vanillin by GC based on the internal standard. The chemical identity was verified by GC-MS, 1H-NMR and 13C-NMR. Some losses during purification occurred. Ethyl acetate was not well suited for alkaline extraction and could be replaced by a more stable solvent such as MTBE.

Example 3: Preparation of $2^{nd}$ Generation Isoeugenol Monooxygenases

The following $2^{nd}$ generation biocatalysts (IEM and helper polypeptides located on two different plasmids) were tested:

| E. coli strain | Plasmid constructs |
| --- | --- |
| BL21(DE3):pIEM1_pG-KJE8 | pIEM1: codon modified isoeugenol monooxygenase of P. nitroreducens Jin1 in pJ414 (T7, amp$^R$, high copy, provider Atum, Newark, CA). pG-KJE8 (araB, pACYC ori, Pzt-1, cm$^R$, dnak, dnaj, grpE, groES, groEL). |
| BL21(DE3):pIEM1_pGro7 | pIEM1: codon modified isoeugenol monooxygenase of P. nitroreducens Jin1 in pJ414 (T7, amp$^R$, high copy). pGro7 (araB, pACYC ori, cm$^R$, groES, groEL. |
| BL21(DE3):pIEM1_pKJE7 | pIEM1: codon modified isoeugenol monooxygenase of P. nitroreducens Jin1 in pJ414 (T7, amp$^R$, high copy). pKJE7 (araB, pACYC ori, cm$^R$, dnak, dnaj, grpE). |
| BL21(DE3):pIEM1_pG-Tf2 | pIEM1: codon modified isoeugenol monooxygenase of P. nitroreducens Jin1 in pJ414 (T7, amp$^R$, high copy). pG-Tf2 (pACYC ori, Pzt-1, cm$^R$, tef, groES, groEL, tig). |
| BL21(DE3):pIEM1_pTf16 | pIEM1: codon modified isoeugenol monooxygenase of P. nitroreducens Jin1 in pJ414 (T7, amp$^R$, high copy). pTf16 (araB, pACYC ori, cm$^R$, tig). |

Figure 4:
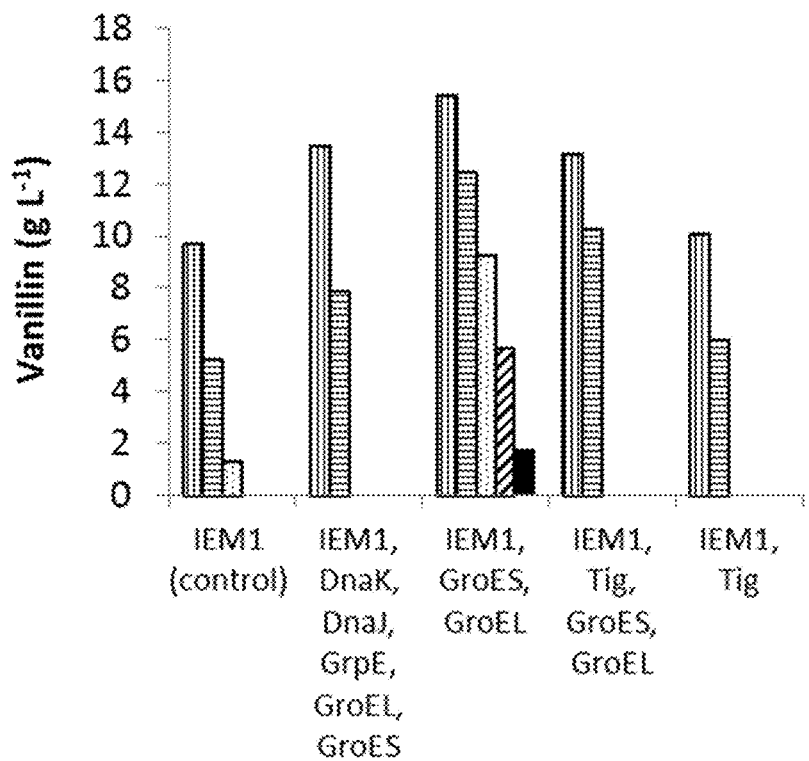
FIG. 4: $2^{nd}$ generation catalysts: Product titers at different catalyst loadings expressed as different optical cell densities: $OD_{600}=18$ (vertical stripes), $OD_{600}=10$ (horizontal stripes), $OD_{600}=5$ (dotted), $OD_{600}=2$ (diagonal stripes), $OD_{600}=1$ (black). The biocatalyst was previously grown in LB medium. IEM1: Isoeugenol monooxygenase of *P. nitroreducens* Jin1. Co-expressed chaperones are also indicated. IEM1 (control) designates the activity of a wildtype isoeugenol monooxygenase of *P. nitroreducens* Jin1 expressed in the absence of any chaperons according to Example 1. Values reflect averaged endpoint measurements within 10% variation.

Freshly grown cells were isolated from an agar plate, grown in 2 mL LB medium containing ampicillin and chloramphenicol under shaking at 37° C. till an optical density $OD_{600}$=1 was reached. 1 mL of this culture was taken to inoculate 200 mL of LB medium containing 100 mg $L^{-1}$ ampicillin and 30 mg $L^{-1}$ chloramphenicol, supplemented with 5 mg $L^{-1}$ of FeCl$_3$ placed in a 1000-mL-flask. Induction of chaperones was at the beginning of the cultivation with 2 mg mL$^{-1}$ of arabinose and if necessary with 5 ng mL$^{-1}$ of tetracycline according to the protocol of the manufacturer (Takara Bio Inc.). Cultivation was at 37° C. under shaking at 180 rpm till an $OD_{600}$ of 0.4 was reached. Temperature was lowered to 20° C. prior to induction with 1 mM of IPTG at $OD_{600}$=0.6. Cells were harvested after an overnight cultivation by centrifugation at 3600 g, re-suspended in cold buffer of 0.1 M glycine NaOH pH 9.5 to the desired optical density. Catalytic activities were tested as described under Example 1. The catalytic activities observed with different constructs are shown in FIG. 4. Higher specific activities were obtained with most of the $2^{nd}$ generation catalysts than with the $1^{st}$ generation catalyst (control). Cells co-expressing the isoeugenol monooxygenase of P. nitroreducens Jin1 and the chaperonins GroES and GroEL were most active. Cells harboring the plasmid pKJE7 showed very weak growth and were not tested for activity.

Example 4: Fed-Batch Cultivation of a $2^{nd}$ Generation Isoeugenol Monooxygenases The strain BL21(DE3):pIEM1_pGro7 was tested under fed-batch culture conditions. Fed-batch cultivation was carried out in a reactor with 3.7 L of working volume (Bioengineering, Switzerland) using a glucose feeding based on dissolved oxygen. A mineral salt medium as described containing 5 g $L^{-1}$ of yeast extract and supplemented with carbenicillin and chloramphenicol at pH 7 served as the growth medium using glycerol instead of glucose as the carbon source. Cultivation was at 37° C. At an $OD_{600}$ of 48, the temperature was lowered to 25° C., and the culture was induced with 1.5 g $L^{-1}$ of arabinose at an $OD_{600}$ of 51. At an $OD_{600}$ of 59, the culture was induced with 1 mM of IPTG. The feeding solution contained 70% sterile, aqueous glycerol. The pH control was with aqueous NH$_3$. The fermentation lasted for 43 h and reached a final $OD_{600}$ of 163. Plasmid stability was determined using agar plates with and without the appropriate antibiotics for selection. Bacterial cells were harvested by centrifugation as previously described, resuspended in 100 mM glycine-NaOH buffer pH 9 and tested for activity. Up to 3.7 g $L^{-1}$ of vanillin were observed by gas chromatography in a reaction carried out as described under Example 1 with a catalyst loading corresponding to an $OD_{600}$ of 5.

Example 5: Preparation of $3^{rd}$ Generation Isoeugenol Monooxygenases

The following $3^{rd}$ generation biocatalysts (IEM and helper polypeptides located on one single polycistronic construct) were prepared and tested:

| E. coli strain | Plasmid construct |
| --- | --- |
| BL21(DE3)T1:pPC1 | Polycistronic construct containing the codon modified isoeugenol monooxygenase of P. nitroreducens Jin1, groEL and groES under the T7 |

| E. coli strain | Plasmid construct |
| --- | --- |
| BL21(DE3)T1:pPC2 | promotor in pJ431 (T7, kan$^R$, low copy; provider Atum, Newark, CA). T1 phage resistance. Sequence elements: Strong RBS-IEM1-strong RBS-groES-native RBS-groEL. Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-spacer-strong RBS-groES-native RBS-groEL |
| BL21(DE3)T1:pPC3 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-medium RBS-groES-native RBS-groEL |
| BL21(DE3)T1:pPC4 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-strong RBS-groES-strong RBS-groEL |
| BL21(DE3)T1:pPC5 | Polycistronic construct containing the codon modified isoeugenol monooxygenase of P. nitroreducens Jin1, groEL and groES under the T7 promotor in pJ431 (T7, kan$^R$, low copy). T1 phage resistance. Sequence elements: Strong RBS-IEM1-weak RBS-groES-native RBS-groEL |

Figure 1:
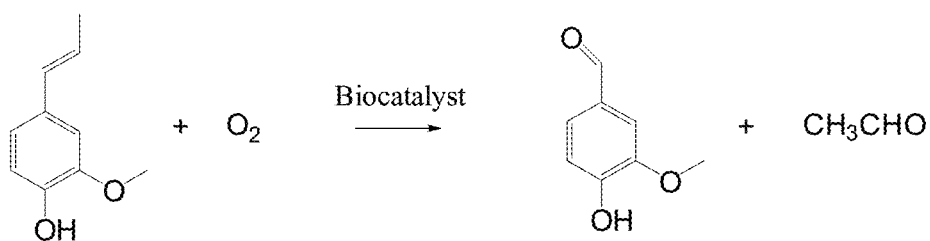
FIG. 1: One step conversion of isoeugenol into vanillin and acetaldehyde.
Figure 2:
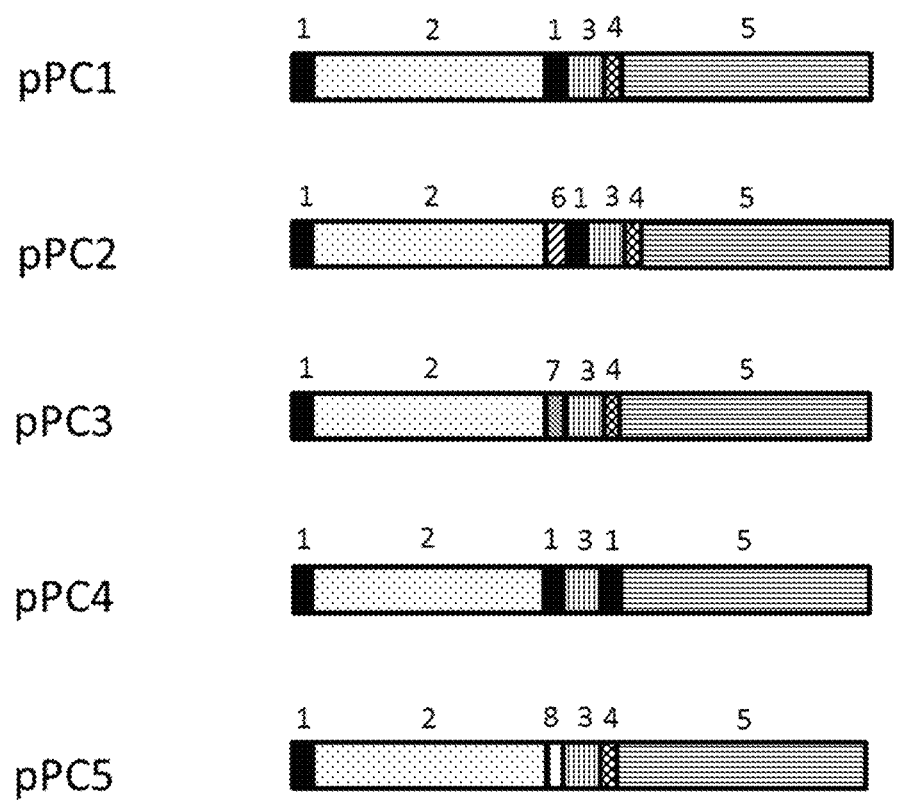
FIG. 2: Polycistronic constructs for co-expressing the isoeugenol monooxygenase (IEM1) of *P. nitroreducens* Jin1 with chaperonins GroES and GroEL using low and high copy plasmids. The plasmid name of the low copy number construct is indicated to the left of each construct. Numbers above the horizontal bar refer to the following elements: 1: RBS (strong); 2: IEM1; 3: GroES; 4: native RBS; 5: GroEL; 6: spacer; 7: RBS (medium); 8: RBS (weak).
Figure 5:
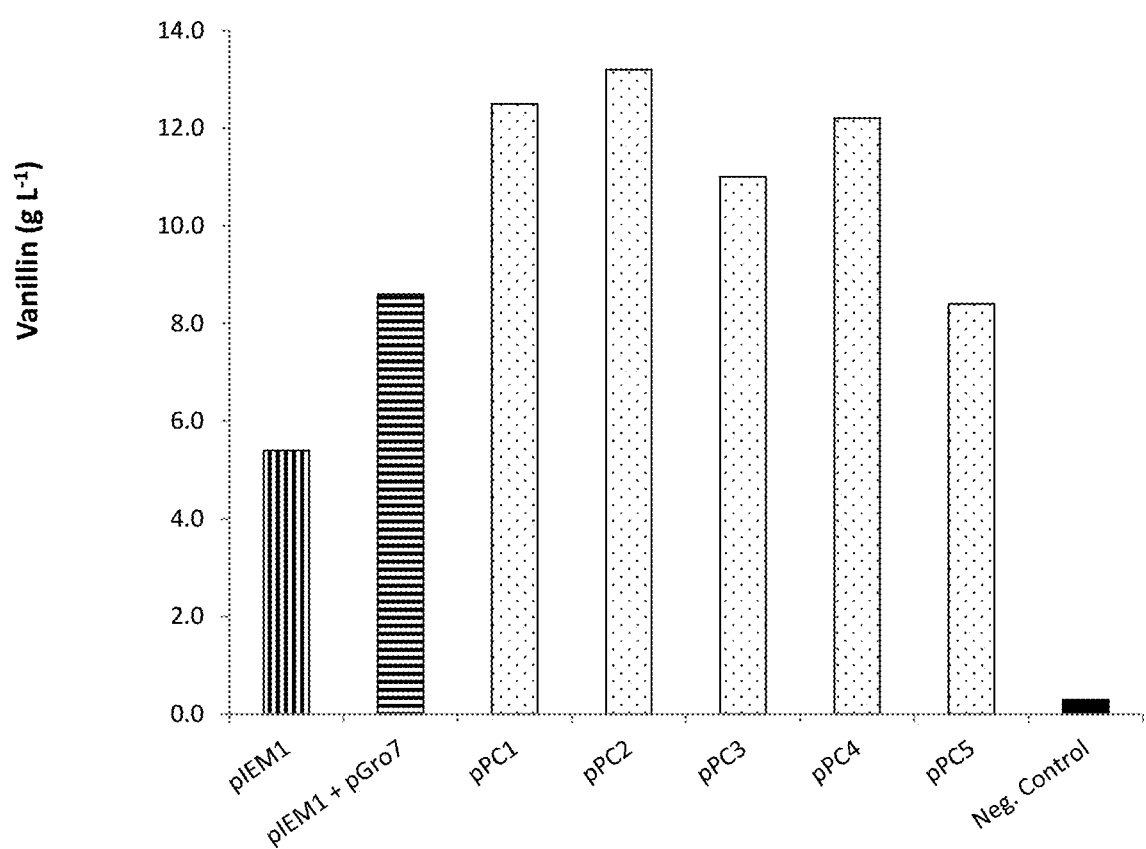
FIG. 5: Product titers from small scale reactions at catalyst loading of $OD_{600}=5$ using one of the $1^{st}$ generation catalysts (vertical stripes), $2^{nd}$ generation catalyst (horizontal stripes), and $3^{rd}$ generation catalysts (dotted). The negative control was obtained with empty cells (filled black). Averaged endpoint concentrations of a double experiment (max 10% variation) are shown.

A schematic representation of the different polycistronic constructs is also given (FIG. 2). Cultivation, induction and activity testes were carried out as described in Example 1. Comparative activity tests with a catalyst loading of an $OD_{600}$ of 5 showed that cells of E. coli expressing one of the polycistronic constructs ($3^{rd}$ generation catalyst) exhibited higher specific catalytic activities compared to the $1^{st}$ and $2^{nd}$ generation catalysts (FIG. 5).

Example 6: Generation of Mutants of the Isoeugenol Monooxygenase of P. putida IE27

Artificial mutants of the isoeugenol monooxygenase of P. putida IE27 (IEM2) were inserted into the plasmid pJ431 (T7, kan$^R$, low copy; provider Atum, Newark, CA) for expression in E. coli BL21(DE3)T1. Alternatively, cells of E. coli producing one of the mutants of P. putida IE27 were co-transformed with the plasmid pGro7 for co-producing the chaperonins GroES and GroEL.

The following mutants were tested:

| Plasmid | Mutant | |
| --- | --- | --- |
| pIEM2c8g | c8g | Thr3Arg |
| pIEM2a13 a | g13a | Asp5Asn |
| pIEM2a67g | a67g | Asn23Asp |
| pIEM2t106t | g106t | Ala36Ser |
| pIEM2t125a | t125a | Phe42Tyr |
| pIEM2a154c | a154c | Thr52Pro |
| pIEM2g222t | g222t | Gln74His |
| pIEM2c253g | c253g | Pro85Ala |
| pIEM2t314a | t314a | Phe105Tyr |
| pIEM2c325a | c325a | Pro109Thr |
| pIEM2g334a | g334a | Glu112Lys |
| pIEM2a434g | a434g | Gln145Arg |
| pIEM2a458t | a458t | Tyr153Phe |
| pIEM2t486a | t486a | His162Gln |
| pIEM2t509a | t509a | Phe170Tyr |
| pIEM2c517g | c517g | Gln173Glu |
| pIEM2t569c | t569c | Leu190Pro |
| pIEM2t598c | t598c | Tyr200His |
| pIEM2a628g | a628g | Lys210Glu |
| pIEM2g761t | g761t | Arg254Leu |
| pIEM2a866t | a866t | Glu289Val |
| pIEM2a947c | a947c | Asp316Ala |
| pIEM2a994g | a994g | Asn332Asp |
| pIEM2a1025g | a1025g | Gln342Arg |
| pIEM2a1037T | a1037t | Tyr346Phe |
| pIEM2c1084a | c1084a | His362Asn |
| pIEM2c1094g | c1094g | Ala365Gly |
| pIEM2a1097t | a1097t | Tyr366Phe |
| pIEM2t1211a | t1211a | Phe404Tyr |
| pIEM2a1219g | a1219g | Lys407Glu |
| pIEM2g1318a | g1318a | Asp440Asn |
| pIEM2g1360t | g1360t | Ala454Ser |
| pIEM2t1426c | t1426c | Ser476Pro |
| pIEM2c154_t222 | a154c, g222t | Thr52Pro, Gln74His |
| pIEM2c154_t222 + pGro7 | a154c, g222t | Thr52Pro, Gln74His, GroES, GroEL |
| pIEM2_c154_a1318 | a154c, g1318a | Thr52Pro, Asp440Asn |
| pIEM2_c154_a1318 + pGro7 | a154c, g1318a | Thr52Pro, Asp440Asn, GroES, GroEL |
| pIEM2_t222_a1318 | g222t, g1318a | Gln74His, Asp440Asn |
| pIEM2_t222_a1318 + pGro7 | g222t, g1318a | Gln74His, Asp440Asn, GroES, GroEL |
| pIEM2_c154_t222_a1318 | a154c, g222t, g1318a | Thr52Pro, Gln74His, Asp440Asn |
| pIEM2_c154_1222_a1318 + pGro7 | a154c, g222t, g1318a | Thr52Pro, Gln74His, Asp440Asn, GroES, GroEL |
| pIEM2 'reference' | wt | Wild type iem of P. putida IE27 in pJ411 |

Figure 6:
FIG. 6: Vanillin titers obtained with single, double and triple mutants of the isoeugenol monooxygenase of *P. putida* IE27 (IEM2). 'Ref' relates to the (inactive) isoeugenol monooxygenase of *P. putida* IE27 used as reference. Cells producing the isoeugenol monooxygenase of *P. nitroreducens* Jin1 (IEM1) served as positive control (C+). Cells containing the empty vector served as negative control (C−). Data points were averaged from a double experiment.
Figure 10:
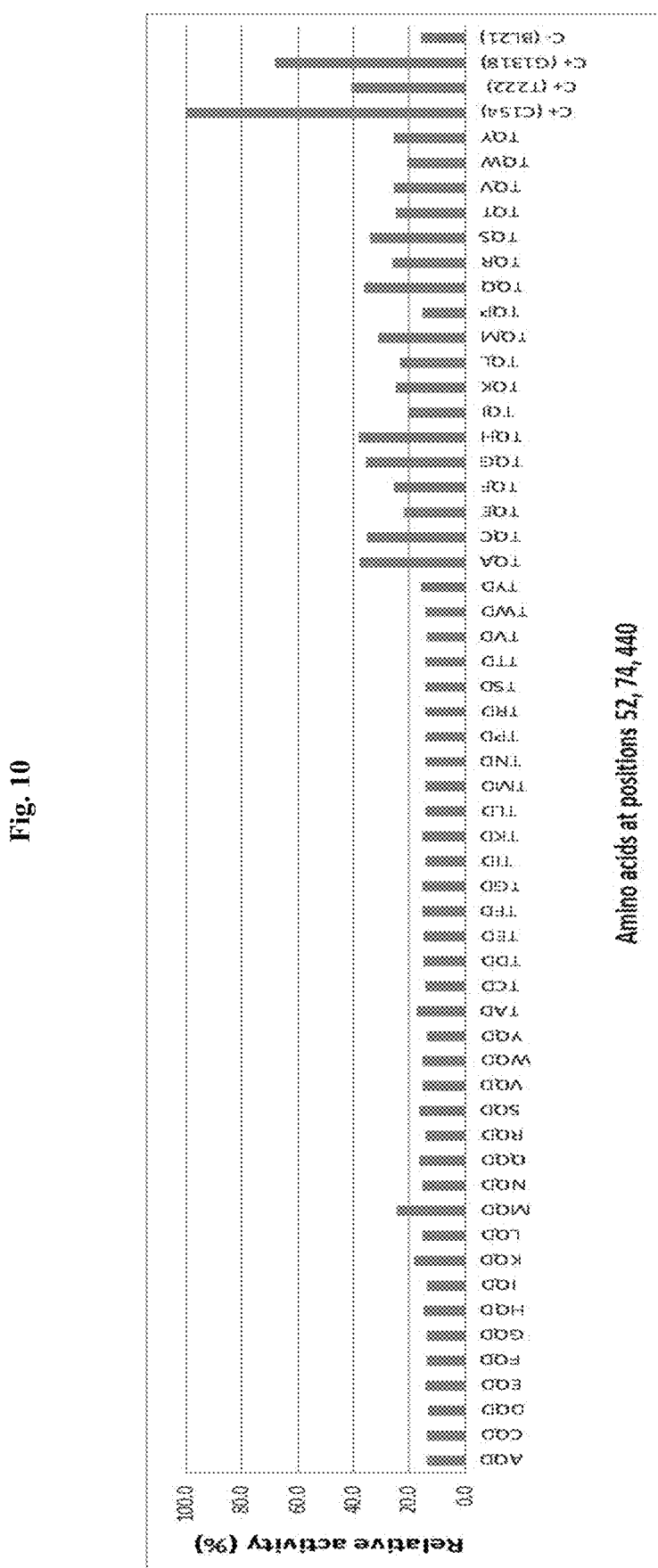
FIG. 10: Relative activity of mutants of the isoeugenol monooxygenase of *P. putida* IE27 obtained by individual saturation mutagenesis at amino acid positions T52, or Q74 or D440. The corresponding amino acids at these positions are indicated on the horizontal axe. The relative activity of each mutant is expressed as the fraction of the averaged vanillin titers obtained with the mutant "C154" (i.e. mutant a154c; corresponding to PQD) under standard assay conditions. For comparison the previously identified mutant "T222" (i.e. mutant g222t, corresponding to THD) and G1318 (i.e. mutant g1318a; corresponding to TQN) are also shown. Empty cells served as the negative control (C−).

A freshly grown colony of E. coli harboring the plasmid encoded mutant was picked from an LB agar plate and grown in 2 mL LB liquid culture with 30 mg L$^{-1}$ of kanamycin at 220 rpm and at 37° C. over night (16 h). 150 µL were then transferred to a flask with 50 mL LB medium containing the required antibiotic and grown at 37° C. under shaking at 200 rpm for about 2 h till an $OD_{600}$ of 0.45 was reached. The temperature was lowered to 20° C. while the culture continued to grow to an $OD_{600}$ of 0.6. After induction with 0.5 mM of IPTG, the culture was grown for another 16 hours under the same conditions. Cells of E. coli containing the mutant isoeugenol monooxygenases of P. putida IE27 were harvested by centrifugation and re-suspended in ice cold 0.1 M glycine buffer pH 9.5 containing 10 v/v % of DMSO to reach a final $OD_{600}$ of 45. In case of E. coli cells containing the isoeugenol monooxygenase of P. nitroreducens Jin1 (used as positive control) the same procedure was applied using 0.1 M glycine buffer, pH 9.0. Into a 20 mL vial were added: 80 mg of isoeugenol, 2 mL of the cell suspension of $OD_{600}$=45. The vial was closed with a punctured aluminum membrane for air circulation. The reaction was stirred with a magnet at 450 rpm at room temperature (23° C.) for 17 h. The reaction was acidified with 3 drops of 15% HCl and extracted with 10 mL of MTBE containing 1 g $L^{-1}$ of tridecane as the internal standard for analysis by GC. The vanillin concentration obtained with the individual mutants and controls is shown in FIG. 6. Further mutants of the isoeugenol monooxygenase of *P. putida* IE27 (IEM) were obtained by individual saturation mutagenesis experiments at amino acid positions T52, or Q74 or D440 performed by a commercial manufacturer. These additional mutants were tested in analogy to the above identified mutants. The relative activity of each mutant as shown in FIG. 10, and is expressed as the fraction of the averaged vanillin titers obtained with the mutant "C154" (i.e. mutant a154c; corresponding to PQD) under standard assay conditions.

Figure 7:
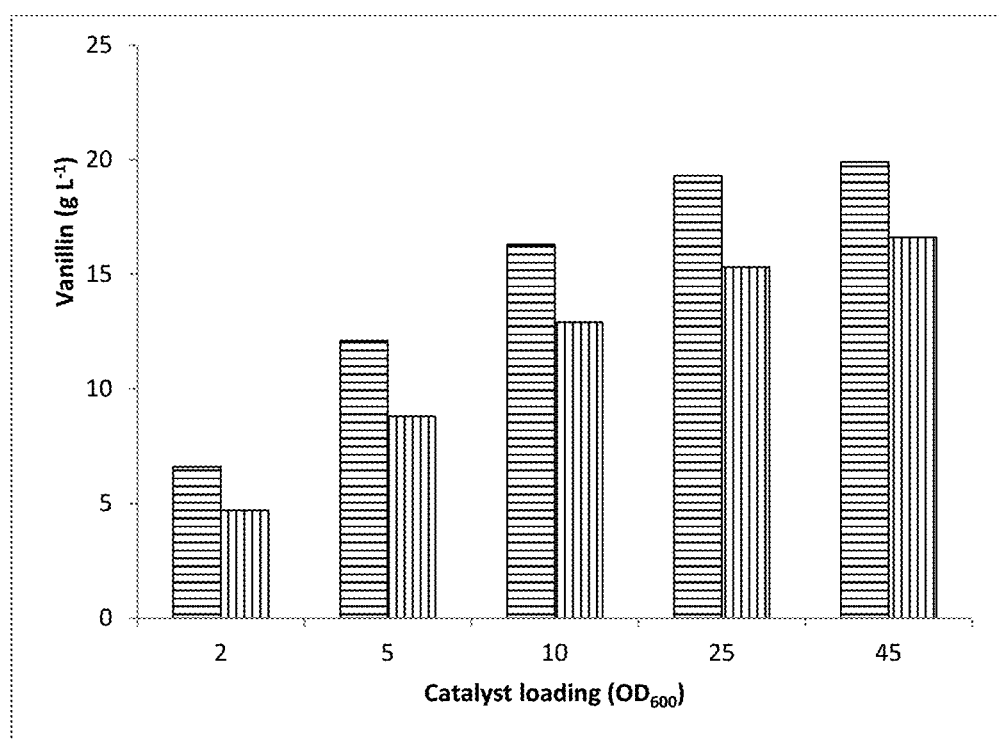
FIG. 7: Biotransformation of isoeugenol into vanillin at different catalyst loading shown for the triple codon mutant of the isoeugenol monooxygenase of *P. putida* IE27 (IEM2) (horizontal stripes), and for the isoeugenol monooxygenase of *P. nitroreducens* Jin1 (IEM1) (vertical stripes). Cells of *E. coli* harboring the two-plasmid-system for co-expressing the isoeugenol monooxygenase and the chaperonins GroES and GroEL served as the catalyst. The isoeugenol monooxygenase of *P. nitroreducens* Jin1 was produced with a high copy construct, while the triple mutant of *P. putida* IE27 was produced with a low copy construct. Averaged product titers of two experiments with variations within less than 10% are shown.
Figure 9:
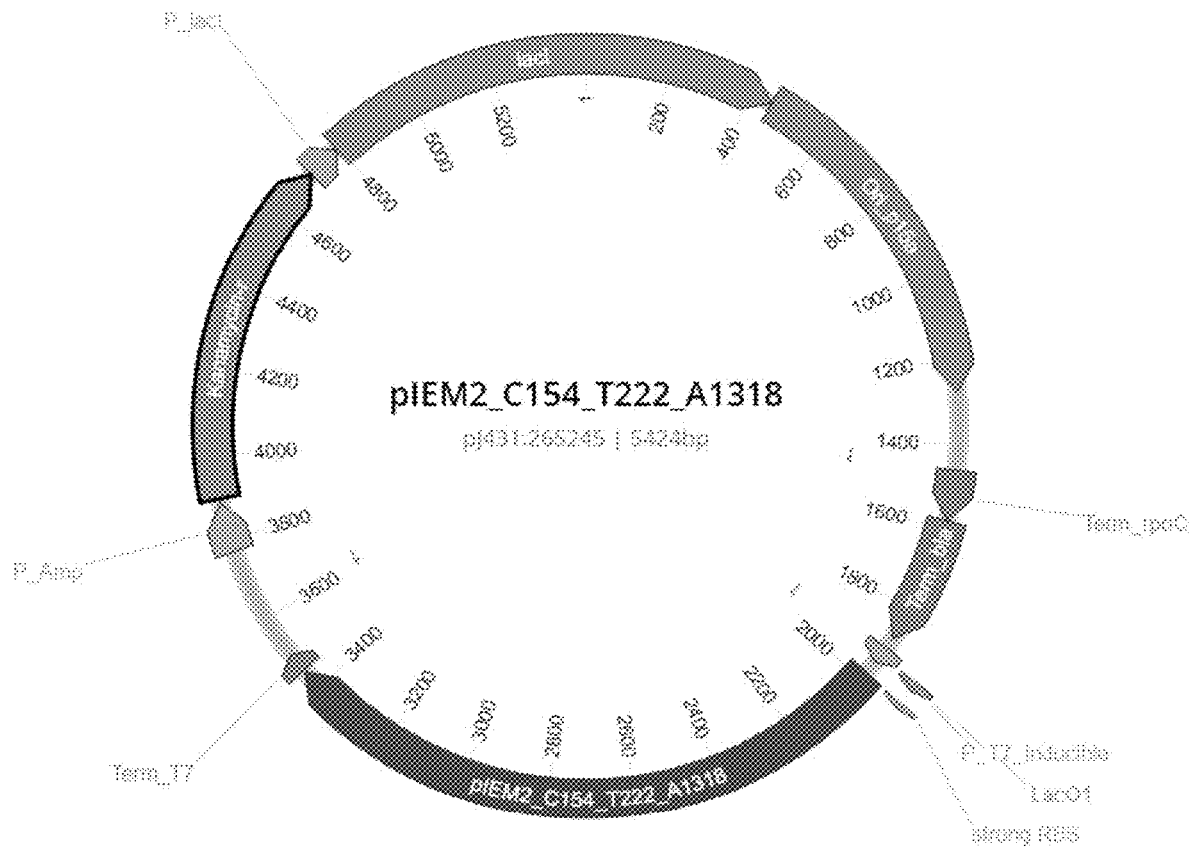
FIG. 9: Annotation of plasmid pIEM2_C154_T222_A1318 for expressing a triple mutant of IEM2 of *Pseudomonas putida* IE27 and corresponding plasmid map.

Example 7: Triple Mutant of the Isoeugenol Monooxygenase of *P. putida* IE27 Co-Expressed with GroES and GroEL A colony of *E. coli* BL21(DE3)T1 harboring the plasmids pIEM2_c154_t222_a1318 (see plasmid map and annotation of FIG. 8 as well as SEQ ID NO:16) and pGro7 was isolated from the agar plate and added to 2 mL of LB medium containing 30 mg/L of kanamycin and 30 mg/L of chloramphenicol. The culture was grown at 37° C. under shaking at 220 rpm for 16 h. 150 μL were transferred to 50 mL of fresh LB medium containing the same antibiotics. Cells were grown at 37° C. under shaking at 220 rpm till an $OD_{600}$ of 0.45 was reached. The culture was induced with 1.5 g/L of arabinose and the temperature lowered to 20° C. for growth under shaking till an $OD_{600}$ of 0.6 was reached. The culture was induced with 0.5 mM of IPTG and grown at 20° C. under shaking at 220 rpm for another 16 h. Cells were harvested by centrifugation and re-suspended in ice cold 0.1 M glycine buffer pH 9.5. Different cell dilutions were prepared corresponding to and $OD_{600}$ of 2 to 45. Into an open 20 mL reaction vial were added 80 mg of isoeugenol, 2 mL of the cell suspension of different optical densities. The reaction was stirred with a magnetic bar at 500 rpm at room temperature for 17 h. Reactions were acidified with 3 drops of 15% HCl and extracted with 10 mL of MTBE containing 1 g/L of tridecane as the internal standard for analysis by GC. The vanillin concentration observed in reactions containing different cell densities is shown in FIG. 7.

Example 8: Triple Mutant of the Isoeugenol Monooxygenase of *P. putida* IE27 Co-Expressed with GroES and GroEL from Different Expression Constructs Derived from the Polycistronic Construct PC1 Triple (SEQ ID NO:25; Containing the Triple Mutant of IEM IE27)

Colonies of *E. coli* cells BL21(DE3)T1 harboring different plasmid constructs (construed according to the general scheme of FIG. 11, and having a nucleotide sequence selected from SEQ ID NO:17 to 24 and corresponding constructs wherein the transcription terminator of the IEM coding sequence was absent) for expressing the triple mutant of the isoeugenol monooxygenase IE27 together with the chaperonins GroES and GroEL were picked from kanamycin containing agar plates and inoculated into 2 mL of a mineral salt medium. The mineral salt medium contained 30 g/L of glycerol, 5 g $L^{-1}$ of $(NH_4)_2HPO_4$, 16 g $L^{-1}$ of $K_2HPO_4$, 2 g $L^{-1}$ of citric acid, 1 g $L^{-1}$ of $MgSO_4$, 30 mg $L^{-1}$ of $CaCl_2$, 5 g/L of yeast extract, trace elements and 50 mg/L of kanamycin.

The cultures were shaken at 37° C. at 230 rpm for 16 hours. 0.25 mL of the culture was transferred to a flask containing 50 mL of the same medium and cultivated at 37° C. at 230 rpm till and optical density $OD_{600}$ of 2.5 was reached. The temperature was lowered to 23° C. and the cultivation continued at 220 rpm till an $OD_{600}$ of 3 was reached. The culture was induced with 0.5 mM of IPTG and kept under the same conditions over night.

At the end of the cultivation samples were taken for determining the optical density at 600 nm, for estimating the cell dry weight using a standard gravimetrical method, and for activity testing. For the activity testing 15 mL of the culture were centrifuged at 3500 g at 4° C. for 35 min and the supernatant was discarded. The cell pellet was frozen for a few hours at −80° C. The frozen pellet was thawn on ice and resuspended in ice-cold 0.1 M of glycine buffer pH 9.5 to a final $OD_{600}$ of 20.

Into a 20 mL flask were added 80 mg of isoeugenol, 1800 μL of ice-cold 0.1 M glycine buffer pH 9.5. Under magnetic stirring were added 200 μL of the cell resuspension ($OD_{600}$=20) to reach a final $OD_{600}$ of 2. The reaction was agitated with a magnetic stirrer at 23° C. at 450 rpm for 16 hours.

Figure 12:
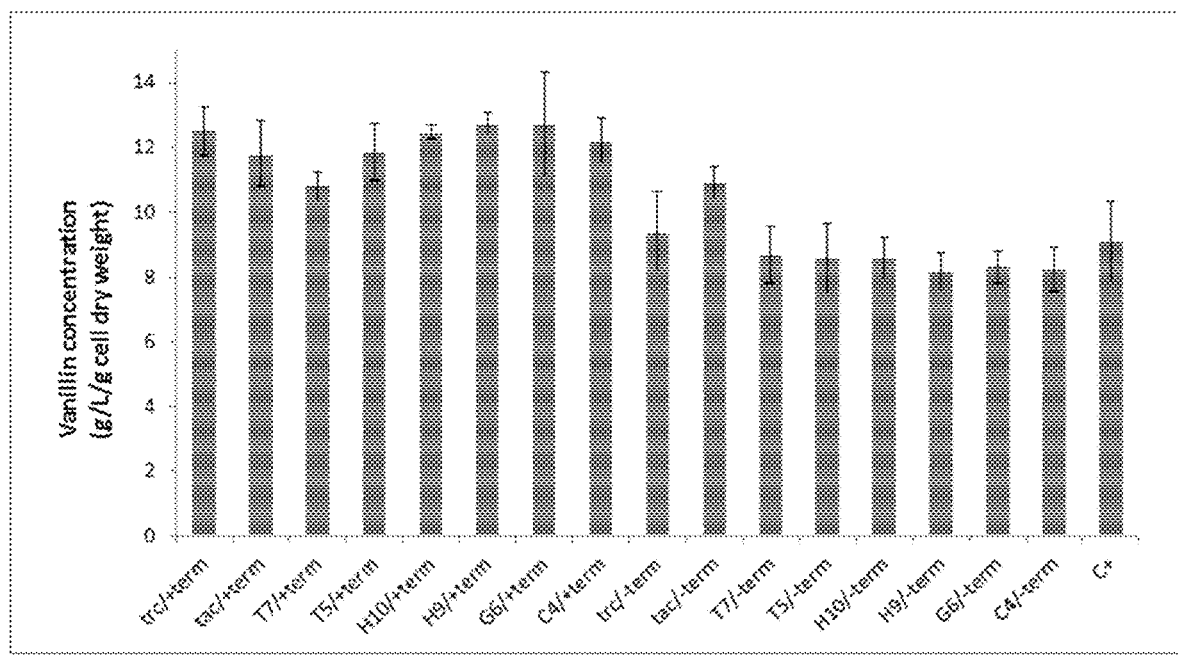

The reaction was acidified with 8 drops (80 μL) of 85% of phosphoric acid prior to extraction with 10 mL of MTBE containing 1 g $L^{-1}$ of tridecane as the internal standard. The vanillin concentration was determined with a gas chromatograph as described. The vanillin concentrations obtained with the different plasmid constructs were normalized with regard to cell dry weight of the cell suspension used in the reaction. The results are shown in FIG. 12.

The content of the documents cross-referenced is incorporated by reference.

Sequences as herein referred to are:

| SEQ ID NO | Name | Source | Type |
| --- | --- | --- | --- |
| 1 | IMG1 codon modified | *P. nitroreducens* Jin1 | NA |
| 2 | IMG1 | *P. nitroreducens* Jin1 | AA |
| 3 | IMG2 wild type | *P. putida* IE27 | NA |
| 4 | IMG2 wild type | *P. putida* IE27 | AA |
| 5 | IMG2 codon modified | *P. putida* IE27 | NA |
| 6 | IMG2 | *P. putida* IE27 | AA |
| 7 | GroEL | *E. coli* | NA |
| 8 | GroEL | *E. coli* | AA |
| 9 | GroES | *E. coli* | NA |
| 10 | GroES | *E. coli* | AA |
| 11 | PC1 | expression construct | NA |
| 12 | PC2 | expression construct | NA |
| 13 | PC3 | expression construct | NA |
| 14 | PC4 | expression construct | NA |
| 15 | PC5 | expression construct | NA |
| 16 | pIEM2_c154_t222_a1318 | expression plasmid | NA |
| 17 | trc/+term | expression construct | NA |
| 18 | tac/+term | expression construct | NA |
| 19 | T7/+term | expression construct | NA |
| 20 | T5/+term | expression construct | NA |
| 21 | H10/+term | expression construct | NA |
| 22 | H9/+term | expression construct | NA |
| 23 | G6/+term | expression construct | NA |
| 24 | C4/+term | expression construct | NA |
| 25 | PC1_triple | expression construct | NA |

NA = Nucleic Acid
AA = Amino Acid

Sequence Listing

SEQ ID NO: 1 -isoeugenol monooxygenase of *P. nitroreducens* Jin1 (codon modified)
```
ATGGCACGTCTGAACCGTAATGATCCGCAACTCGTCGGCACCCTGTTACCAACCCGT
ATTGAGGCTGACCTGTTCGACCTGGAAGTGGACGGCGAAATTCCGAAGTCCATCAA
CGGTACCTTCTACCGTAACACGCCGGAGCCTCAGGTGACGCCGCAGAAATTCCACA
CCTTCATCGATGGTGACGGCATGGCGTCTGCATTTCATTTTGAAGATGGCCACGTGG
ACTTCATCAGCCGCTGGGTTAAAACCGCGCGTTTCACGGCGGAGAGACTGGCACGT
AAAAGCCTGTTCGGTATGTACCGTAATCCGTACACCGATGACGTCTGTGAAGGGT
CTGGATCGTACCGTTGCCAACACGAGCATCATCAGCCATCACGGTAAGGTTCTGGCG
GTGAAAGAAGATGGCTTGCCGTACGAGCTGGACCCACGCACTCTGGAAACCCGTGG
TCGCTTTGACTATGATGGCCAAGTCACCAGCCAGACGCACACCGCGCATCCGAAGT
ATGACCCGGAAACCGGTGACCTGTTGTTCTTTGGCTCCGCAGCCAAGGGTGAGGCAA
CGCCTGATATGGCCTATTACATCGTTGATAAACATGGTAAGGTAACGCATGAGACTT
GGTTCGAGCAACCTATGGCGCCTTTATGCATGATTTTGCTATTACCCGCAATTGGA
GCATCTTCCCGATCATGCCGGCTACCAATTCGTTGAGCCGCTGAAAGCGAAGCAGC
CGATTTACATGTGGGAGCCGGAACTGGGTTCCTATATTGGTGTTCTGCCGCGTCGCG
GTCAAGGTAGCCAGATCCGCTGGCTGAAAGCACCAGCGCTGTGGGTCTTTCACGTCG
TCAACGCCTGGGAAGTGGGCACCAAAATCTACATTGACCTTATGGAGAGCGAAATT
CTGCCATTCCCGTTCCCGAATAGCCAAATCAGCCGTTCGCTCCTGAGAAAGCAGTG
CCGCGTCTGACCCGTTGGGAGATTGATCTGGATAGCAGCAGCGATGAGATTAAGCG
TACGCGTCTGCACGACTTCTTTGCAGAGATGCCGATCATGGATTTTCGTTTTGCGCTG
CAGTGCAACCGCTACGGTTTTATGGGTGTCGATGACCCGCGCAAGCCGCTGGCGCAC
CAACAAGCGGAGAAGATTTTTGCGTACAATAGCCTGGGTATCTGGGACAACCACCG
TGGTGATTATGATTTGTGGTACAGCGGCGAAGCCTCAGCGGCGCAAGAACCGGCTTT
CGTTCCGCGTTCTCCGACTGCAGCGGAAGGCGACGGTTATCTGCTGACCGTTGTGGG
CCGTTTGGACGAGAACCGCAGCGACCTGGTCATTCTGGACACGCAGGACATCCAGA
GCGGTCCGGTTGCGACCATTAAACTGCCGTTTCGCCTGCGTGCGGCCCTGCACGGCT
GTTGGGTTCCGCGTCCGTAA
```

SEQ ID NO: 2 - Isoeugenol monooxygenase of *P. nitroreducens* Jin1 protein
```
MARLNRNDPQLVGTLLPTRIEADLFDLEVDGEIPKSINGTFYRNTPEPQVTPQKFHTFIDG
DGMASAFHFEDGHVDFISRWVKTARFTAERLARKSLFGMYRNPYTDDTSVKGLDRTVA
NTSIISHHGKVLAVKEDGLPYELDPRTLETRGRFDYDGQVTSQTHTAHPKYDPETGDLLF
FGSAAKGEATPDMAYYIVDKHGKVTHETWFEQPYGAFMHDFAITRNWSIFPIMPATNSL
SRLKAKQPIYMWEPELGSYIGVLPRRGQGSQIRWLKAPALWVFHVVNAWEVGTKIYID
LMESEILPFPFPNSQNQPFAPEKAVPRLTRWEIDLDSSSDEIKRTRLHDFFAEMPIMDFRF
ALQCNRYGFMGVDDPRKPLAHQQAEKIFAYNSLGIWDNHRGDYDLWYSGEASAAQEP
AFVPRSPTAAEGDYLLTVVGRLDENRSDLVILDTQDIQSGPVATIKLPFRLRAALHGC
WVPRP
```

SEQ ID NO: 3 - Isoeugenol monooxygenase of *P. putida* IE27 (GenBank Accession AB291707)
```
ATGGCAACGTTTGACCGCAATGATCCCGCAGTTGGCAGGAACGATGTTCCCCACCCG
AATAGAGGCGAATGTCTTTGACCTTGAAATTGAGGGCGAGATCCCACGTGCAATCA
ACGGGAGCTTCTTCCGCAACACCCCCGAACCTCAGGTCACCACGCAACCTTTCCACA
CCTTCATCGATGGGGATGGTTTGGCGTCTGCTTTTCATTTCGAAGATGGCCAGGTCG
ACTTTGTCAGCCGTTGGGTATGTACTCCTCGCTTTGAAGCTGAGCGGTCGGCTCGTA
AATCACTCTTCGGTATGTACCGCAATCCGTTCACTGATGATCCATCGGTAGAAGGTA
TTGATCGTACAGTCGCCAACACCAGTATCATCACTCATCACGGGAAAGTACTGGCCG
CAAAGGAAGATGGACTACCTTATGAGCTTGACCCCCAAACCCTGGAAACCCGAGGT
CGTTATGATTACAAGGGGCAGGTAACCAGCCATACACATACAGCGCACCCTAAGTT
CGACCCCCCAGACAGGTGAAATGTTACTCTTCGGCTCCGCTGCTAAAGGCGAACGAA
CGCTTGATATGGCGTACTATATTGTTGATCGCTACGGCAAGGTGACACATGAGACCT
GGTTTAAGCAGCCTTACGGTGCATTCATGCACGACTTTGCTGTCACGCGCAACTGGT
CAATCTTTCCGATCATGCCTGCGACAAATAGCCTTGAGCGTCTTAAAGCAAAGCAGC
CCATTTACATGTGGGAGCCTGAGCGAGGAAGCTATATAGGAGTACTTCCTCGTCGTG
GTCAGGGCAAGGACATTCGTTGGTTCCGTGCCCCGGCGTTGTGGGTTTTCCATGTCG
TGAATGCTTGGGAGGAAGGGAATAGAATTCTGATTGACTTGATGGAAAGTGAGATT
TTGCCGTTCCCATTCCCGAACTCGCAGAACCTTCCATTTGATCCCTCCAAGGCTGTTC
CGCGTCTAACCCGTTGGGAAATTGATCTCAATAGTGGTAACGATGAGATGAAACGT
ACGCAGCTACACGAATATTTTGCAGAAATGCCTATCATGGATTTCCGTTTTGCGCTC
CAGGATCATCGCTACGCCTACATGGGGGTTGACGATCCTCGTCGCCCCTTAGCTCAT
CAGCAAGCTGAAAAAATCTTTGCCTACAATTCGTTAGGGGTTTGGGACAACCATCGT
AAAGATTATGAACTTTGGTTTACGGGAAAAATGTCTGCAGCGCAGGAACCGGCGTTT
GTTCCTAGAAGCCCAGATGCGCCTGAGGGCGATGGCTACCTACTCAGTGTAGTAGG
GCGGCTCGATGAAGATCGTAGCGATCTAGTTATCCTTGATACGCAATGTTTGGCAGC
TGGGCCTGTGGCCACTGTCAAGCTTCCCTTCCGTCTCCGAGCAGCGTTGCACGGTTG
TTGGCAGTCTAAGAACTGA
```

SEQ ID NO: 4 or 6 - Isoeugenol monooxygenase of *P. putida* IE27 protein
```
MATFDRNDPQLAGTMFPTRIEANVFDLEIEGEIPRAINGSFFRNTPEPQVTTQPFHTFIDG
DGLASAFHFEDGQVDFVSRWVCTPRFEAERSARKSLFGMYRNPFTDDPSVEGIDRTVAN
TSIITHHGKVLAAKEDGLPYELDPQTLETRGRYDYKGQVTSHTHTAHPKFDPQTGEMLL
FGSAAKGERTLDMAYYIVDRYGKVTHETWFKQPYGAFMHDFAVTRNWSIFPIMPATNS
LERLKAKQPIYMWEPERGSYIGVLPRRGQGKDIRWFRAPALWVFHVVNAWEEGNRILI
DLMESEILPFPFPNSQNLPFDPSKAVPRLTRWEIDLNSGNDEMKRTQLHEYFAEMPIMDF
RFALQDHRYAYMGVDDPRRPLAHQQAEKIFAYNSLGVWDNHRKDYELWFTGKMSAA
QEPAFVPRSPDAPEGDYLLSVVGRLDEDRSDLVILDTQCLAAGPVATVKLPFRLRAAL
HGCWQSKN
```

SEQ ID NO: 5 - Isoeugenol monooxygenase of P. putida IE27 (codon modified)
ATGGCCACTTTTGACCGCAATGACCCGCAACTGGCAGGCACCATGTTCCCGACGCGC
ATCGAAGCGAATGTTTTTGATCTGGAGATTGAAGGTGAGATTCCGCGTGCGATCAAC
GGTAGCTTTTTCCGCAACACGCCAGAGCCGCAAGTCACCACGCAGCCGTTTCATACT
TTCATCGACGGCGACGGCCTGGCGTCAGCGTTCCACTTCGAAGATGGCCAGGTCGAC
TTTGTGAGCCGCTGGGTCTGCACCCCGCGTTTCGAGGCAGAGCGCAGCGCGCGTAA
AAGCCTGTTTGGTATGTATCGCAATCCGTTTACGGATGACCCGAGCGTTGAAGGCAT
TGACCGTACCGTGGCGAATACCTCGATCATTACCCACCACGGTAAGGTCCTGGCAGC
AAAAGAAGATGGCTTGCCGTACGAGTTAGATCCGCAGACCCTGGAAACGCGTGGTC
GCTATGACTACAAGGGCCAGGTTACCAGCCATACCCACACGGCTCACCCTAAGTTTG
ATCCGCAAACGGGTGAGATGCTGCTGTTCGGCAGCGCGGCAAAGGGTGAGCGTACC
CTGGACATGGCTACTATATCGTTGACCGTTACGGTAAAGTGACCCATGAAACCTGG
TTCAAGCAACCGTACGCGCCTTTATGCACGACTTCGCAGTCACGCGCAACTGGTCT
ATCTTTCCGATTATGCCGGCCACCAATAGCCTGGAGCGTCTGAAAGCTAAGCAACCG
ATTTACATGTGGGAACCGGAGCGTGGTTCCTACATCGGCGTGCTGCCGCGTCGTGGT
CAGGGTAAAGATATCCGCTGGTTCCGTGCGCCTGCCCTCTGGGTGTTCCACGTTGTG
AACGCATGGAAGAGGGCAATCGTATTCTGATCGATCTGATGGAGAGCGAAATCCT
GCCATTCCCGTTTCCGAACTCTCAGAATCTGCCGTTCGATCCGAGCAAAGCCGTACC
GCGCTTGACCCGTTGGGAGATTGATTTGAACAGCGGTAATGACGAGATGAAGCGTA
CTCAGCTGCACGAATACTTCGCTGAGATGCCGATTATGGACTTTCGTTTCGCGCTGC
AAGATCACCGTTACGCGTATATGGGTGTTGATGATCCACGCCGTCCATTGGCGCATC
AACAAGCGGAAAAGATTTTTGCGTATAACAGCCTGGGTGTTTGGGACAACCATCGT
AAAGACTATGAGCTGTGGTTTACGGGTAAAATGTCCGCGGCTCAGGAACCGGCCTTC
GTGCCGCGCAGCCCGGACGCCCCTGAGGGTGATGGTTATTTGCTGTCCGTCGTGGGT
CGCCTGGATGAAGATCGTAGCGACCTGGTTATCCTGGACACCCAGTGCCTTGCGGCA
GGCCCGGTTGCGACCGTCAAGCTGCCGTTCCGTCTGCGTGCAGCTCTGCATGGTTGT
TGGCAGAGCAAAAACTAA SEQ ID NO: 7 - chaperonin GroEL (GenBank Accession CP009685.1, region
3964433 . . . 3966079)
ATGGCAGCTAAAGACGTAAAATTCGGTAACGACGCTCGTGTGAAAATGCTGCGCGG
CGTAAACGTACTGGCAGATGCAGTGAAAGTTACCCTCGGTCCAAAAGGCCGTAACG
TAGTTCTGGATAAATCTTTCGGTGCACCGACCATCACCAAAGATGGTGTTTCCGTTG
CTCGTGAAATCGAACTGGAAGACAAGTTCGAAAATATGGGTGCGCAGATGGTGAAA
GAAGTTGCCTCTAAAGCAAACGACGCTGCAGGCGACGGTACCACCACTGCAACCGT
ACTGGCTCAGGCTATCATCACTGAAGGTCTGAAAGCTGTTGCTGCGGGCATGAACCC
GATGGACCTGAAACGTGGTATCGACAAAGCGGTTACCGCTGCAGTTGAAGAACTGA
AAGCGCTGTCCGTACCATGCTCTGACTCTAAAGCGATTGCTCAGGTTGGTACCATCT
CCGCTAACTCCGACGAAACCGTAGGTAAACTGATCGCTGAAGCGATGGACAAAGTC
GGTAAAGAAGGCGTTATCACCGTTGAAGACGGTACCGGTCTGCAGGACGAACTGGA
CGTGGTTGAAGGTATGCAGTTCGACCGTGGCTACCTGTCTCCTTACTTCATCAACAA
GCCGGAAACTGGCGCAGTAGAACTGGAAAGCCCGTTCATCCTGCTGGCTGACAAGA
AAATCTCCAACATCCGCGAAATGCTGCCGGTTCTGGAAGCTGTTGCCAAAGCAGGC
AAACCGCTGCTGATCATCGCTGAAGATGTAGAAGGCGAAGCGCTGGCAACTCTGGT
TGTTAACACCATGCGTGGCATCGTGAAAGTCGCTGCGGTTAAAGCACCGGGCTTCGG
CGATCGTCGTAAAGCTATGCTGCAGGATATCGCAACCCTGACTGGCGGTACCGTGAT
CTCTGAAGAGATCGGTATGGAGCTGGAAAAAGCAACCCTGGAAGACCTGGGTCAGG
CTAAACGTGTTGTGATCAACAAAGACACCACCACTATCATCGATGGCGTGGGTGAA
GAAGCTGCAATCCAGGGCCGTGTTGCTCAGATCCGTCAGCAGATTGAAGAAGCAAC
TTCTGACTACGACCGTGAAAAACTGCAGGAACGCGTAGCGAAACTGGCAGGCGGCG
TTGCAGTTATCAAAGTGGGTGCTGCTACCGAAGTTGAAATGAAAGAGAAAAAAGCA
CGCGTTGAAGATGCCCTGCACGCGACCCGTGCTGCGGTAGAAGAAGGCGTGGTTGC
TGGTGGTGGTGTTGCGCTGATCCGCGTAGCGTCTAAACTGGCTGACCTGCGTGGTCA
GAACGAAGACCAGAACGTGGGTATCAAAGTTGCACTGCGTGCAATGGAAGCTCCGC
TGCGTCAGATCGTATTGAACTGCGGCGAAGAACCGTCTGTTGTTGCTAACACCGTTA
AAGGCGGCGACGGCAACTACGGTTACAACGCAGCAACCGAAGAATACGGCAACAT
GATCGACATGGGTATCCTGGATCCAACCAAAGTAACTCGTTCTGCTCTGCAGTACGC
AGCTTCTGTGGCTGGCCTGATGATCACCACCGAATGCATGGTTACCGACCTGCCGAA
AAACGATGCAGCTGACTTAGGCGCTGCTGGCGGTATGGGCGGCATGGGTGGCATGG
GCGGCATGATGTAA SEQ ID NO: 8 - chaperonin GroEL protein
MAAKDVKFGNDARVKMLRGVNVLADAVKVTLGPKGRNVVLDKSFGAPTITKDGVSV
AREIELEDKFENMGAQMVKEVASKANDAAGDGTTTATVLAQAIITEGLKAVAAGMNP
MDLKRGIDKAVTAAVEELKALSVPCSDSKAIAQVGTISANSDETVGKLIAEAMDKVGKE
GVITVEDGTGLQDELDVVEGMQFDRGYLSPYFINKPETGAVELESPFILLADKKISNIRE
MLPVLEAVAKAGKPLLIIAEDVEGEALATLVVNTMRGIVKVAAVKAPGFGDRRKAMLQ
DIATLTGGTVISEEIGMELEKATLEDLGQAKRVVINKDTTTIIDGVGEEAAIQGRVAQIRQ
QIEEATSDYDREKLQERVAKLAGGVAVIKVGAATEVEMKEKKARVEDALHATRAAVE
EGVVAGGGVALIRVASKLADLRGQNEDQNVGIKVALRAMEAPLRQIVLNCGEEPSVVA
NTVKGGDGNYGYNAATEEYGNMIDMGILDPTKVTRSALQYAASVAGLMITTECMVTD
LPKNDAADLGAAGGMGGMGGMGGMM -continued Sequence Listing SEQ ID NO: 9 - chaperonin GroES (GenBank Accession CP009685.1, region
3966123 . . . 3966416)
ATGAATATTCGTCCATTGCATGATCGCGTGATCGTCAAGCGTAAAGAAGTTGAAACT
AAATCTGCTGGCGGCATCGTTCTGACCGGCTCTGCAGCGGCTAAATCCACCCGCGGC
GAAGTGCTGGCTGTCGGCAATGGCCGTATCCTTGAAAATGGCGAAGTGAAGCCGCT
GGATGTGAAAGTTGGCGACATCGTTATTTTCAACGATGGCTACGGTGTGAAATCTGA
GAAGATCGACAATGAAGAAGTGTTGATCATGTCCGAAAGCGACATTCTGGCAATTG
TTGAAGCGTAA SEQ ID NO: 10 - chaperonin GroES protein
MNIRPLHDRVIVKRKEVETKSAGGIVLTGSAAAKSTRGEVLAVGNGRILENGEVKPLDV
KVGDIVIFNDGYGVKSEKIDNEEVLIMSESDILAIVEA SEQ ID NO: 11 - PC1 (polycistroncic construct containing codon modified isoeugenol
monooxygenase of P. nitroreducens Jin 1, groES, groEL)
GAAGGAGATATACATATGGCACGTCTGAACCGTAATGATCCGCAACTCGTCGGCAC
CCTGTTACCAACCCGTATTGAGGCTGACCTGTTCGACCTGGAAGTGGACGGCGAAAT
TCCGAAGTCCATCAACGGTACCTTCTACCGTAACACGCCGGAGCCTCAGGTGACGCC
GCAGAAATTCCACACCTTCATCGATGGTGACGGCATGGCGTCTGCATTTCATTTTGA
AGATGGCCACGTGGACTTCATCAGCCGCTGGGTTAAAACCGCGCGTTTCACGGCGG
AGAGACTGGCACGTAAAAGCCTGTTCGGTATGTACCGTAATCCGTACACCGATGAC
ACGTCTGTGAAGGGTCTGGATCGTACCGTTGCCAACACGAGCATCATCAGCCATCAC
GGTAAGGTTCTGGCGGTGAAAGAAGATGGCTTGCCGTACGAGCTGGACCCACGCAC
TCTGGAAACCCGTGGTCGCTTTGACTATGATGGCCAAGTCACCAGCCAGACGCACAC
CGCGCATCCGAAGTATGACCCGGAAACCGGTGACCTGTTGTTCTTTGGCTCCGCAGC
CAAGGGTGAGGCAACGCCTGATATGGCCTATTACATCGTTGATAAACATGGTAAGG
TAACGCATGAGACTTGGTTCGAGCAACCGTATGGCGCCTTTATGCATGATTTTGCTA
TTACCCGCAATTGGAGCATCTTCCCGATCATGCCGGCTACCAATTCGTTGAGCCGCC
TGAAAGCGAAGCAGCCGATTTACATGTGGGAGCCGGAACTGGGTTCCTATATTGGT
GTTCTGCCGCGTCGCGGTCAAGGTAGCCAGATCCGCTGGCTGAAAGCACCAGCGCT
GTGGGTCTTTCACGTCGTCAACGCCTGGGAAGTGGGCACCAAAATCTACATTGACCT
TATGGAGAGCGAAATTCTGCCATTCCCGTTCCCGAATAGCCAAAATCAGCCGTTCGC
TCCTGAGAAAGCAGTGCCGCGTCTGACCCGTTGGGAGATTGATCTGGATAGCAGCA
GCGATGAGATTAAGCGTACGCGTCTGCACGACTTCTTTGCAGAGATGCCGATCATGG
ATTTTCGTTTTGCGCTGCAGTGCAACCGCTACGGTTTTATGGGTGTCGATGACCCGCG
CAAGCCGCTGGCGCACCAACAAGCGGAGAAGATTTTTGCGTACAATAGCCTGGGTA
TCTGGGACAACCACCGTGGTGATTATGATTTGTGGTACAGCCGGAAGCCTCAGCGG
CGCAAGAACCGGCTTTCGTTCCGCGTTCTCCGACTGCAGCGGAAGGCGACGGTTATC
TGCTGACCGTTGTGGGCCGTTTGGACGAGAACCGCAGCGACCTGGTCATTCTGGACA
CGCAGGACATCCAGAGCGGTCCGGTTGCGACCATTAAACTGCCGTTTCGCCTGCGTG
CGGCCCTGCACGGCTGTTGGGTTCCGCGTCCGTAAGAAGGAGATATACATATGAATA
TTCGTCCATTGCATGATCGCGTGATCGTCAAGCGTAAAGAAGTTGAAACTAAATCTG
CTGGCGGCATCGTTCTGACCGGCTCTGCAGCGGCTAAATCCACCCGCGGCGAAGTGC
TGGCTGTCGGCAATGGCCGTATCCTTGAAAATGGCGAAGTGAAGCCGCTGGATGTG
AAAGTTGGCGACATCGTTATTTTCAACGATGGCTACGGTGTGAAATCTGAGAAGATC
GACAATGAAGAAGTGTTGATCATGTCCGAAAGCGACATTCTGGCAATTGTTGAAGC
GTAATCCGCGCACGACACTGAACATACGAATTTAAGGAATAAAGATAATGGCAGCT
AAAGACGTAAAATTCGGTAACGACGCTCGTGTGAAAATGCTGCGCGGCGTAAACGT
ACTGGCAGATGCAGTGAAAGTTACCCTCGGTCCAAAAGGCCGTAACGTAGTTCTGG
ATAAATCTTTCGGTGCACCGACCATCACCAAAGATGGTGTTTCCGTTGCTCGTGAAA
TCGAACTGGAAGACAAGTTCGAAAATATGGGTGCGCAGATGGTGAAAGAAGTTGCC
TCTAAAGCAAACGACGCTGCAGGCGACGGTACCACCACTGCAACCGTACTGGCTCA
GGCTATCATCACTGAAGGTCTGAAAGCTGTTGCTGCGGGCATGAACCCCGATGGACCT
GAAACGTGGTATCGACAAAGCGGTTACCGCTGCAGTTGAAGAACTGAAAGCGCTGT
CCGTACCATGCTCTGACTCTAAAGCGATTGCTCAGGTTGGTACCATCTCCGCTAACT
CCGACGAAACCGTAGGTAAACTGATCGCTGAAGCGATGGACAAAGTCGGTAAAGAA
GGCGTTATCACCGTTGAAGACGGTACCGGTCTGCAGGACGAACTGGACGTGGTTGA
AGGTATGCAGTTCGACCGTGGCTACCTGTCTCCTTACTTCATCAACAAGCCGGAAAC
TGGCGCAGTAGAACTGGAAAGCCCGTTCATCCTGCTGGCTGACAAGAAAATCTCCA
ACATCCGCGAAATGCTGCCGGTTCTGGAAGCTGTTGCCAAAGCAGGCAAACCGCTG
CTGATCATCGCTGAAGATGTAGAAGGCGAAGCGCTGGCAACTCTGGTTGTTAACACC
ATGCGTGGCATCGTGAAAGTCGCTGCGGTTAAAGCACCGGGCTTCGGCGATCGTCGT
AAAGCTATGCTGCAGGATATCGCAACCCTGACTGGCGGTACCGTGATCTCTGAAGA
GATCGGTATGGAGCTGGAAAAAGCAACCCTGGAAGACCTGGGTCAGGCTAAACGTG
TTGTGATCAACAAAGACACCACCACTATCATCGATGGCGTGGGTGAAGAAGCTGCA
ATCCAGGGCCGTGTTGCTCAGATCCGTCAGCAGATTGAAGAAGCAACTTCTGACTAC
GACCGTGAAAAACTGCAGGAACGCGTAGCGAAACTGGCAGGCGGCGTTGCAGTTAT
CAAAGTGGGTGCTGCTACCGAAGTTGAAATGAAAGAGAAAAAAGCACGCGTTGAAG
ATGCCCTGCACGCGACCCGTGCTGCGGTAGAAGAAGGCGTGGTTGCTGGTGGTGGT
GTTGCGCTGATCCGCGTAGCGTCTAAACTGGCTGACCTGCGTGGTCAGAACGAAGAC
CAGAACGTGGGTATCAAAGTTGCACTGCGTGCAATGGAAGCTCCGCTGCGTCAGAT
CGTATTGAACTGCGGCGAAGAACCGTCGTTGTTGCTAACACCGTTAAAGGCGGCGA
CGGCAACTACGGTTACAACGCAGCAACCGAAGAATACGGCAACATGATCGACATGG
GTATCCTGGATCCAACCAAAGTAACTCGTTCTGCTCTGCAGTACGCAGCTTCTGTGG CTGGCCTGATGATCACCACCGAATGCATGGTTACCGACCTGCCGAAAAACGATGCA
GCTGACTTAGGCGCTGCTGGCGGTATGGGCGGCATGGGTGGCATGGGCGGCATGAT
GTAA SEQ ID NO: 12 - PC2 (polycistroncic construct containing codon modified isoeugenol
monooxygenase of P. nitroreducens Jin 1, groES, groEL)
GAAGGAGATATACATATGGCACGTCTGAACCGTAATGATCCGCAACTCGTCGGCAC
CCTGTTACCAACCCGTATTGAGGCTGACCTGTTCGACCTGGAAGTGGACGGCGAAAT
TCCGAAGTCCATCAACGGTACCTTCTACCGTAACACGCCGGAGCCTCAGGTGACGCC
GCAGAAATTCCACACCTTCATCGATGGTGACGGCATGGCGTCTGCATTTCATTTTGA
AGATGGCCACGTGGACTTCATCAGCCGCTGGGTTAAAACCGCGCGTTTCACGGCGG
AGAGACTGGCACGTAAAAGCCTGTTCGGTATGTACCGTAATCCGTACACCGATGAC
ACGTCTGTGAAGGGTCTGGATCGTACCGTTGCCAACACGAGCATCATCAGCCATCAC
GGTAAGGTTCTGGCGGTGAAAGAAGATGGCTTGCCGTACGAGCTGGACCCACGCAC
TCTGGAAACCCGTGGTCGCTTTGACTATGATGGCCAAGTCACCAGCCAGACGCACAC
CGCGCATCCGAAGTATGACCCGGAAACCGGTGACCTGTTGTTCTTTGGCTCCGCAGC
CAAGGGTGAGGCAACGCCTGATATGGCCTATTACATCGTTGATAAACATGGTAAGG
TAACGCATGAGACTTGGTTCGAGCAACCGTATGGCGCCTTTATGCATGATTTTGCTA
TTACCCGCAATTGGAGCATCTTCCCGATCATGCCGGCTACCAATTCGTTGAGCCGCC
TGAAAGCGAAGCAGCCGATTTACATGTGGGAGCCGGAACTGGGTTCCTATATTGGT
GTTCTGCCGCGTCGCGGTCAAGGTAGCCAGATCCGCTGGCTGAAAGCACCAGCGCT
GTGGGTCTTTCACGTCGTCAACGCCTGGGAAGTGGGCACCAAAATCTACATTGACCT
TATGGAGAGCGAAATTCTGCCATTCCCGTTCCCGAATAGCCAAAATCAGCCGTTCGC
TCCTGAGAAAGCAGTGCCGCGTCTGACCCGTTGGGAGATTGATCTGGATAGCAGCA
GCGATGAGATTAAGCGTACGCGTCTGCACGACTTCTTTGCAGAGATGCCGATCATGG
ATTTTCGTTTTGCGCTGCAGTGCAACCGCTACGGTTTATGGGTGTCGATGACCCGCG
CAAGCCGCTGGCGCACCAACAAGCGGAGAAGATTTTTGCGTACAATAGCCTGGGTA
TCTGGGACAACCACCGTGGTGATTATGATTTGTGGTACAGCGGCGAAGCCTCAGCGG
CGCAAGAACCGGCTTTCGTTCCGCGTTCTCCGACTGCAGCGGAAGGCGACGGTTATC
TGCTGACCGTTGTGGGCCGTTTGGACGAGAACCGCAGCGACCTGGTCATTCTGGACA
CGCAGGACATCCAGAGCGGTCCGGTTGCGACCATTAAACTGCCGTTTCGCCTGCGTG
CGGCCCTGCACGGCTGTTGGGTTCCGCGTCCGTAATCCGCGCACGACACTGAACATA
CGGAAGGAGATATACATATGAATATTCGTCCATTGCATGATCGCGTGATCGTCAAGC
GTAAAGAAGTTGAAACTAAATCTGCTGGCGGCATCGTTCTGACCGGCTCTGCAGCGG
CTAAATCCACCCGCGGCGAAGTGCTGGCTGTCGGCAATGGCCGTATCCTTGAAAATG
GCGAAGTGAAGCCGCTGGATGTGAAAGTTGGCGACATCGTTATTTTCAACGATGGCT
ACGGTGTGAAATCTGAGAAGATCGACAATGAAGAAGTGTTGATCATGTCCGAAAGC
GACATTCTGGCAATTGTTGAAGCGTAATCCGCGCACGACACTGAACATACGAATTTA
AGGAATAAAGATAATGGCAGCTAAAGACGTAAAATTCGGTAACGACGCTCGTGTGA
AAATGCTGCGCGGCGTAAACGTACTGGCAGATGCAGTGAAAGTTACCCTCGGTCCA
AAAGGCCGTAACGTAGTTCTGGATAAATCTTTCGGTGCACCGACCATCACCAAAGAT
GGTGTTTCCGTTGCTCGTGAAATCGAACTGGAAGACAAGTTCGAAAATATGGGTGCG
CAGATGGTGAAAGAAGTTGCCTCTAAAGCAAACGACGCTGCAGGCGACGGTACCAC
CACTGCAACCGTACTGGCTCAGGCTATCATCACTGAAGGTCTGAAAGCTGTTGCTGC
GGGCATGAACCCGATGGACCTGAAACGTGGTATCGACAAAGCGGTTACCGCTGCAG
TTGAAGAACTGAAAGCGCTGTCCGTACCATGCTCTGACTCTAAAGCGATTGCTCAGG
TTGGTACCATCTCCGCTAACTCCGACGAAACCGTAGGTAAACTGATCGCTGAAGCGA
TGGACAAAGTCGGTAAAGAAGGCGTTATCACCGTTGAAGACGGTACCGGTCTGCAG
GACGAACTGGACGTGGTTGAAGGTATGCAGTTCGACCGTGGCTACCTGTCTCCTTAC
TTCATCAACAAGCCGGAAACTGGCGCAGTAGAACTGGAAAGCCCGTTCATCCTGCT
GGCTGACAAGAAAATCTCCAACATCCGCGAAATGCTGCCGGTTCTGGAAGCTGTTGC
CAAAGCAGGCAAACCGCTGCTGATCATCGCTGAAGATGTAGAAGGCGAAGCGCTGG
CAACTCTGGTTGTTAACACCATGCGTGGCATCGTGAAAGTCGCTGCGGTTAAAGCAC
CGGGCTTCGGCGATCGTCGTAAAGCTATGCTGCAGGATATCGCAACCCTGACTGGCG
GTACCGTGATCTCTGAAGAGATCGGTATGGAGCTGGAAAAAGCAACCCTGGAAGAC
CTGGGTCAGGCTAAACGTGTTGTGATCAACAAAGACACCACCACTATCATCGATGGC
GTGGGTGAAGAAGCTGCAATCCAGGGCCGTGTTGCTCAGATCCGTCAGCAGATTGA
AGAAGCAACTTCTGACTACGACCGTGAAAAACTGCAGGAACGCGTAGCGAAACTGG
CAGGCGGCGTTGCAGTTATCAAAGTGGGTGCTGCTACCGAAGTTGAAATGAAAGAG
AAAAAAGCACGCGTTGAAGATGCCCTGCACGCGACCCGTGCTGCGGTAGAAGAAGG
CGTGGTTGCTGGTGGTGGTGTTGCGCTGATCCGCGTAGCGTCTAAACTGGCTGACCT
GCGTGGTCAGAACGAAGACCAGAACGTGGGTATCAAAGTTGCACTGCGTGCAATGG
AAGCTCCGCTGCGTCAGATCGTATTGAACTGCGGCGAAGAACCGTCTGTTGTTGCTA
ACACCGTTAAAGGCGGCGACGGCAACTACGGTTACAACGCAGCAACCGAAGAATAC
GGCAACATGATCGACATGGGTATCCTGGATCCAACCAAAGTAACTCGTTCTGCTCTG
CAGTACGCAGCTTCTGTGGCTGGCCTGATGATCACCACCGAATGCATGGTTACCGAC
CTGCCGAAAAACGATGCAGCTGACTTAGGCGCTGCTGGCGGTATGGGCGGCATGGG
TGGCATGGGCGGCATGATGTAA SEQ ID NO: 13 - PC3 (polycistronic construct containing codon modified isoeugenol
monooxygenase of P. nitroreducens Jin 1, groES, groEL)
GAAGGAGATATACATATGGCACGTCTGAACCGTAATGATCCGCAACTCGTCGGCAC
CCTGTTACCAACCCGTATTGAGGCTGACCTGTTCGACCTGGAAGTGGACGGCGAAAT
TCCGAAGTCCATCAACGGTACCTTCTACCGTAACACGCCGGAGCCTCAGGTGACGCC
GCAGAAATTCCACACCTTCATCGATGGTGACGGCATGGCGTCTGCATTTCATTTTGA
AGATGGCCACGTGGACTTCATCAGCCGCTGGGTTAAAACCGCGCGTTTCACGGCGG
AGAGACTGGCACGTAAAAGCCTGTTCGGTATGTACCGTAATCCGTACACCGATGAC

```
ACGTCTGTGAAGGGTCTGGATCGTACCGTTGCCAACACGAGCATCATCAGCCATCAC
GGTAAGGTTCTGGCGGTGAAAGAAGATGGCTTGCCGTACGAGCTGGACCCACGCAC
TCTGGAAACCCGTGGTCGCTTTGACTATGATGGCCAAGTCACCAGCCAGACGCACAC
CGCGCATCCGAAGTATGACCCGGAAACCGGTGACCTGTTGTTCTTTGGCTCCGCAGC
CAAGGGTGAGGCAACGCCTGATATGGCCTATTACATCGTTGATAAACATGGTAAGG
TAACGCATGAGACTTGGTTCGAGCAACCGTATGGCGCCTTTATGCATGATTTTGCTA
TTACCCGCAATTGGAGCATCTTCCCGATCATGCCGGCTACCAATTCGTTGAGCCGCC
TGAAAGCGAAGCAGCCGATTTACATGTGGGAGCCGGAACTGGGTTCCTATATTGGT
GTTCTGCCGCGTCGCGGTCAAGGTAGCCAGATCCGCTGGCTGAAAGCACCAGCGCT
GTGGGTCTTTCACGTCGTCAACGCCTGGGAAGTGGGCACCAAAATCTACATTGACCT
TATGGAGAGCGAAATTCTGCCATTCCCGTTCCCGAATAGCCAAAATCAGCCGTTCGC
TCCTGAGAAAGCAGTGCCGCGTCTGACCCGTTGGGAGATTGATCTGGATAGCAGCA
GCGATGAGATTAAGCGTACGCGTCTGCACGACTTCTTTGCAGAGATGCCGATCATGG
ATTTTCGTTTTGCGCTGCAGTGCAACCGCTACGGTTTTATGGGTGTCGATGACCCGCG
CAAGCCGCTGGCGCACCAACAAGCGGGAGAAGATTTTTGCGTACAATAGCCTGGGTA
TCTGGGACAACCACCGTGGTGATTATGATTTGTGGTACAGCGGCGAAGCCTCAGCGG
CGCAAGAACCGGCTTTCGTTCCGCGTTCTCCGACTGCAGCGGAAGGCGACGGTTATC
TGCTGACCGTTGTGGGCCGTTTGGACGAGAACCGCAGCGACCTGGTCATTCTGGACA
CGCAGGACATCCAGAGCGGTCCGGTTGCGACCATTAAACTGCCGTTTCGCCTGCGTG
CGGCCCTGCACGGCTGTTGGGTTCCGCGTCCGTAAAATTAGGTAAAAAATAAAAAA
TGAATATTCGTCCATTGCATGATCGCGTGATCGTCAAGCGTAAAGAAGTTGAAACTA
AATCTGCTGGCGGCATCGTTCTGACCGGCTCTGCAGCGGCTAAATCCACCCGCGGCG
AAGTGCTGGCTGTCGGCAATGGCCGTATCCTTGAAAATGGCGAAGTGAAGCCGCTG
GATGTGAAAGTTGGCGACATCGTTATTTTCAACGATGGCTACGGTGTGAAATCTGAG
AAGATCGACAATGAAGAAGTGTTGATCATGTCCGAAAGCGACATTCTGGCAATTGTT
GAAGCGTAATCCGCGCACGACACTGAACATACGAATTTAAGGAATAAAGATAATGG
CAGCTAAAGACGTAAAATTCGGTAACGACGCTCGTGTGAAAATGCTGCGCGGCGTA
AACGTACTGGCAGATGCAGTGAAAGTTACCCTCGGTCCAAAAGGCCGTAACGTAGT
TCTGGATAAATCTTTCGGTGCACCGACCATCACCAAAGATGGTGTTTCCGTTGCTCG
TGAAATCGAACTGGAAGACAAGTTCGAAAATATGGGTGCGCAGATGGTGAAAGAAG
TTGCCTCTAAAGCAAACGACGCTGCAGGCGACGGTACCACCACTGCAACCGTACTG
GCTCAGGCTATCATCACTGAAGGTCTGAAAGCTGTTGCTGCGGGCATGAACCCGATG
GACCTGAAACGTGGTATCGACAAAGCGGTTACCGCTGCAGTTGAAGAACTGAAAGC
GCTGTCCGTACCATGCTCTGACTCTAAAGCGATTGCTCAGGTTGGTACCATCTCCGCT
AACTCCGACGAAACCGTAGGTAAACTGATCGCTGAAGCGATGGACAAAGTCGGTAA
AGAAGGCGTTATCACCGTTGAAGACGGTACCGGTCTGCAGGACGAACTGGACGTGG
TTGAAGGTATGCAGTTCGACCGTGGCTACCTGTCTCCTTACTTCATCAACAAGCCGG
AAACTGGCGCAGTAGAACTGGAAAGCCCGTTCATCCTGCTGGCTGACAAGAAAATC
TCCAACATCCGCGAAATGCTGCCGGTTCTGGAAGCTGTTGCCAAAGCAGGCAAACC
GCTGCTGATCATCGCTGAAGATGTAGAAGGCGAAGCGCTGGCAACTCTGGTTGTTAA
CACCATGCGTGGCATCGTGAAAGTCGCTGCGGTTAAAGCACCGGGCTTCGGCGATC
GTCGTAAAGCTATGCTGCAGGATATCGCAACCCTGACTGGCGGTACCGTGATCTCTG
AAGAGATCGGTATGGAGCTGGAAAAAGCAACCCTGGAAGACCTGGGTCAGGCTAAA
CGTGTTGTGATCAACAAAGACACCACCACTATCATCGATGGCGTGGGTGAAGAAGC
TGCAATCCAGGGCCGTGTTGCTCAGATCCGTCAGCAGATTGAAGAAGCAACTTCTGA
CTACGACCGTGAAAAACTGCAGGAACGCGTAGCGAAACTGGCAGGCGGCGTTGCAG
TTATCAAAGTGGGTGCTGCTACCGAAGTTGAAATGAAAGAGAAAAAGCACGCGTT
GAAGATGCCCTGCACGCGACCCGTGCTGCGGTAGAAGAAGGCGTGGTTGCTGGTGG
TGGTGTTGCGCTGATCCGCGTAGCGTCTAAACTGGCTGACCTGCGTGGTCAGAACGA
AGACCAGAACGTGGGTATCAAAGTTGCACTGCGTGCAATGGAAGCTCCGCTGCGTC
AGATCGTATTGAACTGCGGCGAAGAACCGTCGTTGTTGCTAACACCGTTAAAGGCG
GCGACGGCAACTACGGTTACAACGCAGCAACCGAAGAATACGGCAACATGATCGAC
ATGGGTATCCTGGATCCAACCAAAGTAACTCGTTCTGCTCTGCAGTACGCAGCTTCT
GTGGCTGGCCTGATGATCACCACCGAATGCATGGTTACCGACCTGCCGAAAAACGA
TGCAGCTGACTTAGGCGCTGCTGGCGGTATGGGCGGCATGGGTGGCATGGGCGGCA
TGATGTAA
```

SEQ ID NO: 14 - PC4 (polycistroncic construct containing codon modified isoeugenol monooxygenase of P. nitroreducens Jin 1, groES, groEL)

```
GAAGGAGATATACATATGGCACGTCTGAACCGTAATGATCCGCAACTCGTCGGCAC
CCTGTTACCAACCCGTATTGAGGCTGACCTGTTCGACCTGGAAGTGGACGGCGAAAT
TCCGAAGTCCATCAACGGTACCTTCTACCGTAACACGCCGGAGCCTCAGGTGACGCC
GCAGAAATTCCACACCTTCATCGATGGTGACGGCATGGCGTCTGCATTTCATTTTGA
AGATGGCCACGTGGACTTCATCAGCCGCTGGGTTAAAACCGCGCGTTTCACGGCGG
AGAGACTGGCACGTAAAAGCCTGTTCGGTATGTACCGTAATCCGTACACCGATGAC
ACGTCTGTGAAGGGTCTGGATCGTACCGTTGCCAACACGAGCATCATCAGCCATCAC
GGTAAGGTTCTGGCGGTGAAAGAAGATGGCTTGCCGTACGAGCTGGACCCACGCAC
TCTGGAAACCCGTGGTCGCTTTGACTATGATGGCCAAGTCACCAGCCAGACGCACAC
CGCGCATCCGAAGTATGACCCGGAAACCGGTGACCTGTTGTTCTTTGGCTCCGCAGC
CAAGGGTGAGGCAACGCCTGATATGGCCTATTACATCGTTGATAAACATGGTAAGG
TAACGCATGAGACTTGGTTCGAGCAACCGTATGGCGCCTTTATGCATGATTTTGCTA
TTACCCGCAATTGGAGCATCTTCCCGATCATGCCGGCTACCAATTCGTTGAGCCGCC
TGAAAGCGAAGCAGCCGATTTACATGTGGGAGCCGGAACTGGGTTCCTATATTGGT
GTTCTGCCGCGTCGCGGTCAAGGTAGCCAGATCCGCTGGCTGAAAGCACCAGCGCT
GTGGGTCTTTCACGTCGTCAACGCCTGGGAAGTGGGCACCAAAATCTACATTGACCT
TATGGAGAGCGAAATTCTGCCATTCCCGTTCCCGAATAGCCAAAATCAGCCGTTCGC
TCCTGAGAAAGCAGTGCCGCGTCTGACCCGTTGGGAGATTGATCTGGATAGCAGCA
```

```
GCGATGAGATTAAGCGTACGCGTCTGCACGACTTCTTTGCAGAGATGCCGATCATGG
ATTTTCGTTTTGCGCTGCAGTGCAACCGCTACGGTTTTATGGGTGTCGATGACCCGCG
CAAGCCGCTGGCGCACCAACAAGCGGGAGAAGATTTTTGCGTACAATAGCCTGGGTA
TCTGGGACAACCACCGTGGTGATTATGATTTGTGGTACAGCGGCGAAGCCTCAGCGG
CGCAAGAACCGGCTTTCGTTCCGCGTTCTCCGACTGCAGCGGAAGGCGACGGTTATC
TGCTGACCGTTGTGGGCCGTTTGGACGAGAACCGCAGCGACCTGGTCATTCTGGACA
CGCAGGACATCCAGAGCGGTCCGGTTGCGACCATTAAACTGCCGTTTCGCCTGCGTG
CGGCCCTGCACGGCTGTTGGGTTCCGCGTCCGTAAGAAGGAGATATACATATGAATA
TTCGTCCATTGCATGATCGCGTGATCGTCAAGCGTAAAGAAGTTGAAACTAAATCTG
CTGGCGGCATCGTTCTGACCGGCTCTGCAGCGGCTAAATCCACCCGCGGCGAAGTGC
TGGCTGTCGGCAATGGCCGTATCCTTGAAAATGGCGAAGTGAAGCCGCTGGATGTG
AAAGTTGGCGACATCGTTATTTTCAACGATGGCTACGGTGTGAAATCTGAGAAGATC
GACAATGAAGAAGTGTTGATCATGTCCGAAAGCGACATTCTGGCAATTGTTGAAGC
GTAAGAAGGAGATATACATATGGCAGCTAAAGACGTAAAATTCGGTAACGACGCTC
GTGTGAAAATGCTGCGCGGCGTAAACGTACTGGCAGATGCAGTGAAAGTTACCCTC
GGTCCAAAAGGCCGTAACGTAGTTCTGGATAAATCTTTCGGTGCACCGACCATCACC
AAAGATGGTGTTTCCGTTGCTCGTGAAATCGAACTGGAAGACAAGTTCGAAAATAT
GGGTGCGCAGATGGTGAAAGAAGTTGCCTCTAAAGCAAACGACGCTGCAGGCGACG
GTACCACCACTGCAACCGTACTGGCTCAGGCTATCATCACTGAAGGTCTGAAAGCTG
TTGCTGCGGGCATGAACCCGATGGACCTGAAACGTGGTATCGACAAAGCGGTTACC
GCTGCAGTTGAAGAACTGAAAGCGCTGTCCGTACCATGCTCTGACTCTAAAGCGATT
GCTCAGGTTGGTACCATCTCCGCTAACTCCGACGAAACCGTAGGTAAACTGATCGCT
GAAGCGATGGACAAAGTCGGTAAAGAAGGCGTTATCACCGTTGAAGACGGTACCGG
TCTGCAGGACGAACTGGACGTGGTTGAAGGTATGCAGTTCGACCGTGGCTACCTGTC
TCCTTACTTCATCAACAAGCCGGAAACTGGCGCAGTAGAACTGGAAAGCCCGTTCAT
CCTGCTGGCTGACAAGAAAATCTCCAACATCCGCGAAATGCTGCCGGTTCTGGAAG
CTGTTGCCAAAGCAGGCAAACCGCTGCTGATCATCGCTGAAGATGTAGAAGGCGAA
GCGCTGGCCAACTCTGGTTGTTAACACCATGCGTGGCATCGTGAAAGTGCTGCGGTT
AAAGCACCGGGCTTCGGCGATCGTCGTAAAGCTATGCTGCAGGATATCGCAACCCT
GACTGGCGGTACCGTGATCTCTGAAGAGATCGGTATGGAGCTGGAAAAAGCAACCC
TGGAAGACCTGGGTCAGGCTAAACGTGTTGTGATCAACAAAGACACCACCACTATC
ATCGATGGCGTGGGTGAAGAAGCTGCAATCCAGGGCCGTGTTGCTCAGATCCGTCA
GCAGATTGAAGAAGCAACTTCTGACTACGACCGTGAAAAACTGCAGGAACGCGTAG
CGAAACTGGCAGGCGGCGTTGCAGTTATCAAAGTGGGTGCTGCTACCGAAGTTGAA
ATGAAAGAGAAAAAAGCACGCGTTGAAGATGCCCTGCACGCGACCCGTGCTGCGGT
AGAAGAAGGCGTGGTTGCTGGTGGTGGTGTTGCGCTGATCCGCGTAGCGTCTAAACT
GGCTGACCTGCGTGGTCAGAACGAAGACCAGAACGTGGGTATCAAAGTTGCACTGC
GTGCAATGGAAGCTCCGCTGCGTCAGATCGTATTGAACTGCGGCGAAGAACCGTCT
GTTGTTGCTAACACCGTTAAAGGCGGCGACGGCAACTACGGTTACAACGCAGCAAC
CGAAGAATACGGCAACATGATCGACATGGGTATCCTGGATCCAACCAAAGTAACTC
GTTCTGCTCTGCAGTACGCAGCTTCTGTGGCTGGCCTGATGATCACCACCGAATGCA
TGGTTACCGACCTGCCGAAAAACGATGCAGCTGACTTAGGCGCTGCTGGCGGTATG
GGCGGCATGGGTGGCATGGGCGGCATGATGTAA
```

SEQ ID NO: 15 - PC5 (polycistroncic construct containing codon modified isoeugenol monooxygenase of *P. nitroreducens* Jin 1, groES, groEL)
```
GAAGGAGATATACATATGGCACGTCTGAACCGTAATGATCCGCAACTCGTCGGCAC
CCTGTTACCAACCCGTATTGAGGCTGACCTGTTCGACCTGGAAGTGGACGGCGAAAT
TCCGAAGTCCATCAACGGTACCTTCTACCGTAACACGCCGGAGCCTCAGGTGACGCC
GCAGAAATTCCACACCTTCATCGATGGTGACGGCATGGCGTCTGCATTTCATTTTGA
AGATGGCCACGTGGACTTCATCAGCCGCTGGGTTAAAACCGCGCGTTTCACGGCGG
AGAGACTGGCACGTAAAAGCCTGTTCGGTATGTACCGTAATCCGTACACCGATGAC
ACGTCTGTGAAGGGTCTGGATCGTACCGTTGCCAACACGAGCATCATCAGGCCATCAC
GGTAAGGTTCTGGCGGTGAAAGAAGATGGCTTGCCGTACGAGCTGGACCCACGCAC
TCTGGAAACCCGTGGTCGCTTTGACTATGATGGCCAAGTCACCAGCCAGACGCACAC
CGCGCATCCGAAGTATGACCCGGAAACCGGTGACCTGTTGTTCTTTGGCTCCGCAGC
CAAGGGTGAGGCAACGCCTGATATGGCCTATTACATCGTTGATAAACATGGTAAGG
TAACGCATGAGACTTGGTTCGAGCAACCGTATGGCGCCTTTATGCATGATTTTGCTA
TTACCCGCAATTGGAGCATCTTCCCGATCATGCCGGCTACCAATTCGTTGAGCCGCC
TGAAAGCGAAGCAGCCGATTTACATGTGGGAGCCGGAACTGGGTTCCTATATTGGT
GTTCTGCCGCGTCGCGGTCAAGGTAGCCAGATCCGCTGGCTGAAAGCACCAGCGCT
GTGGGTCTTTCACGTCGTCAACGCCTGGGAAGTGGGCACCAAAATCTACATTGACCT
TATGGAGAGCGAAATTCTGCCATTCCCGTTCCCGAATAGCCAAAATCAGCCGTTCGC
TCCTGAGAAAGCAGTGCCGCGTCTGACCCGTTGGGAGATTGATCTGGATAGCAGCA
GCGATGAGATTAAGCGTACGCGTCTGCACGACTTCTTTGCAGAGATGCCGATCATGG
ATTTTCGTTTTGCGCTGCAGTGCAACCGCTACGGTTTTATGGGTGTCGATGACCCGCG
CAAGCCGCTGGCGCACCAACAAGCGGGAGAAGATTTTTGCGTACAATAGCCTGGGTA
TCTGGGACAACCACCGTGGTGATTATGATTTGTGGTACAGCGGCGAAGCCTCAGCGG
CGCAAGAACCGGCTTTCGTTCCGCGTTCTCCGACTGCAGCGGAAGGCGACGGTTATC
TGCTGACCGTTGTGGGCCGTTTGGACGAGAACCGCAGCGACCTGGTCATTCTGGACA
CGCAGGACATCCAGAGCGGTCCGGTTGCGACCATTAAACTGCCGTTTCGCCTGCGTG
CGGCCCTGCACGGCTGTTGGGTTCCGCGTCCGTAAAAGATAGCAAAAATAAAAAA
TGAATATTCGTCCATTGCATGATCGCGTGATCGTCAAGCGTAAAGAAGTTGAAACTA
AATCTGCTGGCGGCATCGTTCTGACCGGCTCTGCAGCGGCTAAATCCACCCGCGGCG
AAGTGCTGGCTGTCGGCAATGGCCGTATCCTTGAAAATGGCGAAGTGAAGCCGCTG
GATGTGAAAGTTGGCGACATCGTTATTTTCAACGATGGCTACGGTGTGAAATCTGAG
AAGATCGACAATGAAGAAGTGTTGATCATGTCCGAAAGCGACATTCTGGCAATTGTT
```

```
GAAGCGTAATCCGCGCACGACACTGAACATACGAATTTAAGGAATAAAGATAATGG
CAGCTAAAGACGTAAAATTCGGTAACGACGCTCGTGTGAAAATGCTGCGCGGCGTA
AACGTACTGGCAGATGCAGTGAAAGTTACCCTCGGTCCAAAAGGCCGTAACGTAGT
TCTGGATAAATCTTTCGGTGCACCGACCATCACCAAAGATGGTGTTTCCGTTGCTCG
TGAAATCGAACTGGAAGACAAGTTCGAAAATATGGGTGCGCAGATGGTGAAAGAAG
TTGCCTCTAAAGCAAACGACGCTGCAGGCGACGGTACCACCACTGCAACCGTACTG
GCTCAGGCTATCATCACTGAAGGTCTGAAAGCTGTTGCTGCGGGCATGAACCCGATG
GACCTGAAACGTGGTATCGACAAAGCGGTTACCGCTGCAGTTGAAGAACTGAAAGC
GCTGTCCGTACCATGCTCTGACTCTAAAGCGATTGCTCAGGTTGGTACCATCTCCGCT
AACTCCGACGAAACCGTAGGTAAACTGATCGCTGAAGCGATGGACAAAGTCGGTAA
AGAAGGCGTTATCACCGTTGAAGACGGTACCGGTCTGCAGGACGAACTGGACGTGG
TTGAAGGTATGCAGTTCGACCGTGGCTACCTGTCTCCTTACTTCATCAACAAGCCGG
AAACTGGCGCAGTAGAACTGGAAAGCCCGTTCATCCTGCTGGCTGACAAGAAAATC
TCCAACATCCGCGAAATGCTGCCGGTTCTGGAAGCTGTTGCCAAAGCAGGCAAACC
GCTGCTGATCATCGCTGAAGATGTAGAAGGCGAAGCGCTGGCAACTCTGGTTGTTAA
CACCATGCGTGGCATCGTGAAAGTCGCTGCGGTTAAAGCACCGGGCTTCGGCGATC
GTCGTAAAGCTATGCTGCAGGATATCGCAACCCTGACTGGCGGTACCGTGATCTCTG
AAGAGATCGGTATGGAGCTGGAAAAAGCAACCCTGGAAGACCTGGGTCAGGCTAAA
CGTGTTGTGATCAACAAAGACACCACCACTATCATCGATGGCGTGGGTGAAGAAGC
TGCAATCCAGGGCCGTGTTGCTCAGATCCGTCAGCAGATTGAAGAAGCAACTTCTGA
CTACGACCGTGAAAAACTGCAGGAACGCGTAGCGAAACTGGCAGGCGGCGTTGCAG
TTATCAAAGTGGGTGCTGCTACCGAAGTTGAAATGAAAGAGAAAAAAGCACGCGTT
GAAGATGCCCTGCACGCGACCCGTGCTGCGGTAGAAGAAGGCGTGGTTGCTGGTGG
TGGTGTTGCGCTGATCCGCGTAGCGTCTAAACTGGCTGACCTGCTGGTCAGAACGA
AGACCAGAACGTGGGTATCAAAGTTGCACTGCGTGCAATGGAAGCTCCGCTGCGTC
AGATCGTATTGAACTGCGGCGAAGAACCGTCTGTTGTTGCTAACACCGTTAAAGGCG
GCGACGGCAACTACGGTTACAACGCAGCAACCGAAGAATACGGCAACATGATCGAC
ATGGGTATCCTGGATCCAACCAAAGTAACTCGTTCTGCTCTGCAGTACGCAGCTTCT
GTGGCTGGCCTGATGATCACCACCGAATGCATGGTTACCGACCTGCCGAAAAACGA
TGCAGCTGACTTAGGCGCTGCTGGCGGTATGGGCGGCATGGGTGGCATGGGCGGCA
TGATGTAA
```

SEQ ID NO: 16 pIEM2_C154_T222_A1318

```
ttaataagat gatcttcttg agatcgtttt ggtctgcgcg taatctcttg ctctgaaaac          60
gaaaaaaccg ccttgcaggg cggttttcg aaggttctct gagctaccaa ctctttgaac         120
cgaggtaact ggcttggagg agcgcagtca ccaaaacttg tcctttcagt ttagccttaa        180
ccggcgcatg acttcaagac taactcctct aaatcaatta ccagtggctg ctgccagtgg        240
tgcttttgca tgtctttccg ggttggactc aagacgatag ttaccggata aggcgcagcg        300
gtcggactga acgggggggtt cgtgcataca gtccagcttg gagcgaactg cctacccgga       360
actgagtgtc aggcgtggaa tgagacaaac gcggccataa cagcggaatg acaccggtaa       420
accgaaaggc aggaacagga gagcgcacga gggagccgcc aggggggaaac gcctggtatc      480
tttatagtcc tgtcgggttt cgccaccact gatttgagcg tcagatttcg tgatgcttgt       540
cagggggggcg gagcctatgg aaaaacggct ttgccgcggc cctctcactt ccctgttaag      600
tatcttcctg gcatcttcca ggaaatctcc gccccgttcg taagccattt ccgctcgccg      660
cagtcgaacg accgagcgta gcgagtcagt gagcgaggaa gcggaatata tcctgtatca      720
catattctgc tgacgcaccg gtgcagcctt ttttctcctg ccacatgaag cacttcactg      780
acaccctcat cagtgccaac atagtaagcc agtatacact ccgctagcgc tgaggtcccg      840
cagccgaacg accgagcgca gcgagtcagt gagcgaggaa gcggaaggcg agagtaggga      900
actgccaggc atcaaactaa gcagaaggcc cctgacggat ggccttttg cgtttctaca       960
aactcttttct gtgttgtaaa acgacggcca gtcttaagct cgggcccct gggcggttct    1020
gataacgagt aatcgttaat ccgcaaataa cgtaaaaacc cgcttcggcg ggttttttta     1080
tggggggagt ttagggaaag agcatttgtc agaatatttta agggcgcctg tcactttgct    1140
tgatatatga gaattattta accttataaa tgagaaaaaa gcaacgcact ttaaataaga     1200
tacgttgctt tttcgattga tgaacaccta taattaaact attcatctat tatttatgat    1260
tttttgtata tacaatattt ctagtttgtt aaagagaatt aagaaaataa atctcgaaaa    1320
taataaaggg aaaatcagtt tttgatatca aaattataca tgtcaacgat aatacaaaat   1380
ataatacaaa ctataagatg ttatcagtat ttattatgca tttagaataa atttttgtgtc  1440
gcccttccgc gaaattaata cgactcacta taggggaatt gtgagcggat aacaattccc   1500
ctctagaaat aattttgttt aacttttgaa ggagatatac atatggcaac gtttgaccgc   1560
aatgatccgc agttggcagg aacgatgttc cccacccgaa tagaggcgaa tgtctttgac   1620
cttgaaattg agggcgagat cccacgtgca atcaacggga gcttcttccg caacacccc    1680
gaacctcagg tcacccgcga accttccac accttcatcg atgggggatgg tttggcgtca  1740
gcttttcatt tcgaagatgg ccatgtcgac tttgtcagcc gttgggtatg tactcctcgc   1800
tttgaagctg agcggtcggc tcgtaaatca ctcttcggta tgtaccgcaa tccgttcact  1860
gatgatccat cggtagaagg tattgatcgt acagtcgcca acaccagtat catcactcat  1920
cacgggaaag tactggccgc aaaggaagat ggactacctt atgagcttga ccccaaacc    1980
ctggaaccc gaggtcgtta tgattacaag gggcaggtaa ccagccatac acatacagcg   2040
caccctaagt tcgacccca gacaggtgaa atgttactct tcggctccgc tgctaaaggc   2100
gaacgaacgc ttgatatggc gtactatatt gttgatcgct acggcaaggt gacacatgag  2160
acctggttta agcagcctta cggtgcattc atgcacgact ttgctgtcac gcgcaactgg  2220
tcaatctttc cgatcatgcc tgcgacaaat agccttgagc gtcttaaagc aaagcagccc  2280
atttacatgt gggagcctga gcgaggaagc tatataggat tacttcctcg tcgtggtcag  2340
ggcaaggaca ttcgttggtt ccgtgcccgc gcgttgtggg ttttccatgt cgtgaatgct  2400
tgggaggaag ggaatagaat tctgattgac ttgatgaaa gtgagatttt gccgttccca   2460
ttcccgaact cgcagaacct tccatttgat ccctccaagg ctgttccgcg tctaacccgt   2520
tgggaaattg atctcaatag tggtaacgat gagatgaaac gtacgcagct acacgaatat  2580
tttgcagaaa tgcctatcat ggatttccgt tttgcgctcc aggatcatcg ctacgcctac  2640
```

-continued

| Sequence Listing | |
|---|---|
| atgggggttg acgatcctcg tcgcccctta gctcatcagc aagctgaaaa aatctttgcc | 2700 |
| tacaattcgt taggggtttg ggacaaccat cgtaaagatt atgaactttg gtttacggga | 2760 |
| aaaatgtctg cagcgcagga accggcgttt gttcctagaa gcccagatgc gcctgagggc | 2820 |
| gatggctacc tactcagtgt agtagggcgg ctcgatgaaa atcgtagcga tctagttatc | 2880 |
| cttgatacgc aatgtttggc agctgggcct gtggccactg tcaagcttcc cttccgtctc | 2940 |
| cgagcagcgt tgcacggttg ttggcagtct aagaactgag gatccgaatt cgagctcccc | 3000 |
| cctagcataa cccccttggg cctctaaacg ggtcttgagg ggttttttgc ccctgagacg | 3060 |
| cgtcaatcga gttcgtacct aagggcgaca cccctaatt agcccgggcg aaaggcccag | 3120 |
| tctttcgact gagcctttcg ttttatttga tgcctggcag ttccctactc tcgcatgggg | 3180 |
| agtccccaca ctaccatcgg cgctacgcg tttcacttct gagttcggca tggggtcagg | 3240 |
| tgggaccacc gcgctactgc cgccaggcaa acaaggggtg ttatgagcca tattcaggta | 3300 |
| taaatgggct cgcgataatg ttcagaattg gttaattggt tgtaacactg accctatt | 3360 |
| gtttattttt ctaaatacat tcaaatatgt atccgctcat gagacaataa ccctgataaa | 3420 |
| tgcttcaata atattgaaaa aggaagaata tgagccatat tcaacgggaa acgtcgaggc | 3480 |
| cgcgattaaa ttccaacatg gatgctgatt tatatgggta taaatgggct cgcgataatg | 3540 |
| tcgggcaatc aggtgcgaca atctatcgct tgtatgggaa gcccgatgcg ccagagttgt | 3600 |
| ttctgaaaca tggcaaaggt agcgttgcca atgatgttac agatgagatg gtcagactaa | 3660 |
| actggctgac ggaatttatg ccacttccga ccatcaagca ttttatccgt actcctgatg | 3720 |
| atgcatggtt actcaccact gcgatcccg gaaaacagc gttccaggta ttagaagaat | 3780 |
| atcctgattc aggtgaaaat attgttgatg cgctggcagt gttcctgcgc cggttgcact | 3840 |
| cgattcctgt ttgtaattgt cctttaaca gcgatcgcgt atttcgcctc gctcaggcgc | 3900 |
| aatcacgaat gaataacggt ttggttgatg cgagtgattt tgatgacgag cgtaatggct | 3960 |
| ggcctgttga acaagtctgg aaagaaatgc ataaactttt gccattctca ccggattcag | 4020 |
| tcgtcactca tggtgatttc tcacttgata acctatttt tgacgagggg aaattaatag | 4080 |
| gttgtattga tgttggacga tcggaatcg cagaccgata ccaggatctt gccatcctat | 4140 |
| ggaactgcct cggtgagttt tctccttcat tacagaaacg gcttttttcaa aaatatggta | 4200 |
| ttgataatcc tgatatgaat aaattgcagt ttcatttgat gctcgatgag ttttttctaag | 4260 |
| cggcgcgcca tcgaatggcg caaaaccttt cgcggtatgg catgatagcg cccggaagag | 4320 |
| agtcaattca gggtggtgaa tatgaaacca gtaacgttat acgatgtcgc agagtatgcc | 4380 |
| ggtgtctctt atcagaccgt ttcccgcgtg gtgaaccagg ccagccacgt ttctgcgaaa | 4440 |
| acgcgggaaa aagtggaagc ggcgatggcg gagctgaatt acattcccaa ccgcgtggca | 4500 |
| caacaactgg cgggcaaaca gtcgttgctg attggcgttg ccacctccag tctggccctg | 4560 |
| cacgcgccgt cgcaaattgt cgcggcgatt aaatctcgcg ccgatcaact gggtgctcagc | 4620 |
| gtggtggtgt cgatggtaga acgaagcggc gtcgaagcct gtaaagcggc ggtgcacaat | 4680 |
| cttctcgcgc aacgcgtcag tgggctgatc attaactatc cgctgatga ccaggatgcc | 4740 |
| attgctgtgg aagctgcctg cactaatgtt ccggcgttat tcttgatgt ctctgaccag | 4800 |
| acacccatca acagtattat tttctcccat gaggacggta cgcgactggg cgtggagcat | 4860 |
| ctggtcgcat tgggtcacca gcaaatcgcg ctgttagcgg gcccattaag ttctgtctcg | 4920 |
| gcgcgtctgc gtctggctgg ctggcataaa tatctcactc gcaatcaaat tcagccgata | 4980 |
| gcggaacggg aaggcgactg gagtgccatg tccggttttc aacaaaccat gcaaatgctg | 5040 |
| aatgagggca tcgttcccac tgcgatgctg gttgccaacg atcagatggc gctgggcgca | 5100 |
| atgcgcgcca ttaccgagtc cgggctgcgc gttggtgcgg atatctcggt agtgggatac | 5160 |
| gacgataccg aagatagctc atgttatatc ccgccgttaa ccaccatcaa acaggatttt | 5220 |
| cgcctgctgg ggcaaaccag cgtggaccgc ttgctgcaac tctctcaggg ccaggcggtg | 5280 |
| aagggcaatc agctgttgcc agtctcactg gtgaaaagaa aaaccaccct ggcgcccaat | 5340 |
| acgcaaaccg cctctccccg cgcgttggcc gattcattaa tgcagctggc acgacaggtt | 5400 |
| tcccgactgg aaagcgggca gtga | 5424 |

SEQ ID NO: 17: Plasmid construct trc/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAAATCAGTTTTTGATATCAAAATTATACATGTCA
ACGATAATACAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC

```
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCAAGAACTGACTAGCATAACCCCTTGGGGCCTCTAAACGGGTCTTG
AGGGGTTTTTTGGCATCCTGTCCATGACTCGGTGACAATTAATTATCCGGCTCGTATA
ATGTGTGGAATTGTGAGCGGATAACAATTCCCTCTAGAAATAATTTTGTTTAACTTTT
AAAGGAGAGTTATCAATGAATATTCGTCCATTGCATGATCGCGTGATCGTCAAGCGT
AAAGAAGTTGAAACTAAATCTGCTGGCGGCATCGTTCTGACCGGCTCTGCAGCGGCT
AAATCCACCCGCGGCGAAGTGCTGGCTGTCGGCAATGGCCGTATCCTTGAAAATGG
CGAAGTGAAGCCGCTGGATGTGAAAGTTGGCGACATCGTTATTTTCAACGATGGCTA
CGGTGTGAAATCTGAGAAGATCGACAATGAAGAAGTGTTGATCATGTCCGAAAGCG
ACATTCTGGCAATTGTTGAAGCGTAATCCGCGCACGACACTGAACATACGAATTTAA
GGAATAAAGATAATGGCAGCTAAAGACGTAAAATTCGGTAACGACGCTCGTGTGAA
AATGCTGCGCGGCGTAAACGTACTGGCAGATGCAGTGAAAGTTACCCTCGGTCCAA
AAGGCCGTAACGTAGTTCTGGATAAATCTTTCGGTGCACCGACCATCACCAAAGATG
GTGTTTCCGTTGCTCGTGAAATCGAACTGGAAGACAAGTTCGAAAATATGGGTGCGC
AGATGGTGAAAGAAGTTGCCTCTAAAGCAAACGACGCTGCAGGCGACGGTACCACC
ACTGCAACCGTACTGGCTCAGGCTATCATCACTGAAGGTCTGAAAGCTGTTGCTGCG
GGCATGAACCCGATGGACCTGAAACGTGGTATCGACAAAGCGGTTACCGCTGCAGT
TGAAGAACTGAAAGCGCTGTCCGTACCATGCTCTGACTCTAAAGCGATTGCTCAGGT
TGGTACCATCTCCGCTAACTCCGACGAAACCGTAGGTAAACTGATCGCTGAAGCGAT
GGACAAAGTCGGTAAAGAAGGCGTTATCACCGTTGAAGACGGTACCGGTCTGCAGG
ACGAACTGGACGTGGTTGAAGGTATGCAGTTCGACCGTGGCTACCTGTCTCCTTACT
TCATCAACAAGCCGGAAACTGGCGCAGTAGAACTGGAAAGCCCGTTCATCCTGCTG
GCTGACAAGAAAATCTCCAACATCCGCGAAATGCTGCCGGTTCTGGAAGCTGTTGCC
AAAGCAGGCAAACCGCTGCTGATCATCGCTGAAGATGTAGAAGGCGAAGCGCTGGC
AACTCTGGTTGTTAACACCATGCGTGGCATCGTGAAAGTCGCTGCGGTTAAAGCACC
GGGCTTCGGCGATCGTCGTAAAGCTATGCTGCAGGATATCGCAACCCTGACTGGCGG
TACCGTGATCTCTGAAGAGATCGGTATGGAGCTGGAAAAAGCAACCCTGGAAGACC
TGGGTCAGGCTAAACGTGTTGTGATCAACAAAGACACCACCACTATCATCGATGGC
GTGGGTGAAGAAGCTGCAATCCAGGGCCGTGTTGCTCAGATCCGTCAGCAGATTGA
AGAAGCAACTTCTGACTACGACCGTGAAAAACTGCAGGAACGCGTAGCGAAACTGG
CAGGCGGCGTTGCAGTTATCAAAGTGGGTGCTGCTACCGAAGTTGAAATGAAAGAG
AAAAAAGCACGCGTTGAAGATGCCCTGCACGCGACCCGTGCTGCGGTAGAAGAAGG
CGTGGTTGCTGGTGGTGGTGTTGCGCTGATCCGCGTAGCGTCTAAACTGGCTGACCT
GCGTGGTCAGAACGAAGACCAGAACGTGGGTATCAAAGTTGCACTGCGTGCAATGG
AAGCTCCGCTGCGTCAGATCGTATTGAACTGCGGCGAAGAACCGTCTGTTGTTGCTA
ACACCGTTAAAGGCGGCGACGGCAACTACGGTTACAACGCAGCAACCGAAGAATAC
GGCAACATGATCGACATGGGTATCCTGGATCCAACCAAAGTAACTCGTTCTGCTCTG
CAGTACGCAGCTTCTGTGGCTGGCCTGATGATCACCACCGAATGCATGGTTACCGAC
CTGCCGAAAAACGATGCAGCTGACTTAGGCGCTGCTGGCGGTATGGGCGGCATGGG
TGGCATGGGCGGCATGATGTAACCCCTAGCATAACCCCTTGGGGCCTCTAAACGG
GTCTTGAGGGGTTTTTTGCCCCTGAGACGCGTCAATCGAGTTCGTACCTAAGGGCGA
CACCCCCTAATTAGCCCGGGCGAAAGGCCCAGTCTTTCGACTGAGCCTTTCGTTTTA
TTTGATGCCTGGCAGTTCCCTACTCTCGCATGGGGAGTCCCCACATACCATCGGCG
CTACGGCGTTTCACTTCTGAGTTCGGCATGGGGTCAGGTGGGACCACCGCGCTACTG
CCGCCAGGCAAACAAGGGGTGTTATGAGCCATATTCAGGTATAAATGGGCTCGCGA
TAATGTTCAGAATTGGTTAATTGGTTGTAACACTGACCCCTATTTGTTTATTTTTCTA
AATACATTCAAATATGTATCCGCTCATGAGACAATAACCCTGATAAATGCTTCAATA
ATATTGAAAAAGGAAGAATATGAGCCATATTCAACGGGAAACGTCGAGGCGCGAT
TAAATTCCAACATGGATGCTGATTTATATGGGTATAAATGGGCTCGCGATAATGTCG
GGCAATCAGGTGCGACAATCTATCGCTTGTATGGGAAGCCCGATGCGCCAGAGTTGT
TTCTGAAACATGGCAAAGGTAGCGTTGCCAATGATGTTACAGATGAGATGGTCAGA
CTAAACTGGCTGACGGAATTTATGCCACTTCCGACCATCAAGCATTTTATCCGTACT
CCTGATGATGCATGGTTACTCACCACTGCGATCCCCGGAAAAACAGCGTTCCAGGTA
TTAGAAGAATATCCTGATTCAGGTGAAAATATTGTTGATGCGCTGGCAGTGTTCCTG
```

```
CGCCGGTTGCACTCGATTCCTGTTTGTAATTGTCCTTTTAACAGCGATCGCGTATTTC
GCCTCGCTCAGGCGCAATCACGAATGAATAACGGTTTGGTTGATGCGAGTGATTTTG
ATGACGAGCGTAATGGCTGGCCTGTTGAACAAGTCTGGAAAGAAATGCATAAACTT
TTGCCATTCTCACCGGATTCAGTCGTCACTCATGGTGATTTCTCACTTGATAACCTTA
TTTTTGACGAGGGGAAATTAATAGGTTGTATTGATGTTGGACGAGTCGGAATCGCAG
ACCGATACCAGGATCTTGCCATCCTATGGAACTGCCTCGGTGAGTTTTCTCCTTCATT
ACAGAAACGGCTTTTTCAAAAATATGGTATTGATAATCCTGATATGAATAAATTGCA
GTTTCATTTGATGCTCGATGAGTTTTTCTAAGCGGCGCGCCATCGAATGGCGCAAAA
CCTTTCGCGGTATGGCATGATAGCGCCCGGAAGAGAGTCAATTCAGGGTGGTGAAT
ATGAAACCAGTAACGTTATACGATGTCGCAGAGTATGCCGGTGTCTCTTATCAGACC
GTTTCCCGCGTGGTGAACCAGGCCAGCCACGTTTCTGCGAAAACGCGGGAAAAAGT
GGAAGCGGCGATGGCGGAGCTGAATTACATTCCCAACCGCGTGGCACAACAACTGG
CGGGCAAACAGTCGTTGCTGATTGGCGTTGCCACCTCCAGTCTGGCCCTGCACGCGC
CGTCGCAAATTGTCGCGGCGATTAAATCTCGCGCCGATCAACTGGGTGCCAGCGTGG
TGGTGTCGATGGTAGAACGAAGCGGCGTCGAAGCCTGTAAAGCGGCGGTGCACAAT
CTTCTCGCGCAACGCGTCAGTGGGCTGATCATTAACTATCCGCTGGATGACCAGGAT
GCCATTGCTGTGGAAGCTGCCTGCACTAATGTTCCGGCGTTATTTCTTGATGTCTCTG
ACCAGACACCCATCAACAGTATTATTTTCTCCCATGAGGACGGTACGCGACTGGGCG
TGGAGCATCTGGTCGCATTGGGTCACCAGCAAATCGCGCTGTTAGCGGGCCCATTAA
GTTCTGTCTCGGCGCGTCTGCGTCTGGCTGGCTGGCATAAATATCTCACTCGCAATC
AAATTCAGCCGATAGCGGAACGGGAAGGCGACTGGAGTGCCATGTCCGGTTTTCAA
CAAACCATGCAAATGCTGAATGAGGGCATCGTTCCCACTGCGATGCTGGTTGCCAAC
GATCAGATGGCGCTGGGCGCAATGCGCGCCATTACCGAGTCCGGGCTGCGCGTTGG
TGCGGATATCTCGGTAGTGGGATACGACGATACCGAAGATAGCTCATGTTATATCCC
GCCGTTAACCACCATCAAACAGGATTTTCGCCTGCTGGGGCAAACCAGCGTGGACC
GCTTGCTGCAACTCTCTCAGGGCCAGGCGGTGAAGGGCAATCAGCTGTTGCCAGTCT
CACTGGTGAAAAGAAAAACCACCCTGGCGCCCAATACGCAAACCGCCTCTCCCCGC
GCGTTGGCCGATTCATTAATGCAGCTGGCACGACAGGTTTCCCGACTGGAAAGCGG
GCAGTGA

SEQ ID NO: 18: Plasmid construct tac/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAAATCAGTTTTTGATATCAAAATTATACATGTCA
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCGAACCTCAGGTCACCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGGTGGGAAATTGATCTCAATAGTGGTAACGATGAGATGAAAC
GTACGCAGCTACACGAATATTTTGCAGAAATGCCTATCATGGATTTCCGTTTTGCGC
```

Sequence Listing

```
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCCTTGGGGCCTCTAAACGGGTCTTG
AGGGGTTTTTTGGCATCCTGTCCATGACTCGGTGACAATTAATCATCGGCTCGTATA
ATGTGTGGAATTGTGAGCGGATAACAATTCCCTCTAGAAATAATTTTGTTTAACTTTT
AAAGGAGAGTTATCAATGAATATTCGTCCATTGCATGATCGCGTGATCGTCAAGCGT
AAAGAAGTTGAAACTAAATCTGCTGGCGGCATCGTTCTGACCGGCTCTGCAGCGGCT
AAATCCACCCGCGGCGAAGTGCTGGCTGTCGGCAATGGCCGTATCCTTGAAAATGG
CGAAGTGAAGCCGCTGGATGTGAAAGTTGGCGACATCGTTATTTTCAACGATGGCTA
CGGTGTGAAATCTGAGAAGATCGACAATGAAGAAGTGTTGATCATGTCCGAAAGCG
ACATTCTGGCAATTGTTGAAGCGTAATCCGCGCACGACACTGAACATACGAATTTAA
GGAATAAAGATAATGGCAGCTAAAGACGTAAAATTCGGTAACGACGCTCGTGTGAA
AATGCTGCGCGGCGTAAACGTACTGGCAGATGCAGTGAAAGTTACCCTCGGTCCAA
AAGGCCGTAACGTAGTTCTGGATAAATCTTTCGGTGCACCGACCATCACCAAAGATG
GTGTTTCCGTTGCTCGTGAAATCGAACTGGAAGACAAGTTCGAAAATATGGGTGCGC
AGATGGTGAAAGAAGTTGCCTCTAAAGCAAACGACGCTGCAGGCGACGGTACCACC
ACTGCAACCGTACTGGCTCAGGCTATCATCACTGAAGGTCTGAAAGCTGTTGCTGCG
GGCATGAACCCGATGGACCTGAAACGTGGTATCGACAAAGCGGTTACCGCTGCAGT
TGAAGAACTGAAAGCGCTGTCCGTACCATGCTCTGACTCTAAAGCGATTGCTCAGGT
TGGTACCATCTCCGCTAACTCCGACGAAACCGTAGGTAAACTGATCGCTGAAGCGAT
GGACAAAGTCGGTAAAGAAGGCGTTATCACCGTTGAAGACGGTACCGGTCTGCAGG
ACGAACTGGACGTGGTTGAAGGTATGCAGTTCGACCGTGGCTACCTGTCTCCTTACT
TCATCAACAAGCCGGAAACTGGCGCAGTAGAACTGGAAAGCCCGTTCATCCTGCTG
GCTGACAAGAAAATCTCCAACATCCGCGAAATGCTGCCGGTTCTGGAAGCTGTTGCC
AAAGCAGGCAAACCGCTGCTGATCATCGCTGAAGATGTAGAAGGCGAAGCGCTGGC
AACTCTGGTTGTTAACACCATGCGTGGCATCGTGAAAGTCGCTGCGGTTAAAGCACC
GGGCTTCGGCGATCGTCGTAAAGCTATGCTGCAGGATATCGCAACCCTGACTGGCGG
TACCGTGATCTCTGAAGAGATCGGTATGGAGCTGGAAAAAGCAACCCTGGAAGACC
TGGGTCAGGCTAAACGTGTTGTGATCAACAAAGACACCACCACTATCATCGATGGC
GTGGGTGAAGAAGCTGCAATCCAGGGCCGTGTTGCTCAGATCCGTCAGCAGATTGA
AGAAGCAACTTCTGACTACGACCGTGAAAAACTGCAGGAACGCGTAGCGAAACTGG
CAGGCGGCGTTGCAGTTATCAAAGTGGGTGCTGCTACCGAAGTTGAAATGAAAGAG
AAAAAAGCACGCGTTGAAGATGCCCTGCACGCGACCCGTGCTGCGGTAGAAGAAGG
CGTGGTTGCTGGTGGTGGTGTTGCGCTGATCCGCGTAGCGTCTAAACTGGCTGACCT
GCGTGGTCAGAACGAAGACCAGAACGTGGGTATCAAAGTTGCACTGCGTGCAATGG
AAGCTCCGCTGCGTCAGATCGTATTGAACTGCGGCGAAGAACCGTCGTTGTTGCTA
ACACCGTTAAAGGCGGCGACGGCAACTACGGTTACAACGCAGCAACCGAAGAATAC
GGCAACATGATCGACATGGGTATCCTGGATCCAACCAAAGTAACTCGTTCTGCTCTG
CAGTACGCAGCTTCTGTGGCTGGCCTGATGATCACCACCGAATGCATGGTTACCGAC
CTGCCGAAAAACGATGCAGCTGACTTAGGCGCTGCTGGCGGTATGGGCGGCATGGG
TGGCATGGGCGGCATGATGTAACCCCCTAGCATAACCCCTTGGGGCCTCTAAACGG
GTCTTGAGGGGTTTTTTGCCCCTGAGACGCGTCAATCGAGTTCGTACCTAAGGGCGA
CACCCCCTAATTAGCCCGGGCGAAAGGCCCAGTCTTTCGACTGAGCCTTTCGTTTTA
TTTGATGCCTGGCAGTTCCCTACTCTCGCATGGGGAGTCCCCACACTACCATCGGCG
CTACGGCGTTTCACTTCTGAGTTCGGCATGGGGTCAGGTGGGACCACCGCGCTACTG
CCGCCAGGCAAACAAGGGGTGTTATGAGCCATATTCAGGTATAAATGGGCTCGCGA
TAATGTTCAGAATTGGTTAATTGGTTGTAACACTGACCCCTATTTGTTTATTTTTCTA
AATACATTCAAATATGTATCCGCTCATGAGACAATAACCCTGATAAATGCTTCAATA
ATATTGAAAAAGGAAGAATATGAGCCATATTCAACGGGAAACGTCGAGGCCGCGAT
TAAATTCCAACATGGATGCTGATTTATATGGGTATAAATGGGCTCGCGATAATGTCG
GGCAATCAGGTGCGACAATCTATCGCTTGTATGGGAAGCCCGATGCGCCAGAGTTGT
TTCTGAAACATGGCAAAGGTAGCGTTGCCAATGATGTTACAGATGAGATGGTCAGA
CTAAACTGGCTGACGGAATTTATGCCACTTCCGACCATCAAGCATTTTATCCGTACT
CCTGATGATGCATGGTTACTCACCACTGCGATCCCCGGAAAAACAGCGTTCCAGGTA
TTAGAAGAATATCCTGATTCAGGTGAAAATATTGTTGATGCGCTGGCAGTGTTCCTG
CGCCGGTTGCACTCGATTCCTGTTTGTAATTGTCCTTTTAACAGCGATCGCGTATTTC
GCCTCGCTCAGGCGCAATCACGAATGAATAACGGTTTGGTTGATGCGAGTGATTTTG
ATGACGAGCGTAATGGCTGGCCTGTTGAACAAGTCTGGAAAGAAATGCATAAACTT
TTGCCATTCTCACCGGATTCAGTCGTCACTCATGGTGATTTCTCACTTGATAACCTTA
TTTTTGACGAGGGGAAATTAATAGGTTGTATTGATGTTGGACGAGTCGGAATCGCAG
ACCGATACCAGGATCTTGCCATCCTATGGAACTGCCTCGGTGAGTTTTCTCCTTCATT
ACAGAAACGGCTTTTTCAAAAATATGGTATTGATAATCCTGATATGAATAAATTGCA
GTTTCATTTGATGCTCGATGAGTTTTTCTAAGCGGCGCGCCATCGAATGGCGCAAAA
CCTTTCGCGGTATGGCATGATAGCGCCCGGAAGAGAGTCAATTCAGGGTGGTGAAT
ATGAAACCAGTAACGTTATACGATGTCGCAGAGTATGCCGGTGTCTCTTATCAGACC
GTTTCCCGCGTGGTGAACCAGGCCAGCCACGTTTCTGCGAAAACGCGGGAAAAGT
GGAAGCGGCGATGGCGGAGCTGAATTACATTCCCAACCGCGTGGCACAACAACTGG
CGGGCAAACAGTCGTTGCTGATTGGCGTTGCCACCTCCAGTCTGGCCCTGCACGCGC
CGTCGCAAATTGTCGCGGCGATTAAATCTCGCGCCGATCAACTGGGTGCCAGCGTGG
TGGTGTCGATGGTAGAACGAAGCGGCGTCGAAGCCTGTAAAGCGGCGGTGCACAAT
CTTCTCGCGCAACGCGTCAGTGGGCTGATCATTAACTATCCGCTGGATGACCAGGAT
GCCATTGCTGTGGAAGCTGCCTGCACTAATGTTCCGGCGTTATTTCTTGATGTCTCTG
ACCAGACACCCATCAACAGTATTATTTTCTCCCATGAGGACGGTACGCGACTGGGCG
```

```
TGGAGCATCTGGTCGCATTGGGTCACCAGCAAATCGCGCTGTTAGCGGGCCCATTAA
GTTCTGTCTCGGCGCGTCTGCGTCTGGCTGGCTGGCATAAATATCTCACTCGCAATC
AAATTCAGCCGATAGCGGAACGGGAAGGCGACTGGAGTGCCATGTCCGGTTTTCAA
CAAACCATGCAAATGCTGAATGAGGGCATCGTTCCCACTGCGATGCTGGTTGCCAAC
GATCAGATGGCGCTGGGCGCAATGCGCGCCATTACCGAGTCCGGGCTGCGCGTTGG
TGCGGATATCTCGGTAGTGGGATACGACGATACCGAAGATAGCTCATGTTATATCCC
GCCGTTAACCACCATCAAACAGGATTTTCGCCTGCTGGGGCAAACCAGCGTGGACC
GCTTGCTGCAACTCTCTCAGGGCCAGGCGGTGAAGGGCAATCAGCTGTTGCCAGTCT
CACTGGTGAAAAGAAAAACCACCCTGGCGCCCAATACGCAAACCGCCTCTCCCCGC
GCGTTGGCCGATTCATTAATGCAGCTGGCACGACAGGTTTCCCGACTGGAAAGCGG
GCAGTGA

SEQ ID NO: 19: Plasmid construct T7/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAT
AAATCTCGAAAATAATAAAGGGAAAATCAGTTTTTTGATATCAAAATTATACATGTCA
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCTTGGGGCCTCTAAACGGGTCTTG
AGGGGTTTTTTGGCATCCTGTCCATGACTCGGTAATACGACTCACTATAGGGGAATT
GTGAGCGGATAACAATTCCCTCTAGAAATAATTTTGTTTAACTTTTAAAGGAGAGTT
ATCAATGATATTCGTCCATTGCATGATCGCGTGATCGTCAAGCGTAAAGAAGTTGA
AACTAAATCGCTGGCGGCATCGTTCTGACCGGCTCTGCAGCGGCTAAATCCACCCG
CGGCGAAGTGCTGGCTGTCGGCAATGGCGTATCCTTGAAAATGGCGAAGTGAAGC
CGCTGGATGTGAAAGTTGGCGACATCGTTATTTTCAACGATGGCTACGGTGTGAAAT
CTGAGAAGATCGACAATGAAGAAGTGTTGATCATGTCCGAAAGCGACATTCTGGCA
ATTGTTGAAGCGTAATCCGCGCACGACACTGAACATACGAATTTAAGGAATAAGA
TAATGGCAGCTAAAGACGTAAAATTCGGTAACGACGCTCGTGTGAAAATGCTGCGC
GGCGTAAACGTACTGGCAGATGCAGTGAAAGTTACCCTCGGTCCAAAAGGCCGTAA
CGTAGTTCTGGATAAATCTTTCGGTGCACCGACCATCACCAAAGATGGTGTTTCCGT
```

```
TGCTCGTGAAATCGAACTGGAAGACAAGTTCGAAAATATGGGTGCGCAGATGGTGA
AAGAAGTTGCCTCTAAAGCAAACGACGCTGCAGGCGACGGTACCACCACTGCAACC
GTACTGGCTCAGGCTATCATCACTGAAGGTCTGAAAGCTGTTGCTGCGGGCATGAAC
CCGATGGACCTGAAACGTGGTATCGACAAAGCGGTTACCGCTGCAGTTGAAGAACT
GAAAGCGCTGTCCGTACCATGCTCTGACTCTAAAGCGATTGCTCAGGTTGGTACCAT
CTCCGCTAACTCCGACGAAACCGTAGGTAAACTGATCGCTGAAGCGATGGACAAAG
TCGGTAAAGAAGGCGTTATCACCGTTGAAGACGGTACCGGTCTGCAGGACGAACTG
GACGTGGTTGAAGGTATGCAGTTCGACCGTGGCTACCTGTCTCCTTACTTCATCAAC
AAGCCGGAAACTGGCGCAGTAGAACTGGAAAGCCCGTTCATCCTGCTGGCTGACAA
GAAAATCTCCAACATCCGCGAAATGCTGCCGGTTCTGGAAGCTGTTGCCAAAGCAG
GCAAACCGCTGCTGATCATCGCTGAAGATGTAGAAGGCGAAGCGCTGGCAACTCTG
GTTGTTAACACCATGCGTGGCATCGTGAAAGTCGCTGCGGTTAAAGCACCGGGCTTC
GGCGATCGTCGTAAAGCTATGCTGCAGGATATCGCAACCCTGACTGGCGGTACCGTG
ATCTCTGAAGAGATCGGTATGGAGCTGGAAAAAGCAACCCTGGAAGACCTGGGTCA
GGCTAAACGTGTTGTGATCAACAAAGACACCACCACTATCATCGATGGCGTGGGTG
AAGAAGCTGCAATCCAGGGCCGTGTTGCTCAGATCCGTCAGCAGATTGAAGAAGCA
ACTTCTGACTACGACCGTGAAAAACTGCAGGAACGCGTAGCGAAACTGGCAGGCGG
CGTTGCAGTTATCAAAGTGGGTGCTGCTACCGAAGTTGAAATGAAAGAGAAAAAG
CACGCGTTGAAGATGCCCTGCACGCGACCCGTGCTGCGGTAGAAGAAGGCGTGGTT
GCTGGTGGTGGTGTTGCGCTGATCCGCGTAGCGTCTAAACTGGCTGACCTGCGTGGT
CAGAACGAAGACCAGAACGTGGGTATCAAAGTTGCACTGCGTGCAATGGAAGCTCC
GCTGCGTCAGATCGTATTGAACTGCGGCAAGAACCGTCTGTTGTTGCTAACACCGT
TAAAGGCGGCGACGGCAACTACGGTTACAACGCAGCAACCGAAGAATACGGCAAC
ATGATCGACATGGGTATCCTGGATCCAACCAAAGTAACTCGTTCTGCTCTGCAGTAC
GCAGCTTCTGTGGCTGGCCTGATGATCACCACCGAATGCATGGTTACCGACCTGCCG
AAAAACGATGCAGCTGACTTAGGCGCTGCTGGCGGTATGGGCGGCATGGGTGGCAT
GGGCGGCATGATGTAACCCCCTAGCATAACCCCTTGGGGCCTCTAAACGGGTCTTGA
GGGGTTTTTTGCCCCTGAGACGCGTCAATCGAGTTCGTACCTAAGGGCGACACCCCC
TAATTAGCCCGGGCGAAAGGCCCAGTCTTTCGACTGAGCCTTTCGTTTTATTTGATGC
CTGGCAGTTCCCTACTCTCGCATGGGGAGTCCCCACACTACCATCGGCGCTACGGCG
TTTCACTTCTGAGTTCGGCATGGGGTCAGGTGGGACCACCGCGCTACTGCCGCCAGG
CAAACAAGGGGTGTTATGAGCCATATTCAGGTATAAATGGGCTCGCGATAATGTTCA
GAATTGGTTAATTGGTTGTAACACTGACCCCTATTTGTTTATTTTTCTAAATACATTC
AAATATGTATCCGCTCATGAGACAATAACCCTGATAAATGCTTCAATAATATTGAAA
AAGGAAGAATATGAGCCATATTCAACGGGAAACGTCGAGGCCGCGATTAAATTCCA
ACATGGATGCTGATTTATATGGGTATAAATGGGCTCGCGATAATGTCGGGCAATCAG
GTGCGACAATCTATCGCTTGTATGGGAAGCCCGATGCGCCAGAGTTGTTTCTGAAAC
ATGGCAAAGGTAGCGTTGCCAATGATGTTACAGATGAGATGGTCAGACTAAACTGG
CTGACGGAATTTATGCCACTTCCGACCATCAAGCATTTTATCCGTACTCCTGATGATG
CATGGTTACTCACCACTGCGATCCCCGGAAAAACAGCGTTCCAGGTATTAGAAGAAT
ATCCTGATTCAGGTGAAAATATTGTTGATGCGCTGGCAGTGTTCCTGCGCCGGTTGC
ACTCGATTCCTGTTTGTAATTGTCCTTTTAACAGCGATCGCGTATTTCGCCTCGCTCA
GGCGCAATCACGAATGAATAACGGTTTGGTTGATGCGAGTGATTTTGATGACGAGC
GTAATGGCTGGCCTGTTGAACAAGTCTGGAAAGAAATGCATAAACTTTTGCCATTCT
CACCGGATTCAGTCGTCACTCATGGTGATTTCTCACTTGATAACCTTATTTTTGACGA
GGGGAAATTAATAGGTTGTATTGATGTTGGACGAGTCGGAATCGCAGACCGATACC
AGGATCTTGCCATCCTATGGAACTGCCTCGGTGAGTTTTCTCCTTCATTACAGAAAC
GGCTTTTTCAAAAATATGGTATTGATAATCCTGATATGAATAAATTGCAGTTTCATTT
GATGCTCGATGAGTTTTTCTAAGCGGCGCGCCATCGAATGGCGCAAAACCTTTCGCG
GTATGGCATGATAGCGCCCGGAAGAGAGTCAATTCAGGGTGGTGAATATGAAACCA
GTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGC
GATGGCGGAGCTGAATTACATTCCCAACCGCGTGGCACAACAACTGGCGGGCAAAC
AGTCGTTGCTGATTGGCGTTGCCACCTCCAGTCTGGCCCTGCACGCGCCGTCGCAAA
TTGTCGCGGCGATTAAATCTCGCGCCGATCAACTGGGTGCCAGCGTGGTGGTGTCGA
TGGTAGAACGAAGCGGCGTCGAAGCCTGTAAAGCGGCGGTGCACAATCTTCTCGCG
CAACGCGTCAGTGGGCTGATCATTAACTATCCGCTGGATGACCAGGATGCCATTGCT
GTGGAAGCTGCCTGCACTAATGTTCCGGCGTTATTTCTTGATGTCTCTGACCAGACA
CCCATCAACAGTATTATTTTCTCCCATGAGGACGGTACGCGACTGGGCGTGGAGCAT
CTGGTCGCATTGGGTCACCAGCAAATCGCGCTGTTAGCGGGCCCATTAAGTTCTGTC
TCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCAT
GCAAATGCTGAATGAGGGCATCGTTCCCACTGCGATGCTGGTTGCCAACGATCAGAT
GGCGCTGGGCGCAATGCGCGCCATTACCGAGTCCGGGCTGCGCGTTGGTGCGGATA
TCTCGGTAGTGGGATACGACGATACCGAAGATAGCTCATGTTATATCCCGCCGTTAA
CCACCATCAAACAGGATTTTCGCCTGCTGGGGCAAACCAGCGTGGACCGCTTGCTGC
AACTCTCTCAGGGCCAGGCGGTGAAGGGCAATCAGCTGTTGCCAGTCTCACTGGTGA
AAAGAAAAACCACCCTGGCGCCCAATACGCAAACCGCCTCTCCCCGCGCGTTGGCC
GATTCATTAATGCAGCTGGCACGACAGGTTTCCCGACTGGAAAGCGGGCAGTGA

SEQ ID NO: 20: Plasmid construct T5/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
```

Sequence Listing

```
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAATCAGTTTTTGATATCAAAATTATACATGTCA
ACGATAATACAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCCTTGGGGCCTCTAAACGGGTCTTG
AGGGGTTTTTTGGCATCCTGTCCATGACTCGGAAATCATAAAAAATTTATTTGCTTTG
TGAGCGGATAACAATTATAATACCCTCTAGAAATAATTTTGTTTAACTTTTAAAGGA
GAGTTATCAATGAATATTCGTCCATTGCATGATCGCGTGATCGTCAAGCGTAAAGAA
GTTGAAACTAAATCTGCTGGCGGCATCGTTCTGACCGGCTCTGCAGCGGCTAAATCC
ACCCGCGGCGAAGTGCTGGCTGTCGGCAATGGCCGTATCCTTGAAAATGGCGAAGT
GAAGCCGCTGGATGTGAAAGTTGGCGACATCGTTATTTTCAACGATGGCTACGGTGT
GAAATCTGAGAAGATCGACAATGAAGAAGTGTTGATCATGTCCGAAAGCGACATTC
TGGCAATTGTTGAAGCGTAATCCGCGCACGACACTGAACATACGAATTTAAGGAAT
AAAGATAATGGCAGCTAAAGACGTAAAATTCGGTAACGACGCTCGTGTGAAAATGC
TGCGCGGCGTAAACGTACTGGCAGATGCAGTGAAAGTTACCCTCGGTCCAAAAGGC
CGTAACGTAGTTCTGGATAAATCTTTCGGTGCACCGACCATCACCAAAGATGGTGTT
TCCGTTGCTCGTGAAATCGAACTGGAAGACAAGTTCGAAAATATGGGTGCGCAGAT
GGTGAAAGAAGTTGCCTCTAAAGCAAACGACGCTGCAGGCGACGGTACCACCACTG
CAACCGTACTGGCTCAGGCTATCATCACTGAAGGTCTGAAAGCTGTTGCTGCGGGCA
TGAACCCGATGGACCTGAAACGTGGTATCGACAAAGCGGTTACCGCTGCAGTTGAA
GAACTGAAAGCGCTGTCCGTACCATGCTCTGACTCTAAAGCGATTGCTCAGGTTGGT
ACCATCTCCGCTAACTCCGACGAAACCGTAGGTAAACTGATCGCTGAAGCGATGGA
CAAAGTCGGTAAAGAAGGCGTTATCACCGTTGAAGACGGTACCGGTCTGCAGGACG
AACTGGACGTGGTTGAAGGTATGCAGTTCGACCGTGGCTACCTGTCTCCTTACTTCA
TCAACAAGCCGGAAACTGGCGCAGTAGAACTGGAAAGCCCGTTCATCCTGCTGGCT
GACAAGAAAATCTCCAACATCCGCGAAATGCTGCCGGTTCTGGAAGCTGTTGCCAA
AGCAGGCAAACCGCTGCTGATCATCGCTGAAGATGTAGAAGGCGAAGCGCTGGCAA
CTCTGGTTGTTAACACCATGCGTGGCATCGTGAAAGTCGCTGCGGTTAAAGCACCGG
GCTTCGGCGATCGTCGTAAAGCTATGCTGCAGGATATCGCAACCCTGACTGGCGTA
CCGTGATCTCTGAAGAGATCGGTATGGAGCTGGAAAAAGCAACCCTGGAAGACCTG
GGTCAGGCTAAACGTGTTGTGATCAACAAAGACACCACCACTATCATCGATGGCGT
GGGTGAAGAAGCTGCAATCCAGGGCCGTGTTGCTCAGATCCGTCAGCAGATTGAAG
AAGCAACTTCTGACTACGACCGTGAAAACTGCAGGAACGCGTAGCGAAACTGGCA
GGCGGCGTTGCAGTTATCAAAGTGGGTGCTGCTACCGAAGTTGAAATGAAAGAGAA
AAAAGCACGCGTTGAAGATGCCCTGCACGCGACCCGTGCTGCGGTAGAAGAAGGCG
```

TGGTTGCTGGTGGTGGTGTTGCGCTGATCCGCGTAGCGTCTAAACTGGCTGACCTGC
GTGGTCAGAACGAAGACCAGAACGTGGGTATCAAAGTTGCACTGCGTGCAATGGAA
GCTCCGCTGCGTCAGATCGTATTGAACTGCGGCGAAGAACCGTCTGTTGTTGCTAAC
ACCGTTAAAGGCGGCGACGGCAACTACGGTTACAACGCAGCAACCGAAGAATACGG
CAACATGATCGACATGGGTATCCTGGATCCAACCAAAGTAACTCGTTCTGCTCTGCA
GTACGCAGCTTCTGTGGCTGGCCTGATGATCACCACCGAATGCATGGTTACCGACCT
GCCGAAAAACGATGCAGCTGACTTAGGCGCTGCTGGCGGTATGGGCGGCATGGGTG
GCATGGGCGGCATGATGTAACCCCCTAGCATAACCCCTTGGGGCCTCTAAACGGGTC
TTGAGGGGTTTTTTGCCCCTGAGACGCGTCAATCGAGTTCGTACCTAAGGGCGACAC
CCCCTAATTAGCCCGGGCGAAAGGCCCAGTCTTTCGACTGAGCCTTTCGTTTTATTTG
ATGCCTGGCAGTTCCCTACTCTCGCATGGGGAGTCCCCACACTACCATCGGCGCTAC
GGCGTTTCACTTCTGAGTTCGGCATGGGGTCAGGTGGGACCACCGCGCTACTGCCGC
CAGGCAAACAAGGGGTGTTATGAGCCATATTCAGGTATAAATGGGCTCGCGATAAT
GTTCAGAATTGGTTAATTGGTTGTAACACTGACCCCTATTTGTTTATTTTTCTAAATA
CATTCAAATATGTATCCGCTCATGAGACAATAACCCTGATAAATGCTTCAATAATAT
TGAAAAAGGAAGAATATGAGCCATATTCAACGGGAAACGTCGAGGCCGCGATTAAA
TTCCAACATGGATGCTGATTTATATGGGTATAAATGGGCTCGCGATAATGTCGGGCA
ATCAGGTGCGACAATCTATCGCTTGTATGGGAAGCCCGATGCGCCAGAGTTGTTTCT
GAAACATGGCAAAGGTAGCGTTGCCAATGATGTTACAGATGAGATGGTCAGACTAA
ACTGGCTGACGAATTTATGCCACTTCCGACCATCAAGCATTTTATCCGTACTCCTG
ATGATGCATGGTTACTCACCACTGCGATCCCCGGAAAAACAGCGTTCCAGGTATTAG
AAGAATATCCTGATTCAGGTGAAAATATTGTTGATGCGCTGGCAGTGTTCCTGCGCC
GGTTGCACTCGATTCCTGTTTGTAATTGTCCTTTTAACAGCGATCGCGTATTTCGCCT
CGCTCAGGCGCAATCACGAATGAATAACGGTTTGGTTGATGCGAGTGATTTTGATGA
CGAGCGTAATGGCTGGCCTGTTGAACAAGTCTGGAAAGAAATGCATAAACTTTTGCC
ATTCTCACCGGATTCAGTCGTCACTCATGGTGATTTCTCACTTGATAACCTTATTTTT
GACGAGGGGAAATTAATAGGTTGTATTGATGTTGGACGAGTCGGAATCGCAGACCG
ATACCAGGATCTTGCCATCCTATGGAACTGCCTCGGTGAGTTTTCTCCTTCATTACAG
AAACGGCTTTTTCAAAAATATGGTATTGATAATCCTGATATGAATAAATTGCAGTTT
CATTTGATGCTCGATGAGTTTTTCTAAGCGGCGCGCCATCGAATGGCGCAAAACCTT
TCGCGGTATGGCATGATAGCGCCCGGAAGAGAGTCAATTCAGGGTGGTGAATATGA
AACCAGTAACGTTATACGATGTCGCAGAGTATGCCGGTGTCTCTTATCAGACCGTTT
CCCGCGTGGTGAACCAGGCCAGCCACGTTTCTGCGAAAACGCGGGAAAAAGTGGAA
GCGGCGATGGCGGAGCTGAATTACATTCCCAACCGCGTGGCACAACAACTGGCGGG
CAAACAGTCGTTGCTGATTGGCGTTGCCACCTCCAGTCTGGCCCTGCACGCGCCGTC
GCAAATTGTCGCGGCGATTAAATCTCGCGCCGATCAACTGGGTGCCAGCGTGGTGGT
GTCGATGGTAGAACGAAGCGGCGTCGAAGCCTGTAAAGCGGCGGTGCACAATCTTC
TCGCGCAACGCGTCAGTGGGCTGATCATTAACTATCGCTGGATGACCAGGATGCCA
TTGCTGTGGAAGCTGCCTGCACTAATGTTCCGGCGTTATTTCTTGATGTCTCTGACCA
GACACCCATCAACAGTATTATTTTCTCCCATGAAGACGGTACGCGACTGGGCGTGGA
GCATCTGGTCGCATTGGGTCACCAGCAAATCGCGCTGTTAGCGGGCCCATTAAGTTC
TGTCTCGGCGCGTCTGCGTCTGGCTGGCTGGCATAAATATCTCACTCGCAATCAAAT
TCAGCCGATAGCGGAACGGGAAGGCGACTGGAGTGCCATGTCCGGTTTTCAACAAA
CCATGCAAATGCTGAATGAGGGCATCGTTCCCACTGCGATGCTGGTTGCCAACGATC
AGATGGCGCTGGGCGCAATGCGCGCCATTACCGAGTCCGGGCTGCGCGTTGGTGCG
GATATCTCGGTAGTGGGATACGACGATACCGAAGATAGCTCATGTTATATCCCGCCG
TTAACCACCATCAAACAGGATTTTCGCCTGCTGGGGCAAACCAGCGTGGACCGCTTG
CTGCAACTCTCTCAGGGCCAGGCGGTGAAGGGCAATCAGCTGTTGCCAGTCTCACTG
GTGAAAAGAAAAACCACCCTGGCGCCCAATACGCAAACCGCCTCTCCCCGCGCGTT
GGCCGATTCATTAATGCAGCTGGCACGACAGGTTTCCCGACTGGAAAGCGGGCAGT
GA

SEQ ID NO: 21: Plasmid construct H10/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAAATCAGTTTTTGATATCAAAATTATACATGTCA

Sequence Listing

```
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTTCACGCGCAACT
GGTCAATCTTTCCGATCATGCCTGCGACAAATAGCCTTGAGCGTCTTAAAGCAAAGC
AGCCCATTTACATGTGGGAGCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCCTTGGGGCCTCTAAACGGGTCTTG
AGGGGTTTTTTGGCATCCTGTCCATGACTCGGTAATACGACTCACTACGGAAGAATT
GTGAGCGGATAACAATTCCCTCTAGAAATAATTTTGTTTAACTTTTAAAGGAGAGTT
ATCAATGAATATTCGTCCATTGCATGATCGCGTGATCGTCAAGCGTAAAGAAGTTGA
AACTAAATCTGCTGGCGGCATCGTTCTGACCGGCTCTGCAGCGGCTAAATCCACCCG
CGGCGAAGTGCTGGCTGTCGGCAATGGCCGTATCCTTGAAAATGGCGAAGTGAAGC
CGCTGGATGTGAAAGTTGGCGACATCGTTATTTTCAACGATGGCTACGGTGTGAAAT
CTGAGAAGATCGACAATGAAGAAGTGTTGATCATGTCCGAAAGCGACATTCTGGCA
ATTGTTGAAGCGTAATCCGCGCACGACACTGAACATACGAATTTAAGGAATAAAGA
TAATGGCAGCTAAAGACGTAAAATTCGGTAACGACGCTCGTGTGAAAATGCTGCGC
GGCGTAAACGTACTGGCAGATGCAGTGAAAGTTACCCTCGGTCCAAAAGGCCGTAA
CGTAGTTCTGGATAAATCTTTCGGTGCACCGACCATCACCAAAGATGGTGTTTCCGT
TGCTCGTGAAATCGAACTGGAAGACAAGTTCGAAAATATGGGTGCGCAGATGGTGA
AAGAAGTTGCCTCTAAAGCAAACGACGCTGCAGGCGACGGTACCACCACTGCAACC
GTACTGGCTCAGGCTATCATCACTGAAGGTCTGAAAGCTGTTGCTGCGGGCATGAAC
CCGATGGACCTGAAACGTGGTATCGACAAAGCGGTTACCGCTGCAGTTGAAGAACT
GAAAGCGCTGTCCGTACCATGCTCTGACTCTAAAGCGATTGCTCAGGTTGGTACCAT
CTCCGCTAACTCCGACGAAACCGTAGGTAAACTGATCGCTGAAGCGATGGACAAAG
TCGGTAAAGAAGGCGTTATCACCGTTGAAGACGGTACCGGTCTGCAGGACGAACTG
GACGTGGTTGAAGGTATGCAGTTCGACCGTGGCTACCTGTCTCCTTACTTCATCAAC
AAGCCGGAAACTGGCGCAGTAGAACTGGAAAGCCCGTTCATCCTGCTGGCTGACAA
GAAAATCTCCAACATCCGCGAAATGCTGCCGGTTCTGGAAGCTGTTGCCAAAGCAG
GCAAACCGCTGCTGATCATCGCTGAAGATGTAGAAGGCGAAGCGCTGGCAACTCTG
GTTGTTAACACCATGCGTGGCATCGTGAAAGTCGCTGCGGTTAAAGCACCGGGCTTC
GGCGATCGTCGTAAAGCTATGCTGCAGGATATCGCAACCCTGACTGGCGGTACCGTG
ATCTCTGAAGAGATCGGTATGGAGCTGGAAAAAGCAACCCTGGAAGACCTGGGTCA
GGCTAAACGTGTTGTGATCAACAAAGACACCACCACTATCATCGATGGCGTGGGTG
AAGAAGCTGCAATCCAGGGCCGTGTTGCTCAGATCCGTCAGCAGATTGAAGAAGCA
ACTTCTGACTACGACCGTGAAAAACTGCAGGAACGCGTAGCGAAACTGGCAGGCGG
CGTTGCAGTTATCAAAGTGGGTGCTGCTACCGAAGTTGAAATGAAAGAGAAAAAAG
CACGCGTTGAAGATGCCCTGCACGCGACCCGTGCTGCGGTAGAAGAAGGCGTGGTT
GCTGGTGGTGGTGTTGCGCTGATCCGCGTAGCGTCTAAACTGGCTGACCTGCGTGGT
CAGAACGAAGACCAGAACGTGGGTATCAAAGTTGCACTGCGTGCAATGGAAGCTCC
GCTGCGTCAGATCGTATTGAACTGCGGCGAAGAACCGTCTGTTGTTGCTAACACCGT
TAAAGGCGGCGACGGCAACTACGGTTACAACGCAGCAACCGAAGAATACGGCAAC
ATGATCGACATGGGTATCCTGGATCCAACCAAAGTAACTCGTTCTGCTCTGCAGTAC
GCAGCTTCTGTGGCTGGCCTGATGATCACCACCGAATGCATGGTTACCGACCTGCCG
AAAAACGATGCAGCTGACTTAGGCGCTGCTGGCGGTATGGGCGGCATGGGTGGCAT
GGGCGGCATGATGTAACCCCCTAGCATAACCCCTTGGGGCCTCTAAACGGGTCTTGA
GGGGTTTTTTGCCCCTGAGACGCGTCAATCGAGTTCGTACCTAAGGGCGACACCCCC
TAATTAGCCCGGGCGAAAGGCCCAGTCTTTCGACTGAGCCTTTCGTTTTATTTGATGC
CTGGCAGTTCCCTACTCTCGCATGGGGAGTCCCCACACTACCATCGGCGCTACGGCG
TTTCACTTCTGAGTTCGGCATGGGGTCAGGTGGGACCACCGCGCTACTGCCGCCAGG
CAAACAAGGGGTGTTATGAGCCATATTCAGGTATAAATGGGCTCGCGATAATGTTCA
GAATTGGTTAATTGGTTGTAACACTGACCCCTATTTGTTTATTTTTCTAAATACATTC
AAATATGTATCCGCTCATGAGACAATAACCCTGATAAATGCTTCAATAATATTGAAA
AAGGAAGAATATGAGCCATATTCAACGGGAAACGTCGAGGCCGCGATTAAATTCCA
ACATGGGATGCTGATTTATATGGGTATAAATGGGCTCGCGATAATGTCGGGCAATCAG
GTGCGACAATCTATCGCTTGTATGGGAAGCCCGATGCGCCAGAGTTGTTTCTGAAAC
```

```
ATGGCAAAGGTAGCGTTGCCAATGATGTTACAGATGAGATGGTCAGACTAAACTGG
CTGACGGAATTTATGCCACTTCCGACCATCAAGCATTTTATCCGTACTCCTGATGATG
CATGGTTACTCACCACTGCGATCCCCGGAAAAACAGCGTTCCAGGTATTAGAAGAAT
ATCCTGATTCAGGTGAAAATATTGTTGATGCGCTGGCAGTGTTCCTGCGCCGGTTGC
ACTCGATTCCTGTTTGTAATTGTCCTTTTAACAGCGATCGCGTATTTCGCCTCGCTCA
GGCGCAATCACGAATGAATAACGGTTTGGTTGATGCGAGTGATTTTGATGACGAGC
GTAATGGCTGGCCTGTTGAACAAGTCTGGAAAGAAATGCATAAACTTTTGCCATTCT
CACCGGATTCAGTCGTCACTCATGGTGATTTCTCACTTGATAACCTTATTTTTGACGA
GGGGAAATTAATAGGTTGTATTGATGTTGGACGAGTCGGAATCGCAGACCGATACC
AGGATCTTGCCATCCTATGGAACTGCCTCGGTGAGTTTTCTCCTTCATTACAGAAAC
GGCTTTTTCAAAAATATGGTATTGATAATCCTGATATGAATAAATTGCAGTTTCATTT
GATGCTCGATGAGTTTTTCTAAGCGGCGCGCCATCGAATGGCGCAAAACCTTTCGCG
GTATGGCATGATAGCGCCCGGAAGAGAGTCAATTCAGGGTGGTGAATATGAAACCA
GTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGC
GATGGCGGAGCTGAATTACATTCCCAACCGCGTGGCACAACAACTGGCGGGCAAAC
AGTCGTTGCTGATTGGCGTTGCCACCTCCAGTCTGGCCCTGCACGCGCCGTCGCAAA
TTGTCGCGGCGATTAAATCTCGCGCCGATCAACTGGGTGCCAGCGTGGTGGTGTCGA
TGGTAGAACGAAGCGGCGTCGAAGCCTGTAAAGCGGCGGTGCACAATCTTCTCGCG
CAACGCGTCAGTGGGCTGATCATTAACTATCCGTGGATGACCAGGATGCCATTGCT
GTGGAAGCTGCCTGCACTAATGTTCCGGCGTTATTTCTTGATGTCTCTGACCAGACA
CCCATCAACAGTATTATTTTCTCCCATGAGGACGGTACGCGACTGGGCGTGGAGCAT
CTGGTCGCATTGGGTCACCAGCAAATCGCGCTGTTAGCGGGCCCATTAAGTTCTGTC
TCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCAT
GCAAATGCTGAATGAGGGCATCGTTCCCACTGCGATGCTGGTTGCCAACGATCAGAT
GGCGCTGGGCGCAATGCGCGCCATTACCGAGTCCGGGCTGCGCGTTGGTGCGGATA
TCTCGGTAGTGGGATACGACGATACCGAAGATAGCTCATGTTATATCCCGCCGTTAA
CCACCATCAAACAGGATTTTCGCCTGCTGGGGCAAACCAGCGTGGACCGCTTGCTGC
AACTCTCTCAGGGCCAGGCGGTGAAGGGCAATCAGCTGTTGCCAGTCTCACTGGTGA
AAAGAAAAACCACCCTGGCGCCCAATACGCAAACCGCCTCTCCCCGCGCGTTGGCC
GATTCATTAATGCAGCTGGCACGACAGGTTTCCCGACTGGAAAGCGGGCAGTGA

SEQ ID NO: 22: Plasmid construct H9/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAAATCAGTTTTTGATATCAAAATTATACATGTCA
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
```

Sequence Listing

```
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCCTTGGGGCCTCTAAACGGGTCTTG
AGGGGTTTTTTGGCATCCTGTCCATGACTCGGTAATACGACTCACTAATACTGAATT
GTGAGCGGATAACAATTCCCTCTAGAAATAATTTTGTTTAACTTTTAAAGGAGAGTT
ATCAATGAATATTCGTCCATTGCATGATCGCGTGATCGTCAAGCGTAAAGAAGTTGA
AACTAAATCTGCTGGCGGCATCGTTCTGACCGGCTCTGCAGCGGCTAAATCCACCCG
CGGCGAAGTGCTGGCTGTCGGCAATGGCCGTATCCTTGAAAATGGCGAAGTGAAGC
CGCTGGATGTGAAAGTTGGCGACATCGTTATTTTCAACGATGGCTACGGTGTGAAAT
CTGAGAAGATCGACAATGAAGAAGTGTTGATCATGTCCGAAAGCGACATTCTGGCA
ATTGTTGAAGCGTAATCCGCGCACGACACTGAACATACGAATTTAAGGAATAAAGA
TAATGGCAGCTAAAGACGTAAAATTCGGTAACGACGCTCGTGTGAAAATGCTGCGC
GGCGTAAACGTACTGGCGCAGATGCAGTGAAAGTTACCCTCGGTCAAAAGGCCGTAA
CGTAGTTCTGGATAAATCTTTCGGTGCACCGACCATCACCAAAGATGGTGTTTCCGT
TGCTCGTGAAATCGAACTGGAAGACAAGTTCGAAAATATGGGTGCGCAGATGGTGA
AAGAAGTTGCCTCTAAAGCAAACGACGCTGCAGGCGACGGTACCACCACTGCAACC
GTACTGGCTCAGGCTATCATCACTGAAGGTCTGAAAGCTGTTGCTGCGGGCATGAAC
CCGATGGACCTGAAACGTGGTATCGACAAAGCGGTTACCGCTGCAGTTGAAGAACT
GAAAGCGCTGTCCGTACCATGCTCTGACTCTAAAGCGATTGCTCAGGTTGGTACCAT
CTCCGCTAACTCCGACGAAACCGTAGGTAAACTGATCGCTGAAGCGATGGACAAAG
TCGGTAAAGAAGGCGTTATCACCGTTGAAGACGGTACCGGTCTGCAGGACGAACTG
GACGTGGTTGAAGGTATGCAGTTCGACCGTGGCTACCTGTCTCCTTACTTCATCAAC
AAGCCGGAAACTGGCGCAGTAGAACTGGAAAGCCCGTTCATCCTGCTGGCTGACAA
GAAAATCTCCAACATCCGCGAAATGCTGCCGGTTCTGGAAGCTGTTGCCAAAGCAG
GCAAACCGCTGCTGATCATCGCTGAAGATGTAGAAGGCGAAGCGCTGGCAACTCTG
GTTGTTAACACCATGCGTGGCATCGTGAAAGTCGCTGCGGTTAAAGCACCGGGCTTC
GGCGATCGTCGTAAAGCTATGCTGCAGGATATCGCAACCCTGACTGGCGGTACCGTG
ATCTCTGAAGAGATCGGTATGGAGCTGGAAAAAGCAACCCTGGAAGACCTGGGTCA
GGCTAAACGTGTTGTGATCAACAAAGACACCACCACTATCATCGATGGCGTGGGTG
AAGAAGCTGCAATCCAGGGCCGTGTTGCTCAGATCCGTCAGCAGATTGAAGAAGCA
ACTTCTGACTACGACCGTGAAAAACTGCAGGAACGCGTAGCGAAACTGGCAGGCGG
CGTTGCAGTTATCAAAGTGGGTGCTGCTACCGAAGTTGAAATGAAAGAGAAAAAG
CACGCGTTGAAGATGCCCTGCACGCGACCCGTGCTGCGGTAGAAGAAGGCGTGGTT
GCTGGTGGTGGTGTTGCGCTGATCCGCGTAGCGTCTAAACTGGCTGACCTGCGTGGT
CAGAACGAAGACCAGAACGTGGGTATCAAAGTTGCACTGCGTGCAATGGAAGCTCC
GCTGCGTCAGATCGTATTGAACTGCGGCGAAGAACCGTCTGTTGTTGCTAACACCGT
TAAAGGCGGCGACGGCAACTACGGTTACAACGCAGCAACCGAAGAATACGGCAAC
ATGATCGACATGGGTATCCTGGATCCAACCAAAGTAACTCGTTCTGCTCTGCAGTAC
GCAGCTTCTGTGGCTGGCCTGATGATCACCACCGAATGCATGGTTACCGACCTGCCG
AAAAACGATGCAGCTGACTTAGGCGCTGCTGGCGGTATGGGCGGCATGGGTGGCAT
GGGCGGCATGATGTAACCCCCTAGCATAACCCCTTGGGGCCTCTAAACGGGTCTTGA
GGGGTTTTTTGCCCCTGAGACGCGTCAATCGAGTTCGTACCTAAGGGCGACACCCCC
TAATTAGCCCGGGCGAAAGGCCCAGTCTTTCGACTGAGCCTTTCGTTTTATTTGATGC
CTGGCAGTTCCCTACTCTCGCATGGGGAGTCCCCACACTACCATCGGCGCTACGGCG
TTTCACTTCTGAGTTCGGCATGGGGTCAGGTGGGACCACCGCGCTACTGCCGCCAGG
CAAACAAGGGGTGTTATGAGCCATATTCAGGTATAAATGGGCTCGCGATAATGTTCA
GAATTGGTTAATTGGTTGTAACACTGACCCCTATTTGTTTATTTTTCTAAATACATTC
AAATATGTATCCGCTCATGAGACAATAACCCTGATAAATGCTTCAATAATATTGAAA
AAGGAAGAATATGAGCCATATTCAACGGGAAACGTCGAGGCCGCGATTAAATTCCA
ACATGGATGCTGATTTATATGGGTATAAATGGGCTCGCGATAATGTCGGGCAATCAG
GTGCGACAATCTATCGCTTGTATGGGAAGCCCGATGCGCCAGAGTTGTTTCTGAAAC
ATGGCAAAGGTAGCGTTGCCAATGATGTTACAGATGAGATGGTCAGACTAAACTGG
CTGACGGAATTTATGCCACTTCCGACCATCAAGCATTTTATCCGTACTCCTGATGATG
CATGGTTACTCACCACTGCGATCCCGGAAAAACAGCGTTCCAGGTATTAGAAGAAT
ATCCTGATTCAGGTGAAAATATTGTTGATGCGCTGGCAGTGTTCCTGCGCCGGTTGC
ACTCGATTCCTGTTTGTAATTGTCCTTTTAACAGCGATCGCGTATTTCGCCTCGCTCA
GGCGCAATCACGAATGAATAACGGTTTGGTTGATGCGAGTGATTTTGATGACGAGC
GTAATGGCTGGCCTGTTGAACAAGTCTGGAAAGAAATGCATAAACTTTTGCCATTCT
CACCGGATTCAGTCGTCACTCATGGTGATTTCTCACTTGATAACCTTATTTTTGACGA
GGGGAAATTAATAGGTTGTATTGATGTTGGACGAGTCGGAATCGCAGACCGATACC
AGGATCTTGCCATCCTATGGAACTGCCTCGGTGAGTTTTCTCCTTCATTACAGAAAC
GGCTTTTTCAAAAATATGGTATTGATAATCCTGATATGAATAAATTGCAGTTTCATTT
GATGCTCGATGAGTTTTTCTAAGCGGCGCGCCATCGAATGGCGCAAAACCTTTCGCG
GTATGGCATGATAGCGCCCGGAAGAGAGTCAATTCAGGGTGGTGAATATGAAACCA
GTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGC
GATGGCGGAGCTGAATTACATTCCCAACCGCGTGGCACAACAACTGGCGGGCAAAC
AGTCGTTGCTGATTGGCGTTGCCACCTCCAGTCTGGCCCTGCACGCGCCGTCGCAAA
TTGTCGCGGCGATTAAATCTCGCGCCGATCAACTGGGTGCCAGCGTGGTGGTGTCGA
TGGTAGAACGAAGCGGCGTCGAAGCCTGTAAAGCGGCGGTGCACAATCTTCTCGCG
```

| Sequence Listing |
| --- |
| CAACGCGTCAGTGGGCTGATCATTAACTATCCGCTGGATGACCAGGATGCCATTGCT
GTGGAAGCTGCCTGCACTAATGTTCCGGCGTTATTTCTTGATGTCTCTGACCAGACA
CCCATCAACAGTATTATTTTCTCCCATGAGGACGGTACGCGACTGGGCGTGGAGCAT
CTGGTCGCATTGGGTCACCAGCAAATCGCGCTGTTAGCGGGCCCATTAAGTTCTGTC
TCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCAT
GCAAATGCTGAATGAGGGCATCGTTCCCACTGCGATGCTGGTTGCCAACGATCAGAT
GGCGCTGGGCGCAATGCGCGCCATTACCGAGTCCGGGCTGCGCGTTGGTGCGGATA
TCTCGGTAGTGGGATACGACGATACCGAAGATAGCTCATGTTATATCCCGCCGTTAA
CCACCATCAAACAGGATTTTCGCCTGCTGGGGCAAACCAGCGTGGACCGCTTGCTGC
AACTCTCTCAGGGCCAGGCGGTGAAGGGCAATCAGCTGTTGCCAGTCTCACTGGTGA
AAAGAAAAACCACCCTGGCGCCCAATACGCAAACCGCCTCTCCCCGCGCGTTGGCC
GATTCATTAATGCAGCTGGCACGACAGGTTTCCCGACTGGAAAGCGGGCAGTGA SEQ ID NO: 23: Plasmid construct G6/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAAATCAGTTTTTGATATCAAAATTATACATGTCA
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTCGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCCTTGGGGCCTCTAAACGGGTCTTG
AGGGGTTTTTTGCATCCCTGTCCATGACTCGGTAATACGACTCACTATTTCGGAATT
GTGAGCGGATAACAATTCCCTCTAGAAATAATTTTGTTTAACTTTTAAGGAGAGTT
ATCAATGAATATTCGTCATTGCATGATCGCGTGATCGTCAAGCGTAAAGAAGTTGA
AACTAAATCTGCTGGCGGCATCGTTCTGACCGGCTCTGCAGCGGCTAAATCCACCCG
CGGCGAAGTGCTGGCTGTCGGCAATGGCCGTATCCTTGAAAATGGCGAAGTGAAGC
CGCTGGATGTGAAAGTTGGCGACATCGTTATTTTCAACGATGGCTACGGTGTGAAAT
CTGAGAAGATCGACAATGAAGAAGTGTTGATCATGTCCGAAAGCGACATTCTGGCA
ATTGTTGAAGCGTAATCCGCGCACGACACTGAACATACGAATTTAAGGAATAAGA
TAATGGCAGCTAAAGACGTAAAATTCGGTAACGACGCTCGTGTGAAAATGCTGCGC |

```
GGCGTAAACGTACTGGCAGATGCAGTGAAAGTTACCCTCGGTCCAAAAGGCCGTAA
CGTAGTTCTGGATAAATCTTTCGGTGCACCGACCATCACCAAAGATGGTGTTTCCGT
TGCTCGTGAAATCGAACTGGAAGACAAGTTCGAAAATATGGGTGCGCAGATGGTGA
AAGAAGTTGCCTCTAAAGCAAACGACGCTGCAGGCGACGGTACCACCACTGCAACC
GTACTGGCTCAGGCTATCATCACTGAAGGTCTGAAAGCTGTTGCTGCGGGCATGAAC
CCGATGGACCTGAAACGTGGTATCGACAAAGCGGTTACCGCTGCAGTTGAAGAACT
GAAAGCGCTGTCCGTACCATGCTCTGACTCTAAAGCGATTGCTCAGGTTGGTACCAT
CTCCGCTAACTCCGACGAAACCGTAGGTAAACTGATCGCTGAAGCGATGGACAAAG
TCGGTAAAGAAGGCGTTATCACCGTTGAAGACGGTACCGGTCTGCAGGACGAACTG
GACGTGGTTGAAGGTATGCAGTTCGACCGTGGCTACCTGTCTCCTTACTTCATCAAC
AAGCCGGAAACTGGCGCAGTAGAACTGGAAAGCCCGTTCATCCTGCTGGCTGACAA
GAAAATCTCCAACATCCGCGAAATGCTGCCGGTTCTGGAAGCTGTTGCCAAAGCAG
GCAAACCGCTGCTGATCATCGCTGAAGATGTAGAAGGCGAAGCGCTGGCAACTCTG
GTTGTTAACACCATGCGTGGCATCGTGAAAGTCGCTGCGGTTAAAGCACCGGGCTTC
GGCGATCGTCGTAAAGCTATGCTGCAGGATATCGCAACCCTGACTGGCGGTACCGTG
ATCTCTGAAGAGATCGGTATGGAGCTGGAAAAAAGCAACCCTGGAAGACCTGGGTCA
GGCTAAACGTGTTGTGATCAACAAAGACACCACCACTATCATCGATGGCGTGGGTG
AAGAAGCTGCAATCCAGGGCCGTGTTGCTCAGATCCGTCAGCAGATTGAAGAAGCA
ACTTCTGACTACGACCGTGAAAAACTGCAGGAACGCGTAGCGAAACTGGCAGGCGG
CGTTGCAGTTATCAAAGTGGGTGCTGCTACCGAAGTTGAAATGAAAGAGAAAAAAG
CACGCGTTGAAGATGCCCTGCACGCGACCCGTGCTGCGGTAGAAGAAGGCGTGGTT
GCTGGTGGTGGTGTTGCGCTGATCCGCGTAGCGTCTAAACTGGCTGACCTGCGTGGT
CAGAACGAAGACCAGAACGTGGGTATCAAAGTTGCACTGCGTGCAATGGAAGCTCC
GCTGCGTCAGATCGTATTGAACTGCGGCGAAGAACCGTCTGTTGTTGCTAACACCGT
TAAAGGCGGCGACGGCAACTACGGTTACAACGCAGCAACCGAAGAATACGGCAAC
ATGATCGACATGGGTATCCTGGATCCAACCAAAGTAACTCGTTCTGCTCTGCAGTAC
GCAGCTTCTGTGGCTGGCCTGATGATCACCACCGAATGCATGGTTACCGACCTGCCG
AAAAACGATGCAGCTGACTTAGGCGCTGCTGGCGGTATGGGCGGCATGGGTGGCAT
GGGCGGCATGATGTAACCCCCTAGCATAACCCCTTGGGGCCTCTAAACGGGTCTTGA
GGGGTTTTTTGCCCCTGAGACGCGTCAATCGAGTTCGTACCTAAGGGCGACACCCCC
TAATTAGCCCGGGCGAAAGGCCCAGTCTTTCGACTGAGCCTTTCGTTTTATTTGATGC
CTGGCAGTTCCCTACTCTCGCATGGGGAGTCCCCACACTACCATCGGCGCTACGGCG
TTTCACTTCTGAGTTCGGCATGGGGTCAGGTGGGACCACCGCGCTACTGCCGCCAGG
CAAACAAGGGGTGTTATGAGCCATATTCAGGTATAAATGGGCTCGCGATAATGTTCA
GAATTGGTTAATTGGTTGTAACACTGACCCCTATTTGTTTATTTTTCTAAATACATTC
AAATATGTATCCGCTCATGAGACAATAACCCTGATAAATGCTTCAATAATATTGAAA
AAGGAAGAATATGAGCCATATTCAACGGGAAACGTCGAGGCCGCGATTAAATTCCA
ACATGGATGCTGATTTATATGGGTATAAATGGGCTCGCGATAATGTCGGGCAATCAG
GTGCGACAATCTATCGCTTGTATGGGAAGCCCGATGCGCCAGAGTTGTTTCTGAAAC
ATGGCAAAGGTAGCGTTGCCAATGATGTTACAGATGAGATGGTCAGACTAAACTGG
CTGACGGAATTTATGCCACTTCCGACCATCAAGCATTTTATCCGTACTCCTGATGATG
CATGGTTACTCACCACTGCGATCCCCGGAAAAACAGCGTTCCAGGTATTAGAAGAAT
ATCCTGATTCAGGTGAAAATATTGTTGATGCGCTGGCAGTGTTCCTGCGCCGGTTGC
ACTCGATTCCTGTTTGTAATTGTCCTTTTAACAGCGATCGCGTATTTCGCCTCGCTCA
GGCGCAATCACGAATGAATAACGGTTTGGTTGATGCGAGTGATTTTGATGACGAGC
GTAATGGCTGGCCTGTTGAACAAGTCTGGAAAGAAATGCATAAACTTTTGCCATTCT
CACCGGATTCAGTCGTCACTCATGGTGATTTCTCACTTGATAACCTTATTTTTGACGA
GGGGAAATTAATAGGTTGTATTGATGTTGGACGAGTCGGAATCGCAGACCGATACC
AGGATCTTGCCATCCTATGGAACTGCCTCGGTGAGTTTTCTCCTTCATTACAGAAAC
GGCTTTTTCAAAAATATGGTATTGATAATCCTGATATGAATAAATTGCAGTTTCATTT
GATGCTCGATGAGTTTTTCTAAGCGGCGCGCCATCGAATGGCGCAAAACCTTTCGCG
GTATGGCATGATAGCGCCCGGAAGAGAGTCAATTCAGGGTGGTGAATATGAAACCA
GTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGC
GATGGCGGAGCTGAATTACATTCCCAACCGCGTGGCACAACAACTGGCGGGCAAAC
AGTCGTTGCTGATTGGCGTTGCCACCTCCAGTCTGGCCCTGCACGCGCCGTCGCAAA
TTGTCGCGGCGATTAAATCTCGCGCCGATCAACTGGGTGCCAGCGTGGTGGTGTCGA
TGGTAGAACGAAGCGGCGTCGAAGCCTGTAAAGCGGCGGTGCACAATCTTCTCGCG
CAACGCGTCAGTGGGCTGATCATTAACTATCCGCTGGATGACCAGGATGCCATTGCT
GTGGAAGCTGCCTGCACTAATGTTCCGGCGTTATTTCTTGATGTCTCTGACCAGACA
CCCATCAACAGTATTATTTTCTCCCATGAGGACGGTACGCGACTGGGCGTGGAGCAT
CTGGTCGCATTGGGTCACCAGCAAATCGCGCTGTTAGCGGGCCCATTAAGTTCTGTC
TCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCAT
GCAAATGCTGAATGAGGGCATCGTTCCCACTGCGATGCTGGTTGCCAACGATCAGAT
GGCGCTGGGCGCAATGCGCGCCATTACCGAGTCCGGGCTGCGCGTTGGTGCGGATA
TCTCGGTAGTGGGATACGACGATACCGAAGATAGCTCATGTTATATCCCGCCGTTAA
CCACCATCAAACAGGATTTTCGCCTGCTGGGGCAAACCAGCGTGGACCGCTTGCTGC
AACTCTCTCAGGGCCAGGCGGTGAAGGGCAATCAGCTGTTGCCAGTCTCACTGGTGA
AAAGAAAAACCACCCTGGCGCCCAATACGCAAACCGCCTCTCCCCGCGCGTTGGCC
GATTCATTAATGCAGCTGGCACGACAGGTTTCCCGACTGGAAAGCGGGCAGTGA

SEQ ID NO: 24: Plasmid construct C4/+term
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
```

```
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
AAATCTCGAAAATAATAAAGGGAAAATCAGTTTTTGATATCAAAATTATACATGTCA
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGACTAGCATAACCCCTTGGGGCCTCTAAACGGGTCTTG
AGGGGTTTTTGGCATCCTGTCCATGACTCGGTAATACGACTCACTATCAAGGAATT
GTGAGCGGATAACAATTCCCTCTAGAAATAATTTTGTTTAACTTTTAAAGGAGAGTT
ATCAATGAATATTCGTCCATTGCATGATCGCGTGATCGTCAAGCGTAAAGAAGTTGA
AACTAAATCTGCTGGCGGCATCGTTCTGACCGGCTCTGCAGCGGCTAAATCCACCCG
CGGCGAAGTGCTGGCTGTCGGCAATGGCCGTATCCTTGAAAATGGCGAAGTGAAGC
CGCTGGATGTGAAAGTTGGCGACATCGTTATTTTCAACGATGGCTACGGTGTGAAAT
CTGAGAAGATCGACAATGAAGAAGTGTTGATCATGTCCGAAAGCGACATTCTGGCA
ATTGTTGAAGCGTAATCCGCGCACGACACTGAACATACGAATTTAAGGAATAAAGA
TAATGGCAGCTAAAGACGTAAAATTCGGTAACGACGCTCGTGTGAAAATGCTGCGC
GGCGTAAACGTACTGGCAGATGCAGTGAAAGTTACCCTCGGTCCAAAAGGCCGTAA
CGTAGTTCTGGATAAATCTTTCGGTGCACCGACCATCACCAAAGATGGTGTTTCCGT
TGCTCGTGAAATCGAACTGGAAGACAAGTTCGAAAATATGGGTGCGCAGATGGTGA
AAGAAGTTGCCTCTAAAGCAAACGACGCTGCAGGCGACGGTACCACCACTGCAACC
GTACTGGCTCAGGCTATCATCACTGAAGGTCTGAAAGCTGTTGCTGCGGGCATGAAC
CCGATGGACCTGAAACGTGGTATCGACAAAGCGGTTACCGCTGCAGTTGAAGAACT
GAAAGCGCTGTCCGTACCATGCTCTGACTCTAAAGCGATTGCTCAGGTTGGTACCAT
CTCCGCTAACTCCGACGAAACCGTAGGTAAACTGATCGCTGAAGCGATGGACAAAG
TCGGTAAAGAAGGCGTTATCACCGTTGAAGACGGTACCGGTCTGCAGGACGAACTG
GACGTGGTTGAAGGTATGCAGTTCGACCGTGGCTACCTGTCTCCTTACTTCATCAAC
AAGCCGGAAACTGGCGCAGTAGAACTGGAAAGCCCGTTCATCCTGCTGGCTGACAA
GAAAATCTCCAACATCCGCGAAATGCTGCCGGTTCTGGAAGCTGTTGCCAAAGCAG
GCAAACCGCTGCTGATCATCGCTGAAGATGTAGAAGGCGAAGCGCTGGCAACTCTG
GTTGTTAACACCATGCGTGGCATCGTGAAAGTCGCTGCGGTTAAAGCACCGGGCTTC
GGCGATCGTCGTAAAGCTATGCTGCAGGATATCGCAACCCTGACTGGCGGTACCGTG
ATCTCTGAAGAGATCGGTATGGAGCTGGAAAAAGCAACCCTGGAAGACCTGGGTCA
GGCTAAACGTGTTGTGATCAACAAAGACACCACCACTATCATCGATGGCGTGGGTG
AAGAAGCTGCAATCCAGGGCCGTGTTGCTCAGATCCGTCAGCAGATTGAAGAAGCA
ACTTCTGACTACGACCGTGAAAAACTGCAGGAACGCGTAGCGAAACTGGCAGGCGG
```

```
CGTTGCAGTTATCAAAGTGGGTGCTGCTACCGAAGTTGAAATGAAAGAGAAAAAG
CACGCGTTGAAGATGCCCTGCACGCGACCCGTGCTGCGGTAGAAGAAGGCGTGGTT
GCTGGTGGTGGTGTTGCGCTGATCCGCGTAGCGTCTAAACTGGCTGACCTGCGTGGT
CAGAACGAAGACCAGAACGTGGGTATCAAAGTTGCACTGCGTGCAATGGAAGCTCC
GCTGCGTCAGATCGTATTGAACTGCGGCGAAGAACCGTCTGTTGTTGCTAACACCGT
TAAAGGCGGCGACGGCAACTACGGTTACAACGCAGCAACCGAAGAATACGGCAAC
ATGATCGACATGGGTATCCTGGATCCAACCAAAGTAACTCGTTCTGCTCTGCAGTAC
GCAGCTTCTGTGGCTGGCCTGATGATCACCACCGAATGCATGGTTACCGACCTGCCG
AAAAACGATGCAGCTGACTTAGGCGCTGCTGGCGGTATGGGCGGCATGGGTGGCAT
GGGCGGCATGATGTAACCCCCTAGCATAACCCCTTGGGGCCTCTAAACGGGTCTTGA
GGGGTTTTTTGCCCCTGAGACGCGTCAATCGAGTTCGTACCTAAGGGCGACACCCCC
TAATTAGCCCGGGCGAAAGGCCCAGTCTTTCGACTGAGCCTTTCGTTTTATTTGATGC
CTGGCAGTTCCCTACTCTCGCATGGGGAGTCCCCACACTACCATCGGCGCTACGGCG
TTTCACTTCTGAGTTCGGCATGGGGTCAGGTGGGACCACCGCGCTACTGCCGCCAGG
CAAACAAGGGGTGTTATGAGCCATATTCAGGTATAAATGGGCTCGCGATAATGTTCA
GAATTGGTTAATTCGGTTGTAACACTGACCCCTATTTGTTTATTTTTCTAAATACATTC
AAATATGTATCCGCTCATGAGACAATAACCCTGATAAATGCTTCAATAATATTGAAA
AAGGAAGAATATGAGCCATATTCAACGGGAAACGTCGAGGCCGCGATTAAATTCCA
ACATGGATGCTGATTTATATGGGTATAAATGGGCTCGCGATAATGTCGGCAATCAG
GTGCGACAATCTATCGCTTGTATGGGAAGCCCGATGCGCCAGAGTTGTTTCTGAAAC
ATGGCAAAGGTAGCGTTGCCAATGATGTTACAGATGAGATGGTCAGACTAAACTGG
CTGACGGAATTTATGCCACTTCCGACCATCAAGCATTTTATCCGTACTCCTGATGATG
CATGGTTACTCACCACTGCGATCCCCGGAAAAACAGCGTTCCAGGTATTAGAAGAAT
ATCCTGATTCAGGTGAAAATATTGTTGATGCGCTGGCAGTGTTCCTGCGCCGGTTGC
ACTCGATTCCTGTTTGTAATTGTCCTTTTAACAGCGATCGCGTATTTCGCCTCGCTCA
GGCGCAATCACGAATGAATAACGGTTTGGTTGATGCGAGTGATTTTGATGACGAGC
GTAATGGCTGGCCTGTTGAACAAGTCTGGAAAGAAATGCATAAACTTTTGCCATTCT
CACCGGATTCAGTCGTCACTCATGGTGATTTCTCACTTGATAACCTTATTTTTGACGA
GGGGAAATTAATAGGTTGTATTGATGTTGGACGAGTCGGAATCGCAGACCGATACC
AGGATCTTGCCATCCTATGGAACTGCCTCGGTGAGTTTTCTCCTTCATTACAGAAAC
GGCTTTTTCAAAAATATGGTATTGATAATCCTGATATGAATAAATTGCAGTTTCATTT
GATGCTCGATGAGTTTTTCTAAGCGGCGCGCCATCGAATGGCGCAAAACCTTTCGCG
GTATGGCATGATAGCGCCCGGAAGAGAGTCAATTCAGGGTGGTGAATATGAAACCA
GTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGC
GATGGCGGAGCTGAATTACATTCCCAACCGCGTGGCACAACAACTGGCGGGCAAAC
AGTCGTTGCTGATTGGCGTTGCCACCTCCAGTCTGGCCCTGCACGCGCCGTCGCAAA
TTGTCGCGGCGATTAAATCTCGCGCCGATCAACTGGGTGCCAGCGTGGTGGTGTCGA
TGGTAGAACGAAGCGGCGTCGAAGCCTGTAAAGCGGCGGTGCACAATCTTCTCGCG
CAACGCGTCAGTGGGCTGATCATTAACTATCCGCTGGATGACCAGGATGCCATTGCT
GTGGAAGCTGCCTGCACTAATGTTCCGGCGTTATTTCTTGATGTCTCTGACCAGACA
CCCATCAACAGTATTATTTTCTCCCATGAGGACGGTACGCGACTGGGCGTGGAGCAT
CTGGTCGCATTGGGTCACCAGCAAATCGCGCTGTTAGCGGGCCCATTAAGTTCTGTC
TCGGCGCGTCTGCGTCTGGCTGGCTGGCATAAATATCTCACTCGCAATCAAATTCAG
CCGATAGCGGAACGGGAAGGCGACTGGAGTGCCATGTCCGGTTTTCAACAAACCAT
GCAAATGCTGAATGAGGGCATCGTTCCCACTGCGATGCTGGTTGCCAACGATCAGAT
GGCGCTGGGCGCAATGCGCGCCATTACCGAGTCCGGGCTGCGCGTTGGTGCGGATA
TCTCGGTAGTGGGATACGACGATACCGAAGATAGCTCATGTTATATCCCGCCGTTAA
CCACCATCAAACAGGATTTTCGCCTGCTGGGGCAAACCAGCGTGGACCGCTTGCTGC
AACTCTCTCAGGGCCAGGCGGTGAAGGGCAATCAGCTGTTGCCAGTCTCACTGGTGA
AAAGAAAAACCACCCTGGCGCCCAATACGCAAACCGCCTCTCCCCGCGCGTTGGCC
GATTCATTAATGCAGCTGGCACGACAGGTTTCCCGACTGGAAAGCGGGCAGTGA

SEQ ID NO: 25: Plasmid construct PC1_triple
TTAATAAGATGATCTTCTTGAGATCGTTTTGGTCTGCGCGTAATCTCTTGCTCTGAAA
ACGAAAAAACCGCCTTGCAGGGCGGTTTTTCGAAGGTTCTCTGAGCTACCAACTCTT
TGAACCGAGGTAACTGGCTTGGAGGAGCGCAGTCACCAAAACTTGTCCTTTCAGTTT
AGCCTTAACCGGCGCATGACTTCAAGACTAACTCCTCTAAATCAATTACCAGTGGCT
GCTGCCAGTGGTGCTTTTGCATGTCTTTCCGGGTTGGACTCAAGACGATAGTTACCG
GATAAGGCGCAGCGGTCGGACTGAACGGGGGGTTCGTGCATACAGTCCAGCTTGGA
GCGAACTGCCTACCCGGAACTGAGTGTCAGGCGTGGAATGAGACAAACGCGGCCAT
AACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACT
GATTTGAGCGTCAGATTTCGTGATGCTTGTCAGGGGGCGGAGCCTATGGAAAAAC
GGCTTTGCCGCGGCCCTCTCACTTCCCTGTTAAGTATCTTCCTGGCATCTTCCAGGAA
ATCTCCGCCCCGTTCGTAAGCCATTTCCGCTCGCCGCAGTCGAACGACCGAGCGTAG
CGAGTCAGTGAGCGAGGAAGCGGAATATATCCTGTATCACATATTCTGCTGACGCAC
CGGTGCAGCCTTTTTTCTCCTGCCACATGAAGCACTTCACTGACACCCTCATCAGTGC
CAACATAGTAAGCCAGTATACACTCCGCTAGCGCTGAGGTCCCGCAGCCGAACGAC
CGAGCGCAGCGAGTCAGTGAGCGAGGAAGCGGAAGGCGAGAGTAGGGAACTGCCA
GGCATCAAACTAAGCAGAAGGCCCCTGACGGATGGCCTTTTTGCGTTTCTACAAACT
CTTTCTGTGTTGTAAAACGACGGCCAGTCTTAAGCTCGGGCCCCCTGGGCGGTTCTG
ATAACGAGTAATCGTTAATCCGCAAATAACGTAAAAACCCGCTTCGGCGGGTTTTTT
TATGGGGGGAGTTTAGGGAAAGAGCATTTGTCAGAATATTTAAGGGCGCCTGTCACT
TTGCTTGATATATGAGAATTATTTAACCTTATAAATGAGAAAAAAGCAACGCACTTT
AAATAAGATACGTTGCTTTTTCGATTGATGAACACCTATAATTAAACTATTCATCTAT
TATTTATGATTTTTTGTATATACAATATTTCTAGTTTGTTAAAGAGAATTAAGAAAAT
```

-continued

Sequence Listing

```
AAATCTCGAAAATAATAAAGGGAAAATCAGTTTTTGATATCAAAATTATACATGTCA
ACGATAATACAAAATATAATACAAACTATAAGATGTTATCAGTATTTATTATGCATT
TAGAATAAATTTTGTGTCGCCCTTCCGCGAAATTAATACGACTCACTATAGGGGAAT
TGTGAGCGGATAACAATTCCCCTCTAGAAATAATTTTGTTTAACTTTTGAAGGAGAT
ATACATATGGCAACGTTTGACCGCAATGATCCGCAGTTGGCAGGAACGATGTTCCCC
ACCCGAATAGAGGCGAATGTCTTTGACCTTGAAATTGAGGGCGAGATCCCACGTGC
AATCAACGGGAGCTTCTTCCGCAACACCCCCGAACCTCAGGTCACCCCGCAACCTTT
CCACACCTTCATCGATGGGATGGTTTGGCGTCTGCTTTTCATTTCGAAGATGGCCAT
GTCGACTTTGTCAGCCGTTGGGTATGTACTCCTCGCTTTGAAGCTGAGCGGTCGGCT
CGTAAATCACTCTTCGGTATGTACCGCAATCCGTTCACTGATGATCCATCGGTAGAA
GGTATTGATCGTACAGTCGCCAACACCAGTATCATCACTCATCACGGGAAAGTACTG
GCCGCAAAGGAAGATGGACTACCTTATGAGCTTGACCCCCAAACCCTGGAAACCCG
AGGTCGTTATGATTACAAGGGGCAGGTAACCAGCCATACACATACAGCGCACCCTA
AGTTCGACCCCCAGACAGGTGAAATGTTACTCTTCGGCTCCGCTGCTAAAGGCGAAC
GAACGCTTGATATGGCGTACTATATTGTTGATCGCTACGGCAAGGTGACACATGAGA
CCTGGTTTAAGCAGCCTTACGGTGCATTCATGCACGACTTTGCTGTCACGCGCAACT
GGTCAATCTTTCCGATCATGCCTGCGACAAATAGCCTTGAGCGTCTTAAAGCAAAGC
AGCCCATTTACATGTGGGAGCCTGAGCGAGGAAGCTATATAGGAGTACTTCCTCGTC
GTGGTCAGGGCAAGGACATTCGTTGGTTCCGTGCCCCGGCGTTGTGGGTTTTCCATG
TCGTGAATGCTTGGGAGGAAGGGAATAGAATTCTGATTGACTTGATGGAAAGTGAG
ATTTTGCCGTTCCCATTCCCGAACTCGCAGAACCTTCCATTTGATCCCTCCAAGGCTG
TTCCGCGTCTAACCCGTTGGGAAATTGATCTCAATAGTGGTAACGATGAGATGAAAC
GTACGCAGCTACACGAATATTTTGCAGAAATGCCTATCATGGATTTCCGTTTTGCGC
TCCAGGATCATCGCTACGCCTACATGGGGGTTGACGATCCTCGTCGCCCCTTAGCTC
ATCAGCAAGCTGAAAAAATCTTTGCCTACAATTCGTTAGGGGTTTGGGACAACCATC
GTAAAGATTATGAACTTTGGTTTACGGGAAAAATGTCTGCAGCGCAGGAACCGGCG
TTTGTTCCTAGAAGCCCAGATGCGCCTGAGGGCGATGGCTACCTACTCAGTGTAGTA
GGGCGGCTCGATGAAAATCGTAGCGATCTAGTTATCCTTGATACGCAATGTTTGGCA
GCTGGGCCTGTGGCCACTGTCAAGCTTCCCTTCCGTCTCCGAGCAGCGTTGCACGGT
TGTTGGCAGTCTAAGAACTGAGAAGGAGATATACATATGAATATTCGTCCATTGCAT
GATCGCGTGATCGTCAAGCGTAAAGAAGTTGAAACTAAATCTGCTGGCGGCATCGTT
CTGACCGGCTCTGCAGCGGCTAAATCCACCCGCGGCGAAGTGCTGGCTGTCGGCAA
TGGCCGTATCCTTGAAAATGGCGAAGTGAAGCCGCTGGATGTGAAAGTTGGCGACA
TCGTTATTTTCAACGATGGCTACGGTGTGAAATCTGAGAAGATCGACAATGAAGAA
GTGTTGATCATGTCCGAAAGCGACATTCTGGCAATTGTTGAAGCGTAATCCGCGCAC
GACACTGAACATACGAATTTAAGGAATAAAGATAATGGCAGCTAAAGACGTAAAAT
TCGGTAACGACGCTCGTGTGAAAATGCTGCGCGGCGTAAACGTACTGGCAGATGCA
GTGAAAGTTACCCTCGGTCCAAAAGGCCGTAACGTAGTTCTGGATAAATCTTTCGGT
GCACCGACCATCACCAAAGATGGTGTTTCCGTTGCTCGTGAAATCGAACTGGAAGAC
AAGTTCGAAAATATGGGTGCGCAGATGGTGAAAGAAGTTGCCTCTAAAGCAAACGA
CGCTGCAGGCGACGGTACCACCACTGCAACCGTACTGGCTCAGGCTATCATCACTGA
AGGTCTGAAAGCTGTTGCTGCGGGCATGAACCCGATGGACCTGAAACGTGGTATCG
ACAAAGCGGTTACCGCTGCAGTTGAAGAACTGAAAGCGCTGTCCGTACCATGCTCTG
ACTCTAAAGCGATTGCTCAGGTTGGTACCATCTCCGCTAACTCCGACGAAACCGTAG
GTAAACTGATCGCTGAAGCGATGGACAAAGTCGGTAAAGAAGGCGTTATCACCGTT
GAAGACGGTACCGGTCTGCAGGACGAACTGGACGTGGTTGAAGGTATGCAGTTCGA
CCGTGGCTACCTGTCTCCTTACTTCATCAACAAGCCGGAAACTGGCGCAGTAGAACT
GGAAAGCCCGTTCATCCTGCTGGCTGACAAGAAAATCTCCAACATCCGCGAAATGC
TGCCGGTTCTGGAAGCTGTTGCCAAAGCAGGCAAACCGCTGCTGATCATCGCTGAAG
ATGTAGAAGGCGAAGCGCTGGCAACTCTGGTTGTTAACACCATGCGTGGCATCGTG
AAAGTCGCTGCGGTTAAAGCACCGGGCTTCGGCGATCGTCGTAAAGCTATGCTGCA
GGATATCGCAACCCTGACTGGCGGTACCGTGATCTCTGAAGAGATCGGTATGGAGCT
GGGAAAAAGCAACCCTGGAAGACCTGGGTCAGGCTAAACGTGTTGTGATCAACAAAG
ACACCACCACTATCATCGATGGCGTGGGTGAAGAAGCTGCAATCCAGGGCCGTGTT
GCTCAGATCCGTCAGCAGATTGAAGAAGCAACTTCTGACTACGACCGTGAAAAACT
GCAGGAACGCGTAGCGAAACTGGCAGGCGGCGTTGCAGTTATCAAAGTGGGTGCTG
CTACCGAAGTTGAAATGAAAGAGAAAAAAGCACGCGTTGAAGATGCCCTGCACGCG
ACCCGTGCTGCGGTAGAAGAAGGCGTGGTTGCTGGTGGTGGTGTTGCGCTGATCCGC
GTAGCGTCTAAACTGGCTGACCTGCGTGGTCAGAACGAAGACCAGAACGTGGGTAT
CAAAGTTGCACTGCGTGCAATGGAAGCTCCGCTGCGTCAGATCGTATTGAACTGCGG
CGAAGAACCGTCTGTTGTTGCTAACACCGTTAAAGGCGGCGACGGCAACTACGGTT
ACAACGCAGCAACCGAAGAATACGGCAACATGATCGACATGGGTATCCTGGATCCA
ACCAAAGTAACTCGTTCTGCTCTGCAGTACGCAGCTTCTGTGGCTGGCCTGATGATC
ACCACCGAATGCATGGTTACCGACCTGCCGAAAAACGATGCAGCTGACTTAGGCGC
TGCTGGCGGTATGGGCGGCATGGGTGGCATGGGCGGCATGATGTAACCCCCTAGCA
TAACCCCTTGGGGCCTCTAAACGGGTCTTGAGGGGTTTTTTGCGCTGAGACGCGTC
AATCGAGTTCGTACCTAAGGGCGACACCCCCTAATTAGCCCGGGCGAAAGGCCCAG
TCTTTCGACTGAGCCTTTCGTTTTATTTGATGCCTGGCAGTTCCCTACTCTCGCATGG
GGAGTCCCCACACTACCATCGGCGCTACGGCGTTTCACTTCTGAGTTCGGCATGGGG
TCAGGTGGGACCACCGCGCTACTGCCGCCAGGCAAACAAGGGGTGTTATGAGCCAT
ATTCAGGTATAAATGGGCTCGCGATAATGTTCAGAATTGGTTAATTGGTTGTAACAC
TGACCCCTATTTGTTTATTTTTCTAAATACATTCAAATATGTATCCGCTCATGAGACA
ATAACCCTGATAAATGCTTCAATAATATTGAAAAAGGAAGAATATGAGCCATATTC
AACGGGAAACGTCGAGGCCGCGATTAAATTCCAACATGGATGCTGATTTATATGGG
TATAAATGGGCTCGCGATAATGTCGGGCAATCAGGTGCGACAATCTATCGCTTGTAT
GGGAAGCCCGATGCGCCAGAGTTGTTTCTGAAACATGGCAAAGGTAGCGTTGCCAA
TGATGTTACAGATGAGATGGTCAGACTAAACTGGCTGACGGAATTTATGCCACTTCC
```

| Sequence Listing |
|---|
| GACCATCAAGCATTTTATCCGTACTCCTGATGATGCATGGTTACTCACCACTGCGAT
CCCCGGAAAAACAGCGTTCCAGGTATTAGAAGAATATCCTGATTCAGGTGAAATA
TTGTTGATGCGCTGGCAGTGTTCCTGCGCCGGTTGCACTCGATTCCTGTTTGTAATTG
TCCTTTTAACAGCGATCGCGTATTTCGCCTCGCTCAGGCGCAATCACGAATGAATAA
CGGTTTGGTTGATGCGAGTGATTTTGATGACGAGCGTAATGGCTGGCCTGTTGAACA
AGTCTGGAAAGAAATGCATAAACTTTTGCCATTCTCACCGGATTCAGTCGTCACTCA
TGGTGATTTCTCACTTGATAACCTTATTTTTGACGAGGGGAAATTAATAGGTTGTATT
GATGTTGGACGAGTCGGAATCGCAGACCGATACCAGGATCTTGCCATCCTATGGAA
CTGCCTCGGTGAGTTTTCTCCTTCATTACAGAAACGGCTTTTTCAAAATATGGTATT
GATAATCCTGATATGAATAAATTGCAGTTTCATTTGATGCTCGATGAGTTTTTCTAAG
CGGCGCGCCATCGAATGGCGCAAAACCTTTCGCGGTATGGCATGATAGCGCCCGGA
AGAGAGTCAATTCAGGGTGGTGAATATGAAACCAGTAACGTTATACGATGTCGCAG
AGTATGCCGGTGTCTCTTATCAGACCGTTTCCCGCGTGGTGAACCAGGCCAGCCACG
TTTCTGCGAAAACGCGGGAAAAAGTGGAAGCGGCGATGGCGGAGCTGAATTACATT
CCCAACCGCGTGGCACAACAACTGGCGGGCAAACAGTCGTTGCTGATTGGCGTTGC
CACCTCCAGTCTGGCCCTGCACGCGCCGTCGCAAATTGTCGCGGCGATTAAATCTCG
CGCCGATCAACTGGGTGCCAGCGTGGTGGTGTCGATGGTAGAACGAAGCGGCGTCG
AAGCCTGTAAAGCGGCGGTGCACAATCTTCTCGCGCAACGCGTCAGTGGGCTGATC
ATTAACTATCCGCTGGATGACCAGGATGCCATTGCTGTGGAAGCTGCCTGCACTAAT
GTTCCGGCGTTATTTCTTGATGTCTCTGACCAGACACCCATCAACAGTATTATTTTCT
CCCATGAGGACGGTACGCGACTGGGCGTGGAGCATCTGGTCGCATTGGGTCACCAG
CAAATCGCGCTGTTAGCGGGCCCATTAAGTTCTGTCTCGGCGCGTCTGCGTCTGGCT
GGCTGGCATAAATATCTCACTCGCAATCAAATTCAGCCGATAGCGGAACGGGAAGG
CGACTGGAGTGCCATGTCCGGTTTTCAACAAACCATGCAAATGCTGAATGAGGGCAT
CGTTCCCACTGCGATGCTGGTTGCCAACGATCAGATGGCGCTGGGCGCAATGCGCGC
CATTACCGAGTCCGGGCTGCGCGTTGGTGCGGATATCTCGGTAGTGGGATACGACGA
TACCGAAGATAGCTCATGTTATATCCCGCCGTTAACCACCATCAAACAGGATTTTCG
CCTGCTGGGCAAACCAGCGTGGACCGCTTGCTGCAACTCTCTCAGGGCCAGGCGG
TGAAGGGCAATCAGCTGTTGCCAGTCTCACTGGTGAAAAGAAAAACCACCCTGGCG
CCCAATACGCAAACCGCCTCTCCCCGCGCGTTGGCCGATTCATTAATGCAGCTGGCA
CGACAGGTTTCCCGACTGGAAAGCGGGCAGTGA |

What is claimed is:

1. An expression system for a recombinant expression of a polypeptide having isoeugenol oxidizing activity, which expression system comprises a single nucleic acid construct carrying:
   a) a nucleotide sequence (A) encoding a polypeptide having enzymatic isoeugenol oxidizing activity, and
   b) at least one nucleotide sequence (B) encoding helper polypeptides which in cooperation assist in correctly folding the polypeptide, encoded by said nucleotide sequence (A);
   wherein said expression system provides for a co-expression of said nucleotide sequences (A) and (B), and
   wherein said nucleotide sequence (A) encodes an amino acid sequence having at least 90% sequence identity to SEQ ID NO:2, wherein said polypeptide comprises at least one amino acid substitution relative to the amino acid sequence of SEQ ID NO:2;
   wherein said at least nucleotide sequence (B) comprises nucleotide sequences (B1) and (B2), wherein
   a) (B1) encodes a polypeptide having chaperonin activity that comprises an amino acid sequence having at least 70% sequence identity to SEQ ID NO:8; and
   b) (B2) encodes a polypeptide having chaperonin activity that comprises an amino acid sequence having at least 70% sequence identity to SEQ ID NO:10;
   wherein the expression system is a single polycistronic nucleic acid construct.

2. An expression vector comprising a recombinant expression system of claim 1.

3. A non-human host organism or host cell comprising, optionally stably integrated into its genome, the expression vector of claim 2.

4. A non-human host organism or host cell comprising, optionally stably integrated into its genome, an expression system of claim 1.

5. A method for producing an isolated catalytically active polypeptide having isoeugenol oxidizing activity, the method comprising co-expressing said polypeptide having isoeugenol oxidizing activity and helper polypeptides in a host cell system comprising an expression system according to claim 1; and optionally isolating said polypeptide having isoeugenol oxidizing activity.

6. A method of producing vanillin, the method comprising:
   a) performing the method according to claim 5 to produce the polypeptide having isoeugenol oxidizing activity,
   b) contacting isoeugenol with the polypeptide having isoeugenol oxidizing activity in a presence of oxygen to produce vanillin; and
   c) optionally isolating the vanillin produced in step a.

7. The method of the claim 6, the method further comprising chemically or biochemically isomerizing eugenol to isoeugenol, and optionally isolating the isoeugenol.

* * * * *